US008741892B2

(12) United States Patent
Grauert et al.

(10) Patent No.: US 8,741,892 B2
(45) **Date of Patent: *Jun. 3, 2014**

(54) COMPOUNDS

(71) Applicants: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE); Bernd Wellenzohn, Friedrichshafen (DE)

(72) Inventors: Matthias Grauert, Biberach an der Riss (DE); Daniel Bischoff, Biberach an der Riss (DE); Georg Dahmann, Warthausen-Birkenhard (DE); Raimund Kuelzer, Mittelbiberach (DE); Klaus Rudolf, Warthausen (DE); Bernd Wellenzohn, Friedrichshafen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/689,867

(22) Filed: Nov. 30, 2012

(65) Prior Publication Data

US 2013/0143870 A1 Jun. 6, 2013

(30) Foreign Application Priority Data

Dec. 5, 2011 (EP) .................................... 11191924

(51) Int. Cl.

| | |
|---|---|
| ***A01K 43/00*** | (2006.01) |
| ***C07D 223/16*** | (2006.01) |
| ***C07D 513/00*** | (2006.01) |
| ***C07D 487/00*** | (2006.01) |
| ***C07D 401/00*** | (2006.01) |
| ***C07D 413/00*** | (2006.01) |

(52) U.S. Cl.
USPC ...... 514/217.01; 514/406; 514/341; 540/594; 540/568; 540/578; 544/333; 544/368; 546/275.4

(58) Field of Classification Search
None
See application file for complete search history.

(56) References Cited

U.S. PATENT DOCUMENTS

| | | | | |
|---|---|---|---|---|
| 6,166,008 | A * | 12/2000 | Johnson et al. | ............ 514/223.2 |
| 7,582,635 | B2 | 9/2009 | Sun et al. | |
| 8,008,300 | B2 | 8/2011 | Sun et al. | |
| 8,048,890 | B2 | 11/2011 | Buschmann et al. | |
| 2003/0055085 | A1 | 3/2003 | Wagenen et al. | |
| 2004/0186111 | A1 | 9/2004 | Sun et al. | |
| 2005/0256130 | A1 | 11/2005 | Pennell et al. | |
| 2007/0154428 | A1 | 7/2007 | Sato et al. | |
| 2010/0004254 | A1 | 1/2010 | Sun et al. | |
| 2010/0216787 | A1 | 8/2010 | Sato et al. | |
| 2012/0004217 | A1 | 1/2012 | Sun et al. | |
| 2012/0015954 | A1 | 1/2012 | Sun et al. | |
| 2013/0137688 | A1 | 5/2013 | Grauert et al. | |
| 2013/0143870 | A1 | 6/2013 | Grauert et al. | |
| 2013/0150341 | A1 | 6/2013 | Grauert et al. | |
| 2013/0150347 | A1 | 6/2013 | Rudolf et al. | |
| 2013/0150355 | A1 | 6/2013 | Rudolf et al. | |
| 2013/0158011 | A1 | 6/2013 | Rudolf et al. | |
| 2013/0158038 | A1 | 6/2013 | Rudolf et al. | |
| 2013/0184248 | A1 | 7/2013 | Grauert et al. | |

FOREIGN PATENT DOCUMENTS

| | | | |
|---|---|---|---|
| CA | 2476031 | A1 | 9/2003 |
| EP | 0307145 | A1 | 3/1989 |
| EP | 0919232 | A1 | 6/1999 |
| WO | 9749395 | | 12/1997 |
| WO | 0206288 | A1 | 1/2002 |
| WO | 03051833 | A2 | 6/2003 |
| WO | 03053922 | A2 | 7/2003 |
| WO | 03076432 | A1 | 9/2003 |
| WO | 03105853 | A1 | 12/2003 |
| WO | 2004058754 | A1 | 7/2004 |
| WO | 2005030128 | A2 | 4/2005 |
| WO | 2005056015 | A1 | 6/2005 |
| WO | 2005085241 | A1 | 9/2005 |
| WO | 2007021573 | A1 | 2/2007 |
| WO | 2007087135 | A2 | 8/2007 |
| WO | 2008112440 | A1 | 9/2008 |
| WO | 2008145616 | A1 | 12/2008 |
| WO | 2008148840 | A1 | 12/2008 |
| WO | 2008156580 | A1 | 12/2008 |
| WO | 2009143404 | A1 | 11/2009 |

(Continued)

OTHER PUBLICATIONS

Abstract in English for WO2011002067, Publication Date: Jan. 1, 2011.

(Continued)

*Primary Examiner* — Jeffrey H Murray
*Assistant Examiner* — Oluwafemi Masha
(74) *Attorney, Agent, or Firm* — Michael P. Morris; Anthony P. Bottino

(57) ABSTRACT

This invention relates to compounds of formula I

I

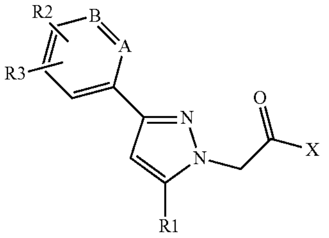

their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment. A, B, X, $R^1$, $R^2$, $R^3$ have meanings given in the description.

3 Claims, No Drawings

(56) References Cited

FOREIGN PATENT DOCUMENTS

| | | | |
|---|---|---|---|
| WO | 2010124055 | A1 | 10/2010 |
| WO | 2010126811 | A1 | 11/2010 |
| WO | 2011002067 | A1 | 1/2011 |
| WO | 2011082010 | A1 | 7/2011 |

OTHER PUBLICATIONS

Adams, C.E. et al., "Chlorpromazine Versus Placebo for Schizophrenia (Review)." The Cochrane Library, 2009, pp. 1-3.
CHEMCATS: Accession No. 0046382561, Oct. 14, 2011.
Dorwald, F. Z. "Side Reactions in Organic Synthesis: A Guide to Successful Synthesis Design." Wiley-VCH Verlag GmbH & Co. KGaA, 2005, pp. 1-390.
Lindsley, C.W., et al., "Discovery of Positive Allosteric Modulators for the Metabotropic Glutamate Receptor Subtype-5 from a Series of N-(1,3-Diphenyl-1H-pyrazol-5-yl) benzamides that Potentiate Receptor Function in Vivo", J. Med. Chem, 2004, 47, pp. 5825-5828.
Shasheva. E. Y. et al., "Reactions of Hydroxyphenyl-substituted 1,2,4-Triazoles with Electrophylic Reagents", Russian Journal of General Chemistry, 2009, vol. 79, No. 10, pp. 2234-2243.
Wermuth, Camille G. "Practice of Medicinal Chemistry, Third Edition." Elsevier Ltd., 2008, Ch. 6, 15, 18, and 20.
International Search Report and Written Opinion for PCT/EP2012/075312 mailed Feb. 7, 2013.
International Search Report and Written Opinion for PCT/EP2012/075313 mailed Feb. 7, 2013.
European Search Report for EP 11193380.0 mailed Mar. 14, 2012.

* cited by examiner

COMPOUNDS

FIELD OF THE INVENTION

This invention relates to substituted pyrazoles and their use as positive allosteric modulators of mGlu5 receptor activity, pharmaceutical compositions containing the same, and methods of using the same as agents for treatment and/or prevention of neurological and psychiatric disorders associated with glutamate dysfunction such as schizophrenia or cognitive decline such as dementia or cognitive impairment.

BACKGROUND OF THE INVENTION

Glutamate is the primary excitatory amino acid in the mammalian central nervous system. Neurotransmission mediated by glutamate has been demonstrated to be critical in many physiological processes, such as synaptic plasticity, long term potentiation involved in both learning and memory as well as sensory perception (Riedel et al., Behav. Brain Res. 2003, 140:1-47). Furthermore, it has been demonstrated that an imbalance of glutamate neurotransmission plays a critical role in the pathophysiology of various neurological and psychiatric diseases.

The excitatory neurotransmission of glutamate is mediated through at least two different classes of receptors, the ionotropic glutamate receptors (NMDA, AMPA and kainate) and the metabotropic glutamate receptors (mGluR). The ionotropic receptors are ligand gated ion channels and are thought to be responsible for the regulating rapid neuronal transmission between two neurons. The metabotropic glutamate receptors are G-protein coupled receptors (GPCRs) which appear to mediate not only synaptic transmission, but also to regulate the extent of neurotransmitter release as well as post synaptic receptor activation.

Disregulation in glutamatergic neurotransmission, for example through altered glutamate release or post-synaptic receptor activation, has been demonstrated in a variety of neurological ans well as psychiatric disorders. Hypofunction of the NMDA receptor has not only been demonstrated in Alzheimer's patients, but is increasingly accepted as the putative cause of schizophrenia (Farber et al., Prog. Brain Res., 1998, 116: 421-437, Coyle et al., Cell. and Mol. Neurobiol. 2006, 26: 365-384). This is supported by clinical studies showing that antagonists of the NMDA receptor induce symptoms indistinguishable to those suffered by schizophrenia patients (Javitt et al., Am J. Psychiatry, 1991, 148: 1301-1308). Therefore, approaches that could potentiate or normalize NMDA receptor signaling have the potential to treat neurological and psychiatric disorders.

mGluR5 belongs to a superfamily of currently eight identified Type III GPCRs, which are unique in that the glutamate ligand binds to a large extracelullar amino-terminal protein domain. This superfamily is further divided into three groups (Group I, II and III) based on amino acid homology as well as the intracellular signalling cascades they regulate (Schoepp et al., Neuropharma, 1999, 38:1431-1476). mGluR5 belongs to group I and is coupled to the phospholipase C signalling cascade which regulates intracellular calcium mobilization.

In the CNS, mGluR5 has been demonstrared to be expressed mainly in the cortex, hippocampus, nucleus accumbens and the caudate-putamen. These brain regions are known to be involved in memory formation and cogntive function as well as emotional response. mGluR5 has been shown to be localized post-synaptically, adjacent to the post-synaptic density (Luj an et al., Eur. J. Neurosci. 1996, 8: 1488-1500). A functional interaction between mGluR5 and the NMDA receptor has also been demonstrated, where activation of mGluR5 potentiates the activation state of the NMDA receptor (Mannaioni et al, NeuroSci., 2001, 21:5925-5924, Rosenbrock et al., Eur. J. Pharma., 2010, 639:40-46). Furthermore, activation of mGluR5 has been demonstrated in pre-clinical in vivo models to rescue cognitive impairment as well as psychotic disturbance induced by NMDA receptor antagonists (Chan et al., Psychopharma. 2008, 198:141-148). Therefore, activation of mGluR5, and thereby potentiation or normalization of the NMDA receptor signaling, is a potential mechanism for the treatment of psychiatric and neurological disorders. Most agonists of mGluR5 bind the orthosteric glutamate binding site. Since the glutamate binding site between the mGluR family members is highly conserved, it has been challenging to develop selective mGluR5 agonists which have acceptable CNS penetration and demonstrate in vivo activity. An alternative approach to achieve selectivity between the mGluR family members is to develop compounds which bind to an allosteric site, which is not as highly conserved between the family members. These allosteric binding compounds would not interfere with the natural glutamate binding and signaling, but modulate the receptor activation state.

Positive allosteric modulators of mGluR5 have recently been identified (O'Brien et al., Mol. Pharma. 2003, 64: 731-740, Lindsley et al., J. Med. Chem. 2004, 47: 5825-5828). These compounds potentiate mGluR5 activity in the presence of bound glutamate. In the absence of bound glutamate, the mGluR5 positive modulators do not demonstrate intrinsic activity. Therefore, these compounds potentiate the natural signaling of mGluR5 as opposed to agonists which activate the receptor in a permanent, unnatural manner. mGluR5 positive allosteric modulators therefore represent an approach to potentiate mGluR5 signaling which in turn potentiates and normalizes the NMDA receptor hypofunction detected in neurological and psychiatric disorders.

US 2005/256130 discloses aryl piperazines.

WO 03/051833 discloses heteroaryl substituted pyrazoles which are shown to be mGluR5 inhibitors.

DETAILED DESCRIPTION OF THE INVENTION

The present invention is directed to compounds of formula I

I

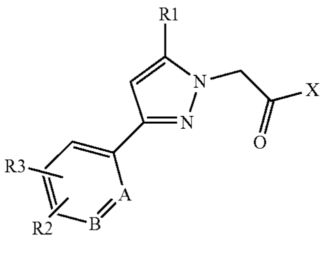

in which

A and B independently represent CH or N;

$R^1$ represents aryl, heteroaryl, $C_{1-8}$alkyl, $C_{3-7}$cycloalkyl, —O—$C_{1-8}$alkyl which latter five groups are optionally substituted with one or more substituents selected from halogen, —CN, $C_{1-3}$alkyl, —O—$C_{1-3}$alkyl;

$R^2$ and $R^3$ independently represent —H, halogen, —CN, —COO—$C_{1-4}$alkyl, $C_{1-5}$alkyl, $C_{3-5}$cycloalkyl, —O—$C_{1-5}$ alkyl which latter four groups are optionally substituted with one or more fluorine atoms;

X represents
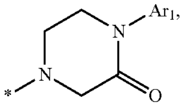
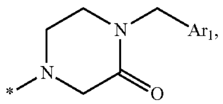
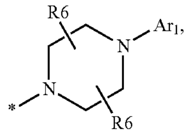
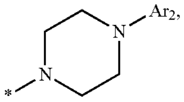
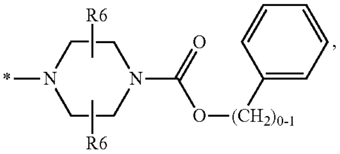
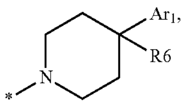
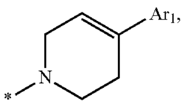
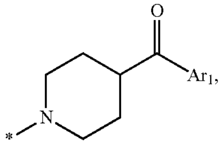
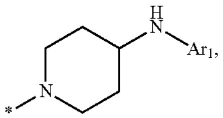
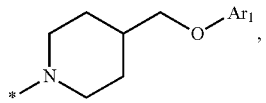
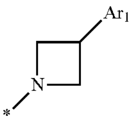
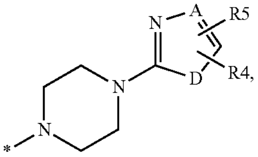
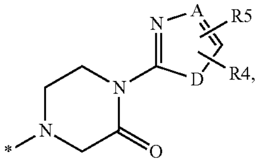
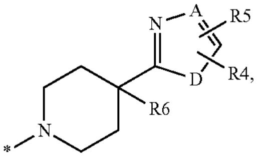
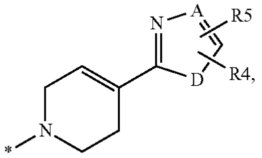
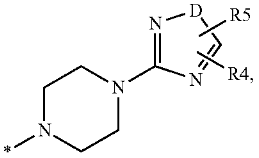
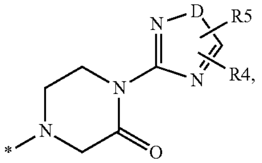
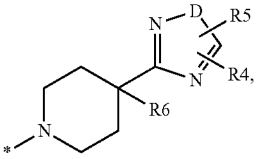
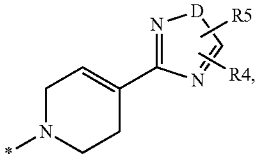
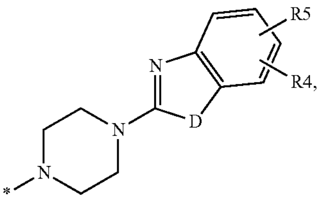
-continued
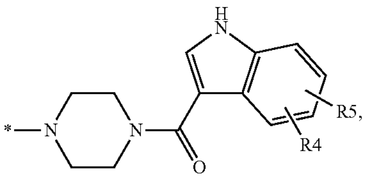
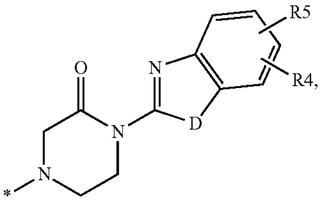
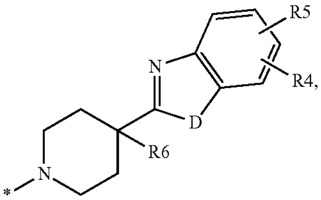
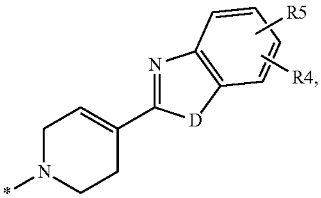
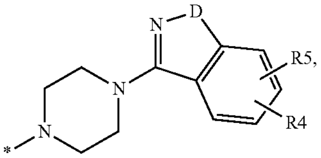
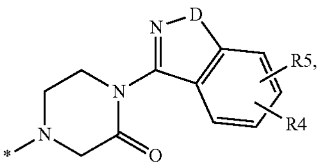
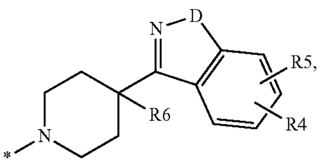
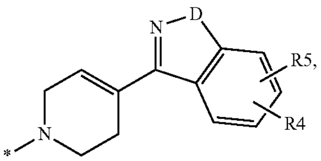
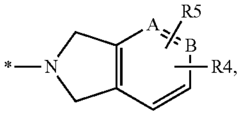
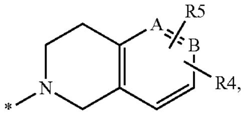
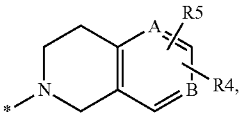
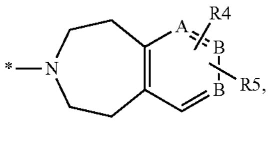

-continued
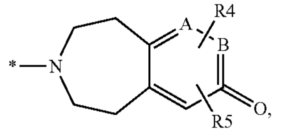
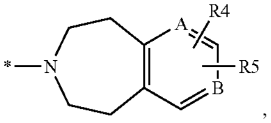
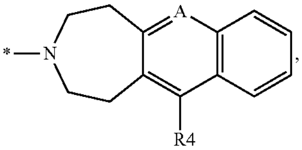
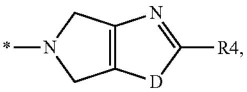
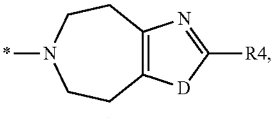
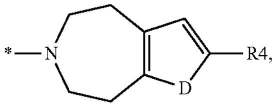
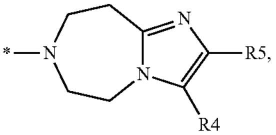
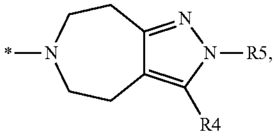
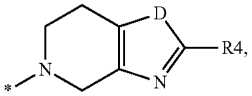
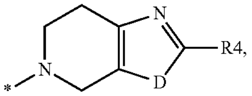
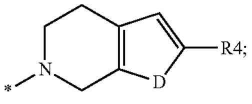
Ar$_1$ represents
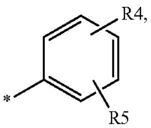
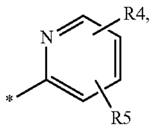
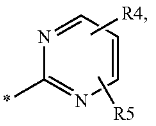
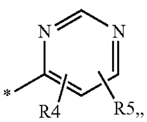
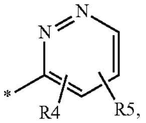
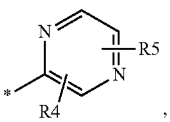
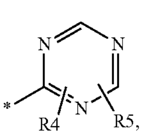
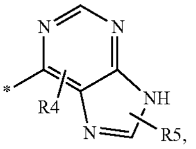
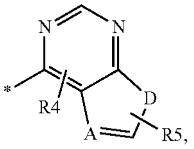
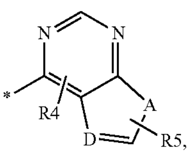
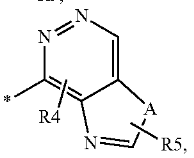
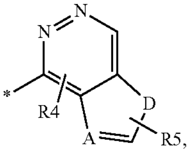
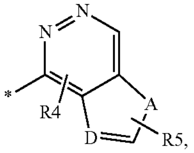
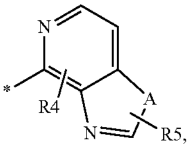
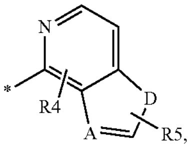
-continued
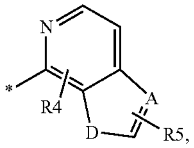
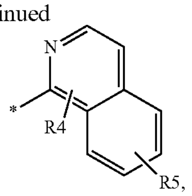
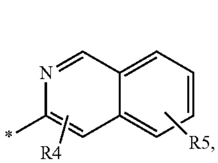
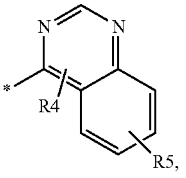
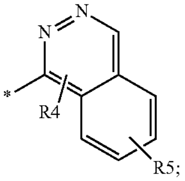
Ar$_2$ represents
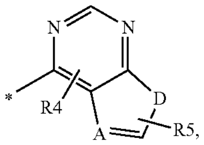
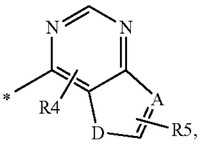
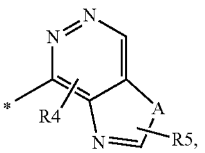
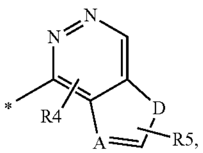
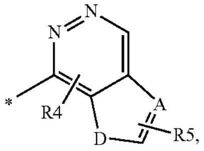
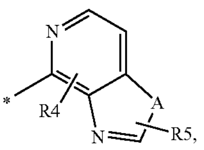
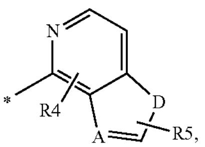
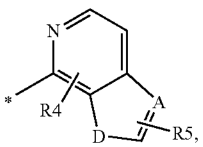
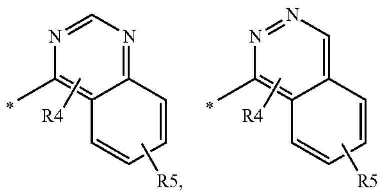
D represents S or O;
$R^4$ and $R^5$ independently represent —H, halogen, —OH, —CN, —$NH_2$, $C_{1-5}$alkyl, phenyl, —NH-phenyl, —NH—$C_{1-5}$alkyl, —N($C_{1-5}$alkyl)$_2$, —O—$C_{1-5}$alkyl, —COO—$C_{1-5}$alkyl, —CONH($C_{1-5}$alkyl), —CON($C_{1-5}$alkyl)$_2$, —NHCONH—$C_{1-5}$alkyl, —NHCON($C_{1-5}$alkyl)$_2$, —NH- CONH—$C_{3-5}$alkenyl, —NHCON($C_{3-5}$alkenyl)$_2$, —NHCO—$C_{1-5}$alkyl which latter eleven groups are optionally substituted with one or more substituents selected from halogen, —OH;

$R^6$ represents —H, $C_{1-3}$alkyl;

or a salt thereof, particularly a physiologically acceptable salt thereof.

In another embodiment, in the general formula I, A, B, D, X, $Ar^1$, $Ar^2$, $R^2$, $R^3$, $R^4$, $R^5$, $R^6$ have the same meaning as defined in any of the preceding embodiments, and $R^1$ represents phenyl, pyridinyl, $C_{1-4}$alkyl, $C_{3-6}$cycloalkyl which latter four groups are optionally substituted with one or more substituents selected from fluoro, $C_{1-3}$alkyl, —O—$C_{1-3}$ alkyl.

In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and X represents

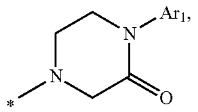
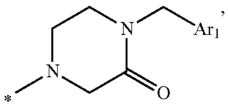
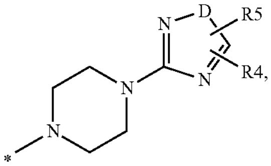
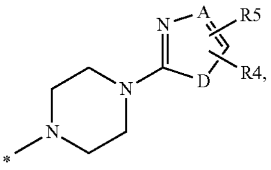
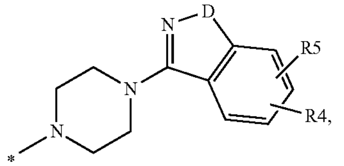
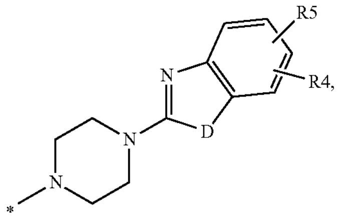
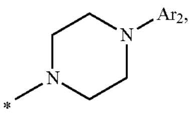
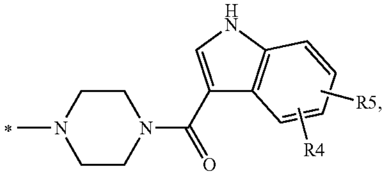
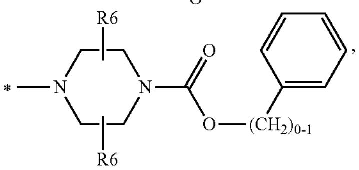
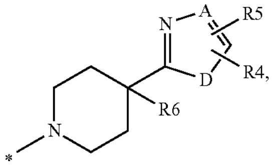
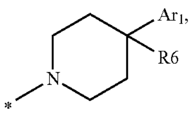

-continued

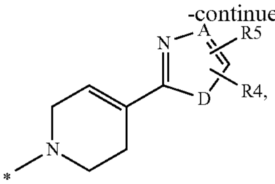
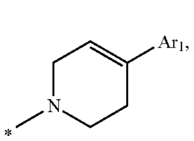
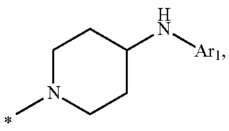
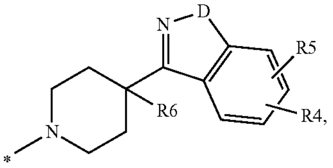
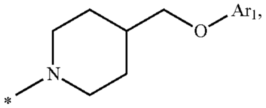
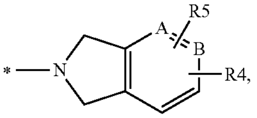
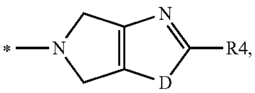
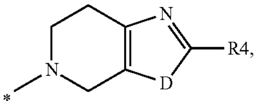
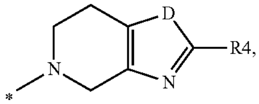
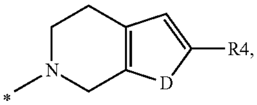
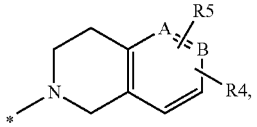
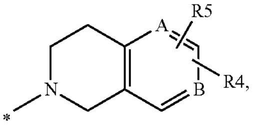
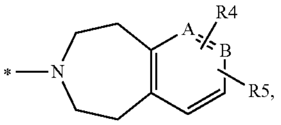
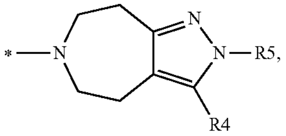
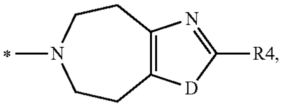
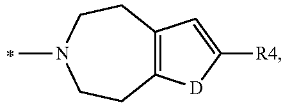
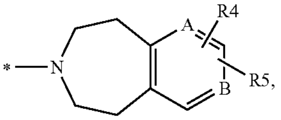
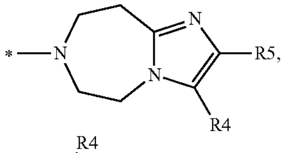
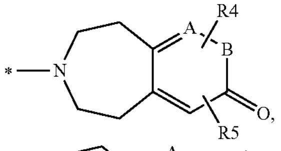
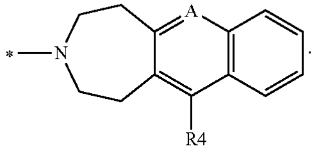

In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and
X represents
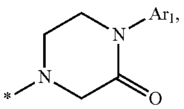
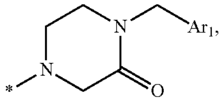
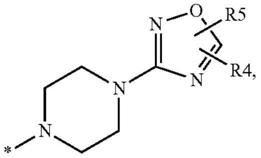
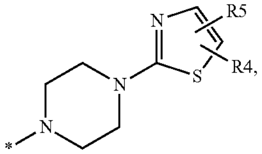
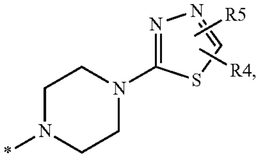
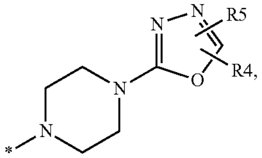
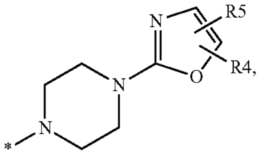
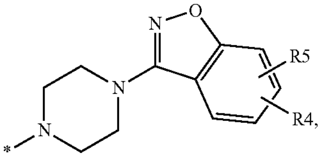
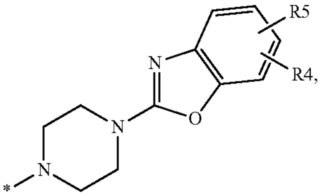
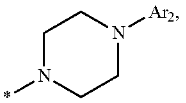
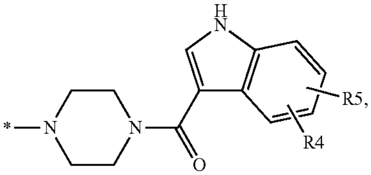
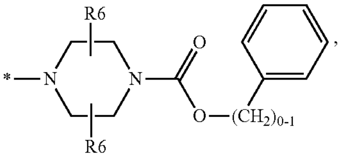
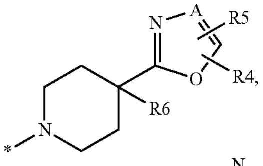
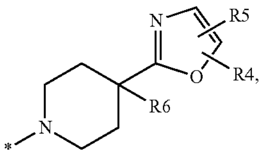
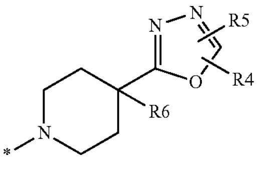
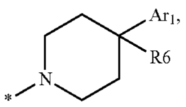
-continued
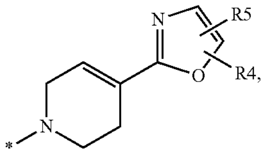
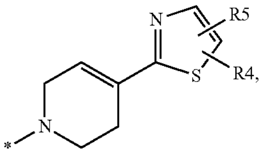
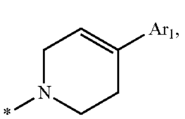
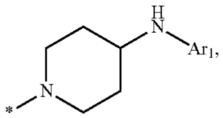
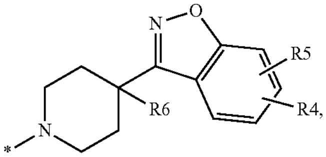
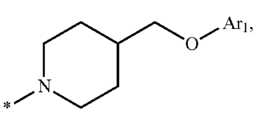
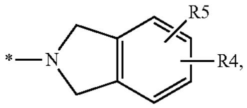
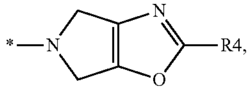
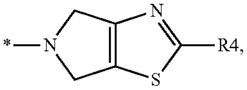
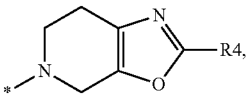
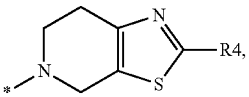
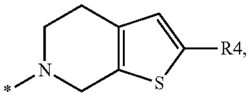
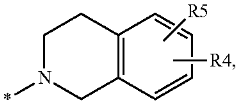
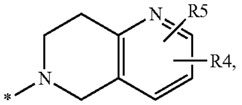
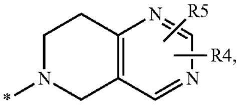
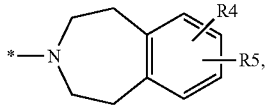
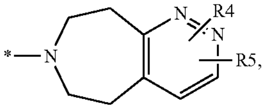
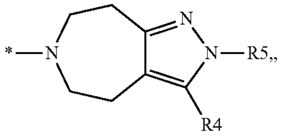
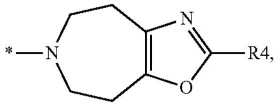
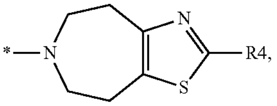
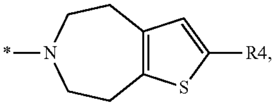
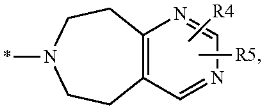
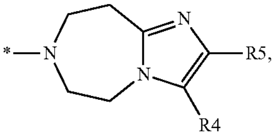
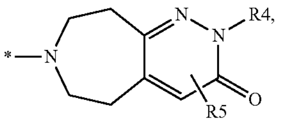

-continued

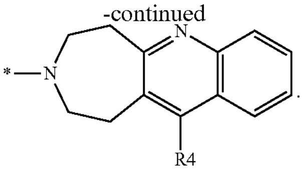

In another embodiment, in the general formula I, A, B, D, X, $Ar^1$, $Ar^2$, $R^1$, $R^2$, $R^3$, $R^4$, $R^5$ have the same meaning as defined in any of the preceding embodiments, and $R^6$ represents hydrogen, methyl.

In another embodiment, in the general formula I, A, B, D, X, $Ar^2$, $R^1$, $R^2$, $R^3$, $R^4$, $R^5$, $R^6$ have the same meaning as defined in any of the preceding embodiments, and $Ar_1$ represents

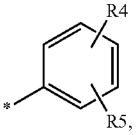
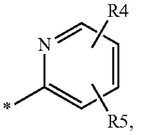
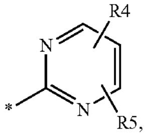
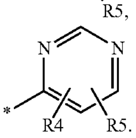

In another embodiment, in the general formula I, A, B, D, X, $Ar^1$, $R^1$, $R^2$, $R^3$, $R^4$, $R^5$, $R^6$ have the same meaning as defined in any of the preceding embodiments, and $Ar_2$ represents

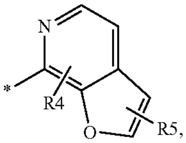
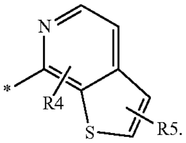

In another embodiment, in the general formula I, A, B, D, X, $Ar^1$, $Ar^2$, $R^1$, $R^2$, $R^3$, $R^6$ have the same meaning as defined in any of the preceding embodiments, and $R^4$ and $R^5$ independently represent —H, —F, —Cl, —Br, —OH, —CN, —$NH_2$, $C_{1-3}$alkyl, phenyl, —NH-phenyl, —NH—$C_{1-3}$alkyl, —N($C_{1-3}$alkyl)$_2$, —O—$C_{1-3}$alkyl, —COO—$C_{1-3}$alkyl, —CONH($C_{1-3}$alkyl), —CON($C_{1-3}$ alkyl)$_2$, —NHCONH—$C_{1-3}$alkyl, —NHCON($C_{1-3}$ alkyl)$_2$, —NHCONH-allyl, —NHCO—$C_{1-3}$alkyl which latter eleven groups are optionally substituted with one or more fluorine atoms.

In another embodiment, in the general formula I, Ar, $R^1$ have the same meaning as defined in any of the preceding embodiments, and the group

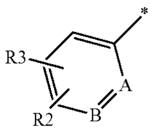

represents phenyl, 2-pyridyl which latter two groups are optionally substituted with one or more substituents selected from fluoro, chloro, bromo, —CN, $C_{1-3}$alkyl, $C_{3-5}$cycloalkyl, —O—$C_{1-3}$ alkyl, —COO—$C_{1-4}$alkyl which latter four groups are optionally substituted with one or more fluorine atoms.

In another embodiment, in the general formula I, A, B, D, X, $Ar^1$, $Ar^2$, $R^2$, $R^3$, $R^4$, $R^5$, $R^6$ have the same meaning as defined in any of the preceding embodiments, and $R^1$ represents phenyl, methyl, ethyl, propyl, iso-propyl, cyclopropyl, cyclohexyl,

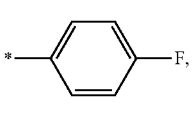
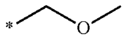
,
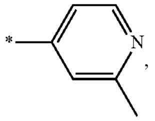
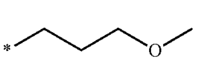
,
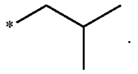
.

In another embodiment, in the general formula I, A, B, D, $Ar^1$, $Ar^2$, $R^1$, $R^2$, $R^3$, $R^4$, $R^5$, $R^6$ have the same meaning as defined in any of the preceding embodiments, and X represents

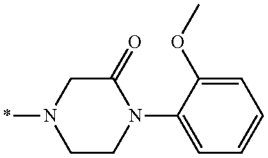
,
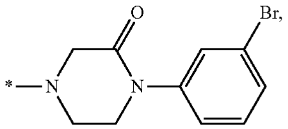
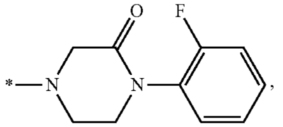
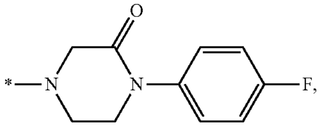
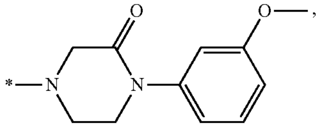
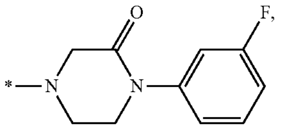
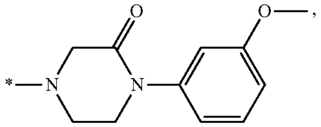
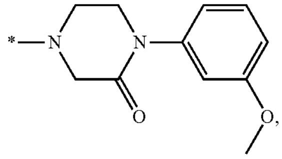
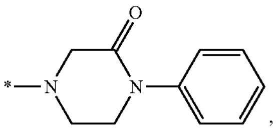
, -continued
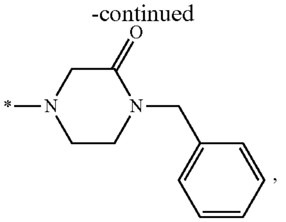
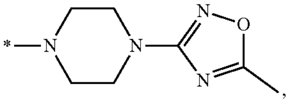
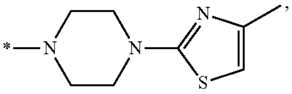
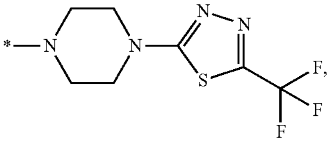
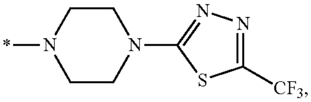
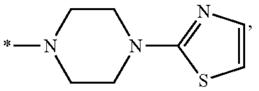
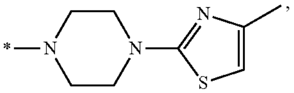
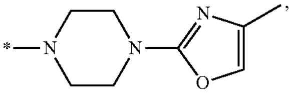
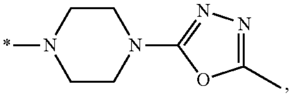
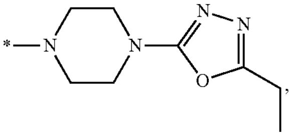
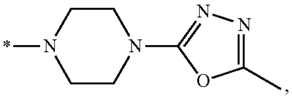
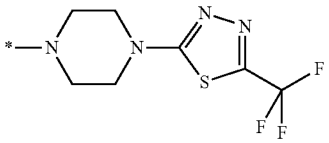
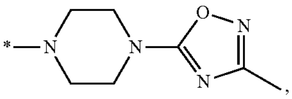
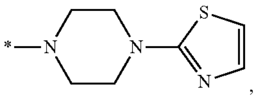
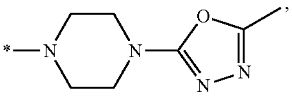
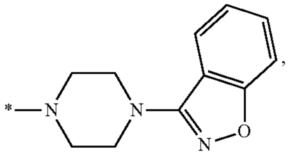
-continued
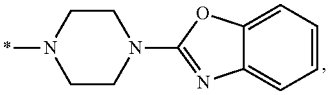
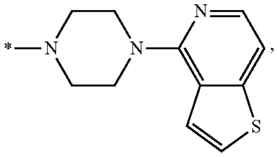
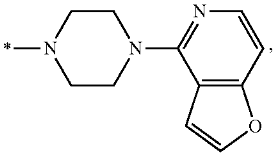
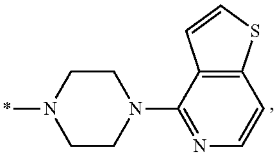
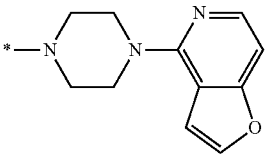
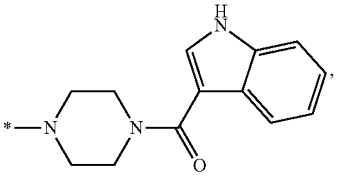
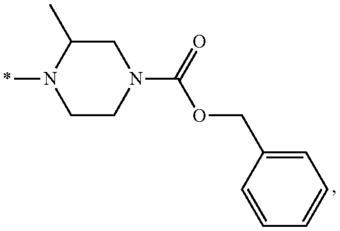
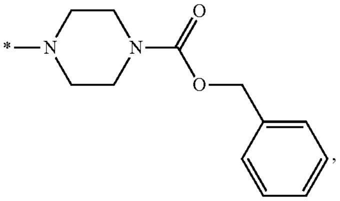
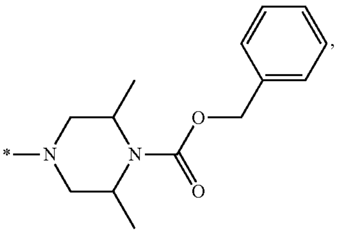
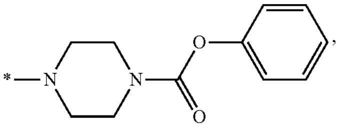
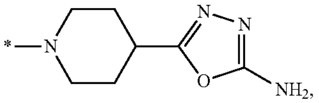
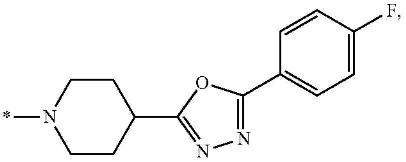

-continued
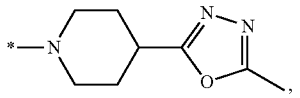
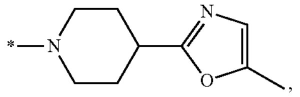
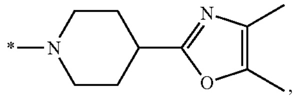
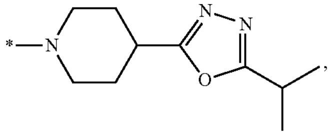
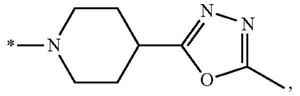
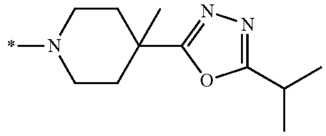
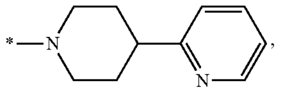
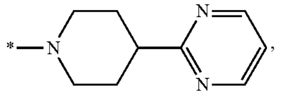
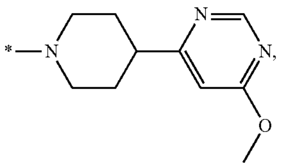
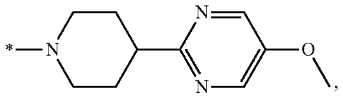
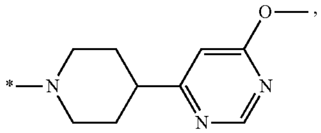
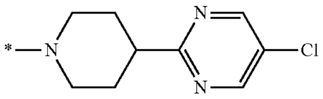
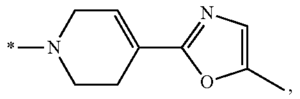
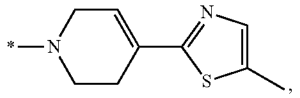
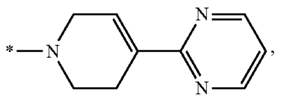
-continued
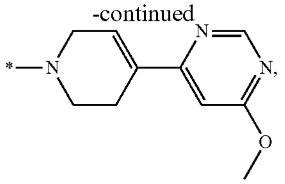
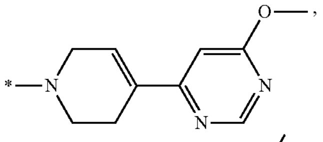
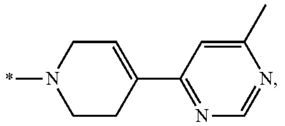
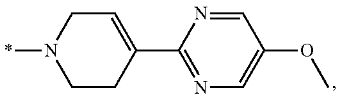
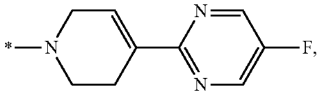
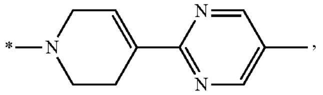
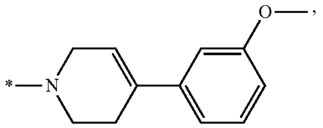
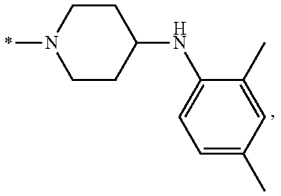
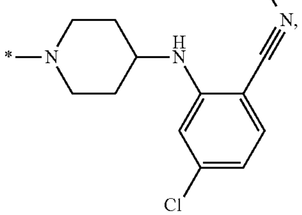
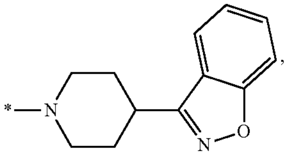
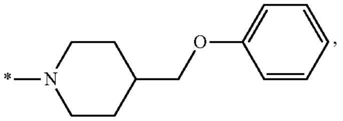
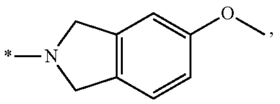 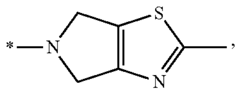
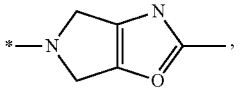 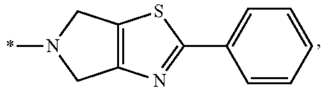

-continued
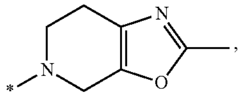,
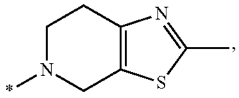,
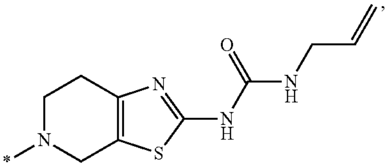,
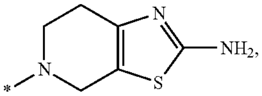,
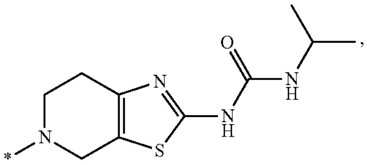,
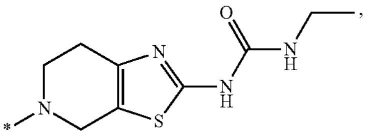,
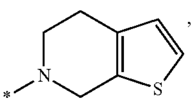,
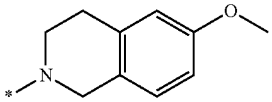,
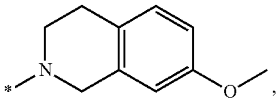,
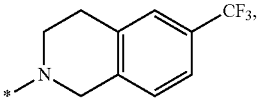,
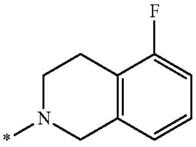,
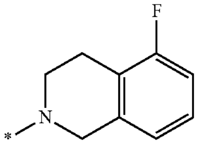,
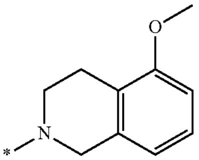,
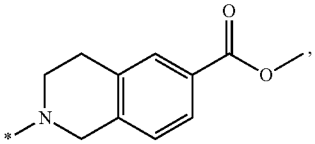,
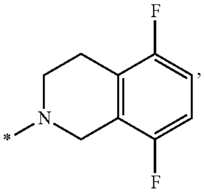,
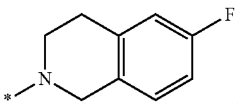,
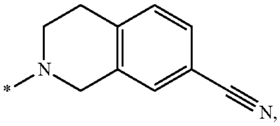,
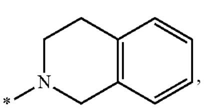,
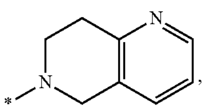,
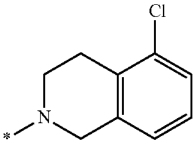,
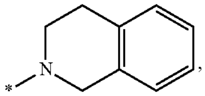,
-continued
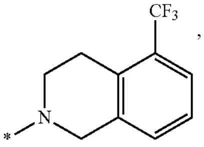,
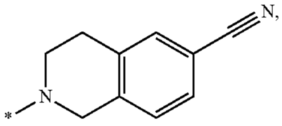,
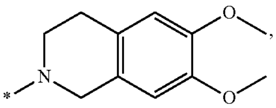,
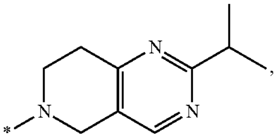,
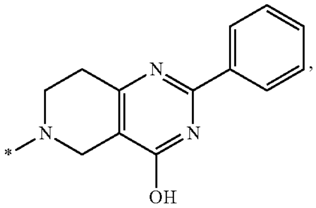,
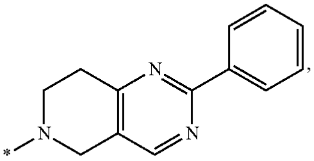,
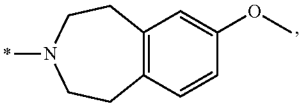,
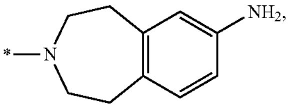,
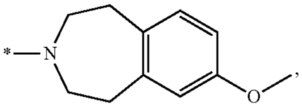,
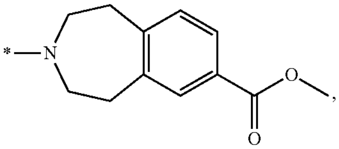,
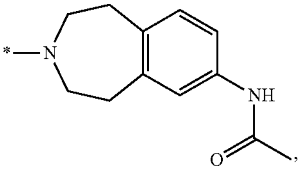,
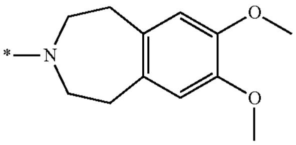
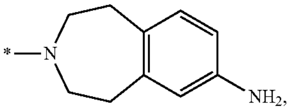,
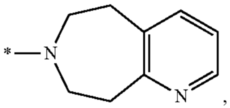,
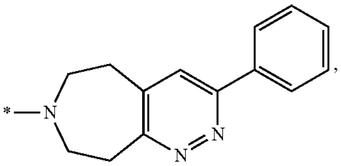, -continued

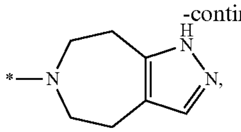, 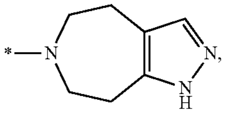,

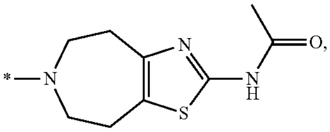,

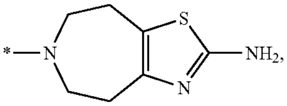, 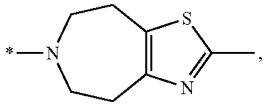,

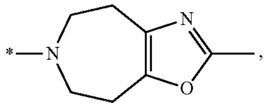, 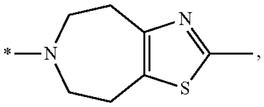,

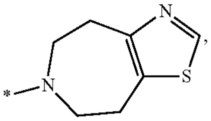, 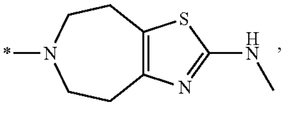,

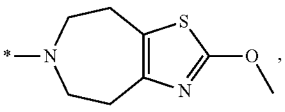, 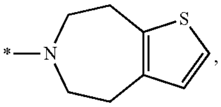,

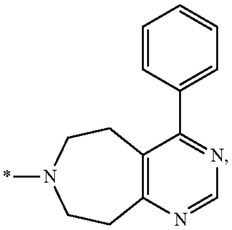,

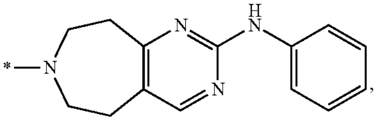,

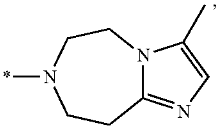, 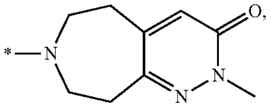,

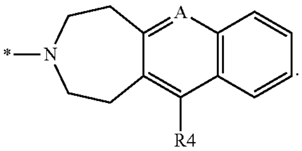.

In another embodiment, in the general formula I, Ar, $R^1$ have the same meaning as defined in any of the preceding embodiments, and A represents N or CH;

B represents CH.

In another embodiment, in the general formula I, A, B, D, X, $Ar^1$, $Ar^2$, $R^1$, $R^4$, $R^5$, $R^6$ have the same meaning as defined in any of the preceding embodiments, and $R^2$ and $R^3$ independently represent —H, chloro, fluoro, —CN, $C_{1-3}$alkyl, —O—$C_{1-3}$alkyl which latter two groups are optionally substituted with one or more fluorine atoms.

In another embodiment, in the general formula I, Ar, $R^1$ have the same meaning as defined in any of the preceding embodiments, and the group

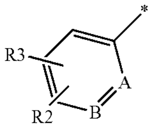

represents

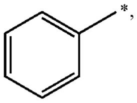, 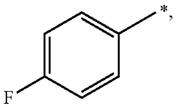, 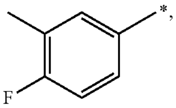,

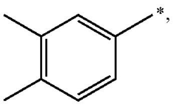, 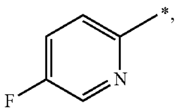,

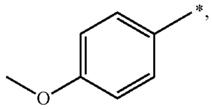, 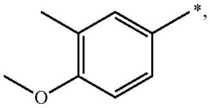,

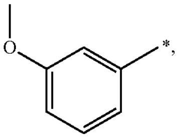, 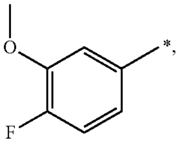, 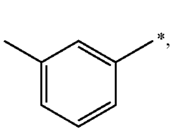,

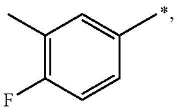, 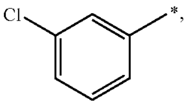, 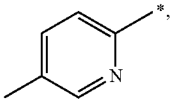,

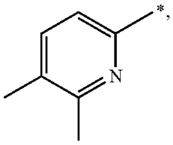, 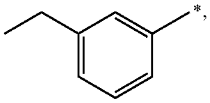, 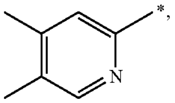,

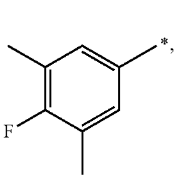, 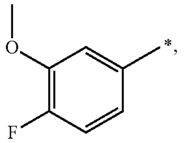, 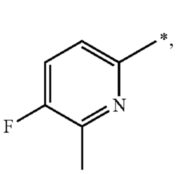,

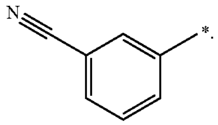.

A further embodiment of the present invention comprises compounds of formula I in which A represents N or CH;

B represents CH;

$R^1$ represents phenyl, methyl, ethyl, propyl, iso-propyl, cyclopropyl, cyclohexyl,
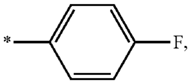 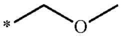, 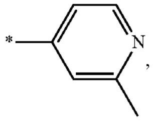
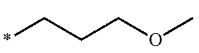, 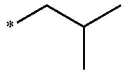;
X represents
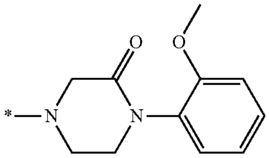, 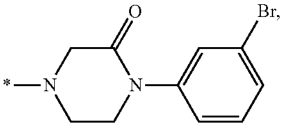
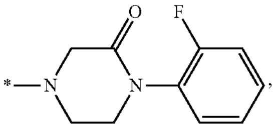
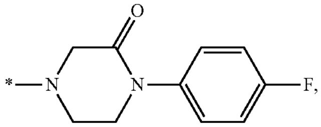
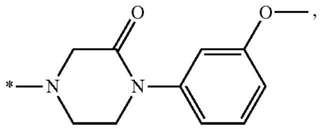
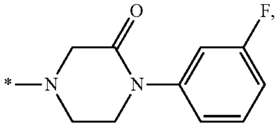
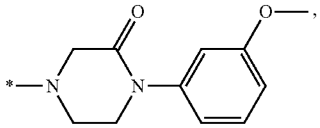
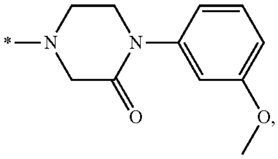 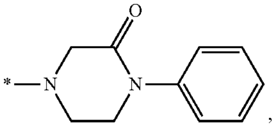,
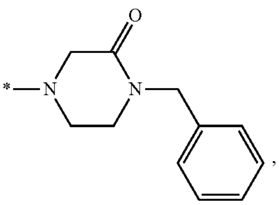
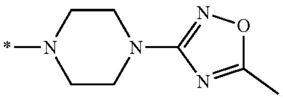,
-continued
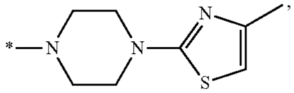
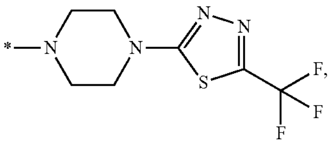
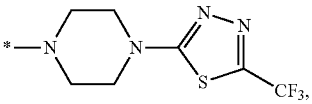
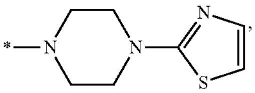 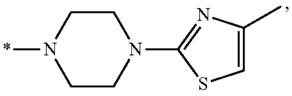
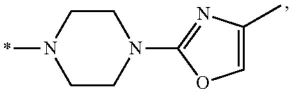
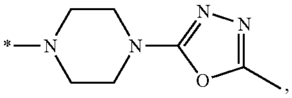
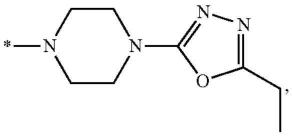
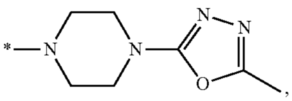
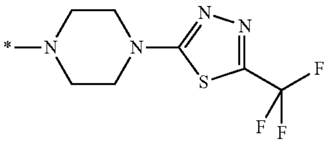
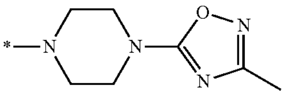, 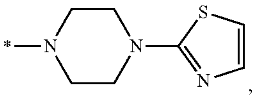,
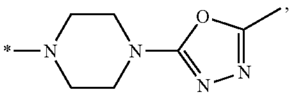
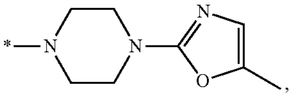
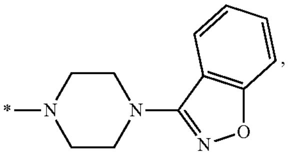
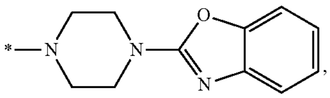

-continued
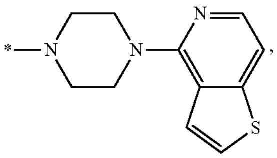,
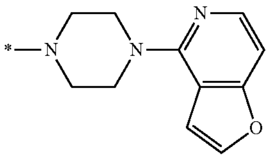,
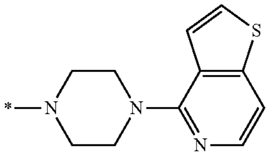,
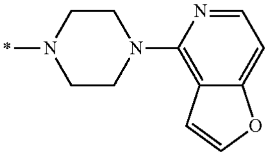
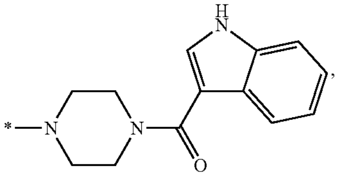,
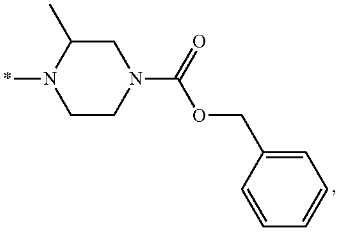,
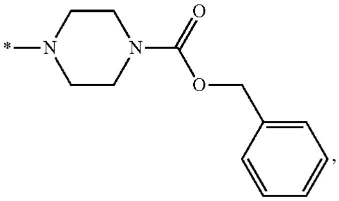,
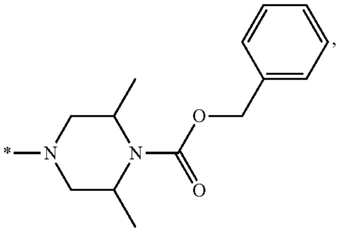,
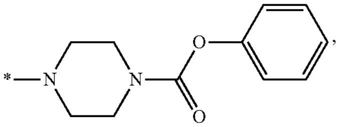,
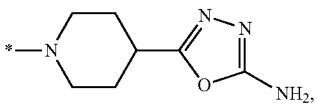,
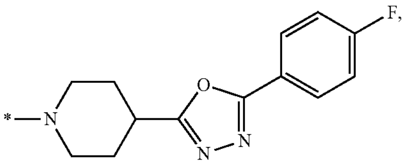
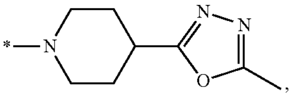,
-continued
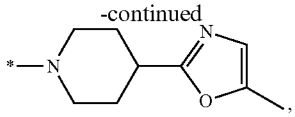,
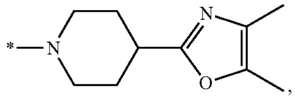,
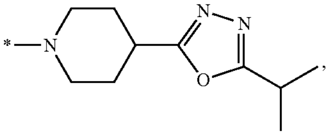,
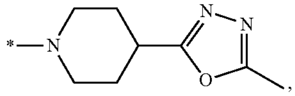,
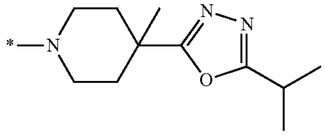
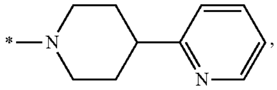,
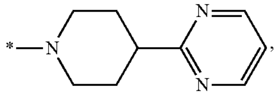,
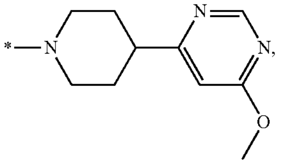
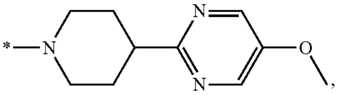,
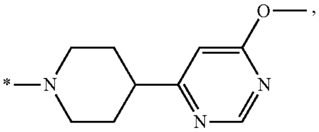,
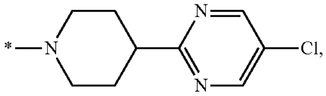
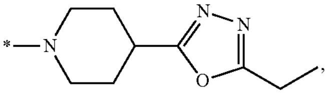,
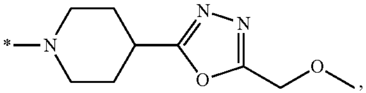,
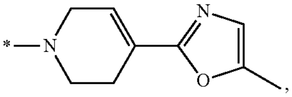,
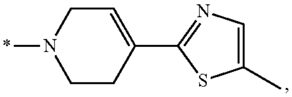,
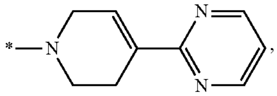, -continued
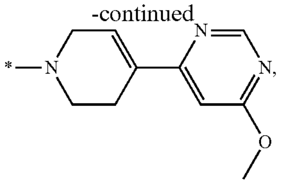
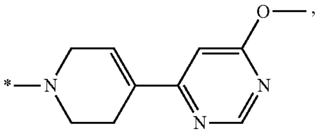
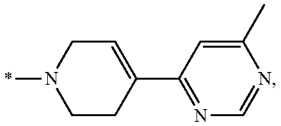
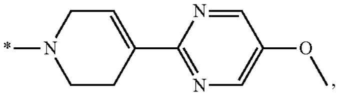
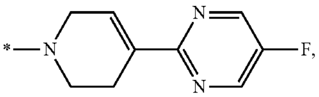
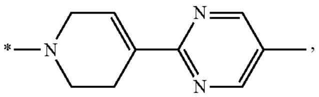
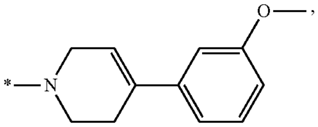
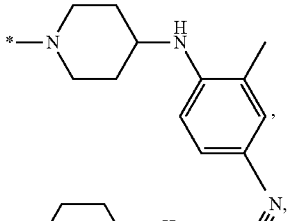
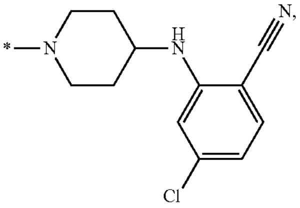
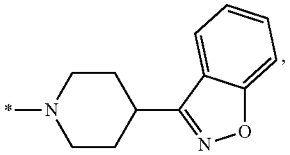
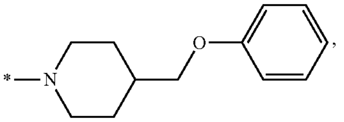
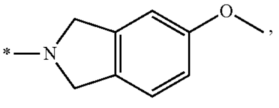
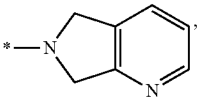
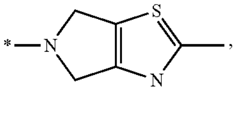
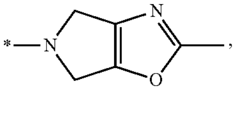
-continued
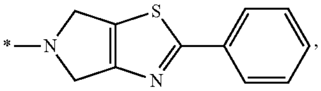
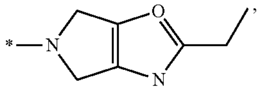
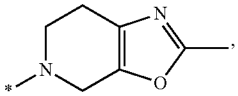
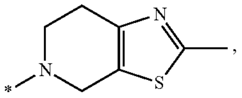
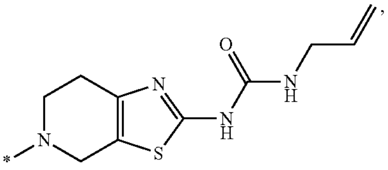
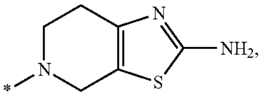
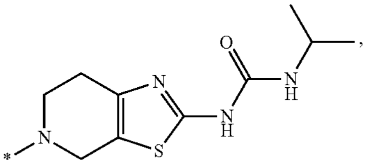
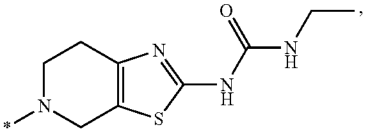
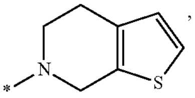
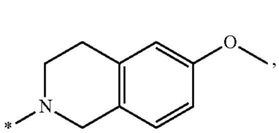
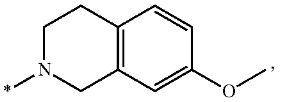
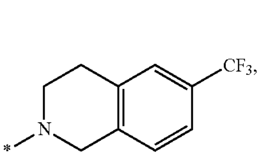
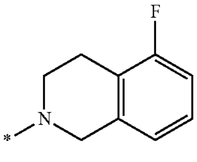
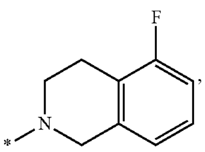
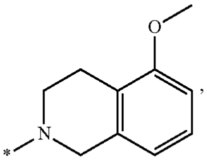
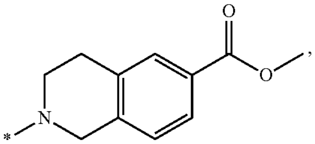
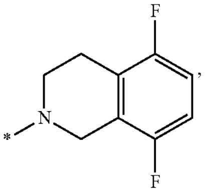
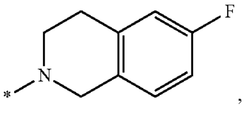
,
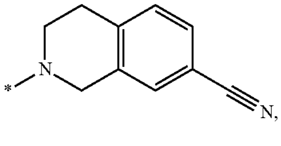

-continued
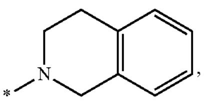,
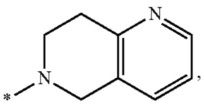,
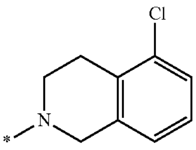,
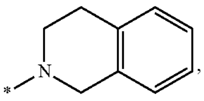,
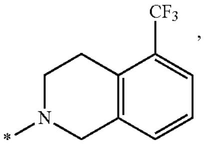,
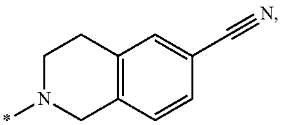,
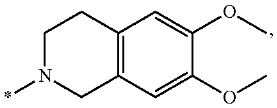,
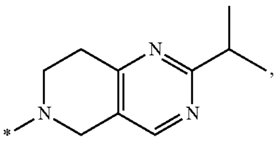,
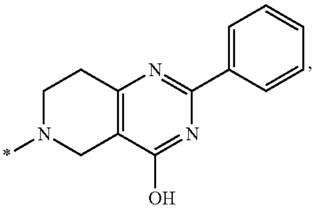,
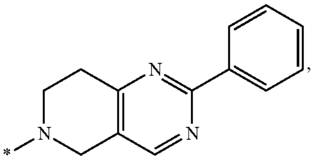,
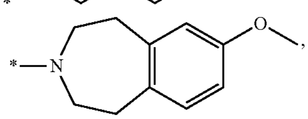,
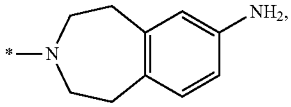,
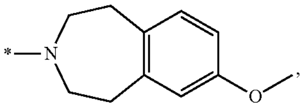,
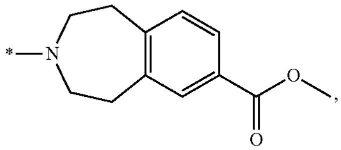,
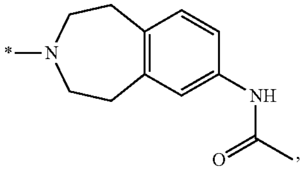,
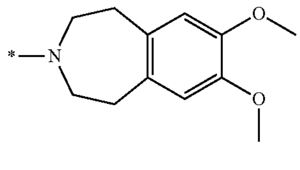
-continued
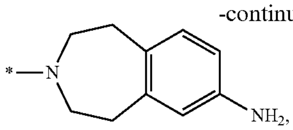,
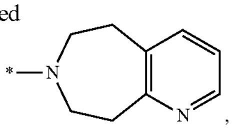,
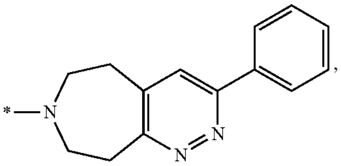,
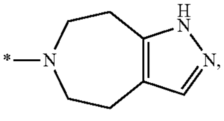,
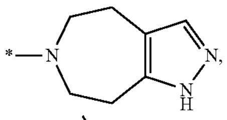,
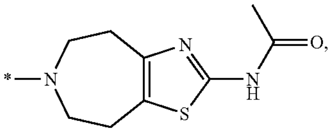,
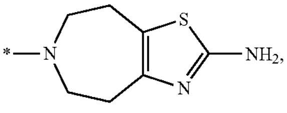,
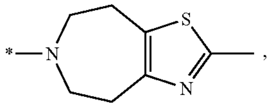,
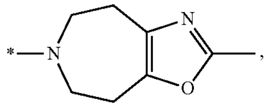,
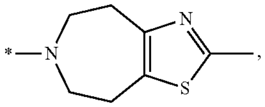,
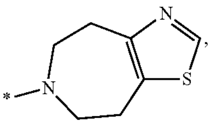,
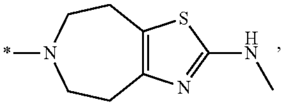,
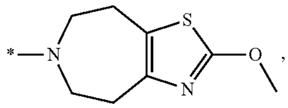,
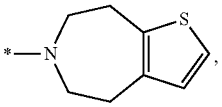,
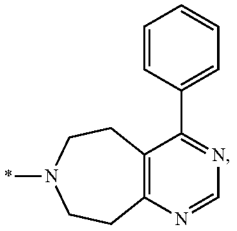,
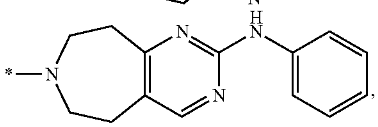,
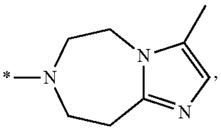,
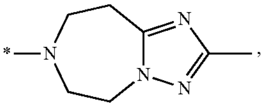,
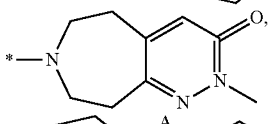,
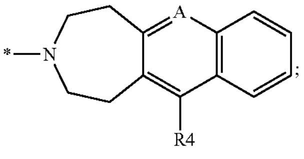;

the group
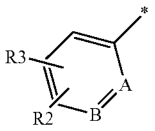
represents
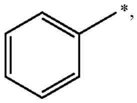, 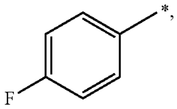, 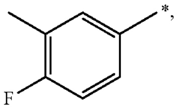, 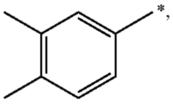, 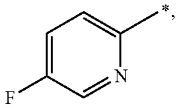, 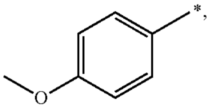, 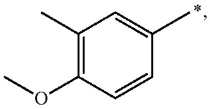, 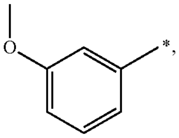, 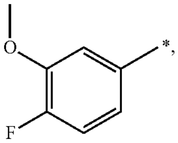, 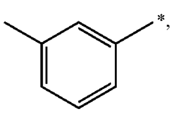, 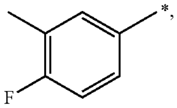, 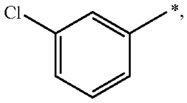, 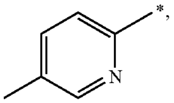, 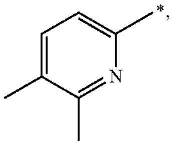, 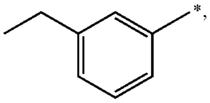, 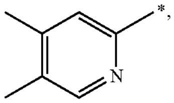, 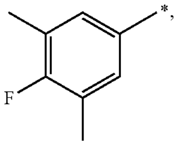, 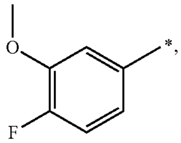, 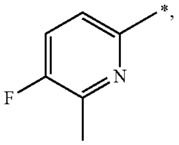, 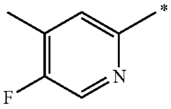 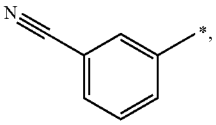, 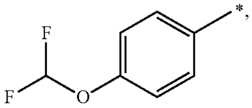, 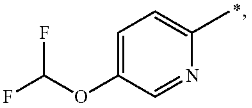, 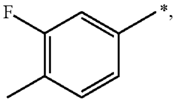, 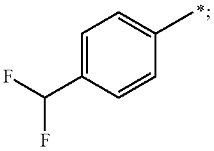;
or a salt thereof, particularly a physiologically acceptable salt thereof.
A further embodiment of the present invention comprises compounds of formula I in which
A represents N or CH;
B represents CH;
$R^1$ represents phenyl, methyl, ethyl, propyl, iso-propyl, cyclopropyl, cyclohexyl,
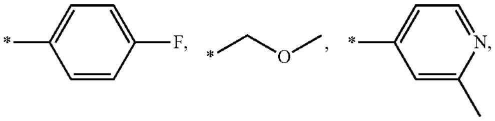
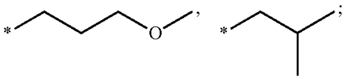;
X represents
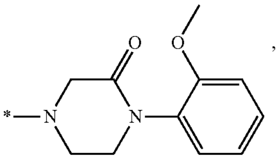, 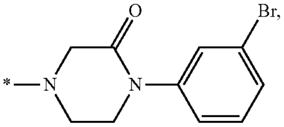, 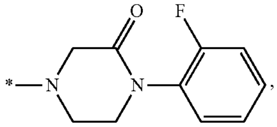, 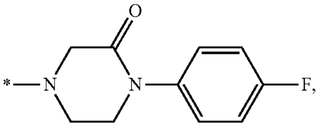, 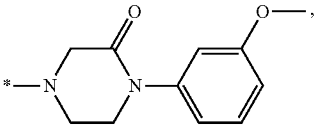, 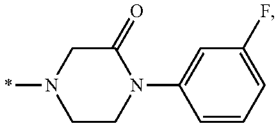, 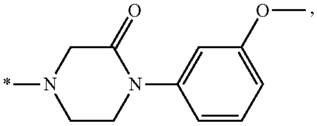, 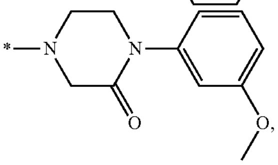, 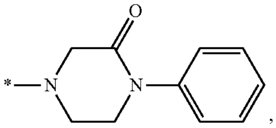, 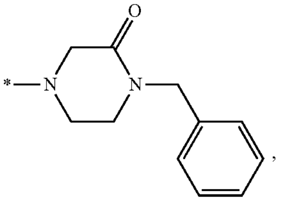, 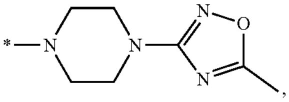, -continued
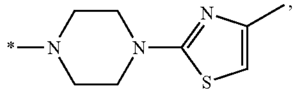
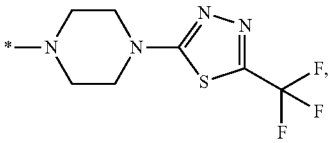
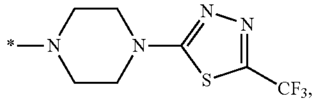
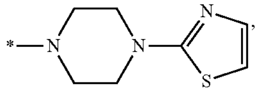
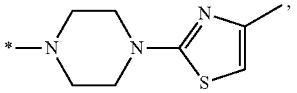
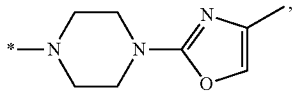
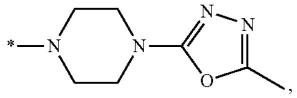
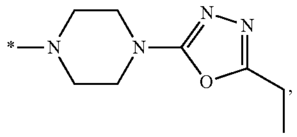
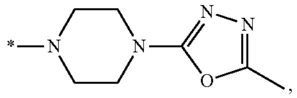
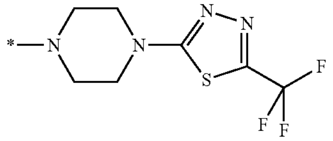
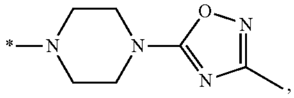
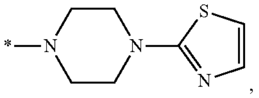
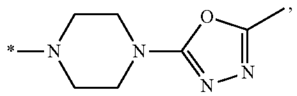
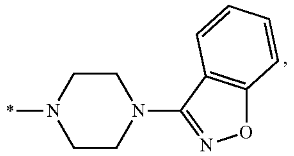
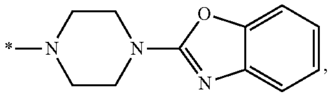
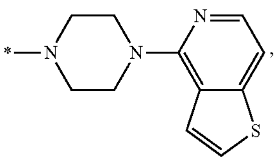
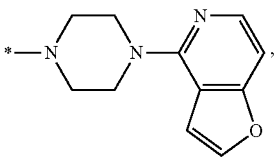
-continued
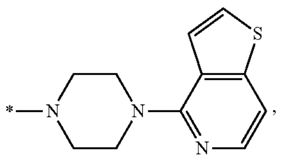
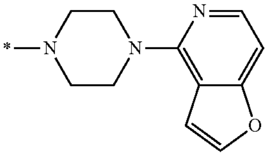
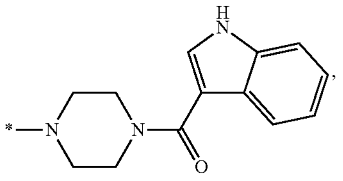
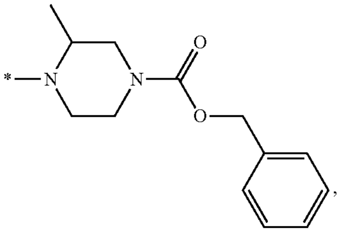
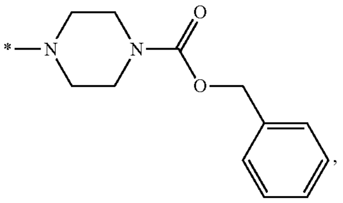
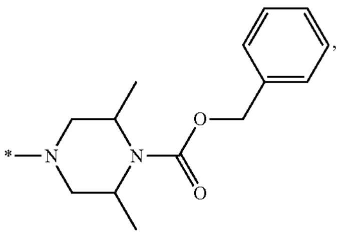
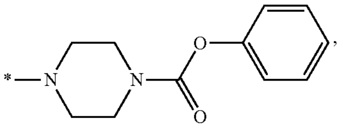
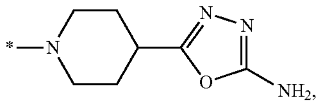
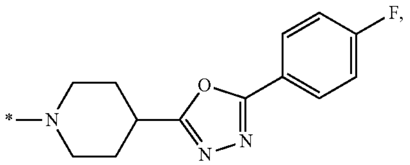
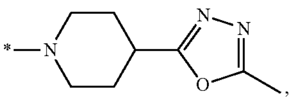
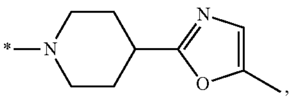

-continued
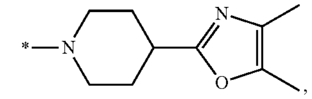
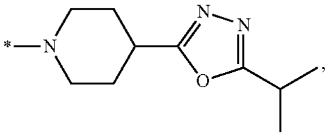
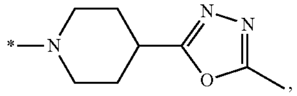
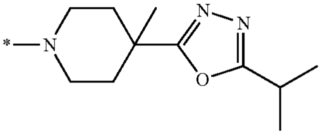
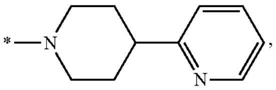
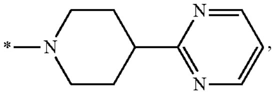
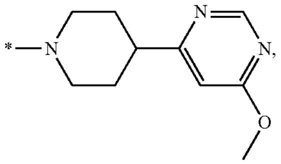
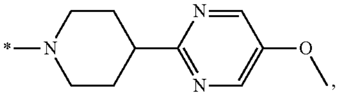
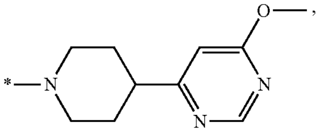
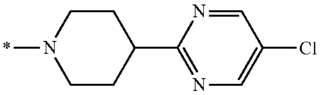
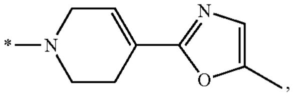
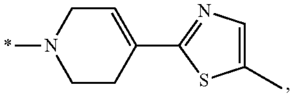
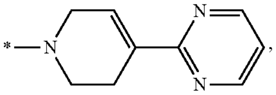
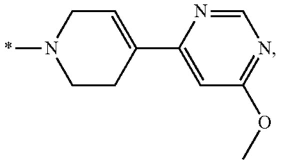
-continued
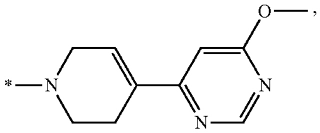
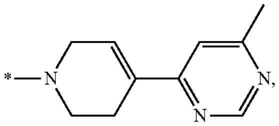
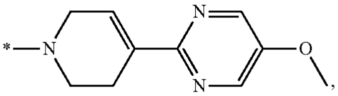
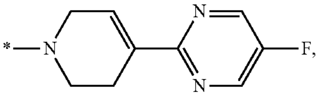
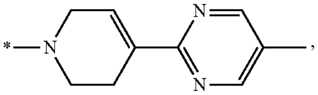
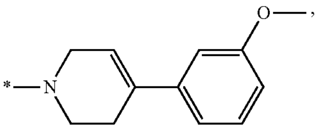
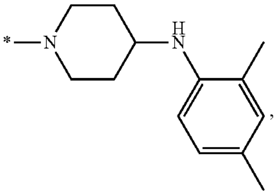
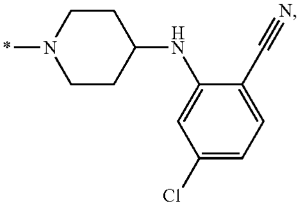
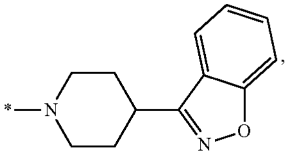
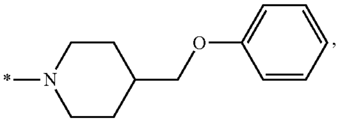
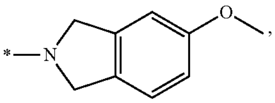
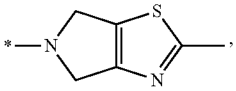
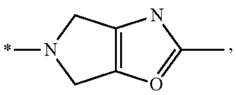
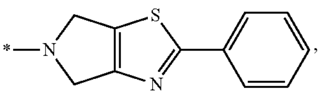
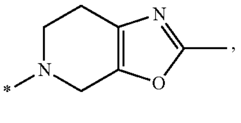
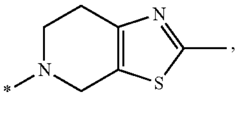

-continued
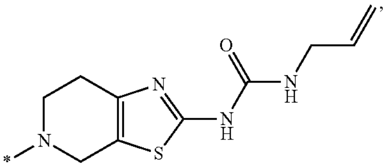
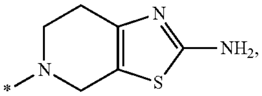
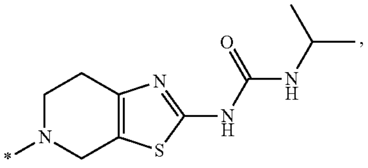
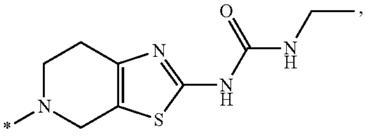
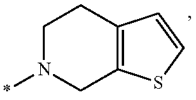
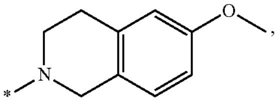
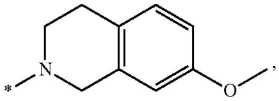
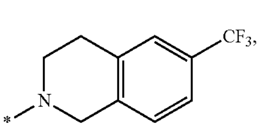
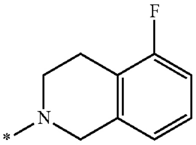
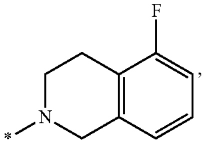
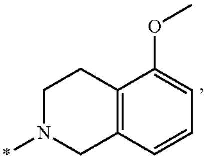
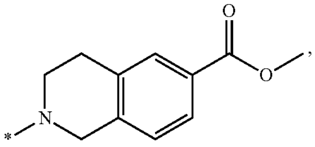
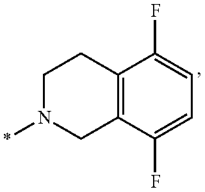
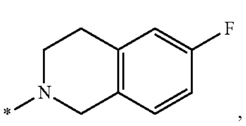
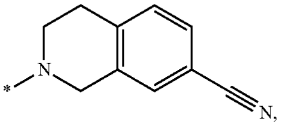
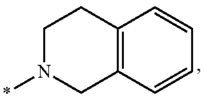
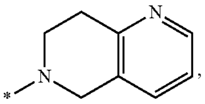
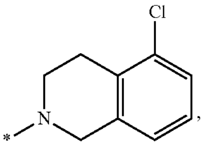
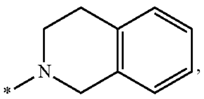
-continued
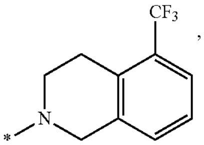
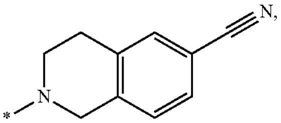
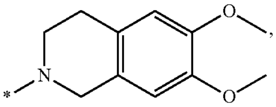
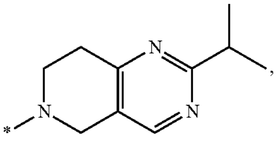
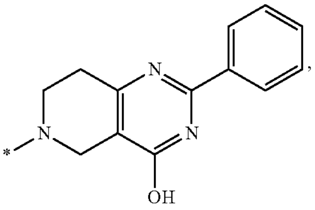
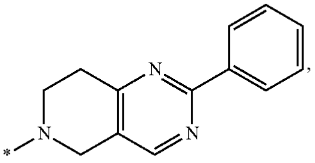
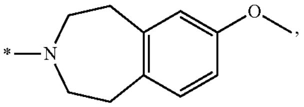
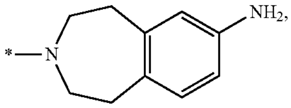
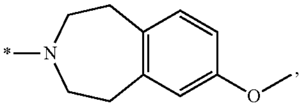
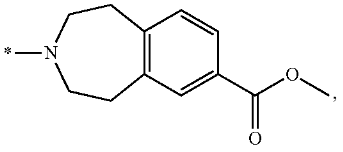
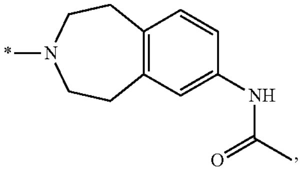
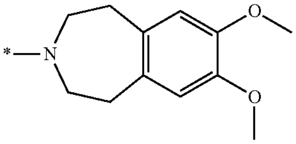
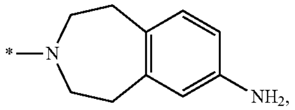
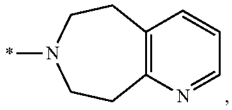
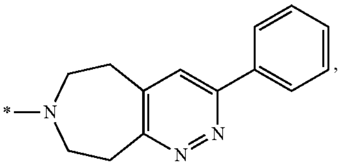

-continued

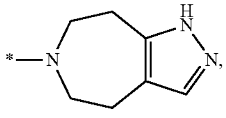, 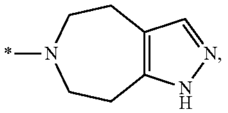,

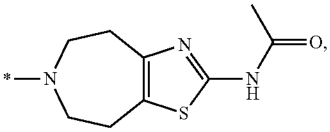,

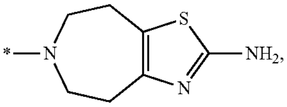, 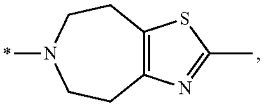,

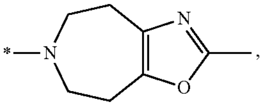, 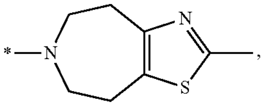,

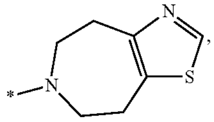, 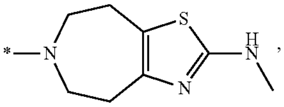,

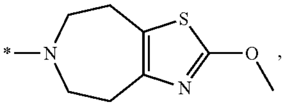, 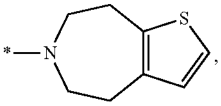,

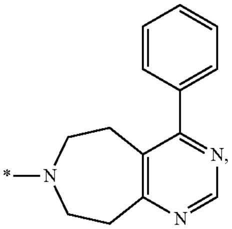,

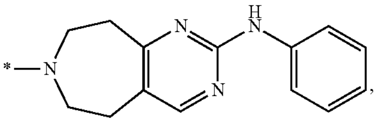,

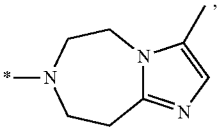, 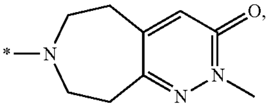,

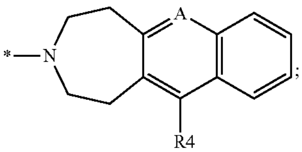;

the group

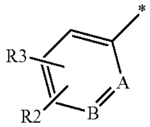

represents

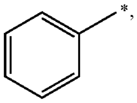, 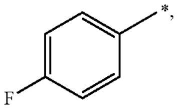, 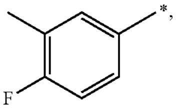, 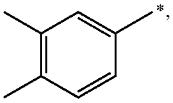, 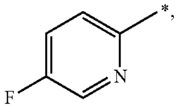, 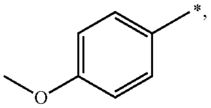, 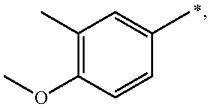, 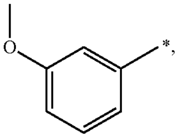, 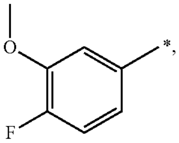, 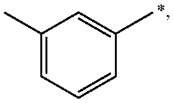, 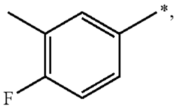, 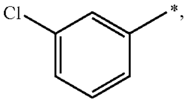, 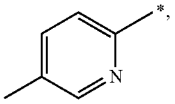, 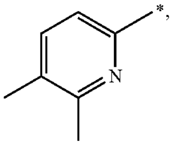, 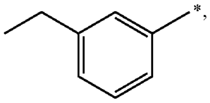, 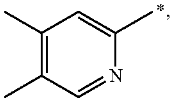, 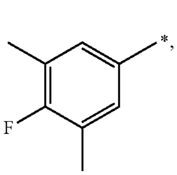, 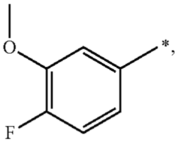, 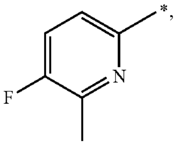, 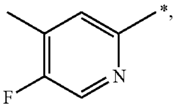, 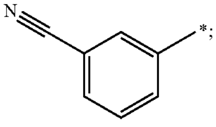;

or a salt thereof, particularly a physiologically acceptable salt thereof.

TERMS AND DEFINITIONS USED

General Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached.

For example, the term "3-carboxypropyl-group" represents the following substituent:

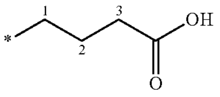

wherein the carboxy group is attached to the third carbon atom of the propyl group. The terms "1-methylpropyl-", "2,2-dimethylpropyl-" or "cyclopropylmethyl-" group represent the following groups:

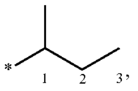

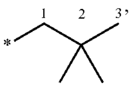

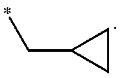

The asterisk may be used in sub-formulas to indicate the bond which is connected to the core molecule as defined.

Stereochemistry/Solvates/Hydrates:

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine(2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine(2,2',2''-nitrilotris(ethanol)), tromethamine, zinc hydroxide, acetic acid, 2.2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts,) also comprise a part of the invention.

Halogen:

The term halogen generally denotes fluorine, chlorine, bromine and iodine.

Alkyl:

The term "$C_{1-8}$-alkyl", either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$.

Alkenyl:

The term "$C_{2-n}$-alkenyl", is used for a group as defined in the definition for "$C_{1-n}$-alkyl" with at least two carbon atoms, if at least two of those carbon atoms of said group are bonded to each other by a double bond.

Cycloalkyl:

The term "$C_{3-7}$-cycloalkyl", either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

Aryl:

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

Heteroaryl:

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

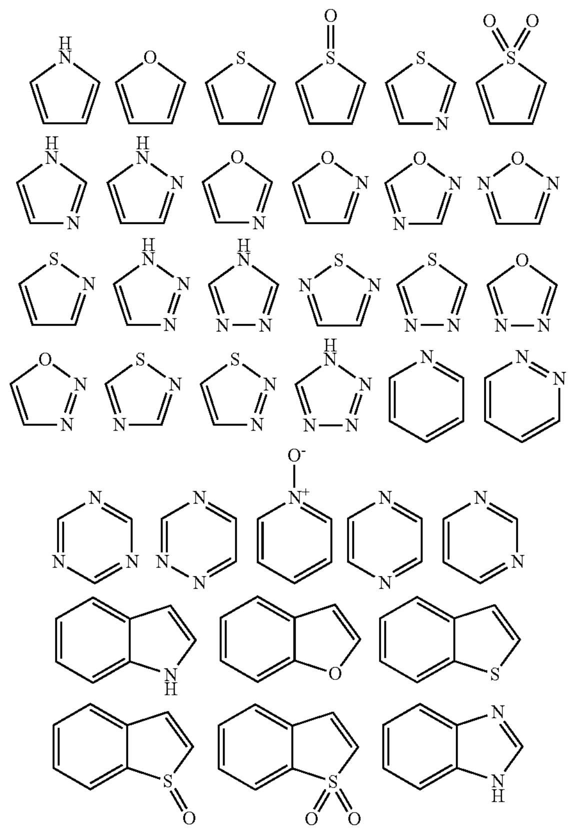

-continued

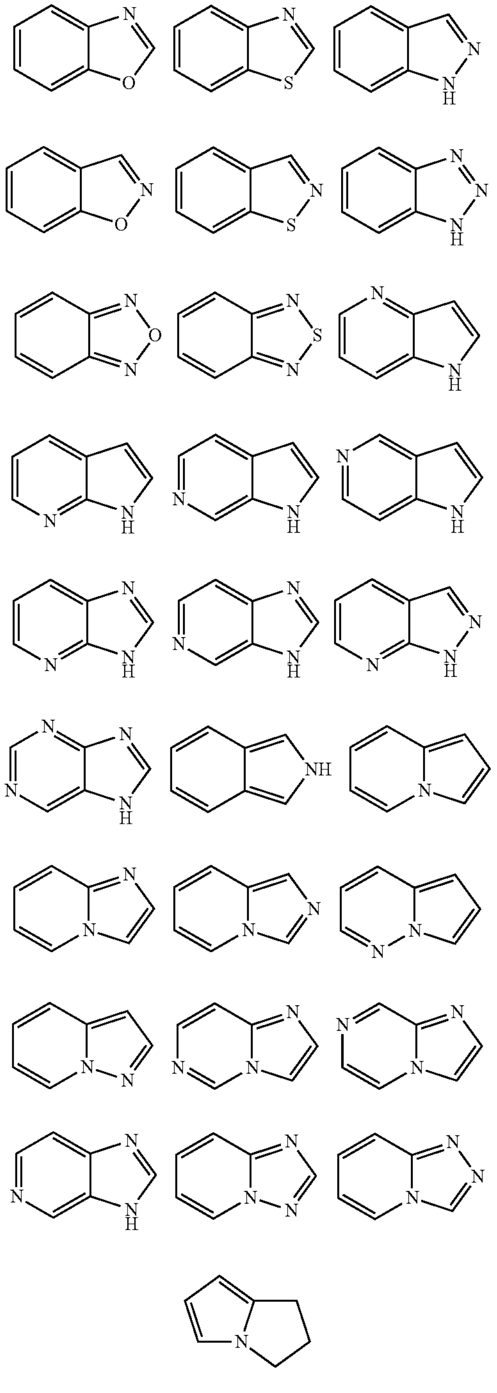

Many of the terms given above may be used repeatedly in the definition of a formula or group and in each case have one of the meanings given above, independently of one another.

General Method of Preparation

Compounds of the present invention can be prepared in accordance with techniques that are well known to those skilled in the art.

Compounds of the present invention can be synthesized according to the following scheme:

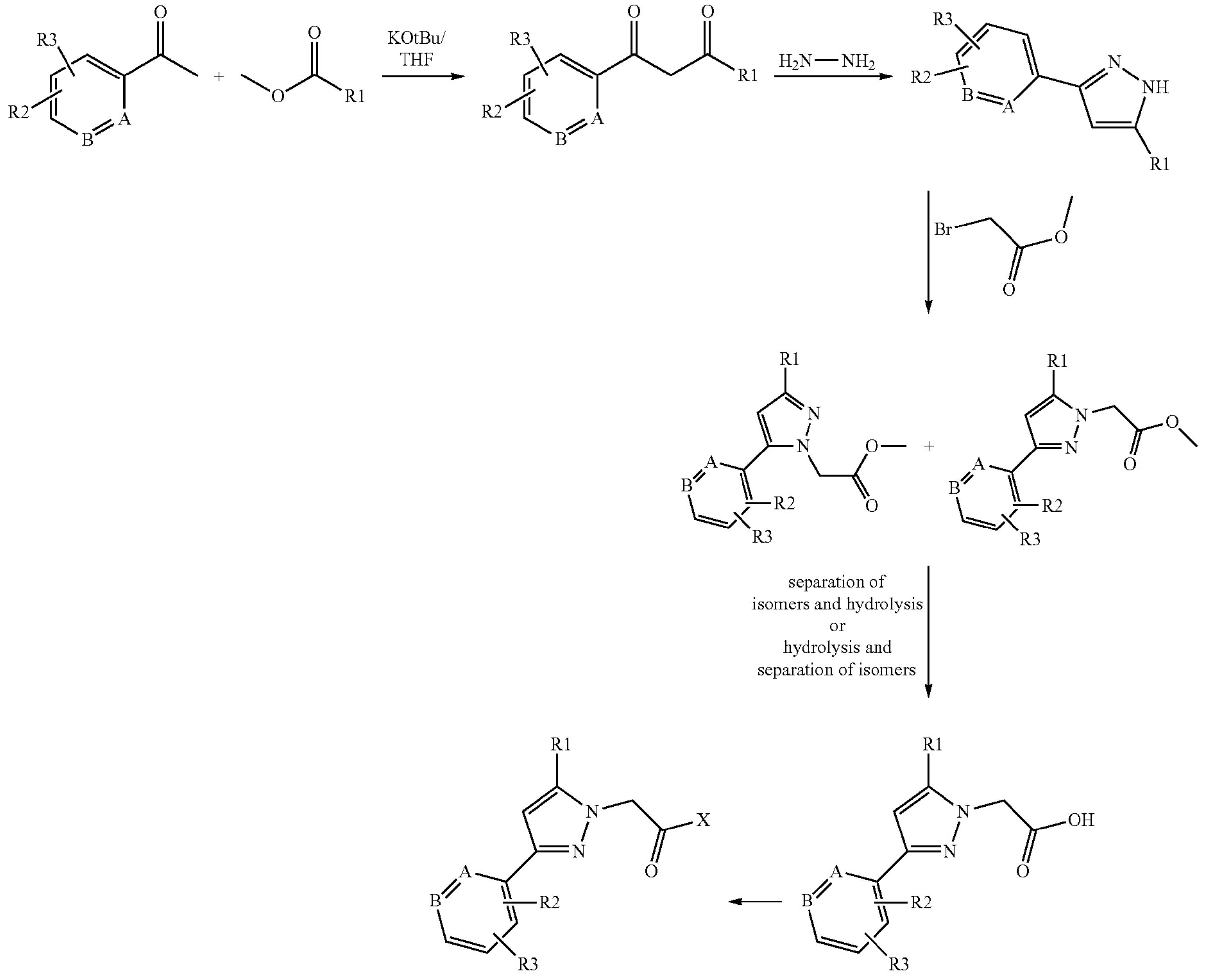

Aryl ketones were deprotonated with potassium tert butoxide and condensed with a methylesters to form a di-keton. Then, the di-keton was condensed with hydrazine to yield a pyrazole-system. The pyrazoles were coupled with 2-bromoacetic acid methyl ester under basic conditions to yield the desired pyrazol-1-yl-acetic acid methyl ester together with different quantities of the isomeric system. The pyrazol-1-yl-acetic acid methyl ester was hydrolyzed with LiOH to the corresponding acid. The isomeres were either separated before or after hydrolysis of the ester. Finally, the pyrazol-1-yl-acetic acids were coupled with an amine to the desired products.

Biological Assay

The positive modulation of mGluR5 is measured in a HEK 293 cell line expressing human recombinant mGluR5 and is detected with calcium based FLIPR assay. The cells are cultured with DMEM supplemented with 10% FCS, 2 μg/mL tetracycline, 100 μg/mL hygromycin and 500 μg/mL geneticin. The cell culture media is exchanged for tetracycline-free cell culture media 3-7 days before the assay. One day before the assay the cell culture medium is exchanged to DMEM without glutamine and phenol red and supplemented with 10% FCS, 100 μg/mL hygromycin and 500 μg/mL geneticin. On the assay day, the medium of the subconfluent cultures is removed and the cells are detached by addition of 2.5 ml EDTA (0.02%) per 175 cm2 culture flask for 1 minute. The cells are resuspend in Ringer solution (140 mM NaCl, 5 mM KCl, 2.5 mM CaCl2, 1.5 mM MgCl2, 5 mM Glucose, 10 mM Hepes; adjusted to pH 7.4 with NaOH), pooled and Ringer solution added to adjust the volume to 50 mL. The cell suspension is centrifuged for 5 mM at 1500 U/min (425 g). The supernatant is removed and the cells washed a second time with 50 ml fresh Ringer solution and centrifuged again as before. The supernatant is again removed and the pellet resuspended in Ringer solution to 1,000,000 cells/ml (1×10^6 cells/mL). The cells are plated onto BD BioCoat Poly-D-Lysine 384 well plates (20.000 cells/well; 20 μl/well). The lid covered plates are then incubated until use at 37° C./10% CO2. For dye loading, 20 μl of Calcium-4 assay kit solution (prepared according to the manufacturer's description in Ringer solution) are added to the cells and the plates are incubated for 80 mM 37° C. and then 10 mM at room temperature.

Controls, Compound Dilution and Assay Execution:
 Each assay plate contained wells with "high" and "low" controls:
 Low controls 1% DMSO/ringer solution+basal glutamate activation (defined as 100% CTL).
 High controls 10 μM CDPPB+basal glutamate activation (defined as 200% CTL).

Test compounds are dissolved and diluted in DMSO to 100-fold the desired concentrations. In a second step, the compounds are diluted in Ringer solution such that the compounds are 4-fold more concentrated than the desired final assay concentration. The final DMSO concentration was 1%.

20 µl of each compound solution are then transferred to the assay plate and the Ca2+ kinetic is measured to determine any intrinsic compound activity. After 5 mM incubation in the FLIPR device, the second stimulation with 20 µl of glutamate in Ringer solution (glutamate concentration adjusted to approximately 5% basal stimulation of the maximal possible glutamate effect) is added and the kinetic Ca2+ response of the wells was measured for the modulation effect.

Analysis:

The peak height of the Ca release related fluorescence signal (9-66) is used for the EC50. The EC50 of the modulation is calculated over a nonlinear regression with GraphPad Prism (Table 1).

TABLE 1

| Example | EC50 [nM] | Example | EC50 [nM] | Example | EC50 [nM] | Example | EC50 [nM] |
|---|---|---|---|---|---|---|---|
| 7.01.001 | 1429 | 7.01.080 | 277 | 7.02.061 | 96 | 7.02.139 | 101 |
| 7.01.002 | 592 | 7.01.081 | 30 | 7.02.062 | 323 | 7.02.140 | 51 |
| 7.01.003 | 1785 | 7.01.082 | 66 | 7.02.063 | 1728 | 7.02.141 | 138 |
| 7.01.004 | 390 | 7.01.083 | 86 | 7.02.064 | 177 | 7.02.142 | 27 |
| 7.01.005 | 381 | 7.01.084 | 34 | 7.02.065 | 194 | 7.02.143 | 48 |
| 7.01.006 | 870 | 7.01.085 | 26 | 7.02.066 | 24 | 7.02.144 | 68 |
| 7.01.007 | 1539 | 7.01.086 | 274 | 7.02.067 | 6 | 7.02.145 | 15 |
| 7.01.008 | 1184 | 7.01.087 | 125 | 7.02.068 | 199 | 7.02.146 | 295 |
| 7.01.009 | 1535 | 7.01.088 | 29 | 7.02.069 | 187 | 7.02.147 | 572 |
| 7.01.010 | 695 | 7.01.089 | 22 | 7.02.070 | 40 | 7.02.148 | 15 |
| 7.01.011 | 1974 | 7.01.090 | 240 | 7.02.071 | 71 | 7.02.149 | 42 |
| 7.01.012 | 829 | 7.01.091 | 37 | 7.02.072 | 251 | 7.02.150 | 28 |
| 7.01.013 | 617 | 7.01.092 | 33 | 7.02.073 | 627 | 7.02.151 | 211 |
| 7.01.014 | 463 | 7.01.093 | 35 | 7.02.074 | 171 | 7.02.152 | 67 |
| 7.01.015 | 1805 | 7.01.094 | 90 | 7.02.075 | 318 | 7.02.153 | 15 |
| 7.01.016 | 143 | 7.01.095 | 53 | 7.02.076 | 293 | 7.02.154 | 108 |
| 7.01.018 | 538 | 7.01.096 | 22 | 7.02.077 | 1799 | 7.02.155 | 92 |
| 7.01.019 | 1661 | 7.01.097 | 109 | 7.02.078 | 232 | 7.02.156 | 170 |
| 7.01.020 | 258 | 7.01.098 | 477 | 7.02.079 | 182 | 7.02.157 | 430 |
| 7.01.021 | 1530 | 7.02.001 | 55 | 7.02.080 | 321 | 7.02.158 | 116 |
| 7.01.022 | 511 | 7.02.002 | 1175 | 7.02.081 | 991 | 7.02.159 | 44 |
| 7.01.023 | 166 | 7.02.003 | 925 | 7.02.082 | 291 | 7.02.160 | 23 |
| 7.01.024 | 1157 | 7.02.004 | 689 | 7.02.083 | 35 | 7.02.161 | 35 |
| 7.01.025 | 1865 | 7.02.005 | 1256 | 7.02.084 | 73 | 7.02.162 | 120 |
| 7.01.026 | 503 | 7.02.006 | 1954 | 7.02.085 | 42 | 7.02.163 | 122 |
| 7.01.027 | 1022 | 7.02.007 | 600 | 7.02.086 | 11 | 7.02.164 | 46 |
| 7.01.028 | 1303 | 7.02.008 | 997 | 7.02.087 | 28 | 7.02.165 | 18 |
| 7.01.029 | 796 | 7.02.009 | 220 | 7.02.088 | 254 | 7.02.166 | 149 |
| 7.01.030 | 484 | 7.02.010 | 13 | 7.02.089 | 59 | 7.02.167 | 370 |
| 7.01.031 | 1865 | 7.02.011 | 37 | 7.02.090 | 41 | 7.02.168 | 604 |
| 7.01.032 | 710 | 7.02.012 | 47 | 7.02.091 | 115 | 7.02.169 | 20 |
| 7.01.033 | 1531 | 7.02.013 | 92 | 7.02.092 | 369 | 7.02.170 | 30 |
| 7.01.034 | 398 | 7.02.014 | 21 | 7.02.093 | 120 | 7.02.171 | 68 |
| 7.01.035 | 205 | 7.02.015 | 15 | 7.02.094 | 49 | 7.02.172 | 64 |
| 7.01.036 | 1322 | 7.02.016 | 110 | 7.02.095 | 6 | 7.02.173 | 38 |
| 7.01.037 | 188 | 7.02.017 | 68 | 7.02.096 | 10 | 7.02.174 | 39 |
| 7.01.038 | 359 | 7.02.018 | 693 | 7.02.097 | 8 | 7.02.175 | 59 |
| 7.01.039 | 752 | 7.02.019 | 36 | 7.02.098 | 12 | 7.02.176 | 221 |
| 7.01.041 | 1550 | 7.02.020 | 21 | 7.02.099 | 18 | 7.02.177 | 111 |
| 7.01.042 | 285 | 7.02.021 | 55 | 7.02.100 | 4 | 7.02.178 | 69 |
| 7.01.043 | 40 | 7.02.022 | 11 | 7.02.101 | 14 | 7.02.179 | 236 |
| 7.01.044 | 1853 | 7.02.023 | 12 | 7.02.102 | 27 | 7.02.180 | 1070 |
| 7.01.045 | 689 | 7.02.024 | 29 | 7.02.103 | 34 | 7.02.181 | 398 |
| 7.01.046 | 1002 | 7.02.025 | 148 | 7.02.104 | 48 | 7.02.182 | 65 |
| 7.01.047 | 789 | 7.02.026 | 83 | 7.02.105 | 242 | 7.02.183 | 330 |
| 7.01.048 | 573 | 7.02.027 | 58 | 7.02.106 | 10 | 7.02.184 | 132 |
| 7.01.049 | 652 | 7.02.028 | 943 | 7.02.107 | 39 | 7.02.185 | 258 |
| 7.01.050 | 652 | 7.02.029 | 329 | 7.02.108 | 127 | 7.02.186 | 326 |
| 7.01.051 | 1441 | 7.02.030 | 1761 | 7.02.109 | 61 | 7.02.187 | 1610 |
| 7.01.052 | 31 | 7.02.031 | 1244 | 7.02.110 | 156 | 7.02.188 | 19 |
| 7.01.053 | 914 | 7.02.032 | 37 | 7.02.111 | 334 | 7.02.189 | 15 |
| 7.01.054 | 53 | 7.02.033 | 29 | 7.02.112 | 404 | 7.02.190 | 29 |
| 7.01.055 | 53 | 7.02.034 | 42 | 7.02.113 | 637 | 7.02.191 | 80 |
| 7.01.056 | 253 | 7.02.035 | 35 | 7.02.114 | 29 | 7.02.192 | 82 |
| 7.01.057 | 740 | 7.02.036 | 136 | 7.02.115 | 8 | 7.02.193 | 290 |
| 7.01.058 | 279 | 7.02.037 | 194 | 7.02.116 | 21 | 7.02.194 | 63 |
| 7.01.059 | 32 | 7.02.038 | 210 | 7.02.117 | 66 | 7.02.195 | 2 |
| 7.01.060 | 101 | 7.02.039 | 915 | 7.02.118 | 127 | 7.02.196 | 43 |
| 7.01.061 | 163 | 7.02.040 | 1696 | 7.02.119 | 12 | 7.02.197 | 90 |
| 7.01.062 | 242 | 7.02.041 | 1216 | 7.02.120 | 21 | 7.02.198 | 6 |
| 7.01.063 | 334 | 7.02.042 | 192 | 7.02.121 | 49 | 7.02.199 | 16 |
| 7.01.064 | 1230 | 7.02.043 | 1736 | 7.02.122 | 38 | 7.02.200 | 24 |
| 7.01.065 | 173 | 7.02.044 | 735 | 7.02.123 | 71 | 7.02.201 | 171 |
| 7.01.066 | 153 | 7.02.045 | 1411 | 7.02.124 | 68 | 7.02.202 | 19 |
| 7.01.067 | 122 | 7.02.046 | 881 | 7.02.125 | 253 | 7.02.203 | 178 |

TABLE 1-continued

| Example | EC50 [nM] | Example | EC50 [nM] | Example | EC50 [nM] | Example | EC50 [nM] |
|---|---|---|---|---|---|---|---|
| 7.01.068 | 236 | 7.02.047 | 221 | 7.02.126 | 68 | 7.02.204 | 47 |
| 7.01.069 | 380 | 7.02.048 | 31 | 7.02.127 | 200 | 7.02.205 | 18 |
| 7.01.070 | 128 | 7.02.049 | 157 | 7.02.128 | 140 | 7.02.206 | 6 |
| 7.01.071 | 233 | 7.02.050 | 183 | 7.02.128 | 159 | 7.02.207 | 70 |
| 7.01.072 | 245 | 7.02.051 | 190 | 7.02.129 | 156 | 7.02.208 | 36 |
| 7.01.073 | 84 | 7.02.052 | 297 | 7.02.130 | 57 | 7.02.209 | 61 |
| 7.01.074 | 91 | 7.02.053 | 552 | 7.02.131 | 8 | 7.02.210 | 145 |
| 7.01.075 | 87 | 7.02.054 | 186 | 7.02.132 | 186 | 7.02.211 | 13 |
| 7.01.076 | 412 | 7.02.055 | 42 | 7.02.133 | 276 | 7.02.212 | 3 |
| 7.01.077 | 110 | 7.02.056 | 245 | 7.02.134 | 15 | 7.02.213 | 26 |
| 7.01.078 | 78 | 7.02.057 | 913 | 7.02.135 | 45 | 7.02.214 | 11 |
| 7.01.079 | 447 | 7.02.058 | 750 | 7.02.136 | 141 | 7.02.215 | 9 |
| 7.02.218 | 54 | 7.02.059 | 287 | 7.02.137 | 352 | 7.02.216 | 6 |
| 7.02.219 | 209 | 7.02.060 | 760 | 7.02.138 | 44 | 7.02.217 | 56 |
| 7.02.220 | 290 | 7.02.231 | 19 | 7.02.242 | 45 | 7.02.253 | 41 |
| 7.02.221 | 4 | 7.02.232 | 104 | 7.02.243 | 164 | 7.02.254 | 281 |
| 7.02.222 | 23 | 7.02.233 | 280 | 7.02.244 | 48 | 7.02.255 | 7 |
| 7.02.223 | 13 | 7.02.234 | 200 | 7.02.245 | 236 | 7.02.256 | 11 |
| 7.02.224 | 2 | 7.02.235 | 30 | 7.02.246 | 62 | 7.02.257 | 16 |
| 7.02.225 | 17 | 7.02.236 | 69 | 7.02.247 | 172 | 7.02.258 | 31 |
| 7.02.226 | 11 | 7.02.237 | 111 | 7.02.248 | 290 | 7.02.259 | 10 |
| 7.02.227 | 35 | 7.02.238 | 146 | 7.02.249 | 184 | 7.02.260 | 26 |
| 7.02.228 | 398 | 7.02.239 | 842 | 7.02.250 | 65 | | |
| 7.02.229 | 31 | 7.02.240 | 85 | 7.02.251 | 34 | | |
| 7.02.230 | 878 | 7.02.241 | 76 | 7.02.252 | 69 | | |

Method of Treatment

The present invention is directed to compounds of general formula I which are useful in the treatment of a disease and/or condition wherein the activity of an mGluR5 positive modulator is of therapeutic benefit, including but not limited to the treatment of psychotic disorders, cognitive disorders and dementias.

The compounds of general formula I are useful for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

Therefore, the present invention also relates to a compound of general formula I as a medicament.

A further aspect of the present invention relates to the use of a compound of general formula I for the treatment of a disease and/or condition wherein the activity of mGluR5 positive modulator is of therapeutic benefit.

Furthermore, the present invention relates to the use of a compound of general formula I for the treatment of psychotic disorders, cognitive disorders and dementias.

Furthermore, the present invention relates to the use of a compound of general formula I for the treatment of psychotic disorders including schizophrenia, schizoaffective disorder and substance induced psychotic disorder; cognitive disorders and dementias including age-associated learning and memory impairments or losses, post stroke dementia, deficits in concentration, mild cognitive impairment, the cognitive dysfunction in Alzheimers disease, and the cognitive dysfunction of schizophrenia.

In a further aspect of the present invention the present invention relates to methods for the treatment or prevention of above mentioned diseases and conditions, which method comprises the administration of an effective amount of a compound of general formula I to a human being.

Dosage

The dose range of the compounds of general formula I applicable per day is usually from 0.1 to 5000 mg, preferably from 0.1 to 1000 mg, more preferably from 5 to 500 mg, most preferably, 10 or 100 mg. Each dosage unit may conveniently contain from 0.1 to 500 mg, preferably 10 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Pharmaceutical Compositions

Suitable preparations for administering the compounds of formula will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) should be in the range from 1 to 99 wt.-%, preferably 10 to 90 wt.-%, more preferably 20 to 70 wt.-%, of the composition as a whole. Suitable tablets may be obtained, for example, by mixing one or more compounds according to formula I with known excipients, for example inert diluents, carriers, disintegrants, adjuvants, surfactants, binders and/or lubricants. The tablets may also consist of several layers. A further aspect of the invention is a pharmaceutical formulation including a compound of formula I in admixture with a pharmaceutically acceptable adjuvant, diluent or carrier.

Combination Therapy

In another aspect the present invention relates to a combination therapy in which an active compound according to the present invention is administered together with another active compound. Accordingly, the invention also refers to pharmaceutical formulations that provide such a combination of active ingredients, whereby one of which is an active compound of the present invention. Such combinations may be fixed dose combinations (the active ingredients that are to be combined are subject of the same pharmaceutical formulation) or free dose combinations (active ingredients are in separate pharmaceutical formulations).

Consequently, a further aspect of the present invention refers to a combination of each of the active compounds of the present invention, preferably at least one active compound according to the present invention, with another active compound for example selected from the group of antipsychotics such as haloperidol, clozapine, risperidone, quetiapine, aripripazole, and olanzapine; antidepressants such as selective serotonin re-uptake inhibitors and dual serotonin/noradrenaline re-uptake inhibitors; mood stabilizers such as lithium valproate and lamotrigine; beta-secretase inhibitors; gamma-secretase inhibitors; gamma-secretase modulators; amyloid aggregation inhibitors such as e.g. scyllo-inositol; directly or indirectly acting neuroprotective and/or disease-modifying substances; anti-oxidants, such as e.g. vitamin E, ginko biloba or ginkolide; anti-inflammatory substances, such as e.g. Cox inhibitors, NSAIDs additionally or exclusively having Aβ (Abeta) lowering properties; HMG-CoA reductase inhibitors, such as statins; acetylcholine esterase inhibitors, such as donepezil, rivastigmine, tacrine, galantamine; NMDA receptor antagonists such as e.g. memantine; AMPA receptor agonists; AMPA receptor positive modulators, AMPkines, glycine transporter 1 inhibitors; monoamine receptor reuptake inhibitors; substances modulating the concentration or release of neurotransmitters; substances inducing the secretion of growth hormone such as ibutamoren mesylate and capromorelin; CB-1 receptor antagonists or inverse agonists; antibiotics such as minocyclin or rifampicin; PDE1, PDE2, PDE4, PDE5, PDE9 or PDE10 inhibitors, GABAA receptor inverse agonists; GABAA alpha5 receptor inverse agonists; GABAA receptor antagonists; nicotinic receptor agonists or partial agonists or positive modulators; alpha4beta2 nicotinic receptor agonists or partial agonists or positive modulators; alpha7 nicotinic receptor agonists or partial agonists; histamine receptor H3 antagonists; 5-HT4 receptor agonists or partial agonists; 5-HT6 receptor antagonists; alpha2-adrenoreceptor antagonists, calcium antagonists; muscarinic receptor M1 agonists or partial agonists or positive modulators; muscarinic receptor M2 antagonists; muscarinic receptor M4 antagonists; muscarinic receptor M4 positive allosteric modulators; metabotropic glutamate receptor 5 positive allosteric modulators; metabotropic glutamate receptor 2 antagonists; metabotropic glutamate receptor 2/3 agonists; metabotropic glutamate receptor 2 positive allosteric modulators and other substances that modulate receptors or enzymes in a manner such that the efficacy and/or safety of the active compounds according to the invention is increased and/or unwanted side effects are reduced.

The active compounds according to the invention may also be used in combination with immunotherapies such as e.g. active immunisation with Abeta or parts thereof or passive immunisation with humanised anti-Abeta antibodies, nanobodies or antibody fragments for the treatment of the above mentioned diseases and conditions.

The active compounds according to the invention also may be combined with antipsychotics like haloperidol, flupentixol, fluspirilene, chlorprothixene, prothipendyl, levomepromazine, clozapine, olanzapine, quetiapine, risperidone, paliperidone, amisulpride, ziprasidone, aripiprazol, sulpiride, zotepine, sertindole, fluphenazine, perphenazine, perazine, promazine, chlorpromazine, levomepromazine, benperidol, bromperidol, pimozid, melperone, pipamperone, iloperidone, asenapine, perospirone, blonanserin, lurasidone.

The active compounds according to the invention also may be combined with antidepressants like amitriptyline imipramine hydrochloride, imipramine maleate, lofepramine, desipramine, doxepin, trimipramine.

Or the active compounds according to the invention also may be combined with serotonin (5-HT) reuptake inhibitors such as alaproclate, citalopram escitalopram, clomipramine, duloxetine, femoxetine, fenfluramine, norfenfluramine, fluoxetine, fluvoxamine, indalpine, milnacipran, paroxetine, sertraline, trazodone, venlafaxine, zimelidine, bicifadine, desvenlafaxine, brasofensme and tesofensine.

The combinations according to the present invention may be provided simultaneously in one and the same dosage form, i.e. in form of a combination preparation, for example the two components may be incorporated in one tablet, e.g. in different layers of said tablet. The combination may be also provided separately, in form of a free combination, i.e. the active compounds of the present invention are provided in one dosage form and one or more of the above mentioned combination partners is provided in another dosage form. These two dosage forms may be equal dosage forms, for example a co-administration of two tablets, one containing a therapeutically effective amount of the active compound of the present invention and one containing a therapeutically effective amount of the above mentioned combination partner. It is also possible to combine different administration forms, if desired. Any type of suitable administration forms may be provided.

The active compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

The dosage or administration forms are not limited, in the frame of the present invention any suitable dosage form may be used. Exemplarily the dosage forms may be selected from solid preparations such as patches, tablets, capsules, pills, pellets, dragees, powders, troches, suppositories, liquid preparations such as solutions, suspensions, emulsions, drops, syrups, elixirs, or gaseous preparations such as aerosols, sprays and the like.

The dosage forms are advantageously formulated in dosage units, each dosage unit being adapted to supply a single dose of each active component being present. Depending from the administration route and dosage form the ingredients are selected accordingly.

The dosage for the above-mentioned combination partners may be expediently 1/5 of the normally recommended lowest dose up to 1/1 of the normally recommended dose.

The dosage forms are administered to the patient for example 1, 2, 3, or 4 times daily depending on the nature of the formulation. In case of retarding or extended release formulations or other pharmaceutical formulations, the same may be applied differently (e.g. once weekly or monthly etc.). It is preferred that the active compounds of the invention be administered either three or fewer times, more preferably once or twice daily.

Experimental Section

Preparation of Examples for Compounds of the General Formula I

Unless otherwise stated, one or more tautomeric forms of compounds of the examples described hereinafter may be prepared in situ and/or isolated. All tautomeric forms of compounds of the examples described hereinafter should be considered to be disclosed.

The invention is illustrated by way of the following examples, in which the following abbreviations may be employed:

ABBREVIATIONS

RT room temperature
THF tetrahydrofuran
KOtBu Potassium tert-butanolate
PFTU pentafluorphenol-tetramethyluronium hexafluorophosphat
ACN acetonitrile
MeOH methanol
DIPEA diisopropylamine
DEA diethylamine
EtOAC ethyl acetate
DMF dimethylformamide
TBTU [(Benzotriazol-1-yloxy)-dimethylamino-methylene]-dimethyl-ammonium tetrafluoro borate
HATU (O-(7-Azobenzotriazol-1-yl)-1,1,3,3-tetramethyluroniumhexafluorophosphate
conc. concentrated
min. minutes
DCM dichlormethane
TFA: trifluoro acetic acid
LDA lithium diisopropylamide
Dess-Martin (1,1,1-triacetoxy)-1,1-dihydro-1,2-benziodoxol-3(1H)-one
DDQ 2,3-dichlor-5,6-dicyan-p-benzochinon Analytical Methods All compounds specified in the examples below gave the correct mass spectra matching the theoretical isotope pattern. For practical reasons, only one of the major isotope peaks is given as representative data for the mass spectrum.

List of HPLC Purification Methods

Method 1:

Gilson HPLC

Eluent:

A: water with 0.10% TFA

B: methanol

Gradient

| time in min | % A | % B | flow in ml/min |
|---|---|---|---|
| 00.00 | 90 | 10 | 50 |
| 02.00 | 90 | 10 | 50 |
| 11.00 | 0 | 100 | 50 |
| 14.00 | 0 | 100 | 50 |

Column:

Sunfire C18, 30×100 mm, 10 μm (temperature: isocratic 60° C.).

List of HPLC-Analytical HPLC Methods:

Method A:

Waters ZQ 2000MS, Agilent HP100, binäre pumps

Eluent:

A: water with 0.10% TFA

B: methanol

Gradient:

| time in min | % A | % B | flow in ml/min |
|---|---|---|---|
| 0.00 | 95 | 5 | 1.50 |
| 1.30 | 0 | 100 | 1.50 |
| 2.50 | 0 | 100 | 1.50 |
| 2.60 | 95 | 5 | 1.50 |

Column:

Sunfire C18, 4.6×50 mm, 3.5 μm (temperature: isocratic 40° C.).

Diodenarray Detection:

210-400 nm

Method B:

Waters ZQ 2000MS, Agilent HP100, binäre pumps

Eluent:

A: water with 0.10% TFA

B: acetonitrile with 0.08% TFA

Gradient:

| time in min | % A | % B | flow in ml/min |
|---|---|---|---|
| 0.00 | 95 | 5 | 1.50 |
| 2.00 | 0 | 100 | 1.50 |
| 2.50 | 0 | 100 | 1.50 |
| 2.60 | 95 | 5 | 1.50 |

Column:

Sunfire C18, 4.6×50 mm, 3.5 μm (temperature: isocratic 40° C.).

Diodenarray Detection:

210-500 nm

Method C:

Waters Acquity with diodenarraydetector and massdetector

Eluent:

A: water with 0.10% TFA

B: methanol

Gradient

| time in min | % A | % B | flow in ml/min |
|---|---|---|---|
| 0.00 | 99 | 1 | 1.20 |
| 0.05 | 99 | 1 | 1.20 |
| 1.05 | 0 | 100 | 1.20 |
| 1.25 | 0 | 100 | 1.20 |

Column:

Sunfire C18, 2.1×30 mm, 2.5 μm (temperature: isocratic 60° C.).

Diodenarray Detection:

210-400 nm.

Method D:

Waters Acquity with diodenarraydetector

Eluent:

A: water with 0.13% TFA

B: methanol with 0.05% TFA

Gradient:

| time in min | % A | % B | flow in ml/min |
|---|---|---|---|
| 0.00 | 99 | 1 | 1.20 |
| 0.05 | 99 | 1 | 1.20 |
| 1.05 | 0 | 100 | 1.20 |
| 1.25 | 0 | 100 | 1.20 |

Column:

Sunfire C18, 2.1×30 mm, 2.5 μm (temperature: isocratic 60° C.).

Method E:

Waters Alliance with diodenarraydetector and massdetector

Eluent:

A: water with 0.10% TFA

B: methanol

Gradient:

| time in min | % A | % B | flow in ml/min |
|---|---|---|---|
| 0.00 | 95 | 5 | 4.90 |
| 1.60 | 0 | 100 | 4.90 |
| 2.20 | 95 | 5 | 4.90 |

Column:

Sunfire C18, 4.6×30 mm, 3.5 μm (temperature: isocratic 60° C.).

Method F:

Waters Alliance with DA and MS-detector

Eluent:

A: water with 0.10% $NH_3$

D: methanol

Gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

Column:

Waters XBridge™ C18 3.5 μm, 4.6×30 mm (temperature: isocratic 60° C.).

Method G:

Waters ZQ 2000MS, Alliance 2695

Eluent:

A: water with 0.10% TFA

B: methanol

Gradient:

| time in min | % A | % B | flow in ml/min |
|---|---|---|---|
| 0.00 | 95 | 5 | 1.50 |
| 1.30 | 0 | 100 | 1.50 |
| 3.00 | 0 | 100 | 1.50 |
| 3.40 | 95 | 5 | 1.50 |

Column:

Sunfire C18, 4.6×50 mm, 3.5 μm (temperature: isocratic 40° C.).

Diodenarray Detection:

210-500 nm

Method H:

Agilent 1200 System

Eluent:

A: water with 0.10% formicacid

B: acetonitril 0.10% formicacid

Gradient:

| time in min | % A | % B | flow in ml/min |
|---|---|---|---|
| 0.00 | 95 | 5 | 1.60 |
| 0.10 | 95 | 5 | 1.60 |
| 1.75 | 5 | 95 | 1.60 |
| 1.90 | 5 | 95 | 1.60 |
| 1.95 | 95 | 5 | 1.60 |
| 2.00 | 95 | 5 | 1.60 |

Column:

Zorbax StableBond C18, 3.0×30 mm, 1.8 μm (temperature: isocratic 25° C.).

Detection:

254 nm

Method I:

Waters Acquity with diodenarraydetector and massdetector

Eluent:

A: water with 0.10% TFA

B: methanol

Gradient:

| time in min | % A | % B | flow in ml/min |
|---|---|---|---|
| 0.00 | 99 | 1 | 1.30 |
| 0.15 | 99 | 1 | 1.30 |
| 1.10 | 0 | 100 | 1.30 |
| 1.25 | 0 | 100 | 1.30 |

Column:

Sunfire C18, 2.1×30 mm, 2.5 μm (temperature: isocratic 60° C.).

Diodenarray Detection:

210-400 nm.

Method J:

Waters ZQ MS, Alliance 2690/2695 HPLC, Waters 996/2996 diodenarraydetector

Eluent:

A: water with 0.10% TFA

D: methanol

Gradient:

| time in min | % A | % D | flow in ml/min |
|---|---|---|---|
| 0.00 | 95 | 5 | 4.00 |
| 0.20 | 95 | 5 | 4.00 |
| 1.60 | 0 | 100 | 4.00 |
| 2.10 | 0 | 100 | 4.00 |

Column:

Waters XBridge™ C18 3.5 μm, 4.6×20 mm IS™ (temperature: isocratic 40° C.).

Diodenarray Detection:

210-400 nm.

Method K:

Agilent 1200 mit DA- and MS-Detektor

Eluent:

A: water with 0.10% $NH_3$

B: methanol

Gradient:

| time in min | % A | % B | flow in ml/min |
|---|---|---|---|
| 0.00 | 95 | 5 | 2.20 |
| 0.30 | 95 | 5 | 2.20 |
| 1.50 | 0 | 100 | 2.20 |
| 1.60 | 0 | 100 | 2.40 |
| 1.80 | 0 | 100 | 2.40 |

Column:

Xbridge C18, 3×30 mm, 2.5 μm (temperature: isocratic 60° C.).

Method L:

Waters Alliance with diodenarraydetector and massdetector

Eluent:

A: water with 0.10% TFA

B: methanol with 0.10% TFA

Gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |
| 1.85 | 95 | 5 | 4.00 |

Column:

XBridge C18, 4.6×30 mm, 3.5 μm (temperature: isocratic 60° C.).

Method M:

Waters Acquity with diodenarraydetector and massdetector

Eluent:

A: water with 0.13% TFA

B: methanol with 0.08% TFA

Gradient:

| time in min | % A | % B | flow in ml/min |
|---|---|---|---|
| 0.00 | 99 | 1 | 1.30 |
| 0.05 | 99 | 1 | 1.30 |
| 0.35 | 0 | 100 | 1.30 |
| 0.50 | 0 | 100 | 1.30 |

Column:

Xbridge BEH C18, 2.1×30 mm, 1.7 μm (temperature: isocratic 60° C.).

Diodenarray Detection:

210-400 nm.

Method N:

Waters Alliance with DA and MS-detector

Eluent:

A: water with 0.10% $NH_3$

D: methanol with 0.10% $NH_3$

Gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

Column:

Waters XBridge C18 3.5 μm, 4.6×30 mm (temperature: isocratic 60° C.).

Method O:

Waters ZMD, Alliance 2690/2695 HPLC, Waters 996/2996 diodenarraydetector

Eluent:

A: water with 0.10% TFA

B: acetonitril with 0.10% TFA

Gradient:

| time in min | % A | % B | flow in ml/min |
|---|---|---|---|
| 0.00 | 95 | 5 | 2.80 |
| 0.30 | 95 | 5 | 2.80 |
| 1.60 | 2 | 98 | 2.80 |
| 1.90 | 2 | 98 | 2.80 |
| 2.00 | 95 | 5 | 2.50 |

Column:

Merck Chromolith™ Flash RP-18e, 3 mm×100 mm (temperature: isocratic 25° C.)

Method P:

Waters ZQ 2000MS, Agilent HP100, binäre pumps

Eluent:

A: water with 0.10% TFA

B: methanol

Gradient:

| time in min | % A | % B | flow in ml/min |
|---|---|---|---|
| 0.00 | 80 | 20 | 2.00 |
| 1.70 | 0 | 100 | 2.00 |
| 2.50 | 0 | 100 | 2.00 |
| 2.60 | 80 | 20 | 2.00 |

Column:

Sunfire C18, 4.6×50 mm, 3.5 μm (temperature: isocratic 60° C.).

Diodenarray Detection:

210-500 nm

Method Q:

Agilent 1100 with DA and MS-detector

Eluent:

A: water with 0.1% TFA

D: methanol

Gradient:

| time in min | % A | % D | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.25 | 0 | 100 | 4.00 |

Column:
Stable Bond C18 3.5 μm, 4.6×30 mm (temperature: isocratic 60° C.).
Method R:
Agilent 1100 with DA and MS-detector
Eluent:
A: water with 0.1% TFA
D: methanol with 0.1% TFA
Gradient:

| time in min | % A | % D | flow in ml/min |
|---|---|---|---|
| 0.00 | 95 | 5 | 4.00 |
| 0.15 | 95 | 5 | 4.00 |
| 1.70 | 0 | 100 | 4.00 |
| 2.25 | 0 | 100 | 4.00 |

Column:
Sunfire C18 3.5 μm, 4.6×30 mm (temperature: isocratic 60° C.).
Method S:
Agilent 1200 with DA and MS-detector
Eluent:
A: water with 0.2% TFA
D: methanol
Gradient:

| time in min | % A | % D | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 |

Column:
Stable Bond C18, 1.8 μm, 3×30 mm (temperature: isocratic 60° C.).
Method T:
Waters Alliance with diodenarraydetector and massdetector
Eluent:
A: water with 0.10% TFA
B: methanol
Gradient:

| time in min | % A | % B | flow in ml/min |
|---|---|---|---|
| 0.00 | 95 | 5 | 4.80 |
| 1.60 | 0 | 100 | 4.80 |
| 1.85 | 0 | 100 | 4.80 |
| 1.90 | 95 | 5 | 4.80 |

Column:
XBridge C18, 4.6×30 mm, 3.5 μm (temperature: isocratic 60° C.).
Method U:
Waters Acquity with diodenarraydetector and massdetector
Eluent:
A: water with 0.10% TFA
B: methanol
Gradient:

| time in min | % A | % B | flow in ml/min |
|---|---|---|---|
| 0.00 | 99 | 1 | 1.40 |
| 0.05 | 99 | 1 | 1.40 |
| 1.00 | 0 | 100 | 1.40 |
| 1.25 | 0 | 100 | 1.40 |

Column:
Xbridge C18, 2.1×20 mm, 2.5 μm (temperature: isocratic 60° C.).
Diodenarray Detection:
210-400 nm.
Method V:
Agilent 1200 with DA and MS-detector
Eluent:
A: water with 0.2% TFA
D: methanol
Gradient:

| time in min | % A | % D | flow in ml/min |
|---|---|---|---|
| 0.00 | 95 | 5 | 2.20 |
| 0.05 | 95 | 5 | 2.20 |
| 1.40 | 0 | 100 | 2.20 |
| 1.80 | 0 | 100 | 2.20 |

Column:
Sunfire C18, 2.5 μm, 3×30 mm (temperature: isocratic 60° C.).
Method W:
Waters Alliance with diodenarraydetector and massdetector
Eluent:
A: water with 0.10% TFA
B: methanol
Gradient:

| time in min | % A | % B | flow in ml/min |
|---|---|---|---|
| 0.00 | 95 | 5 | 4.00 |
| 1.60 | 0 | 100 | 4.00 |
| 1.85 | 0 | 100 | 4.00 |
| 1.90 | 95 | 5 | 4.00 |

Column:
XBridge C18, 4.6×30 mm, 3.5 μm (temperature: isocratic 60° C.).
Method X:
Waters Acquity with diodenarraydetector and massdetector
Eluent:
A: water with 0.13% TFA
B: methanol with 0.05% TFA
Gradient:

| time in min | % A | % B | flow in ml/min |
|---|---|---|---|
| 0.00 | 99 | 1 | 1.30 |
| 0.05 | 99 | 1 | 1.30 |
| 0.35 | 0 | 100 | 1.30 |
| 0.50 | 0 | 100 | 1.30 |

Column:

Xbridge BEH C18, 2.1×30 mm, 1.7 μm (temperature: isocratic 60° C.).

Diodenarray Detection:

210-400 nm.

Method Y:

Waters Alliance with diodenarraydetector and massdetector

Eluent:

A: water with 0.10% TFA

B: methanol

Gradient:

| time in min | % A | % B | flow in ml/min |
|---|---|---|---|
| 0.00 | 95 | 5 | 4.00 |
| 1.60 | 0 | 100 | 4.00 |
| 1.85 | 95 | 5 | 4.00 |
| 1.90 | 95 | 5 | 4.00 |

Column:

Sunfire C18, 4.6×30 mm, 3.5 μm (temperature: isocratic 60° C.).

Method Z:

Waters Acquity with diodenarraydetector and massdetector

Eluent:

A: water with 0.1% TFA

B: methanol

Gradient

| time in min | % A | % B | flow in ml/min |
|---|---|---|---|
| 0.00 | 99 | 1 | 1.50 |
| 0.05 | 99 | 1 | 1.50 |
| 1.05 | 0 | 100 | 1.50 |
| 1.20 | 0 | 100 | 1.50 |

Column:

Xbridge BEH Phenyl, 2.1×30 mm, 1.7 μm (temperature: isocratic 60° C.)

Method AA:

Waters Acquity with diodenarraydetector and massdetector

Eluent:

A: water with 0.1% TFA

B: methanol

Gradient

| time in min | % A | % B | flow in ml/min |
|---|---|---|---|
| 0.00 | 99 | 1 | 1.50 |
| 0.05 | 99 | 1 | 1.50 |
| 1.00 | 0 | 100 | 1.50 |
| 1.10 | 0 | 100 | 1.50 |

Column:

Xbridge Phenyl, 2.1×20 mm, 2.5 μm (temperature: isocratic 60° C.)

Method AB:

Waters Alliance with DA and MS-detector

Eluent:

A: water with 0.10% $NH_3$

D: methanol with 0.10% $NH_3$

Gradient:

| time in min | % A | % D | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

Column:

Waters XBridge™ 3.5 μm, 4.6×30 mm (temperature: isocratic 60° C.).

Method AC:

Waters Alliance with diodenarraydetector and massdetector

Eluent:

A: water with 0.10% NH3

B: methanol

Gradient:

| time in min | % A | % B | flow in ml/min |
|---|---|---|---|
| 0.00 | 95 | 5 | 4.00 |
| 0.20 | 95 | 5 | 4.00 |
| 1.50 | 0 | 100 | 4.00 |
| 1.75 | 0 | 100 | 4.00 |

Column:

XBridge C18, 4.6×30 mm, 3.5 μm (temperature: isocratic 60° C.).

Method AD:

Waters SQD MS, Aquility UPLC, diodenarray: 210-500 nm

Eluent:

A: water with 0.10% TFA

B: acetonitrile with 0.08% TFA

Gradient:

| time in min | % A | % B | flow in ml/min |
|---|---|---|---|
| 0.00 | 95 | 5 | 1.50 |
| 0.70 | 0 | 100 | 1.50 |
| 0.70 | 0 | 100 | 1.50 |
| 0.81 | 95 | 5 | 1.50 |
| 1.90 | 0 | 100 | 0.20 |

Column:

Ascentis Express C18, 2.1×50 mm, 2.7 μm (temperature: isocratic 60° C.).

Method AE:

Applied Biosystem: LCM/MS API 2000, HPLC: Shimadzu Prominence dual wavelength: 220 and 260 nm Eluent:

A: water with 0.05% TFA

B: acetonitrile

Gradient:

| time in min | % A | % B | flow in ml/min |
|---|---|---|---|
| 0.01 | 90 | 10 | 1.20 |
| 1.50 | 70 | 30 | 1.20 |
| 3.00 | 10 | 90 | 1.20 |
| 4.00 | 10 | 90 | 1.20 |
| 5.00 | 90 | 10 | 1.20 |

Column:

Gemini C18, 4.6×50 mm, 2.7 μm (temperature: isocratic 20° C.).

Method AF:

Agilent 1200 with DA and MS-detector

Eluent:

A: water with 0.2% TFA

B: methanol

Gradient:

| time in min | % A | % B | flow in ml/min |
|---|---|---|---|
| 0.00 | 95 | 5 | 1.80 |
| 0.05 | 95 | 5 | 1.80 |
| 1.70 | 0 | 100 | 1.80 |
| 1.75 | 0 | 100 | 2.50 |

Column:

Sunfire C18, 2.5 μm, 3×30 mm (temperature: isocratic 60° C.).

Method AG:

Eluent:

A: acetonitril 95% and water 5% with 0.1% TFA

B: water 95% and acetonitril 5% with 0.1% TFA

Gradient:

| time in min | % A | % B | flow in ml/min |
|---|---|---|---|
| 00.00 | 20 | 80 | |
| 15.00 | 80 | 20 | |
| 20.00 | 80 | 20 | |

Column:

Zorbax 300 SB-C8 (Agilent) 3.5 μm; 4.6×150 mm (temperature: isocratic 60° C.).

Method AH:

Waters ZQ 2000MS, Agilent HP100, binäre pumps

Eluent:

A: water with 0.10% TFA

B: methanol

Gradient:

| time in min | % A | % B | flow in ml/min |
|---|---|---|---|
| 0.00 | 95 | 5 | 1.50 |
| 1.30 | 0 | 100 | 1.50 |
| 2.50 | 0 | 100 | 1.50 |
| 2.60 | 95 | 5 | 1.50 |

Column:

Sunfire C18, 4.6×50 mm, 3.5 μm (temperature: isocratic 60° C.).

Diodenarray Detection:

210-500 nm

Synthesis of Intermediates

6.01. Synthesis of Building Blocks

6.01.01 5,6,7,8-Tetrahydro-4H-thiazolo-[4,5-d]-azepin-2-ylamine hydrobromide

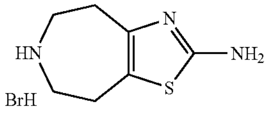 [SMILES: Br ; Nc1nc2c(s1)CCNCC2]

6.01.01.1 5-Bromo-azepan-4-one hydrobromide

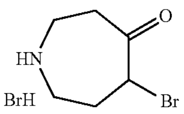

32 mL 62% HBr solution in 50 mL conc. acetic acid was added to 50 g hexahydro-azepin-4-on hydrochloride in 600 mL conc. acetic acid. Then 17.2 mL bromine in 50 mL conc. acetic acid was dropped to the reaction. The solvent was removed and the residue was crystallized from a mixture of DCM/MeOH (8/2) to give 79 g of the desired compound.

$(M+H)^+$: 192

6.01.01.2 5,6,7,8-Tetrahydro-4H-thiazolo-[4,5-d]-azepin-2-ylamine hydrobromide

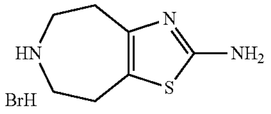 [SMILES: Br ; Nc1nc2c(s1)CCNCC2]

1.44 g thiourea was added to 4 g 5-bromo-azepan-4-one hydrobromide in 50 mL ethanol and stirred 3 h at 80° C. and over the weekend at RT. The precipitate was filtered and dried to yield 3.8 g of the product.

$R_t$: 0.61 min (method F)

$(M+H)^+$: 170

By using the same synthesis strategy as for 5,6,7,8-Tetrahydro-4H-thiazolo-[4,5-d]-azepin-2-ylamine hydrobromide the following compounds were obtained:

| Examples | Product | MS m/z $[M + H]^+$ | HPLC Method | Rt min |
|---|---|---|---|---|
| 6.01.02 | 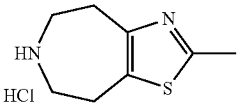 | 169 | Method H | 0.33 |

-continued

| Examples | Product | MS m/z [M + H]+ | HPLC Method | Rt min |
|---|---|---|---|---|
| 6.01.03 | 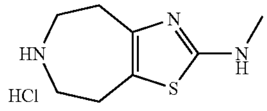 | 184 | Method N | 0.69 |

6.01.04.01 4-Chloro-6-methoxy-pyrimidine

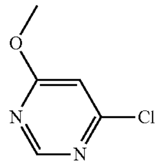

3.1 g sodiummethanolate was added to 7.2 g 4,6-dichlorpyrimidine in 150 mL methanol at 0° C. The reaction was warmed to RT and stirred additional 3 h. Water and EtOAC were added and the layers were separated. The organic layer was dried and evaporated to give 7.1 g of the desired product.

$R_t$: 0.85 min (method L), $(M+H)^+$: 144

6.01.12.01 4-Hydroxy-4-pyrimidin-2-yl-piperidine-1-carboxylic acid tert-butyl ester

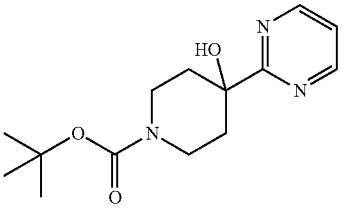 [SMILES: CC(C)(C)OC(=O)N1CCC(O)(c2ncccn2)CC1]

9.9 mL 1.6 mol/L n-buthyllithium solution in hexane was added to 3.85 g 2-tributylstannanyl-pyrimidine at −78° C. The reaction was stirred 30 min. at −78° C. and 2.1 g 1-carboxylic acid tert-butyl ester-4-piperidone in 10 mL THF was added. The reaction was warmed up and stirred over night at RT. Then, the reaction was cooled to 0° C. and water was added slowly. EtOAC was added and the layers were separated. The organic layer was washed one time with water and two times with a saturated ammonia chloride solution. Then, the organic layer was dried and evaporated. The residue was purified by HPLC to yield 448 mg.

$R_t$: 1.21 min (method J), $(M+H)^+$: 133/162/180

6.01.04.02 4-(6-Methoxy-pyrimidin-4-yl)-3,6-dihydro-2H-pyridine-1-carboxylic acid tert-butyl ester

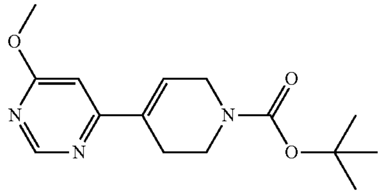 [SMILES: COc1cc(C2=CCN(C(=O)OC(C)(C)C)CC2)ncn1]

0.5 g tetrakis(triphenylphosphine) palladium was added to 1.3 g 4-chloro-6-methoxy-pyrimidine and 4-(4,4,5,5-tetramethyl-(1,3,2)dioxaborolan-2-yl)-3,6-dihydro-2H-pyridine-1-carboxylic acid tert-butyl ester) and 9 mL 2 mol/L sodiumcarbonate in 40 mL dioxane. The reaction was stirred 15 min. under microwave conditions. Water was added and the reaction was extracted with DCM. The organic layer was dried and evaporated. The residue was purified by HPLC to give 1.44 g of the desired product.

$R_t$: 1.38 min (method L)

$(M+H)^+$: 292

By using the same synthesis strategy as for 4-(6-methoxy-pyrimidin-4-yl)-piperidine-1-carboxylic acid tert-butyl ester the following compound was obtained:

| Examples | Product | MS m/z [M + H]+ | HPLC Method | Rt min |
|---|---|---|---|---|
| 6.01.05.02 | 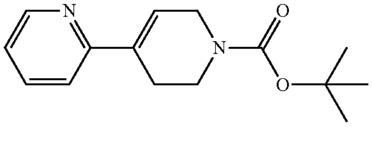 [SMILES: CC(C)(C)OC(=O)N1CC=C(c2ccccn2)CC1] | 163//205/261 | method J | 1.02 |
| 6.01.06.02 | 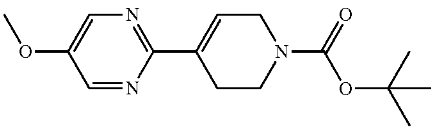 [SMILES: COc1cnc(C2=CCN(C(=O)OC(C)(C)C)CC2)nc1] | 292 | method I | 0.96 |

-continued

| Examples | Product | MS m/z [M + H]$^+$ | HPLC Method | Rt min |
|---|---|---|---|---|
| 6.01.07.02 | 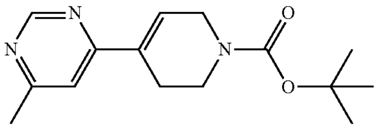 [SMILES: Cc1cc(C2=CCN(C(=O)OC(C)(C)C)CC2)ncn1] | 276 | method I | 0.82 |
| 6.01.08.02 | 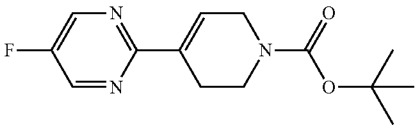 [SMILES: CC(C)(C)OC(=O)N1CC=C(c2ncc(F)cn2)CC1] | 280 | method I | 0.92 |
| 6.01.09.02 | 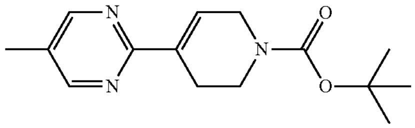 [SMILES: Cc1cnc(C2=CCN(C(=O)OC(C)(C)C)CC2)nc1] | 276 | | |
| 6.01.10.02 | 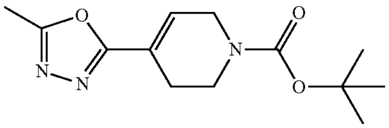 [SMILES: Cc1nnc(C2=CCN(C(=O)OC(C)(C)C)CC2)o1] | 266 | method I | 0.86 |
| 6.01.11.02 | 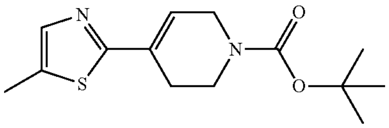 [SMILES: Cc1cnc(C2=CCN(C(=O)OC(C)(C)C)CC2)s1] | 281 | method I | 0.90 |

6.01.12.02 4-Pyrimidin-2-yl-3,6-dihydro-2H-pyridine-1-carboxylic acid tert-butyl ester

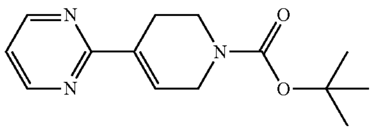 [SMILES: CC(C)(C)OC(=O)N1CC=C(c2ncccn2)CC1]

110 mg 4-hydroxy-4-pyrimidin-2-yl-piperidine-1-carboxylic acid tert-butyl ester was dissolved in 2.5 mL pyridine and 0.18 ml phosphoroxychloride was added. The reaction was stirred one day at RT. The reaction was decomposed with water and extracted with DCM. The organic layer was dried and the solvent was removed to give 84 mg of the desired compound.

$R_t$: 1.33 min (method J)

$(M+H)^+$: 162/206/262

6.01.04.03 4-(6-Methoxy-pyrimidin-4-yl)-piperidine-1-carboxylic acid tert-butyl ester

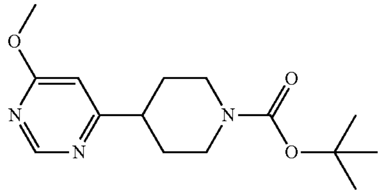 [SMILES: COc1cc(C2CCN(C(=O)OC(C)(C)C)CC2)ncn1]

150 mg palladium charcoal was added to 765 mg 4-(6-methoxy-pyrimidin-4-yl)-3,6-dihydro-2H-pyridine-1-carboxylic acid tert-butyl ester in 90 mL methanol. The reaction was stirred 3.5 h at RT and 3 bar hydrogen. Then, the reaction was filtered and evaporated to give 769 mg of the desired product.

$R_t$: 1.31 min (method J)

$(M+H)^+$: 194/238/294

By using the same synthesis strategy as for 4-(6-methoxy-pyrimidin-4-yl)-piperidine-1-carboxylic acid tert-butyl ester the following compound was obtained:

| Examples | Product | MS m/z [M + H]$^+$ | HPLC Method | Rt min |
|---|---|---|---|---|
| 6.01.05.03 | 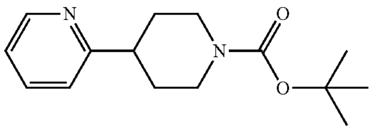 | 263//207/163 | method J | 1.04 |

-continued

| Examples | Product | MS m/z [M + H]$^+$ | HPLC Method | Rt min |
|---|---|---|---|---|
| 6.01.06.03 | 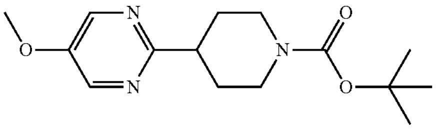 | 294 | method I | 0.91 |
| 6.01.11.03 | 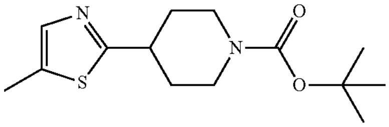 [SMILES: Cc1cnc(C2CCN(C(=O)OC(C)(C)C)CC2)s1] | 283 | method I | 0.86 |

6.01.04 4-Methoxy-6-piperidin-4-yl-pyrimidine

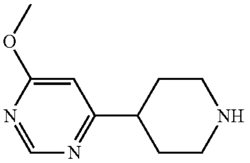

1.16 g 4-(6-Methoxy-pyrimidin-4-yl)-piperidine-1-carboxylic acid tert-butyl ester were stirred in 2 mL 4 mol/L HCl solution in dioxane for 40 min. The mixture was diluted with dioxane and basified with sodiumcarbonate. The suspension was filtered and the filtrate was concentrated to give 0.24 g of the desired product.

$R_t$: 1.31 min (method L)

$(M+H)^+$: 194/238/294

By using the same synthesis strategy as for 1',2',3',4',5',6'-hexahydro-(2,4')bipyridinyl hydrochlorid the following compounds were obtained:

| Examples | Product | MS m/z [M + H]$^+$ | HPLC Method | Rt min |
|---|---|---|---|---|
| 6.01.05 | 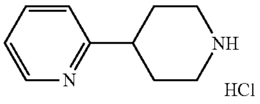 [SMILES: c1ccc(C2CCNCC2)nc1 ; Cl] | 263/ 207/ 163 | method J | 1.04 |
| 6.01.06 | 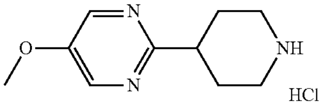 | 194 | method I | 0.45 |
| 6.01.07 | 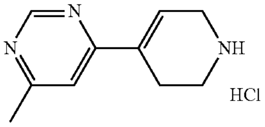 | 176 | method F | 0.87 |
| 6.01.08 | 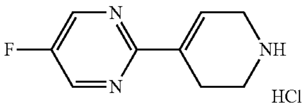 [SMILES: Fc1cnc(C2=CCNCC2)nc1 ; Cl] | 180 | method F | 0.96 |

-continued

| Examples | Product | MS m/z [M + H]$^+$ | HPLC Method | Rt min |
|---|---|---|---|---|
| 6.01.09 | 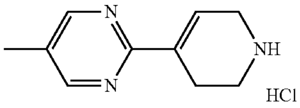 | 176 | method F | 0.95 |
| 6.01.10 | 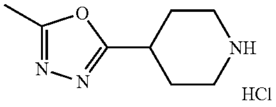 | 166 | method F | 0.44 |
| 6.01.11 | 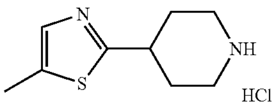 | 183 | method I | 0.35 |
| 6.01.15 | 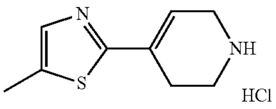 | 181 | method I | 0.52 |

6.01.16.01 3-Bromo-piperidin-4-one hydrobromide

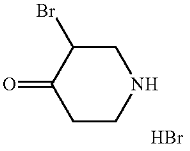

4.7 mL 33% HBr in acetic acid, 11.4 g bromine in 30 mL acetic acid was added slowly to a stirred solution of 10 g piperidine-4,4-diol in 60 mL acetic acid at RT. The reaction mixture was stirred additional 45 min at ambient temperature and the acetic acid was completely removed under reduced pressure. The residue was dissolved in 200 mL acetone and refluxed for 1 hour, cooled, filtered and washed with acetone and dried to give 15.2 g of the desired product (M+H)+: 180.

6.01.16.02 4,5,6,7-Tetrahydro-thiazolo(5,4-c)pyridin-2-ylamine dihydrobromide

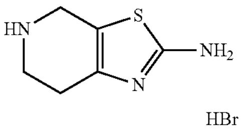

4.55 g thiourea was added to 15.2 g 3-Bromo-piperidin-4-one hydrobromide in 152 mL ethanol and refluxed for 20 h. The reaction was cooled and the solid was filtered, washed with ethanol and dried to give 15.8 g of the desired product.

(M+H)+: 184

6.01.16.03 2-Amino-6,7-dihydro-4H-thiazolo(5,4-c) pyridine-5-carboxylic acid tert-butyl ester

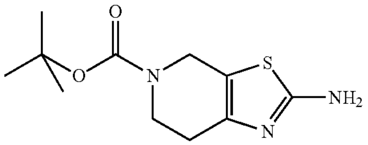 [SMILES: CC(C)(C)OC(=O)N1CCc2nc(N)sc2C1]

15.8 g 4,5,6,7-tetrahydro-thiazolo(5,4-c)pyridin-2-ylamine and 100 mL dioxane was added to 15.2 g potassium carbonate in 158 mL water. 13.1 g di tert-butyl dicarbonate in 58 mL dioxane was added at 0° C. The reaction mixture was allowed to stir for 3 h at ambient temperature. The reaction mixture was diluted with water and the solid was filtered through silica gel, washed with water (2×50 mL) to afford the desired product. The filtrate was concentrated, diluted with waterand extracted with ethyl acetat. The organic layer was dried over magnesium sulfate and concentrated to afford 11.6 g desired product.

1H NMR (400 MHz, DMSO-d6): δ 1.41 (s, 9H), 2.43 (t, 2H), 3.56 (t, 2H), 4.28 (s, 2H), 6.80 (s, 2H)

(M+H)+: 256

By using the same synthesis strategy as for 2-amino-6,7-dihydro-4H-thiazolo(5,4-c)pyridine-5-carboxylic acid tert-butyl ester the following compound was obtained:

| Examples | Product | MS m/z [M + H]$^+$ | HPLC Method | Rt min |
|---|---|---|---|---|
| 6.01.17.01 | 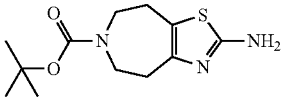 [SMILES: CC(C)(C)OC(=O)N1CCc2nc(N)sc2CC1] | 270 | | |

6.01.16.04 2-Phenoxycarbonylamino-6,7-dihydro-4H-thiazolo(5,4-c)pyridine-5-carboxylic acid tert-butyl ester

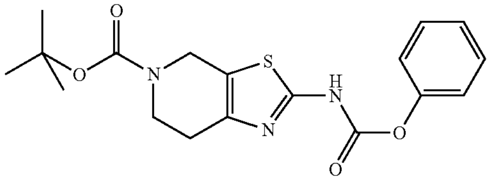 [SMILES: CC(C)(C)OC(=O)N1CCc2nc(NC(=O)Oc3ccccc3)sc2C1]

39 g calcium carbonate and 36.8 g phenyl chloroformate in 250 mL THF was added to a stirred solution of 50 g 2-amino-6,7-dihydro-4H-thiazolo (5,4-c)pyridine-5-carboxylic acid tert-butyl ester in 1 L THF. The reaction mixture was allowed to stir for 15 h. The reaction mixture was filtered through silica gel and the filtrate was concentrated under reduced pressure. The residue was diluted with water and extracted with ethyl acetate and the organic layer was dried over magnesium sulfate. The organic layer was concentrated under reduced pressure. The residue was washed with 20% ethyl acetate in hexane to give 60 g of the desired product.

1H NMR (400 MHz, CDCl3): δ 1.44 (s, 9H), 2.81 (s, 2H), 3.66 (s, 2H), 4.53 (s, 2H), 7.18 (d, 2H), 7.25-7.30 (m, 1H), 7.41 (t, 2H), 11.99 (br s, 1H)

(M+H)+: 376

6.01.16.05 2-(3-allyl-ureido)-6,7-dihydro-4H-thiazolo(5,4-c)pyridine-5-carboxylic acid tert-butyl ester

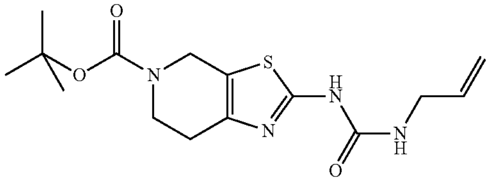 [SMILES: C=CCNC(=O)Nc1nc2c(s1)CN(C(=O)OC(C)(C)C)CC2]

45 mg allylamin was added to 200 mg 2-phenoxycarbonylamino-6,7-dihydro-4H-thiazolo (5,4-c) pyridine-5-carboxylic acid tert-butyl ester in 25 mL DMF. The reaction was stirred for 12 h at RT, diluted with water and extracted with ethyl acetate. The organic layer was washed with brine solution and concentrated. The residue was purified by column chromatographie (silica gel, eluent: 40% ethylacetate in hexane) to give 179 mg of desired product. (M+H)+: 339

6.01.16 1-allyl-3-(4,5,6,7-tetrahydro-thiazolo(5,4-c) pyridin-2-yl)-urea

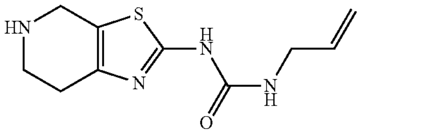 [SMILES: C=CCNC(=O)Nc1nc2c(s1)CNCC2]

10% TFA in 60 ml chloroform was added to 2.5 g 2-(3-allyl-ureido)-6,7-dihydro-4H-thiazolo (5,4-c) pyridine-5-carboxylic acid tert-butyl ester in 28 ml chloroform and stirred for 2 h at RT. The mixture was concentrated, the residue was diluted with chloroform and basified with 2.5 M aqueous potassium carbonate solution and extracted with chloroform. The organic layer was concentrated. The residue was washed with a mixture 50% ethyl acetate and 50% hexane to yield 1.7 g of the desired product. (M+H)+: 239

6.01.17.02 2-acetylamino-4,5,7,8-tetrahydro-thiazolo (4,5-d)azepine-6-carboxylic acid tert-butyl ester

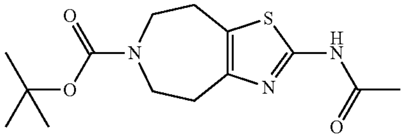 [SMILES: CC(=O)Nc1nc2c(s1)CCN(C(=O)OC(C)(C)C)CC2]

95 mg acetyl chloride was added to 312 mg 2-Amino-4,5,7,8-tetrahydro-thiazolo (4,5-d) azepine-6-carboxylic acid tert-butyl ester in 5 mL pyridine at 15° C. The reaction was stirred 3 h at RT. The reaction was diluted with dichlormethane and 1 mL water was added. The solution was filtered over 40 mL Alox and 100 mL Extrelut and evaporated to give 127 mg desired product. (M+H)+: 312

By using the same synthesis strategy as for 1-allyl-3-(4,5,6,7-tetrahydro-thiazolo (5,4-c) pyridin-2-yl)-urea the following compounds were obtained:

| Examples | Product | MS m/z [M + H]$^+$ | HPLC Method | Rt min |
|---|---|---|---|---|
| 6.01.17 | 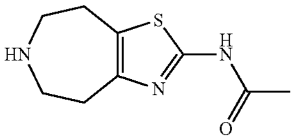 | 212 | | |

6.01.18 4-(5-Isopropyl-(1,3,4) oxadiazol-2-yl)-4-methyl-piperidine

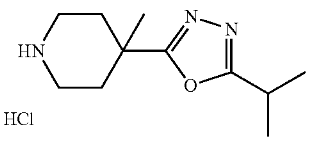

HCl 6.01.18.01 4-methyl-piperidine-1,4-dicarboxylic acid 1-tert-butyl ester 4-methyl ester

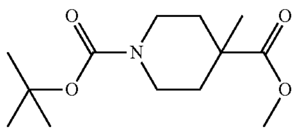 [SMILES: COC(=O)C1(C)CCN(C(=O)OC(C)(C)C)CC1]

137 mL Diisopropylamine in 3390 mL THF was cooled to 0° C. and 360 mL n-buthyllithium was added dropwise under nitrogen. The reaction was cooled to −78° C. and a solution of 180 mL piperidine-1,4-dicarboxylic acid 1-tert-butyl ester 4-methyl ester in 1800 mL THF was added dropwise over 1 h. The reaction was stirred at −78° C. for 2 h and then 168 mL methyliodide in 300 mL THF was added in one portion. The mixture was stirred 2 h at −78° C. and then allowed to warm to RT. The reaction was quenched with saturated aqueous sodium sulfate solution, the organig phase was separated, dried and evaporated. The residue was purified by chromatography on silica gel to give 155 g of the desired product.

$R_f$: 0.3 (petrolether/EtOAC=10/1)

1H NMR (TH03330-021-1, 400 MHz, CDCl3): δ3.67-3.65 (m, 2H, CH2), 3.62 (s, 3H, CH3), 2.93-2.87 (m, 2H, CH2), 2.00-1.95 (m, 2H, CH2), 1.37 (s, 9H, 3CH3), 1.31-1.25 (m, 2H, CH2), 1.12 (s, 3H, CH3).

6.0.1.18.02 4-hydrazinocarbonyl-4-methyl-piperidine-1-carboxylic acid tert-butyl ester

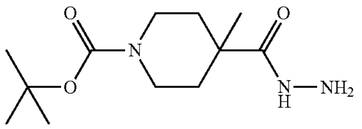 [SMILES: CC(C)(C)OC(=O)N1CCC(C)(C(=O)NN)CC1]

100 g 4-methyl-piperidine-1,4-dicarboxylic acid 1-tert-butyl ester 4-methyl ester was dissolved in 100 mL methanol and 300 mL hydrazine monohydrate was added. The mixture was reflux overnight. The reaction was cooled to RT and then concentrated to dryness under vacuum to give compound 89 g desired product.

$R_f$: 0.2 (DCM/MeOH=20/1)

By using the same synthesis strategy as for 4-hydrazinocarbonyl-4-methyl-piperidine-1-carboxylic acid tert-butyl ester the following compound was obtained:

| Examples | Product | NMR | Rf |
|---|---|---|---|
| 6.01.19.02 | 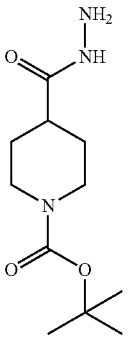 [SMILES: CC(C)(C)OC(=O)N1CCC(C(=O)NN)CC1] | $^1$H-NMR: (400 MHz, MeOD): δ 4.08 (d, J = 13.2 Hz, 2H, CH2), 2.27 (br, 2H, NH2), 2.38-2.29 (m, 1H, CH), 1.72-1.68 (m, 2H, CH2), 1.63-1.56 (m, 2H, CH2), 1.45 (s, 9H, 3CH3). | 0.2 (DCM/MeOH = 20/1) |

6.01.18.03 4-(5-isopropyl-(1,3,4)oxadiazol-2-yl)-4-methyl-piperidine-1-carboxylic acid tert-butyl ester

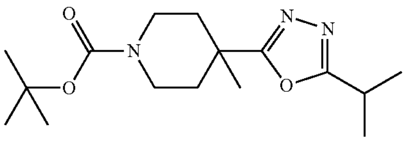 [SMILES: CC(C)c1nnc(C2(C)CCN(C(=O)OC(C)(C)C)CC2)o1]

30 g 4-hydrazinocarbonyl-4-methyl-piperidine-1-carboxylic acid tert-butyl ester was refluxed with 150 mL 1,1,1-trimethoxy-2-methyl-propane overnight. The excess of reagent was removed under vacuum and the residue was purified by chromatography on silica gel to give 19 g of the desired product.

1H NMR (TH03330-027-1, 400 MHz, CDCl3): δ 3.76-3.75 (m, 2H, CH2), 3.31-3.30 (m, 1H, CH), 3.22-3.17 (m, 2H, CH2), 2.18-2.15 (m, 2H, CH2), 1.68-1.62 (m, 2H, CH2), 1.45-1.38 (m, 9H, BocH), 1.37 (s, 9H, CH3).

By using the same synthesis strategy as for 4-(5-isopropyl-(1,3,4)oxadiazol-2-yl)-4-methyl-piperidine-1-carboxylic acid tert-butyl ester the following compound was obtained:

| Examples | Product | NMR | Rf |
|---|---|---|---|
| 6.01.19.03 | 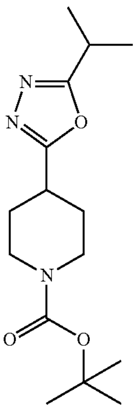 [SMILES: CC(C)c1nnc(C2CCN(C(=O)OC(C)(C)C)CC2)o1] | $^1$H-NMR (400 MHz, MeOD): δ 4.08-4.04 (m, 2H, CH2), 3.20-3.13 (m, 2H, 2CH), 3.01 (br, 2H, CH2), 2.07-2.03 (m, 2H, CH2), 1.75-1.68 (m, 2H, CH2), 1.46 (s, 9H, 3CH3), 1.36 (d, J = 6.8 Hz, 6H, 2CH3). | 0.3 (DCM/MeOH = 20/1) |

6.01.18 4-(5-Isopropyl-(1,3,4)oxadiazol-2-yl)-4-methyl-piperidine

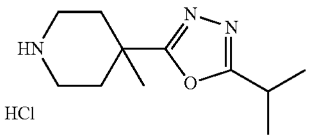

150 mL saturated dioxane-HCl was added to 19 g 4-(5-isopropyl-(1,3,4)oxadiazol-2-yl)-4-methyl-piperidine-1-carboxylic acid tert-butyl ester in 100 mL dioxane at 0° C. The mixture was stirred at RT for 2 h. The precipitate was filtered and washed with ethyl acetate to give 15.1 g of the desired product.

1H NMR (TH03335-030-4, 400 MHz, MeOD): δ 3.38-3.33 (m, 2H, CH2), 3.22-3.16 (m, 1H, CH), 3.13-3.10 (m, 2H, CH2), 2.44-2.39 (m, 2H, CH2), 2.03-1.95 (m, 2H, CH2), 1.46 (s, 3H, CH3), 1.38 (d, J=7.2 Hz, 6H, 2CH3).

By using the same synthesis strategy as for 4-(5-isopropyl-(1,3,4)oxadiazol-2-yl)-piperidine-1-carboxylic acid tert-butyl ester the following compound was obtained:

| Examples | Product | MS m/z [M + H]$^+$ |
|---|---|---|
| 6.01.19 | 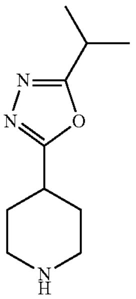 | $^1$H-NMR (400 MHz, MeOD): δ 3.49-3.44 (m, 2H, CH2), 3.38-3.34 (m, 1H, CH), 3.22-3.16 (m, 3H, CH2/CH), 2.36-2.32 (m, 2H, CH2), 2.09-2.02 (m, 2H, CH2), 1.37 (d, J = 7.2 Hz, 6H, CH3). |

6.01.20.01 2-methylamino-4,5,7,8-tetrahydro-thiazolo(4,5-d)azepine-6-carboxylic acid tert-butyl ester

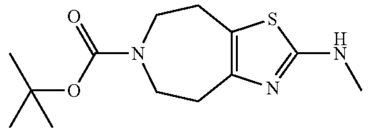 [SMILES: CNc1nc2c(s1)CCN(C(=O)OC(C)(C)C)CC2]

104 mg 60% sodium hydrid was added to 700 mg 2-amino-4,5,7,8-tetrahydro-thiazolo (4,5-d) azepine-6-carboxylic acid tert-butyl ester in 1.5 mL THF at 0° C. Then, 162 μL methyliodide was dropped to the mixture. The reaction was stirred over night at RT. The solvent was removed and the residue was purified by HPLC and 121 mg of the desired product was obtained.

(M+H)+: 284

6.01.21 4-phenyl-6,7,8,9-tetrahydro-5H-pyrimido[4,5-d]azepine hydrochloride

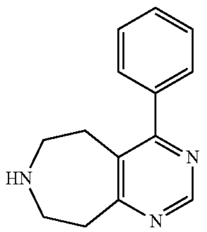 [SMILES: c1ccc(-c2ncnc3c2CCNCC3)cc1]

6.01.21.01 (1-benzyl-5-chloro-2,3,6,7-tetrahydro-1H-azepin-4-yl)-phenyl-methanol

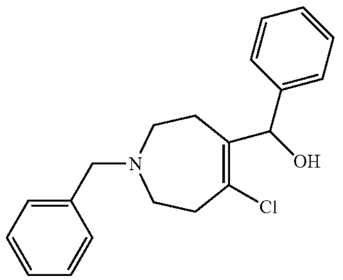 [SMILES: OC(C1=C(Cl)CCN(Cc2ccccc2)CC1)c1ccccc1]

136.6 g brombenzol in 300 mL diethylether was added to 21.2 g magnesium in 100 mL diethylether. The Grignard reaction is initiated with a small amount of iodine, kept at reflux by adding the bromebenzole and stirred additional 15 min for compleation. Then, 21.2 g 1-benzyl-5-chloro-2,3,6,7-tetrahydro-1H-azepine-4-carbaldehyde in 300 mL diethylether was added. The mixture was stirred 2 h in a warm water bath and quenched with 200 ml 6 M HCl solution at 0° C. The reaction was filtered and the filtrate was washed with diethylether and water. The filtrate was dissolved in sodium carbonate solution and chloroform. The layers were separated and the organic layer was washed with water and evaporated to give 89.9 g of the desired product. Fp: 124° C.

6.01.21.02 (1-benzyl-5-chloro-2,3,6,7-tetrahydro-1H-azepin-4-yl)-phenyl-methanone

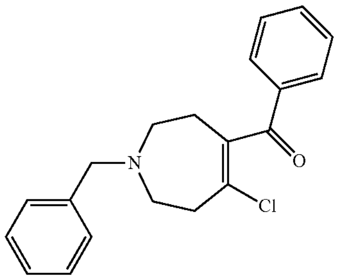 [SMILES: O=C(C1=C(Cl)CCN(Cc2ccccc2)CC1)c1ccccc1]

89 g (1-benzyl-5-chloro-2,3,6,7-tetrahydro-1H-azepin-4-yl)-phenyl-methanol in 800 mL dichlormethane was dropped to 115.4 g pyridiniumchlorchromate in 600 mL dichlormethane. The reaction was stirred 2.5 days at RT. Potassiumcarbonate-solution was added to the reaction. The mixture was stirred 2 h at RT and filtered over celite. The layers were separated and the organic layer was washed with water. The solvent was removed and the residue was purified by chromatography on silica gel (toluol/EE: 8.5:1.5). The solvent was removed and 64.6 g of the desired compound was obtained. $R_f$: 0.5 (toluol/EE: 8.5:1.5)

6.01.21.03 7-benzyl-4-phenyl-6,7,8,9-tetrahydro-5H-pyrimido[4,5-d]azepine

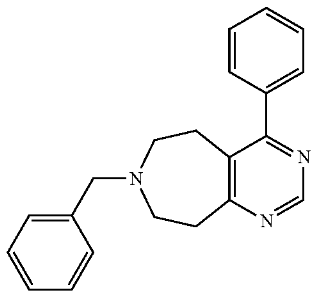 [SMILES: c1ccc(CN2CCc3ncnc(-c4ccccc4)c3CC2)cc1]

16.8 g sodium was added to 500 mL ethanol at 10° C. Then, 48.5 g formamidine hydrochloride was added and the reaction was stirred 15 min at 6° C. 28 g (1-benzyl-5-chloro-2,3,6,7-tetrahydro-1H-azepin-4-yl)-phenyl-methanone was added and the reaction was stirred 17.5 h at RT and 1 h at 40° C. The mixture was filtered and the solvent was removed. The residue was dissolved in ethyl acetate. The layers were separated and the organic layer was washed with water and evaporated. The residue was crystalysed with diethylether to yield 10.7 g of the desired product. Fp: 81-82° C.

6.01.21.04 4-phenyl-6,7,8,9-tetrahydro-5H-pyrimido[4,5-d]azepine hydrochloride

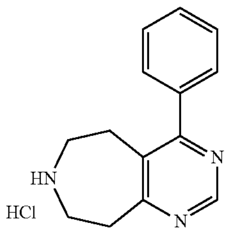 [SMILES: Cl ; c1ccc(-c2ncnc3c2CCNCC3)cc1]

Palladium charcoal was added to 17 g 7-benzyl-4-phenyl-6,7,8,9-tetrahydro-5H-pyrimido[4,5-d]azepine in 250 mL ethanol and 54 mL 1 mol/L HCl solution. The reaction was stirred at 80° C. and 5 bar hydrogen. The mixture was filtered and evaporated to give 13.15 g of the desired product.

6.01.22 4-(5-Methyl-oxazol-2-yl)-piperidine

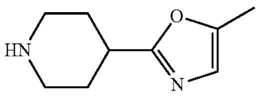

6.01.22.01 N-(2-Hydroxy-propyl)-isonicotinamide

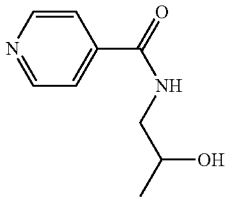

289 g 1-amino-propan-2-ol was added to 75 g isonicotinoyl chloride and 549 mL triethylamine in 2 L anhydrous dichlormethane at 0° C. under nitrogen atmosphere. After 30 min at 0° C. the reaction was concentrated under vacuum and the residue was re-suspended in 5 L ethyl acetate. The precipitate was removed by filtration. The filtrate was concentrate and recrystallized from ethyl acetate to give 154 g of the desired product.

$R_f$: 0.4 (dichlormethane:20/methanol:1)

$(M+H)^+$: 181

6.01.22.02 N-(2-Oxo-propyl)-isonicotinamide

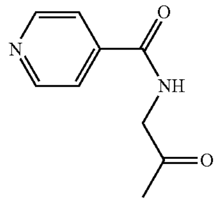

A solution of 154 g N-(2-hydroxy-propyl)-isonicotinamide in 800 mL dichlormethane was added dropwise to a solution of 438 g Dess-Martin reagent in 1.2 L dichlormethane at 0° C. under nitrogen atmosphere. After 30 min at 0° C., the solution was stirred at RT for 4 h. The mixture was concentrated under vacuum and the resulting crude product was purified by flash chromatography (silica gel) to give 91 g of the desired product.

$R_f$: 0.55 (dichlormethane/methanol:20/1), $(M+H)^+$: 179

6.01.22.03 4-(5-Methyl-oxazol-2-yl)-piperidine

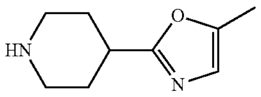

20 g N-(2-oxo-propyl)-isonicotinamide was dissolved in 200 mL phosphoroxychloride at 0° C. and the mixture was heated to 120° C. overnight. The reaction was quenched with cold water and then extracted with ethyl acetate. The organic layer was washed with brine, dried and concentrated under vacuum. The resulting crude product was purified by flash chromatography (silica gel) to give compound 10.5 g of the desired product.

$R_f$: 0.35 (petrolether/ethyl acetate:1/1), (M+H)+: 167

6.01.23 4-(5-Methyl-oxazol-2-yl)-1,2,3,6-tetrahydropyridine hydrochloride

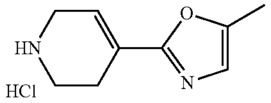

6.01.23.01 1-Benzyl-4-(5-methyl-oxazol-2-yl)-pyridinium

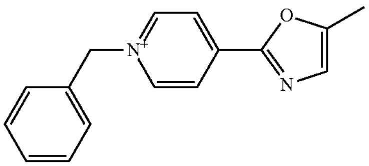 [SMILES: Cc1cnc(-c2cc[n+](Cc3ccccc3)cc2)o1]

141 g benzylbromide was added to 66 g 4-(5-methyl-oxazol-2-yl)-piperidine at RT and the mixture was heated at reflux overnight. The precipitate was collected by filtration and washed with acetone, dried under vacuum to give compound 126 g desired product.

$R_f$: 0.00 (petrolether/ethyl acetate:1/1), $(M+H)^+$: 252

6.01.23.02 1-Benzyl-4-(5-methyl-oxazol-2-yl)-1,2,3,6-tetrahydro-pyridine

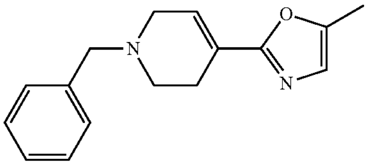 [SMILES: Cc1cnc(C2=CCN(Cc3ccccc3)CC2)o1]

21.6 g sodium borohydride was added to 130 g 1-benzyl-4-(5-methyl-oxazol-2-yl)-pyridinium in 1.5 L ethanol at 0° C. under nitrogen atmosphere. After 30 min at 0° C., the solution was stirred at RT for 2 h. The mixture was concentrated and treated with water and ethyl acetate. The organic layers were separated and aqueous layer was extracted with ethyl acetate. The organic layer was washed with brine, dried over sodium sulfate and concentrated under vacuum. The resulting crude product was purified by flash chromatography (silica gel) to give 81.2 g of the desired product. $R_f$: 0.3 (petrolether/ethyl acetate:1/1), $(M+H)^+$: 255

6.01.23.03 4-(5-Methyl-oxazol-2-yl)-1,2,3,6-tetrahydro-pyridine hydrochloride

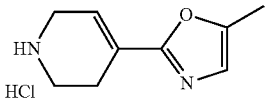

20 g 1-chloroethyl chloroformate was added to 24 g 1-benzyl-4-(5-methyl-oxazol-2-yl)-1,2,3,6-tetrahydro-pyridine in 200 mL anhydrous dichlormethane at 0° C. under nitrogen atmosphere. After 2 h, the solution was concentrated and 200 mL anhydrous methanol was added. The mixture was heated at reflux for 4 h and concentrated. The resulting crude product was re-crystallized from dichlormethane to give 16 g of the desired product.

$R_f$: 0.0 (petrolether/ethyl acetate:1/1)

$(M+H)^+$: 165

6.01.24 5,6-Dimethyl-pyridine-2-carboxylic acid methyl ester

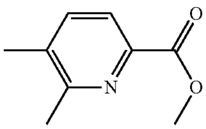

77.4 ml 2 mol/L trimethylsilyldiazomethan in hexane was added to 5,6-dimethyl-pyridine-2-carboxylic acid in 150 mL methanol and 600 mL dichlormethane at −5° C. and the reaction was stirred for 0.5 h. After warming to RT the solvent was removed and the residue was purified by chromatorgaphie on Silica (cyclohexane/ethyl acetate:7/3) to give 12.8 g of the desired product.

$R_t$: 0.49 (method M), $(M+H)^+$: 166

6.01.25 2-Methyl-isonicotinic acid methyl ester

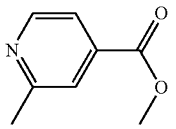

5 g 2-methyl-isonicotinic acid was stirred 24 h at 50° C. in 150 mL 1.3 mol/L HCl in methanol. The solvent was removed and water was added to the residue. The mixture was basified with saturated sodiumhydrogencarbonate solution and extracted with ethylacetate. The organic layer was dried with magnesiumsulfate and evaporated to give 4.5 g of the desired product.

$R_t$: 0.36 (method S), $(M+H)^+$: 152

6.01.26
1-(5-Methyl-(1,2,4)oxadiazol-3-yl)-piperazine hydrochloride

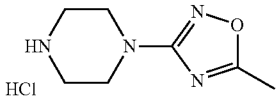

6.01.26.01 4-Cyano-piperazine-1-carboxylic acid tert-butyl ester

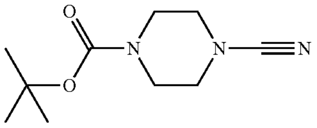

3.76 g bromcyane was added to 6 g piperazine-1-carboxylic acid tert-butyl ester and 6.3 mL DIPEA in 30 mL dichlormethane at 0° C. The reaction was stirred 1.5 h at 0° C. Water and dichlormethane was added and the layers were separated. The organic layer was washed with brine and water and evaporated to give 6.8 g of the desired product.

$R_t$: 1.13 (method AB), $(M+H-56)^+$: 156

6.01.26.02 4-(5-Methyl-(1,2,4)-oxadiazol-3-yl)-piperazine-1-carboxylic acid tert-butyl ester

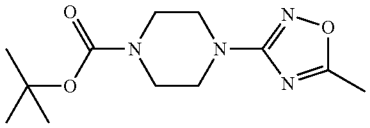 [SMILES: Cc1nc(N2CCN(C(=O)OC(C)(C)C)CC2)no1]

5.3 mL triethylamine and 2.6 g hydroxylamine hydrochloride were added to 6.8 g 4-cyano-piperazine-1-carboxylic acid tert-butyl ester in 50 mL ethanol. The reaction was stirred 2 h at 80° C. The solvent was removed and 50 mL pyridine and 3.7 mL acetic anhydride were added to the residue and stirred at 80° C. over night. The mixture was evaporated. Water was added and the precipitate was filtered and purified by chromatography on silica gel (cyclohexane/ethyl acetate: 2/1) to give 3.35 g of the desired product.

$R_t$: 1.30 (method AB), $(M+H)^+$: 269

6.01.26.03
1-(5-Methyl-(1,2,4)oxadiazol-3-yl)-piperazine hydrochloride

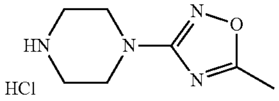

20 mL 4 mol/L HCl solution in dioxane was added to 3.35 g 4-(5-methyl-(1,2,4) oxadiazol-3-yl)-piperazine-1-carboxylic acid tert-butyl ester dissolved in 20 mL dioxane was stirred over night. The mixture was diluted with diethylether and the precipitate was filtered and washed with diethylether to give 2.5 g of the desired product.

$R_t$: 0.72 min (method AB), $(M+H)^+$: 169

6.01.27 1-(4-Methyl-oxazol-2-yl)-piperazine hydrochloride

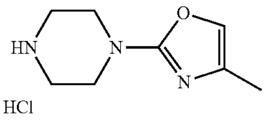

6.01.27.01 4-(4-Methyl-oxazol-2-yl)-piperazine-1-carboxylic acid tert-butyl ester

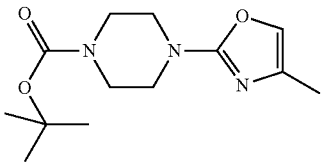 [SMILES: Cc1coc(N2CCN(C(=O)OC(C)(C)C)CC2)n1]

17 mL 2 mol/L aqueous sodium hydroxide solution was dropped to 6.7 g 4-cyano-piperazine-1-carboxylic acid tert-butyl ester and 2.5 mL 1-hydroxy-propan-2-one in 10 mL THF. The reaction was stirred 12 h at RT and over night at 75° C. The reaction was cooled, water was added and the mixture was diluted with diethylether. The precipitate was filtered to give 1.32 g of the desired product.

$R_t$: 1.30 min. (method AB)

$(M+H)^+$: 269

6.01.27.02
1-(3-Methyl-(1,2,4)oxadiazol-5-yl)-piperazine hydrochloride

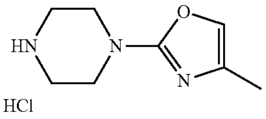

80.9 mL 1 mol/L zinc chloride solution in diethylether was dropped to 11.4 g 4-cyano-piperazine-1-carboxylic acid tert-butyl ester. The reaction was stirred over night at 150° C. The precipitate was filtered and the filtrate was concentrated and purified by chromatography on silica gel (dichlormethane/methanol/ammonia: 9/1/0.1%). Diethylether was added to the residue and the precipitate was filtered to give 1 g of the desired product. The residue was dissolved in diethylether and hydrogen chloride in was added. The precipitate was filtered to give 0.9 g of the desired product.

$R_t$: 0.67 min (method F)

$(M+H)^+$: 169

6.01.28
2-Methyl-5,6-dihydro-4H-pyrrolo[3,4-d]-oxazole hydroiodide

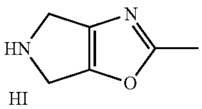

6.01.28.01 1-Benzyl-2,5-dihydro-1H-pyrrole

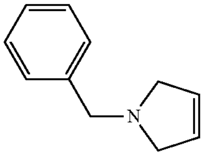 [SMILES: C1=CCN(Cc2ccccc2)C1]

The compound was produced according to patent application EP 18499770 A1; yield: 70%

$R_t$: 10.95 min. (method AG)

$(M+H)^+$: 161

6.01.28.02
Benzyl-2,5-dihydro-1H-pyrrole-1-carboxylate

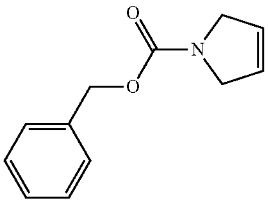 [SMILES: O=C(OCc1ccccc1)N1CC=CC1]

43 mL benzyloxycarbonyl chloride in 135 mL dichlormethane was added to 17.6 g 1-benzyl-2,5-dihydro-1H-pyrrole in 135 mL dichlormethane at 0° C. in 60 min. The mixture was stirred 3 h at RT and washed with saturated sodium hydrogencarbonate solution. The organic layer was dried and evaporated. The residue was purified by chromatography on silica gel (hexane/ethyl acetate: 5/1) to give 19.7 g of the desired product.

$R_t$: 16.50 min. (method AG)

$(M+H)^+$: 204

6.01.28.03 Benzyl
6-oxa-3-azabicyclo[3.1.0]hexane-3-carboxylate

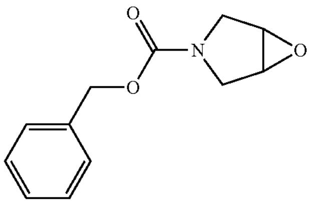 [SMILES: O=C(OCc1ccccc1)N1CC2OC2C1]

The compound was produced according patent application WO2004/99201 A1; yield: 89%

$R_t$: 5.36 min. (method AG), $(M+H)^+$: 220

6.01.28.04 Benzyl
3-amino-4-hydroxypyrrolidine-1-carboxylate

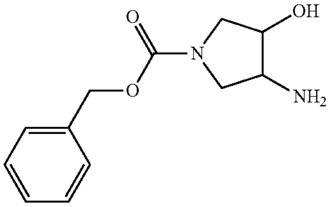 [SMILES: NC1CN(C(=O)OCc2ccccc2)CC1O]

6.5 g benzyl 6-oxa-3-azabicyclo[3.1.0]hexane-3-carboxylate in 80 mL 33% aqueous ammonia solution was stirred 20 h in a closed vessel. The reaction was cooled and extracted with dichlormethane. The organic layer was washed with sodium chloride solution and evaporated to give 6.1 g of the desired product.

$R_t$: 2.37 min. (method AG)

$(M+H)^+$: 237

6.01.28.05 Benzyl
3-acetamido-4-hydroxypyrrolidine-1-carboxylate

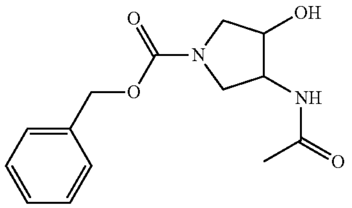 [SMILES: CC(=O)NC1CN(C(=O)OCc2ccccc2)CC1O]

3.24 g acetic anhydride was added to 7.1 g benzyl 3-amino-4-hydroxypyrrolidine-1-carboxylate in 100 mL dichlormethane at 0-5° C. The mixture was stirred 2 h at RT, 100 mL diethylether was added and the mixture was stirred for 15 min. The precipitate was filtered to give 7.6 g of the desired product.

$R_t$: 4.14 min. (method AG)

$(M+H)^+$: 279

6.01.28.06 Benzyl 3-acetamido-4-oxopyrrolidine-1-carboxylate

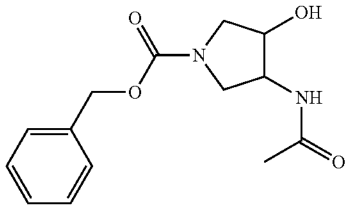 [SMILES: CC(=O)NC1CN(C(=O)OCc2ccccc2)CC1O]

Pyidin-sulphur trioxide in 6.5 mL DMSO was added to 1.34 g benzyl-3-acetamido-4-hydroxypyrrolidine-1-carboxylate and 2.5 mL DIPEA in 8 mL dichlormethane at 0° C. The reaction was stirred 1 h at RT. Water was added and the mixture was extracted with ethyl acetate. The organic layer was washed with water and sodium chloride solution and evaporated. The residue was purified by chromatography on silica gel (ethyl acetate) to give 1.1 g of the desired product. $(M+H)^+$: 277

6.01.28.07 2-Methyl-4,6-dihydro-pyrrolo[3,4-d]oxazole-5-carboxylic acid benzyl ester

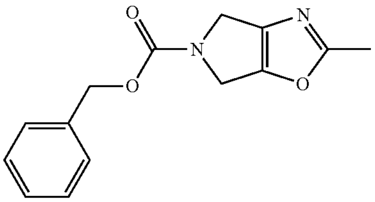 [SMILES: Cc1nc2c(o1)CN(C(=O)OCc1ccccc1)C2]

8.5 g methoxycarbonylsulfamoyl)triethylammoniumhydroxid was added to 4.7 g benzyl 3-acetamido-4-oxopyrrolidine-1-carboxylate in 180 mL THF. The reaction was stirred 1 h at 65° C. and evaporated. The residue was purified on silica gel (hexane/ethyl acetate:1/1) to give 1.4 g of the desired product.

$R_t$: 1.29 min (method Y), $(M+H)^+$: 259

6.01.28.08 2-methyl-5,6-dihydro-4H-pyrrolo[3,4-d]oxazole hydroiodide

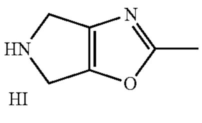

0.6 mL trimethylsilyliodide was added to 400 mg 2-methyl-4,6-dihydro-pyrrolo[3,4-d]oxazole-5-carboxylic acid benzyl ester in 30 mL acetonitrile. The reaction was stirred 4 h at RT. The solvent was removed to give 390 mg of the desired product.

$R_t$: 0.49 min (method AB)

$(M+H)^+$: 125

6.01.29 5-fluoro-4-methyl-pyridine-2-carboxylic acid methyl ester

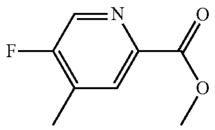

18 g 2-bromo-5-fluoro-4-methyl-pyridine, 1.5 g 1,1'-bis(diphenylphosphino)ferrocene dichloropalladium (II) and 18 g sodium acetate was stirred 17 h at 80° C. in an atmosphere of 5 bar carbon monoxide. The reaction was filtered and the solvent was removed. Diethylether was added to the residue and the mixture was filtered. The filtrate was evaporated to give 12 g of the desired product.

$R_t$: 0.90 min. (method W)

$(M+H)^+$: 170

By using the same synthesis strategy as for 5-fluoro-4-methyl-pyridine-2-carboxylic acid methyl ester the following compound was obtained:

| Example | Product | MS m/z $[M+H]^+$ | HPLC Method | Rt min |
|---|---|---|---|---|
| 6.01.30 | 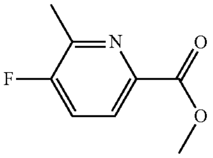 | 170 | method W | 0.87 |

6.01.31 3-phenyl-6,7,8,9-tetrahydro-5H-1,2,7-triaza-benzocycloheptene dihydrochloride

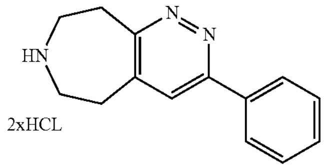 [SMILES: c1ccc(-c2cc3c(nn2)CCNCC3)cc1]

6.01.31.01 4-ethoxycarbonylmethyl-5-oxo-azepane-1,4-dicarboxylic acid 1-tert-butyl ester 4-ethyl ester

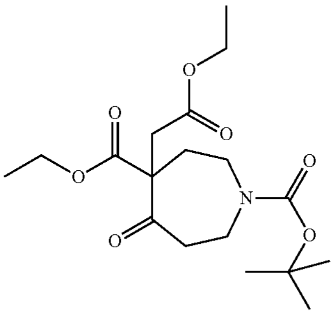 [SMILES: CCOC(=O)CC1(C(=O)OCC)CCN(C(=O)OC(C)(C)C)CCC1=O]

6.7 g potassium carbonate was added to 7 g 5-oxo-azepane-1,4-dicarboxylic acid 1-tert-butyl ester 4-ethyl ester in 50 mL DMF and stirred at RT. After 30 min 6.1 g ethyl bromoacetate was added and the reaction was stirred at RT over night. The reaction was diluted with water and extracted with ethyl acetate/hexane (1/1). The organic phase was washed with brine, dried and concentrated. The residue was purified by column chromatography on silica gel (15% ethyl acetate in hexane) to give 5.6 g of the desired product.

$(M+H)^+=372$ 6.01.31.024-carboxymethyl-5-oxo-azepane-1-carboxylic acid tert-butyl ester

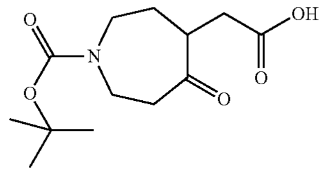 [SMILES: CC(C)(C)OC(=O)N1CCC(=O)C(CC(=O)O)CC1]

23.3 g sodium hydroxide in 218 mL water was added to 38 g 4-ethoxycarbonylmethyl-5-oxo-azepane-1,4-dicarboxylic acid 1-tert-butyl ester 4-ethyl ester in 155 mL THF. The reaction was stirred over night at RT, THF was removed and the mixture was extracted with dichlormethane. The aqueous part was acidified with 3M HCl to pH 3 at 0° C. The aqueous solution was extracted with dichloromethane, dried over magnesium sulfate, concentrated under reduced pressure to give 18.2 g of the desired product.

$(M+H)^+=272$ 6.01.31.03 3-oxo-2,3,4,4a,5,6,8,9-octahydro-1,2,7-triaza-benzocycloheptene-7-carboxylic cid tert-butyl ester

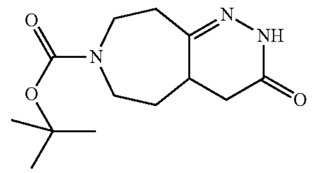 [SMILES: CC(C)(C)OC(=O)N1CCC2=NNC(=O)CC2CC1]

60 mL acetic acid was added to 16 g 4-carboxymethyl-5-oxo-azepane-1-carboxylic acid tert-butyl ester in 120 mL THF at 5° C. 14 mL hydrazine hydrate was added to the reaction and the mixture was refluxed over night. After completion of the reaction, volatiles were removed and the residue was basified with sodium carbonate and extracted with chloroform. The organic layer was dried and concentrated under reduced pressure to afford 11 g of the desired product $(M+H)^+=268$ 6.01.31.04 3-oxo-2,3,5,6,8,9-hexahydro-1,2,7-triaza-benzocycloheptene-7-carboxylic acid ert-butyl ester

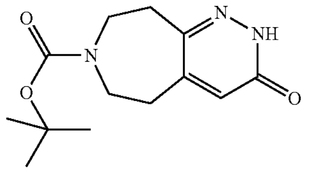 [SMILES: CC(C)(C)OC(=O)N1CCc2cc(=O)[nH]nc2CC1]

7 g 3-oxo-2,3,4,4a,5,6,8,9-octahydro-1,2,7-triaza-benzocycloheptene-7-carboxylic cid tert-butyl ester was dissolved in 70 mL toluene and 6.7 g manganese dioxide was added to the reaction mixture. It was heated at reflux for 48 h. After completion of the reaction, the reaction mixture was diluted with chloroform and filtered through celite. The filtrate was concentrated and purified by column chromatography to afford 5.5 g of the desired product. $(M+H)^+=266$ 6.01.31.05 3-chloro-5,6,8,9-tetrahydro-1,2,7-triaza-benzocycloheptene-7-carboxylic acid tert-butyl ester

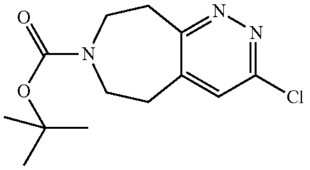 [SMILES: CC(C)(C)OC(=O)N1CCc2cc(Cl)nnc2CC1]

11 g 3-oxo-2,3,5,6,8,9-hexahydro-1,2,7-triaza-benzocycloheptene-7-carboxylic acid ert-butyl ester in 90 ml phosphor oxychloride was refluxed overnight. The phosphor oxychloride was quenched with 8.7 g sodium carbonate to pH 8 and 100 mL water was added to the reaction mixture. Di-tert.butyl-dicarbonate was added to the reaction mixture and stirred over night. The solution was extracted with 50% ethyl acetate in hexane. The extracted organic layer was dried, concentrated under reduced pressure and purified by column chromatography to afford 8.0 g of the desired product. $(M+H)^+=284$ 6.01.31.06 3-phenyl-5,6,8,9-tetrahydro-1,2,7-triaza-benzocycloheptene-7-carboxylic acid tert-butyl ester

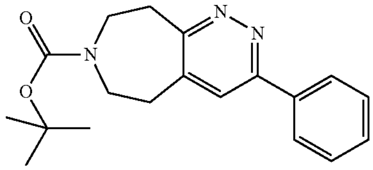 [SMILES: CC(C)(C)OC(=O)N1CCc2cc(-c3ccccc3)nnc2CC1]

5 g phenylboronic acid in 30 mL dioxane was added to 3.2 g 3-chloro-5,6,8,9-tetrahydro-1,2,7-triaza-benzocycloheptene-7-carboxylic acid tert-butyl ester and 388 mg (1,1'-bis (diphenyl-phosphinoferrocene)palladium(II)dichloride in 50 mL dioxane under argon. The reaction was stirred at 90° C. over night. The mixture was cooled to RT diluted with water and extracted with ethyl acetate. The organic layer was washed with aqueous sodium hydroxide and brine. The solvent was removed and the precipitate was purified by column chromatographie to yield 5.5 g of the desired product. $(M+H)^+=325$ 6.01.31.07 3-phenyl-6,7,8,9-tetrahydro-5H-1,2,7-triaza-benzocycloheptene dihydrochloride

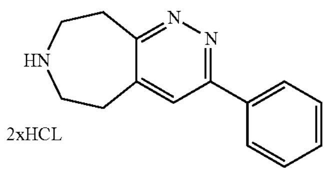 [SMILES: c1ccc(-c2cc3c(nn2)CCNCC3)cc1]

40 mL hydrogen chloride in dioxane was added to 5.5 g 3-phenyl-5,6,8,9-tetrahydro-1,2,7-triaza-benzocyclohep-tene-7-carboxylic acid tert-butyl ester in 40 mL dioxane at 5° C. The reaction was stirred over night. The solvent was removed and co-evaporated with ethyl acetate to yield 3.7 g of the desired product. $R_t$: 4.09 min (method AE), $(M+H)^+$: 226

6.01.32 2-methyl-2,5,6,7,8,9-hexahydro-1,2,7-triaza-benzocyclohepten-3-one hydrochloride

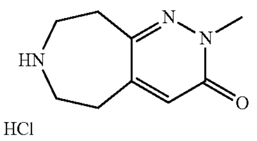

6.01.32.01 2-methyl-3-oxo-2,3,4,4a,5,6,8,9-octahy-dro-1,2,7-triaza-benzocycloheptene-7-carboxylic acid tert-butyl ester

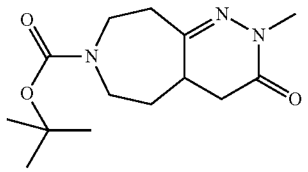 [SMILES: CN1N=C2CCN(C(=O)OC(C)(C)C)CCC2CC1=O]

36 mL acetic acid was added to 10.5 g 4-carboxymethyl-5-oxo-azepane-1-carboxylic acid tert-butyl ester in 75 mL THF at 5° C. 3.1 mL methylhydrazine was added to the mixture and refluxed for 3 h. The mixture was diluted with water and extracted with ethyl acetate. The organic layer was washed with brine. The crude product was purified by column chromatography on silica gel to yield 6.9 g of the desired product. $(M+H)^+$: 282

6.01.32.02 2-methyl-3-oxo-2,3,5,6,8,9-hexahydro-1,2,7-triaza-benzocycloheptene-7-carboxylic acid tert-butyl ester

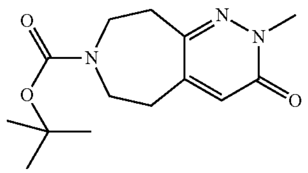 [SMILES: Cn1nc2c(cc1=O)CCN(C(=O)OC(C)(C)C)CC2]

3 g DDQ was added to 2.5 g 2-methyl-3-oxo-2,3,4,4a,5,6,8,9-octahydro-1,2,7-triaza-benzocycloheptene-7-carboxylic acid tert-butyl ester in 25 mL dioxane. The reaction was refluxed for 12 h. Then aqueous potassium carbonate solution was added and the mixture was extracted with chloroform. The organic layer was washed with brine. The crude product was purified by column chromatography on silica gel to yield 1.3 g of the desired product.

$(M+H)^+$: 280

6.01.32.03 2-Methyl-2,5,6,7,8,9-hexahydro-1,2,7-triaza-benzocyclohepten-3-one hydrochloride

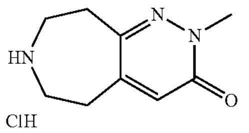

40 mL dioxane solution of hydrogen chloride was added to 5.5 g 3-phenyl-5,6,8,9-tetrahydro-1,2,7-triaza-benzocyclo-heptene-7-carboxylic acid tert-butyl ester in 40 mL dioxane at 5° C. The reaction was stirred over night. The solvent was removed and co-evaporated with ethyl acetate to yield 3.7 g of the desired product. $(M+H)^+$: 180, $R_t$: 7.84 min (method AE)

6.01.33 2,7-dimethyl-5,6,7,8-tetrahydro-4H-thiazolo [4,5-d]azepine dihydrobromide

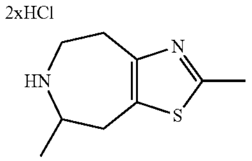

6.01.33.01 5-bromo-7-methyl-azepan-4-one hydro-bromide/3-bromo-7-methyl-azepan-4-one hydrobro-mide (mixture of isomeres)

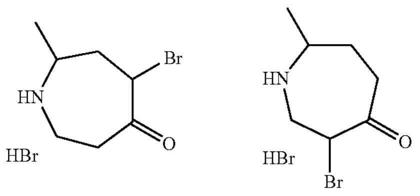

9.8 mL bromine was added to 30 g 7-methyl-azepan-4-one hydrobromide in 180 mL acetic acid. The reaction was stirred over night at RT. The reaction was evaporated to yield 33 g of the desired product as isomere mixture. $R_f$: 0.4 (DCM/MeOH=20/1), $(M+H)^+$=206

6.01.33.02 2,7-dimethyl-5,6,7,8-tetrahydro-4H-thiazolo[4,5-d]azepine hydrobromide 2,6-dimethyl-5,6,7,8-tetrahydro-4H-thiazolo[5,4-c]azepine hydrobromide isomere mixture

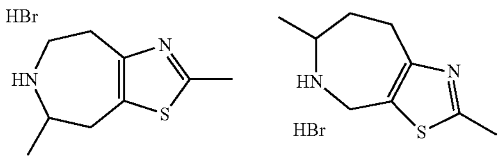

A mixture of 33 g 5-bromo-7-methyl-azepan-4-one hydrobromide and 3-bromo-7-methyl-azepan-4-one hydrobromide and 8.6 g thioacetamide in 400 mL dry EtOH was refluxed overnight. The reaction mixture was concentrated to give 30 g of the desired product, which was used for the next step without further purification. $R_f$: 0.2 (DCM/MeOH=20/1), $(M+H)^+=183$ 6.01.33.03 2,7-Dimethyl-4,5,7,8-tetrahydro-thiazolo[4,5-d]azepine-6-carboxylic acid tert-butyl ester

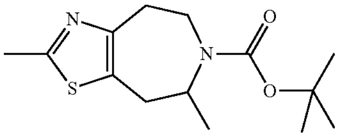 [SMILES: Cc1nc2c(s1)CC(C)N(C(=O)OC(C)(C)C)CC2]

A mixture of 30 g 2,7-dimethyl-5,6,7,8-tetrahydro-4H-thiazolo[4,5-d]azepine hydrobromide and 2,6-dimethyl-5,6,7,8-tetrahydro-4H-thiazolo[5,4-c]azepine hydrobromide, 38.5 g di-tert.butyl-dicarbonate and 9.1 g sodium hydroxide in 300 mL water and 500 mL tetrahydrofuran was stirred at RT for 3 h. The reaction mixture was extracted with ethyl acetate. The organic layer was washed with brine, dried over sodium sulfate and evaporated to dryness. The residue was purified by pre-HPLC to give 7.7 g of the desired product. $R_f$: 0.6 (DCM/MeOH=20/1), $(M+H)^+=283$ 6.01.33.04 2,7-dimethyl-5,6,7,8-tetrahydro-4H-thiazolo[4,5-d]azepine dihydrobromide

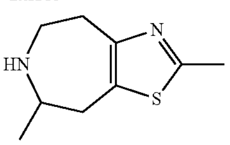

54 ml 4 mol/L HCL in ethyl acetate was added to 7.7 g 2,7-Dimethyl-4,5,7,8-tetrahydro-thiazolo[4,5-d]azepine-6-carboxylic acid tert-butyl ester in 100 mL ethyl acetate. The reaction was stirred 2 h at RT and evaporated to give 6.2 g of the desired product.

$R_f$: 0.2 (DCM/MeOH=20/1), $(M+H)^+=183$ 6.01.34 phenyl-(6,7,8,9-tetrahydro-5H-pyrimido[4,5-d]azepin-2-yl)-amine

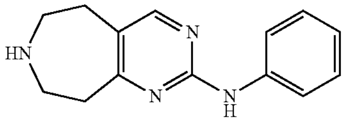 [SMILES: c1ccc(Nc2ncc3c(n2)CCNCC3)cc1]

6.01.34.01 1-benzyl-5-chloro-2,3,6,7-tetrahydro-1H-azepine-4-carbaldehyde hydrochloride

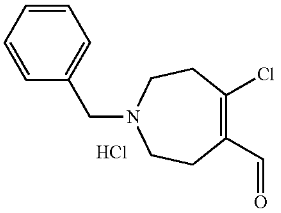 [SMILES: O=CC1=C(Cl)CCN(Cc2ccccc2)CC1 ; Cl]

77 mL phosphoroxychloride was added to 62 mL DMF at 8-18° C. 84 mL dichlormethane was added and 50 g 1-benzyl 4-azepanone hydrochloride. The reaction was stirred over night at RT. The mixture was added to 300 mL ice water and extracted with dichlormethane. The organic layer was evaporated to give 23.3 g of the desired product. $(M+H)^+=287$ 6.01.34.02 (7-benzyl-6,7,8,9-tetrahydro-5H-pyrimido[4,5-d]azepin-2-yl)-phenyl-amine

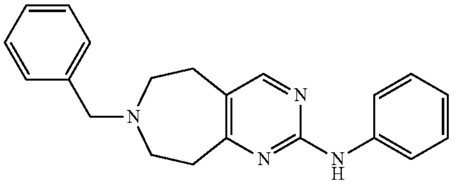 [SMILES: c1ccc(CN2CCc3cnc(Nc4ccccc4)nc3CC2)cc1]

1 g 1-benzyl-5-chloro-2,3,6,7-tetrahydro-1H-azepine-4-carbaldehyde hydrochloride was added to 1 g phenylguanidine carbonate salt and 1 g sodium ethanolate in 25 mL ethanol. The reaction was stirred 4 h at 70° C. The mixture was filtered over silica gel and the solvent was removed. The residue was purified by chromatography on silica gel (dichlormethane/MeOH/ammonia: 19/1/0.1) to yield 300 mg of the desired product.

$R_f$: 0.55 (DCM/MeOH/ammonia=19/1/0.1), $(M+H)^+=331$ 6.01.34.03 phenyl-(6,7,8,9-tetrahydro-5H-pyrimido[4,5-d]azepin-2-yl)-amine

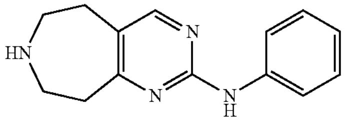 [SMILES: c1ccc(Nc2ncc3c(n2)CCNCC3)cc1]

150 mg (7-benzyl-6,7,8,9-tetrahydro-5H-pyrimido[4,5-d]azepin-2-yl)-phenyl-amine and 20 mg palladium on charcoal in 10 mL was stirred 1 day under 3 bar of a hydrogen atmosphere. The mixture was filtered and evaporated to yield 84 mg of the desired product. $(M+H)^+=241$ 6.01.35 3-methyl-6,7,8,9-tetrahydro-5H-imidazo[1,2-a][1,4]diazepine dihydrochloride

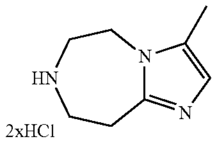

6.01.35.01 5-oxo-[1,4]diazepane-1-carboxylic acid tert-butyl ester

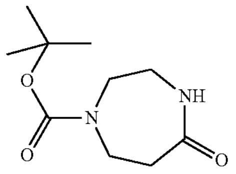

0.38 g trimethyl-oxonium tetrafluoro borate was added to 0.5 g 5-oxo-perhydro-1,4-diazepine-1-carboxylic acid tert-butyl ester in 15 mL THF. The reaction was stirred over night at RT. The reaction mixture was washed with saturated aqueous sodiumhydrogencarbonate solution and water. The organic layer was dried and evaporated to give 428 mg of the desired product.

$(M+H)^+$: 229, $R_t$: 0.82 min (method J)

6.01.35.02 3-methyl-5,6,8,9-tetrahydro-imidazo[1,2-a][1,4]diazepine-7-carboxylic acid tert-butyl ester

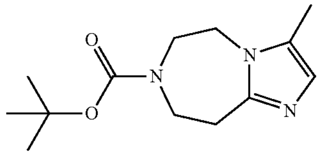 [SMILES: Cc1cnc2n1CCN(C(=O)OC(C)(C)C)CC2]

0.6 mL propargylamin was added to 429 mg 5-oxo-[1,4]diazepane-1-carboxylic acid tert-butyl ester in 20 mL methanol. The reaction was refluxed 5 h and evaporated to give 468 mg of the desired product. $(M+H)^+$: 252, $R_t$: 0.88 min (method J)

6.01.35.03 3-methyl-6,7,8,9-tetrahydro-5H-imidazo[1,2-a][1,4]diazepine dihydrochloride

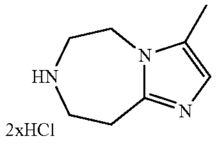

1.89 g 3-methyl-5,6,8,9-tetrahydro-imidazo[1,2-a][1,4]diazepine-7-carboxylic acid tert-butyl ester was stirred in 40 mL 4 mol/L HCl solution in dioxane over night. The mixture was concentrated to give 1.67 g of the desired product. $R_t$: 0.62 min (method AC), $(M+H)^+$: 152

6.01.36 N-(2,3,4,5-Tetrahydro-1H-benzo[d]azepin-7-yl)-acetamide

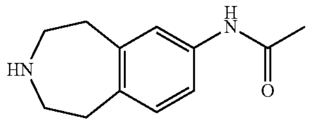

6.01.36.01 N-[3-(2,2,2-Trifluoro-acetyl)-2,3,4,5-tetrahydro-1H-benzo[d]azepin-7-yl]-acetamide

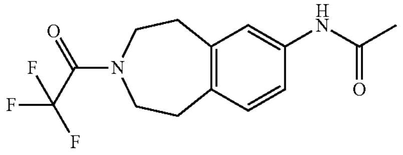 [SMILES: CC(=O)Nc1ccc2c(c1)CCN(C(=O)C(F)(F)F)CC2]

2.75 mL acetanhydride was added to 5 g 3-trifluoracetyl-7-amino-1,2,4,5-tetrahydro-benzo[D]azepine in concentrated acetic acid. The mixture was stirred 17 h at RT, diluted with water and stirred for another 1 h at RT. The precipitate was filtered, washed with water and dried to give 5.35 g of the desired product. $R_f$: 0.46 (DCM/MeOH=19/1), $(M+H)^+$=301

6.01.36.02 N-(2,3,4,5-Tetrahydro-1H-benzo[d]azepin-7-yl)-acetamide

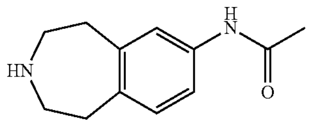

29.2 g potassiumcarbonate in 100 mL of water was added to 17.5 g N-[3-(2,2,2-Trifluoro-acetyl)-2,3,4,5-tetrahydro-1H-benzo[d]azepin-7-yl]-acetamide in 400 mL MeOH and 50 mL THF at 5° C. The reaction mixture was stirred in the ice bath for 2 h and 2 h at RT. The solvent was removed and the residue was extracted with brine and dichloromethane, the organic fraction was dried and the solvent removed to yield 14.9 g of the desired product.

$R_f$: 0.12 (DCM/MeOH=9/1), $(M+H)^+$=205

6.01.37 2-Methoxy-5,6,7,8-tetrahydro-thiazolo[4,5-d]azepine

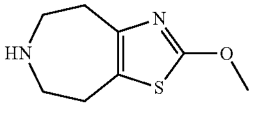

6.01.37.01 Diazo-acetic acid ethyl ester

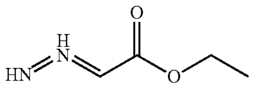

11.4 g sodium nitrite in water was added to 20 g Amino-acetic acid ethyl ester hydrochloride and 5.88 g sodium acetate in 50 mL water at 0° C. The reaction was stirred 10 min. at RT. 3 mL of 10% sulfuric acid was added and the mixture was extracted with ethyl acetate. The organic layer was washed with 10% sodium carbonate, dried and evaporated to give 9 g of the desired product.

$R_f$: 0.40 (petrol ether/ethyl acetate=6/4), $(M+H)^+$=116

6.01.37.02 5-Oxo-azepane-1,4-dicarboxylic acid 1-tert-butyl ester 4-ethyl ester

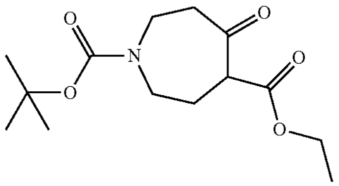 [SMILES: CCOC(=O)C1CCN(C(=O)OC(C)(C)C)CCC1=O]

3 mL boron trifluoride etherate was added to 4 g 4-oxo-piperidine-1-carboxylic acid tert-butyl ester in 30 mL diethyl ether at −30° C. Then 3.5 g diazo-acetic acid ethyl ester in diethyl ether was added at the same temperature and stirred for 30 min. The reaction was poured in to ice water and the organic layer was separated, washed with aqueous sodium-carbonate solution, dried and evaporated to give 3 g of the desired product.

$R_f$: 0.20 (petrol ether/ethyl acetate=6/4), $(M+H)^+$=286

6.01.37.03 Azepan-4-one hydrochloride

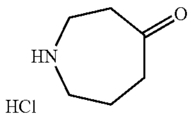

20 g 5-Oxo-azepane-1,4-dicarboxylic acid 1-tert-butyl ester 4-ethyl ester was stirred over night at 110° C. in 200 mL 6 M hydrochloric acid. The reaction was concentrated to yield 11 g of the desired product. $R_f$: 0.20 (dichlormethane/methanol=9/1), $(M+H)^+$=114

6.01.37.04 1-Benzyl-azepan-4-one

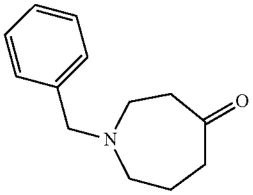 [SMILES: O=C1CCCN(Cc2ccccc2)CC1]

6 mL benzyl bromide was added to 5 g azepane-4-one hydrochloride and 18.5 g potassium carbonate in 50 mL THF and 25 mL water. The mixture was stirred 5 h at 50° C., evaporated, diluted with water and extracted with ethyl acetate. The organic layer was evaporated. The residue was purified by chromatographie on silica gel (petrolether/ethyl acetate:8/2) to give 5 g of the desired product. $R_f$: 0.40 (hexane/ethyl acetate=1/1), $(M+H)^+$=204

6.01.37.05 1-Benzyl-5-bromo-azepan-4-one

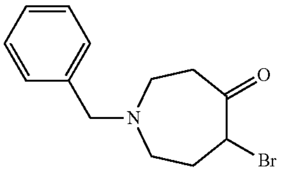 [SMILES: O=C1CCN(Cc2ccccc2)CCC1Br]

33% hydrobromic acid in conc. acetic acid and 1.97 g bromine was added to 5 g 1-benzyl-azepane-4-one in 15 mL conc. acetic acid. The reaction was stirred 2 h at RT and completely concentrated under reduced pressure. The residue was diluted with ethyl acetate and refluxed for 1 h and crystallized with ethyl acetate to give 4 g of the desired product.

$R_f$: 0.40 (hexane/ethyl acetate=1/1), $(M+H)^+$=282/84

6.01.37.06 6-Benzyl-5,6,7,8-tetrahydro-thiazolo[4,5-d]azepine-2-ylamine

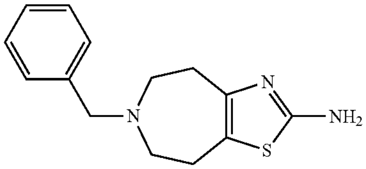 [SMILES: Nc1nc2c(s1)CCN(Cc1ccccc1)CC2]

2.7 g thiourea was added to 5 g 1-benzyl-5-bromo-azepan-4-one in 50 ml ethanol. The reaction was refluxed 5 h and concentrated. The residue was diluted with water and extracted with ethyl acetate. The organic layer was concentrated to give 4 g of the desired product.

$R_f$: 0.4 (hexane/ethyl acetate=1/1)

$(M+H)^+$=262

6.01.37.07 6-Benzyl-2-chloro-5,6,7,8-tetrahydro-thiazolo[4,5-d]azepine

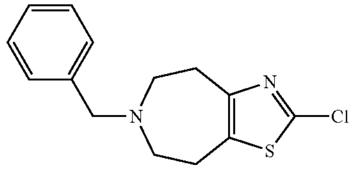 [SMILES: Clc1nc2c(s1)CCN(Cc1ccccc1)CC2]

6 mL hydrochloric acid was added at 0° C. to 6 g 6-benzyl-5,6,7,8-tetrahydro-thiazolo[4,5-d]azepine-2-ylamine in 80 mL acetonitrile. The reaction was stirred for 15 min. and 1.9 g sodium nitrite was added. After 30 min. 2.75 g copper(I) chloride was added and the mixture was stirred 2 h at RT. The reaction was evaporated, water was added and the mixture was extracted with ethyl acetate. The organic layer was evaporated. The residue was purified by chromatographie on silica gel (hexane/ethyl acetate:9/1) to give 4 g of the desired product.

$R_f$: 0.6 (hexane/ethyl acetate=1/1)

$(M+H)^+$=281

6.01.37.08 6-Benzyl-2-methoxy-5,6,7,8-tetrahydro-thiazolo[4,5-d]azepine

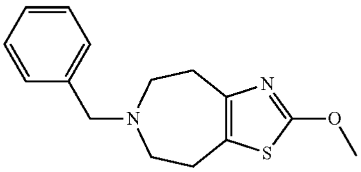 [SMILES: COc1nc2c(s1)CCN(Cc1ccccc1)CC2]

3.87 g sodium methoxide was added to 4 g 6-Benzyl-2-chloro-5,6,7,8-tetrahydro-thiazolo[4,5-d]azepine in 40 mL methanol. The reaction was heated to 80° C. in a sealed tube. After completion of the reaction the solvent was removed, water was added and extracted with ethyl acetate. The organic layer was evaporated and the residue was purified by chromatographie on silica gel (petrolether/ethyl acetate:8/2) to give 3 g of the desired product.

$R_f$: 0.4 (hexane/ethyl acetate=1/1)

$(M+H)^+=277$ 6.01.37.09 2-Methoxy-5,6,7,8-tetrahydro-thiazolo[4,5-d]azepine-6-carboxylic acid 1-chloro-ethyl ester

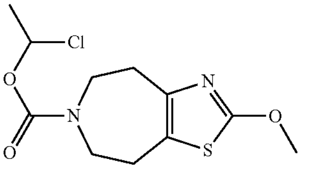 [SMILES: COc1nc2c(s1)CCN(C(=O)OC(C)Cl)CC2]

12.5 g 1-chloroethylchloroformic acid was added to 8 g 6-benzyl-2-methoxy-5,6,7,8-tetrahydro-thiazolo[4,5-d]azepine and 24 mL DIPEA in 80 mL ethyl acetate at 0° C. The reaction was stirred 3 h at RT and evaporated to give 7 g of the desired product.

$R_f$: 0.6 (hexane/ethyl acetate=1/1), $(M+H)^+=293$ 6.01.37.10 2-Methoxy-5,6,7,8-tetrahydro-thiazolo[4,5-d]azepine

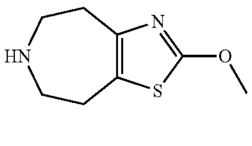

7 g 2-Methoxy-5,6,7,8-tetrahydro-thiazolo[4,5-d]azepine-6-carboxylic acid 1-chloro-ethyl ester in 70 mL methanol was heated 15 min. at 40° C. and concentrated. The residue was purified by chromatography (dichlormethane/methanol:6/4) to give 4 g of the desired product.

$R_f$: 0.2 (DCM/MeOH=1/1), $(M+H)^+=187$ 6.01.38. 5,6,7,8-Tetrahydro-4H-oxazolo[4,5-d]azepin-2-ylamine

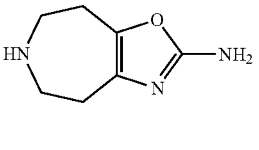 [SMILES: Nc1nc2c(o1)CCNCC2]

6.6 g urea was added to 6 g 5-bromo-azepan-4-one hydrobromide and heated 24 h at 70° C. 4 M aqueous sodium hydroxide was added and the mixture was extracted with chloroform and ethyl acetate. The combined organic layers were evaporated to give 800 mg of the desired product.

$R_t$: 0.39 min (method B), $(M+H)^+$: 154

6.01.39 11-Methyl-2,3,4,5-tetrahydro-1H-azepino[4,5-b]quinoline

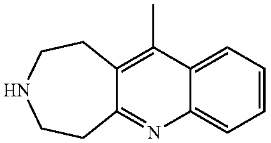 [SMILES: Cc1c2c(nc3ccccc13)CCNCC2]

110 g azepin-4-on hydrochloride and 99.5 g 2-aminoacetophenone was refluxed for 2 days in 1.5 L 2 M aqueous hydrochloride acid. The mixture was cooled to RT, 2 M aqueous sodium hydroxyde solution was added and the mixture was extracted with chloroform. The organic layer was dried and evaporated. The residue was purified by chromatographie on silica gel (100% methanol) to yield 64 g of the desired product. $R_f$: 0.1 (methanol), $(M+H)^+$: 213

6.01.40. 2-Methyl-5,6,7,8-tetrahydro-4H-oxazolo[4,5-d]azepine hydrochloride

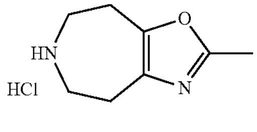

6.01.40.01 N-benzyl-N-(but-3-enyl)-but-3-en-1-amine

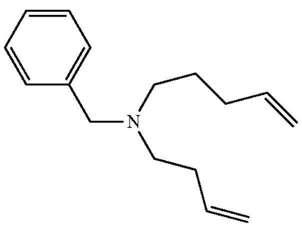 [SMILES: C=CCCCN(CCC=C)Cc1ccccc1]

12 g Benzylamine and 25 g 4-bromo-1-buten were added to a suspension of 46 g potassium carbonate in 150 mL DMF and the mixture was heated at 50° C. for 16 h. The reaction mixture was cooled to RT, diluted with ethyl acetate, washed with water and brine, dried, concentrated, and purified by chromatographie on silica gel (hexane/ethyl acetate 50:1) to yield 18.3 g of the desired product. $(M+H)^+$: 230

6.01.40.02 benzyl dibut-3-enylcarbamate

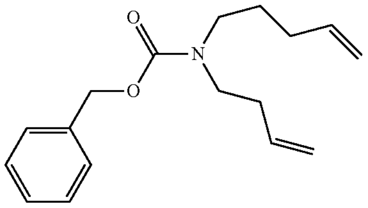 [SMILES: C=CCCCN(CCC=C)C(=O)OCc1ccccc1]

11.2 mL benzylchloroformate was added to 14 g N-benzyl-N-(but-3-enyl)-but-3-en-1-amine in 100 mL toluene at 0° C. After being heated at 70° C. for 3 h, the reaction mixture was cooled to RT, basified with saturated aqueous sodium hydrogencarbonate solution, extracted with ethyl acetate, washed with brine, dried, concentrated, and purified by chromatographie on silica gel (hexane/ethyl acetate 20:1) to yield 16.8 g of the desired product. $(M+H)^+$: 274

6.01.40.03 benzyl 2,3,6,7-tetrahydro-1H-azepine-1-carboxylate

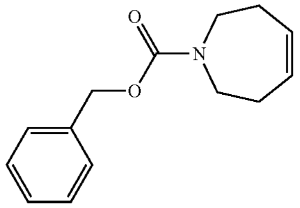 [SMILES: O=C(OCc1ccccc1)N1CCC=CCC1]

0.15 g Grubb's 2 catalyst was added to a solution of 8 g benzyl dibut-3-enylcarbamate in 680 mL toluene and heated at 50° C. for 5 h. The solvent was removed and the residue was purified by chromatographie on silica gel (ethyl acetate/hexane 1:5) to yield 6.6 g of the desired product.

$(M+H)^+$: 232

6.01.40.04 benzyl 8-oxa-4-azabicyclo[5.1.0]octane-4-carboxylate

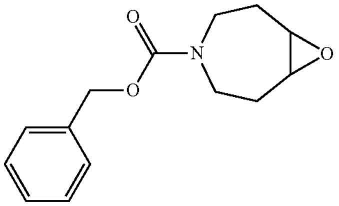 [SMILES: O=C(OCc1ccccc1)N1CCC2OC2CC1]

18 g m-chloroperbenzoic acid was added to 10 g benzyl 2,3,6,7-tetrahydro-1H-azepine-1-carboxylate in 250 ml dichloromethane at 0° C. in several portions. The mixture was allowed to warm to RT over 2 h. 1 L ethyl acetate was added and the solution was extracted with aqueous sodium bicarbonate, 1N aqueous sodium hydroxide and brine. The organic layer was evaporated and the residue was purified by chromatographie on silica gel (ethyl acetae/hexanes 1:5) to yield 10.4 g of the desired product.

6.01.40.05 4-Amino-5-hydroxy-azepane-1-carboxylic acid benzyl ester

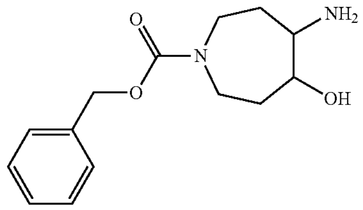 [SMILES: NC1CCN(C(=O)OCc2ccccc2)CCC1O]

3 g benzyl 8-oxa-4-azabicyclo[5.1.0]octane-4-carboxylate in 70 mL 30% aqueous ammonia was stirred at 65° C. in a sealed vessel overnight. The reaction was extracted with dichloromethane. The organic layer was washed with brine, dried over sodium sulfate filtered and concentrated to yield 3.1 g of the desired product. $(M+H)^+$: 265

6.01.40.06 4-Acetylamino-5-hydroxy-azepane-1-carboxylic acid benzyl ester

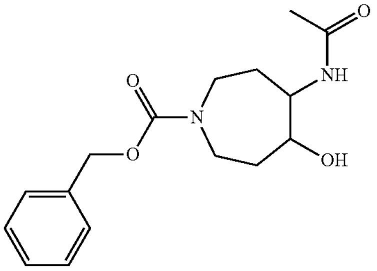 [SMILES: CC(=O)NC1CCN(C(=O)OCc2ccccc2)CCC1O]

3 mL acetic anhydride was added to 8.4 g benzyl 4-amino-5-hydroxy-azepane-1-carboxylic acid benzyl ester in 115 ml dichloromethane at 0° C. After 1 h at RT, saturated sodium bicarbonate was added. The phases were separated and the aqueous phase was extracted with dichloromethane. The combined organic phase was washed with brine, dried over sodium sulphate, filtered and concentrated. The residue was purified by chromatographie on silica gel (ethyl acetate/hexane 2:1) to yield 4.5 g of the desired product. $(M+H)^+$: 307

6.01.40.07 4-Acetylamino-5-oxo-azepane-1-carboxylic acid benzyl ester

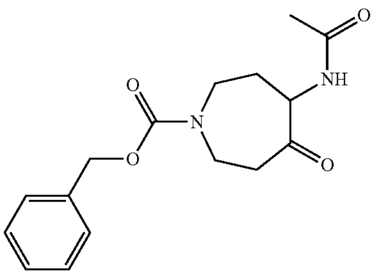 [SMILES: CC(=O)NC1CCN(C(=O)OCc2ccccc2)CCC1=O]

11 g Dess Martin Periodane was added to 6.2 g 4-acetylamino-5-hydroxy-azepane-1-carboxylic acid benzyl ester in 100 mL dichloromethane and stirred for 1 h at RT. The mixture was diluted with dichloromethane and washed with 2 mol/L sodium hydroxide solution. The organic layere was washed with brine, dried and concentrated. The residue was purified by chromatographie on silica gel (EtOAc) to yield 5.5 g of the desired product. $(M+H)^+$: 305

6.01.40.08 Benzyl 2-methyl-4,5,7,8-tetrahydrooxazolo[4,5-d]azepine-6-carboxylate

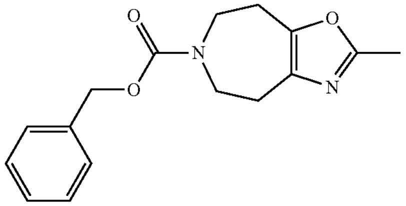 [SMILES: Cc1nc2c(o1)CCN(C(=O)OCc1ccccc1)CC2]

3 g 4-acetylamino-5-oxo-azepane-1-carboxylic acid benzyl ester in 100 mL tetrahydrofuran and 3.8 g (methoxycarbonylsulfamoyl)triethylammonium hydroxide were heated in a sealed tube at 75° C. for 1 h. The solvent was evaporated and the residue was purified by chromatographie on silica gel (ethyl acetate/hexane 1:2) to yield 23 g of the desired product. $(M+H)^+$: 287

6.01.40.09 2-Methyl-5,6,7,8-tetrahydro-4H-oxazolo[4,5-d]azepine hydrochloride

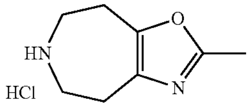

A solution of 25 g of benzyl 2-methyl-4,5,7,8-tetrahydrooxazolo[4,5-d]azepine-6-carboxylate in 500 ml 2-propanol was stirred under hydrogen atmosphere (1 atm) in the presence of 450 mg of 5% palladium/charcoal (50% water) at RT overnight. After filtration over celite the filtrate was concentrated. The residue was diluted in a mixture of dichloromethane and diethylether and 2 mol/L hydrochloric acid in diethylether was added. The precipitate was filtered and dried to yield 15.5 g of the desired product. $R_t$: 0.86 min (method F), $(M+H)^+$: 153

6.02. Synthesis of pyrazol-1yl-acids 6.02.01.01 1,3-Bis-(4-fluoro-phenyl)-1,3-propandione

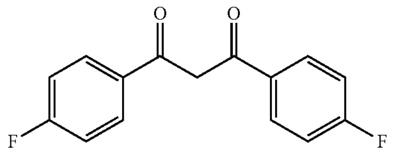 [SMILES: O=C(CC(=O)c1ccc(F)cc1)c1ccc(F)cc1]

9.27 g KOtBu was added to 109 mg 18-Krone-6 and 5 mL 4-fluoracetophenone in 150 mL THF. After 30 min at RT 10.7 g 4-fluoro-benzoic acid methyl ester was added and stirred for 3 h at RT. The reaction was decomposed with water and filtered, the filtrate was concentrated and the residue was purified by chromatography on silica gel (cyclohexane/EE: 98:2). The solvent was removed and 3.9 g of the desired compound was obtained. (M+H)+: 261.

1H-NMR, DMSO 8.30-8.23 (m, 3H, 3/CH), 8.10-8.01 (m, 1H, CH), 3.88-3.85 (s, 1H, CH2)

By using the same synthesis strategy as for 1,3-Bis-(4-fluoro-phenyl)-1,3-propandione the following compounds were obtained:

| Examples | Product | MS m/z $[M+H]^+$ | HPLC Method | Rt min |
|---|---|---|---|---|
| 6.02.01.02 | 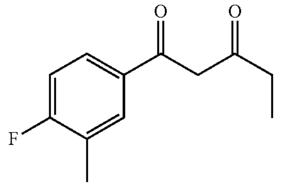 | 209 | method C | 1.05 |
| 6.02.01.03 | 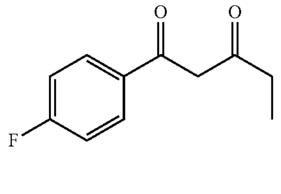 | 195 | method C | 1.00 |

-continued
| Examples | Product | MS m/z [M + H]+ | HPLC Method | Rt min |
|---|---|---|---|---|
| 6.02.01.04 | 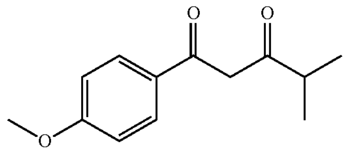 [SMILES: COc1ccc(C(=O)CC(=O)C(C)C)cc1] | 221 | method J | 1.48 |
| 6.02.01.05 | 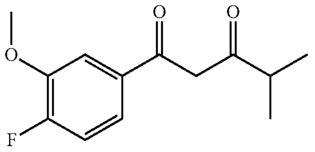 [SMILES: COc1cc(C(=O)CC(=O)C(C)C)ccc1F] | 239 | $^1$H-NMR: DMSO 6.60-6.56 (s, 1H, CH), 2.71-2.63 (m, 1H, CH), 1.18-1.15 (d, 6H, 2/CH3) | |
| 6.02.01.06 | 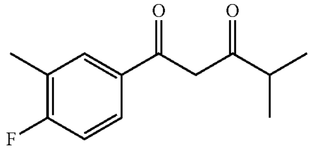 [SMILES: Cc1cc(C(=O)CC(=O)C(C)C)ccc1F] | 223 | method J | 1.59 |
| 6.02.01.07 | 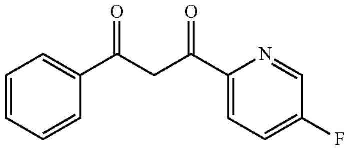 [SMILES: O=C(CC(=O)c1ccc(F)cn1)c1ccccc1] | 243 | method D | 1.08 |
| 6.02.01.08 | 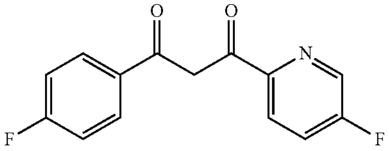 [SMILES: O=C(CC(=O)c1ccc(F)cn1)c1ccc(F)cc1] | 262 | method D | 1.09 |
| 6.02.01.09 | 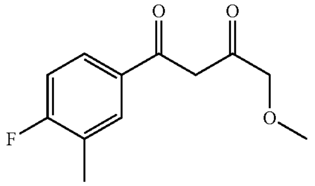 [SMILES: COCC(=O)CC(=O)c1ccc(F)c(C)c1] | 225 | method T | 1.20 |
| 6.02.01.10 | 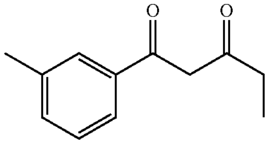 | 191 | method U | 0.81 |
| 6.02.01.11 | 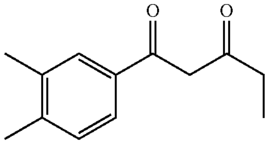 | 205 | method U | 0.86 |
| 6.02.01.12 | 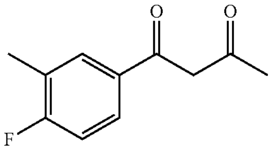 | 195 | method S | 1.20 |

-continued
| Examples | Product | MS m/z $[M + H]^+$ | HPLC Method | Rt min |
|---|---|---|---|---|
| 6.02.01.13 | 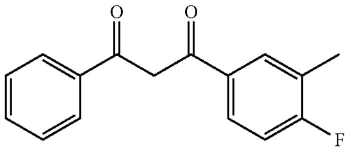 [SMILES: Cc1cc(C(=O)CC(=O)c2ccccc2)ccc1F] | 257 | method I | 1.16 |
| 6.02.01.14 | 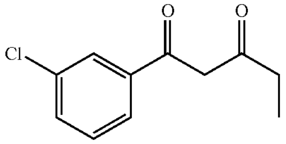 | 211/13 | method U | 0.89 |
| 6.02.01.15 | 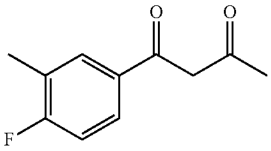 | 195 | method S | 1.20 |
| 6.02.01.16 | 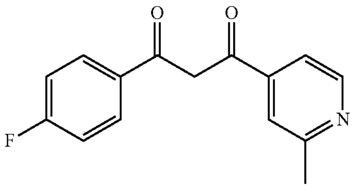 [SMILES: Cc1cc(C(=O)CC(=O)c2ccc(F)cc2)ccn1] | 240 | method S | 1.02 |
| 6.02.01.17 | 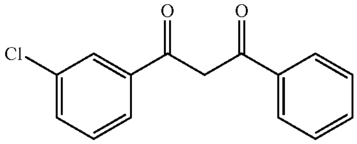 [SMILES: O=C(CC(=O)c1cccc(Cl)c1)c1ccccc1] | 259 | method W | 1.69 |
| 6.02.01.18 | 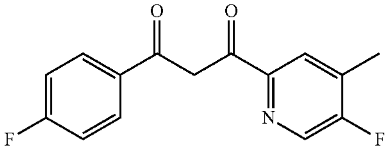 [SMILES: Cc1cc(C(=O)CC(=O)c2ccc(F)cc2)ncc1F] | 258 | method W | 1.63 |
| 6.02.01.19 | 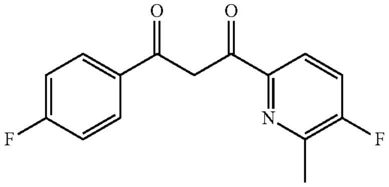 [SMILES: Cc1nc(C(=O)CC(=O)c2ccc(F)cc2)ccc1F] | 258 | Method W | 1.64 |
| 6.02.01.20 | 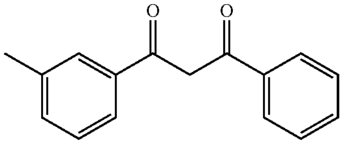 [SMILES: Cc1cccc(C(=O)CC(=O)c2ccccc2)c1] | 239 | method T | 1.56 |
| 6.02.01.21 | 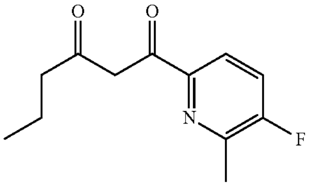 [SMILES: CCCC(=O)CC(=O)c1ccc(F)c(C)n1] | 224 | method AB | 0.94 |

-continued

| Examples | Product | MS m/z $[M+H]^+$ | HPLC Method | Rt min |
|---|---|---|---|---|
| 6.02.01.22 | 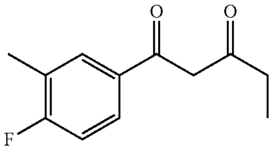 | 209 | method A | 0.96 |
| 6.02.01.23 | 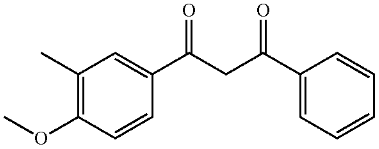 [SMILES: COc1ccc(C(=O)CC(=O)c2ccccc2)cc1C] | 269 | method R | 1.66 |
| 6.02.01.24 | 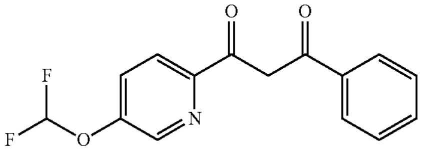 [SMILES: O=C(CC(=O)c1ccc(OC(F)F)cn1)c1ccccc1] | 292 | method AB | 0.97 |
| 6.02.01.25 | 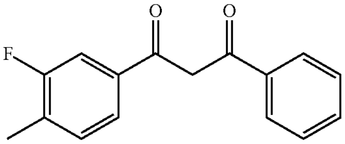 [SMILES: Cc1ccc(C(=O)CC(=O)c2ccccc2)cc1F] | 257 | method A | 1.05 |
| 6.02.01.26 | 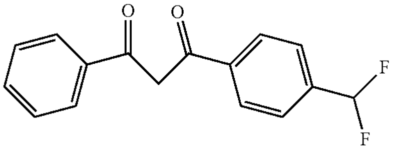 [SMILES: O=C(CC(=O)c1ccc(C(F)F)cc1)c1ccccc1] | 275 | method A | 1.00 |

6.02.01.21 1-(4-fluoro-3-methyl-phenyl)-3-phenyl-1,3-propanedione

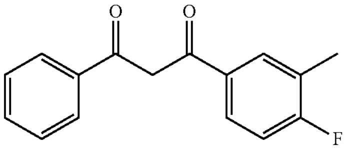 [SMILES: Cc1cc(C(=O)CC(=O)c2ccccc2)ccc1F]

6.02.01.09 1-(4-fluoro-3-methyl-phenyl)-3-phenyl-1,3-propanedione 17.3 g KOtBu was dissolved in 500 mL THF and 9 mL acetophenone was added. After 15 min at RT 25.9 g 4-fluoro-3-methyl-benzoic acid methyl ester was added and stirred for 3 h at RT. The solvent was removed and the residue was purified by chromatography on silica gel (cyclohexane/EE: 98:2). After combination of the desired fractions and removal of the solvent 19.3 g of the desired compound was obtained. $(M+H)^+$: 257

By using the same synthesis strategy as for 1-(4-fluoro-3-methyl-phenyl)-3-phenyl-1,3-propanedione the following compounds were obtained:

| Examples | Product | MS m/z $[M+H]^+$ | HPLC Method | Rt min |
|---|---|---|---|---|
| 6.02.01.22 | 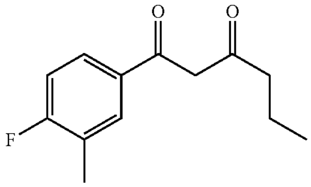 [SMILES: CCCC(=O)CC(=O)c1ccc(F)c(C)c1] | 223 | method I | 1.03 |

-continued
| Examples | Product | MS m/z $[M + H]^+$ | HPLC Method | Rt min |
|---|---|---|---|---|
| 6.02.01.23 | 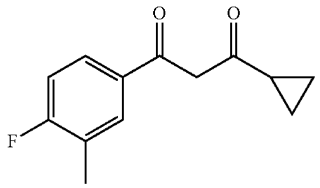 [SMILES: Cc1cc(C(=O)CC(=O)C2CC2)ccc1F] | 221 | method J | 1.53 |
| 6.02.01.24 | 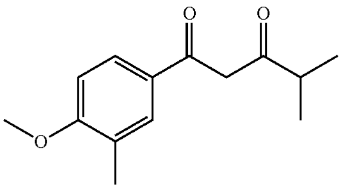 [SMILES: COc1ccc(C(=O)CC(=O)C(C)C)cc1C] | 235 | $^1$H-NMR: 6.48 (s, 1H, CH), 3.88 (s, 3H, CH3), 2.20 (s, 3H, CH3) | |
| 6.02.01.25 | 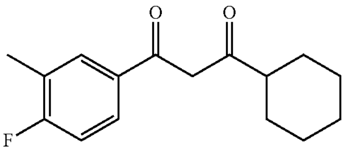 [SMILES: Cc1cc(C(=O)CC(=O)C2CCCCC2)ccc1F] | 263 | method J | 1.73 |
| 6.02.01.26 | 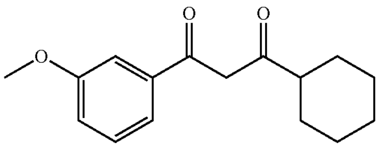 [SMILES: COc1cccc(C(=O)CC(=O)C2CCCCC2)c1] | 261 | method J | 1.67 |
| 6.02.01.27 | 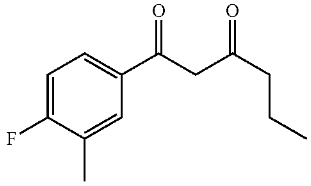 [SMILES: CCCC(=O)CC(=O)c1ccc(F)c(C)c1] | 223 | method I | 1.03 |
| 6.02.01.28 | 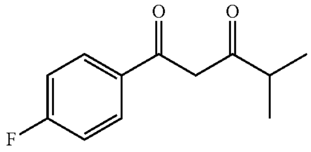 | 209 | method I | 1.45 |
| 6.02.01.29 | 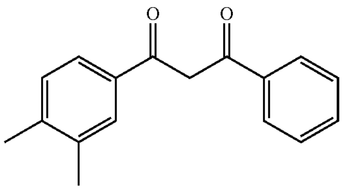 [SMILES: Cc1ccc(C(=O)CC(=O)c2ccccc2)cc1C] | 253 | method I | 1.06 |
| 6.02.01.30 | 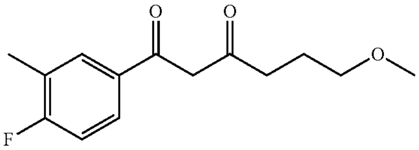 | 253 | method W | 1.50 |

-continued
| Examples | Product | MS m/z [M + H]+ | HPLC Method | Rt min |
|---|---|---|---|---|
| 6.02.01.31 | 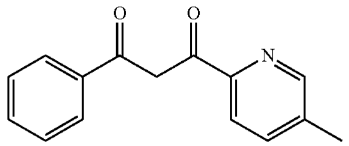 [SMILES: Cc1ccc(C(=O)CC(=O)c2ccccc2)nc1] | 240 | method I | 1.02 |
| 6.02.01.32 | 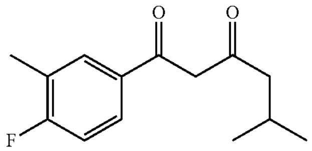 [SMILES: Cc1cc(C(=O)CC(=O)CC(C)C)ccc1F] | 237 | method W | 1.67 |
| 6.02.01.33 | 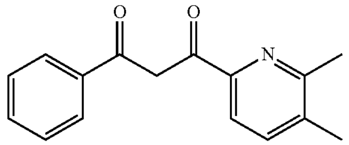 [SMILES: Cc1ccc(C(=O)CC(=O)c2ccccc2)nc1C] | 254 | method I | 0.98 |
| 6.02.01.34 | 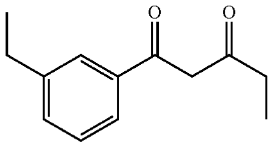 | 205 | method U | 0.89 |
| 6.02.01.35 | 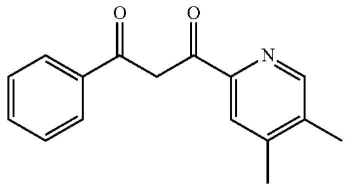 [SMILES: Cc1cnc(C(=O)CC(=O)c2ccccc2)cc1C] | 254 | method I | 0.98 |
| 6.02.01.36 | 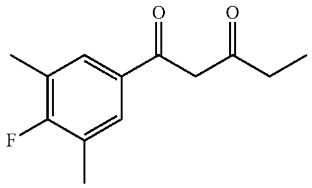 [SMILES: CCC(=O)CC(=O)c1cc(C)c(F)c(C)c1] | 223 | method W | 1.63 |
| 6.02.01.37 | 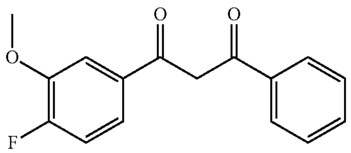 [SMILES: COc1cc(C(=O)CC(=O)c2ccccc2)ccc1F] | 273 | method I | 1.00 |
| 6.02.01.38 | 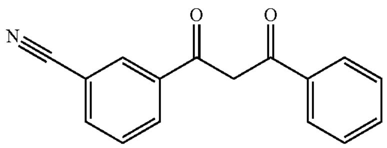 [SMILES: N#Cc1cccc(C(=O)CC(=O)c2ccccc2)c1] | 250 | method Y | 1.58 |
| 6.02.01.39 | 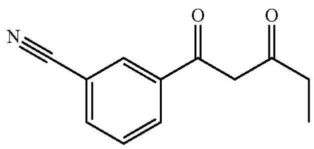 | 202 | method Y | 1.38 |

6.02.02.01 3,5-Bis-(4-fluoro-phenyl)-1H-pyrazole

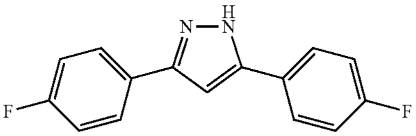 [SMILES: Fc1ccc(-c2cc(-c3ccc(F)cc3)[nH]n2)cc1]

3.9 g 1,3-Bis-(4-fluoro-phenyl)-1,3-propandione was dissolved in 45 mL of a solution of 1 N hydrazine in THF and stirred for 2 h at 75° C. The solvent was removed to give 3.6 g of the desired compound. $R_t$: 1.03 min (method D), $(M+H)^+$: 257

By using the same synthesis strategy as for 3,5-Bis-(4-fluoro-phenyl)-1H-pyrazole the following compounds were obtained:

| Examples | Product | MS m/z $[M + H]^+$ | HPLC Method | Rt min |
|---|---|---|---|---|
| 6.02.02.02 | 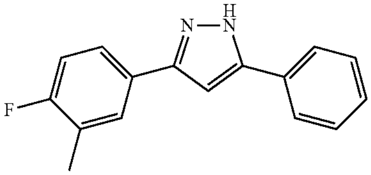 [SMILES: Cc1cc(-c2cc(-c3ccccc3)[nH]n2)ccc1F] | 253 | method D | 1.07 |
| 6.02.02.03 | 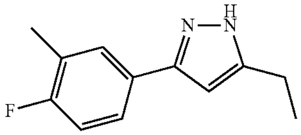 | 206 | method C | 0.93 |
| 6.02.02.04 | 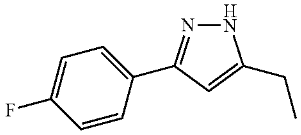 | 191 | method C | 0.87 |
| 6.02.02.05 | 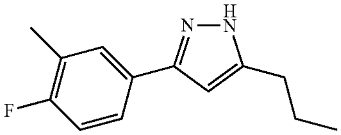 [SMILES: CCCc1cc(-c2ccc(F)c(C)c2)n[nH]1] | 219 | method I | 0.93 |
| 6.02.02.06 | 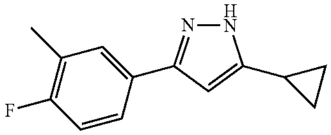 [SMILES: Cc1cc(-c2cc(C3CC3)[nH]n2)ccc1F] | 217 | method J | 1.38 |
| 6.02.02.07 | 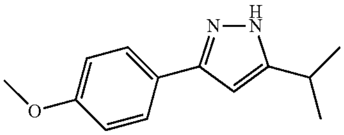 [SMILES: COc1ccc(-c2cc(C(C)C)[nH]n2)cc1] | 217 | method J | 1.27 |
| 6.02.02.08 | 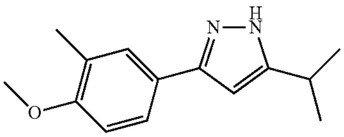 [SMILES: COc1ccc(-c2cc(C(C)C)[nH]n2)cc1C] | 231 | method J | 1.54 |
| 6.02.02.09 | 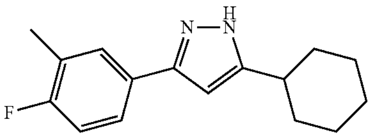 [SMILES: Cc1cc(-c2cc(C3CCCCC3)[nH]n2)ccc1F] | 259 | method J | 1.39 |

-continued
| Examples | Product | MS m/z $[M + H]^+$ | HPLC Method | Rt min |
|---|---|---|---|---|
| 6.02.02.10 | 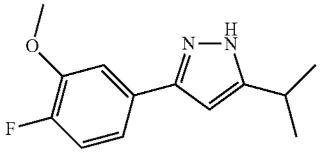 [SMILES: COc1cc(-c2cc(C(C)C)[nH]n2)ccc1F] | 335 | method J | 1.35 |
| 6.02.02.11 | 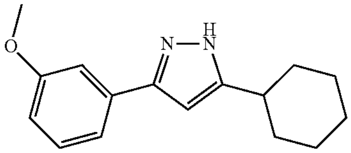 [SMILES: COc1cccc(-c2cc(C3CCCCC3)[nH]n2)c1] | 257 | method J | 1.51 |
| 6.02.02.12 | 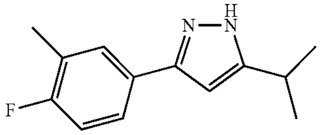 [SMILES: Cc1cc(-c2cc(C(C)C)[nH]n2)ccc1F] | 219 | method J | 1.44 |
| 6.02.02.13 | 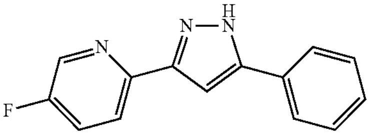 [SMILES: Fc1ccc(-c2cc(-c3ccccc3)[nH]n2)nc1] | 240 | method D | 0.97 |
| 6.02.02.14 | 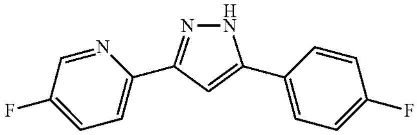 [SMILES: Fc1ccc(-c2cc(-c3ccc(F)cn3)n[nH]2)cc1] | 258 | method D | 0.95 |
| 6.02.02.15 | 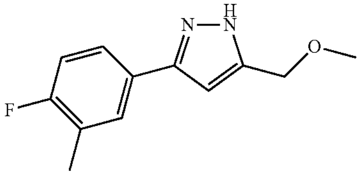 [SMILES: COCc1cc(-c2ccc(F)c(C)c2)n[nH]1] | 221 | method S | 1.10 |
| 6.02.02.16 | 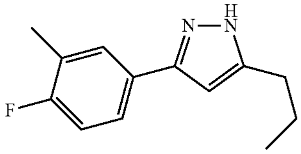 [SMILES: CCCc1cc(-c2ccc(F)c(C)c2)n[nH]1] | 219 | method I | 0.93 |
| 6.02.02.17 | 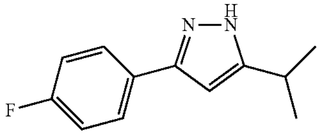 | 205 | method T | 1.26 |
| 6.02.02.18 | 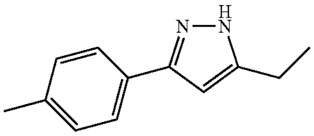 | 187 | method T | 1.20 |

-continued
| Examples | Product | MS m/z $[M + H]^+$ | HPLC Method | Rt min |
|---|---|---|---|---|
| 6.02.02.19 | 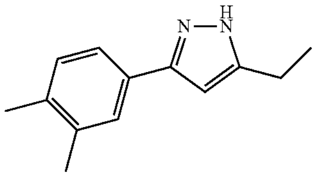 | 201 | method U | 0.71 |
| 6.02.02.20 | 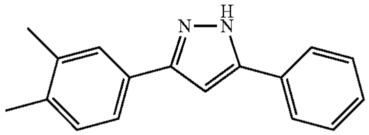 [SMILES: Cc1ccc(-c2cc(-c3ccccc3)[nH]n2)cc1C] | 249 | method I | 1.06 |
| 6.02.02.21 | 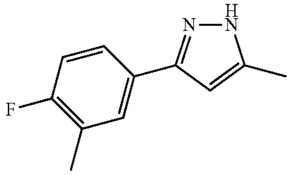 | 191 | method S | 1.10 |
| 6.02.02.22 | 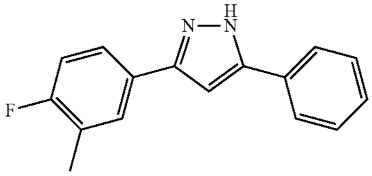 [SMILES: Cc1cc(-c2cc(-c3ccccc3)[nH]n2)ccc1F] | 253 | method I | 0.99 |
| 6.02.02.23 | 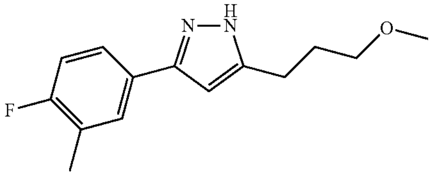 [SMILES: COCCCc1cc(-c2ccc(F)c(C)c2)n[nH]1] | 249 | method U | 0.76 |
| 6.02.02.24 | 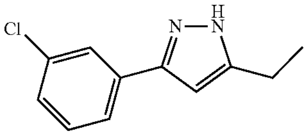 | 207 | method U | 0.81 |
| 6.02.02.25 | 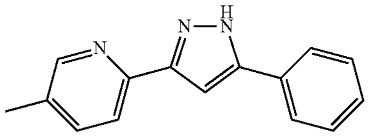 [SMILES: Cc1ccc(-c2cc(-c3ccccc3)[nH]n2)nc1] | 236 | method I | 0.68 |
| 6.02.02.26 | 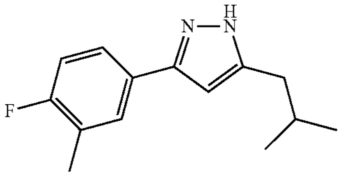 [SMILES: Cc1cc(-c2cc(CC(C)C)[nH]n2)ccc1F] | 233 | method W | 1.52 |
| 6.02.02.27 | 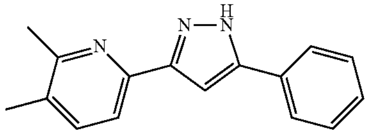 [SMILES: Cc1ccc(-c2cc(-c3ccccc3)[nH]n2)nc1C] | 250 | method I | 0.64 |

-continued
| Examples | Product | MS m/z [M + H]+ | HPLC Method | Rt min |
|---|---|---|---|---|
| 6.02.02.28 | 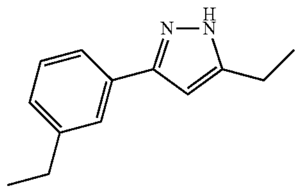 | 201 | method U | 0.78 |
| 6.02.02.29 | 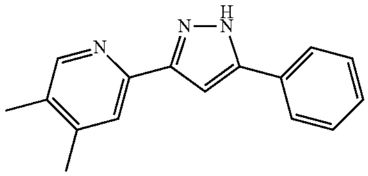 [SMILES: Cc1cnc(-c2cc(-c3ccccc3)[nH]n2)cc1C] | 308 | method I | 0.69 |
| 6.02.02.30 | 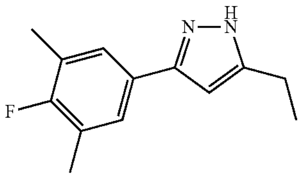 [SMILES: CCc1cc(-c2cc(C)c(F)c(C)c2)n[nH]1] | 219 | method W | 1.45 |
| 6.02.02.31 | 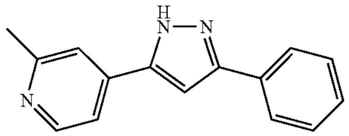 [SMILES: Cc1cc(-c2cc(-c3ccccc3)n[nH]2)ccn1] | 236 | method S | 0.84 |
| 6.02.02..32 | 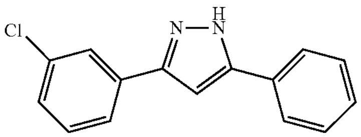 [SMILES: Clc1cccc(-c2cc(-c3ccccc3)[nH]n2)c1] | 255 | method W | 1.50 |
| 6.02.02.33 | 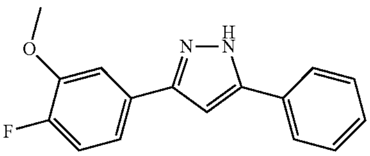 [SMILES: COc1cc(-c2cc(-c3ccccc3)[nH]n2)ccc1F] | 269 | method Z | 0.76 |
| 6.02.02.34 | 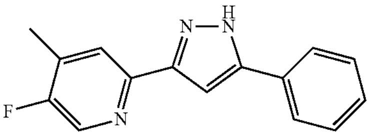 [SMILES: Cc1cc(-c2cc(-c3ccccc3)[nH]n2)ncc1F] | 254 | method W | 1.35 |
| 6.02.02.35 | 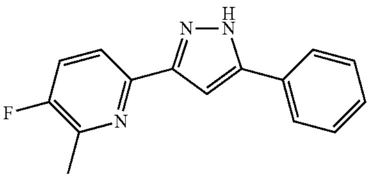 [SMILES: Cc1nc(-c2cc(-c3ccccc3)[nH]n2)ccc1F] | 254 | method W | 1.39 |

-continued
| Examples | Product | MS m/z [M + H]+ | HPLC Method | Rt min |
|---|---|---|---|---|
| 6.02.02.36 | 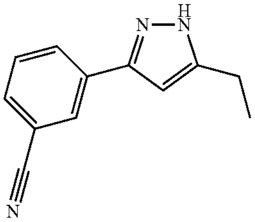 | 198 | method Y | 1.24 |
| 6.02.02.37 | 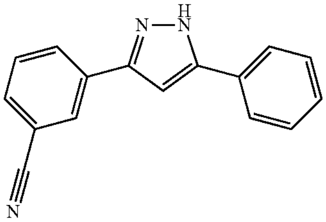 [SMILES: N#Cc1cccc(-c2cc(-c3ccccc3)[nH]n2)c1] | 246 | method Y | 1.41 |
| 6.02.02.38 | 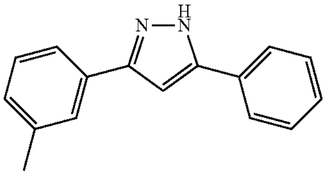 [SMILES: Cc1cccc(-c2cc(-c3ccccc3)[nH]n2)c1] | 235 | method U | 0.85 |
| 6.02.02.39 | 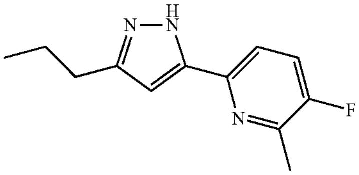 [SMILES: CCCc1cc(-c2ccc(F)c(C)n2)[nH]n1] | 220 | method AB | 0.78 |
| 6.02.02.40 | 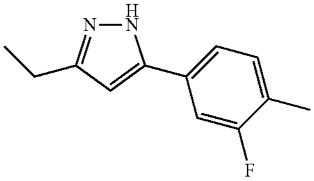 | 205 | method T | 0.86 |
| 6.02.02.41 | 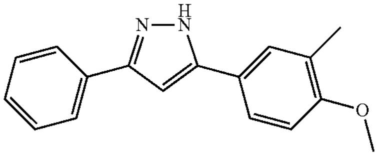 [SMILES: COc1ccc(-c2cc(-c3ccccc3)n[nH]2)cc1C] | 265 | method Y | 1.51 |
| 6.02.02.42 | 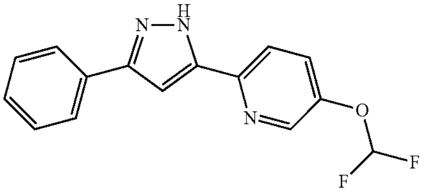 [SMILES: FC(F)Oc1ccc(-c2cc(-c3ccccc3)n[nH]2)nc1] | 288 | method AB | 0.85 |

-continued

| Examples | Product | MS m/z [M + H]+ | HPLC Method | Rt min |
|---|---|---|---|---|
| 6.02.02.43 | 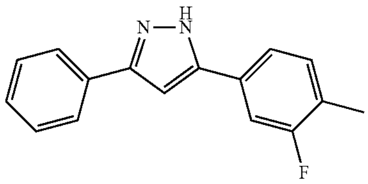 [SMILES: Cc1ccc(-c2cc(-c3ccccc3)n[nH]2)cc1F] | 253 | method Y | 0.97 |
| 6.02.02.44 | 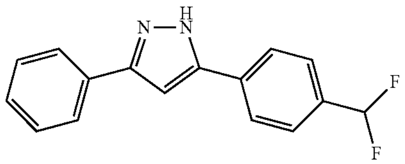 [SMILES: FC(F)c1ccc(-c2cc(-c3ccccc3)n[nH]2)cc1] | 271 | method Y | 0.95 |

6.02.02.39 5-phenyl-1H-pyrazole-3-carboxylic acid methyl ester

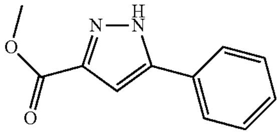

983 mg hydrazine acetate was added to 2 g 2,4-Dioxo-4-phenyl-butyric acid methyl ester in 10 mL concentrated acetic acid. The mixture was stirred over night at RT. Then water was added. The precipitate was filtered, stirred with diisopropylether and again filtered to give 1.3 g desired product. $R_t$: 1.39 min (method O), $(M+H)^+$: 203

6.02.03.01 3-(4-fluoro-3-methyl-phenyl)-5-phenyl-pyrazol-1-yl-acetic acid methyl ester

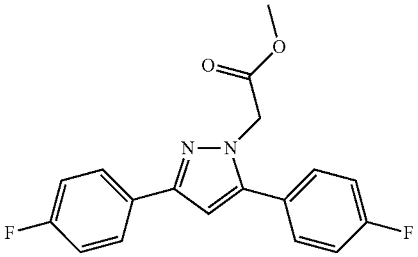 [SMILES: COC(=O)Cn1nc(-c2ccc(F)cc2)cc1-c1ccc(F)cc1]

3.6 g 3,5-Bis-(4-fluoro-phenyl)-1H-pyrazole, 8.8 g $K_2CO_3$ and 1.34 mL 2-bromoacetic acid methyl ester were dissolved in 100 mL acetone and stirred over night under reflux. $K_2CO_3$ was filtered and the solvent was removed. The residue was purified by HPLC (method 1) to yield 2.6 g of the desired product.

By using the same synthesis strategy as for 3-(4-fluoro-3-methyl-phenyl)-5-phenyl-pyrazol-1-yl-acetic acid methyl ester the following compounds were obtained:

| Examples | Product | MS m/z [M + H]+ | HPLC Method | Rt min |
|---|---|---|---|---|
| 6.02.03.02 | 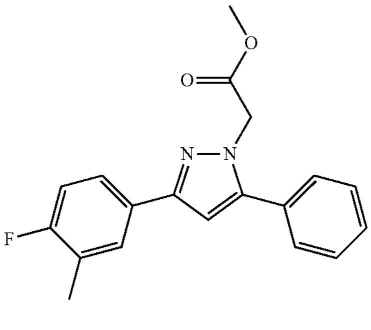 [SMILES: COC(=O)Cn1nc(-c2ccc(F)c(C)c2)cc1-c1ccccc1] | 325 | method I | 0.97 |

-continued
| Examples | Product | MS m/z [M + H]$^+$ | HPLC Method | Rt min |
|---|---|---|---|---|
| 6.02.03.03 | 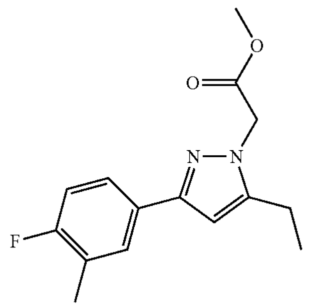 [SMILES: CCc1cc(-c2ccc(F)c(C)c2)nn1CC(=O)OC] | 277 | method C | 0.98 |
| 6.02.03.04 | 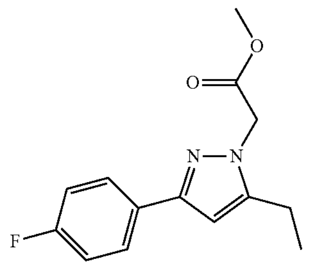 [SMILES: CCc1cc(-c2ccc(F)cc2)nn1CC(=O)OC] | 263 | method C | 0.92 |
| 6.02.03.05 | 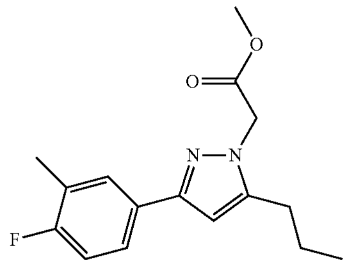 [SMILES: CCCc1cc(-c2ccc(F)c(C)c2)nn1CC(=O)OC] | 291 | method I | 0.97 |
| 6.02.03.06 | 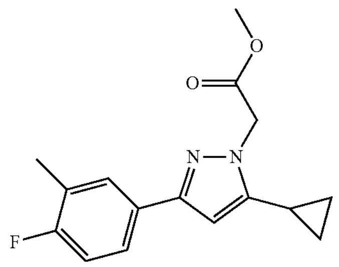 [SMILES: COC(=O)Cn1nc(-c2ccc(F)c(C)c2)cc1C1CC1] | 289 | method J | 1.41 |
| 6.02.03.07 | 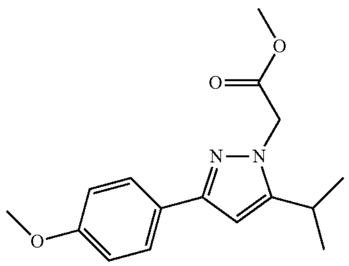 [SMILES: COC(=O)Cn1nc(-c2ccc(OC)cc2)cc1C(C)C] | 289 | method J | 1.36 |

-continued
| Examples | Product | MS m/z [M + H]+ | HPLC Method | Rt min |
|---|---|---|---|---|
| 6.02.03.08 | 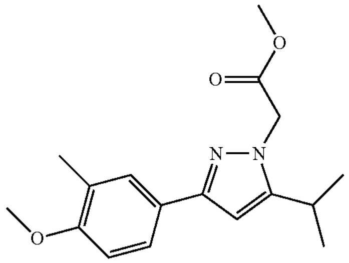 [SMILES: COC(=O)Cn1nc(-c2ccc(OC)c(C)c2)cc1C(C)C] | 289 | method J | 1.54 |
| 6.02.03.09 | 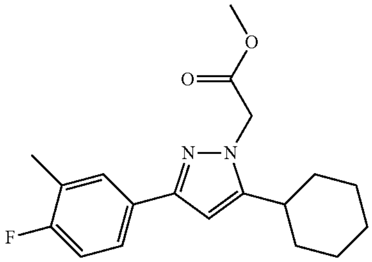 [SMILES: COC(=O)Cn1nc(-c2ccc(F)c(C)c2)cc1C1CCCCC1] | 331 | method J | 1.62 |
| 6.02.03.10 | 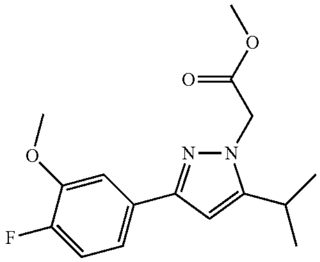 [SMILES: COC(=O)Cn1nc(-c2ccc(F)c(OC)c2)cc1C(C)C] | 307 | method L | 1.39 |
| 6.02.03.11 | 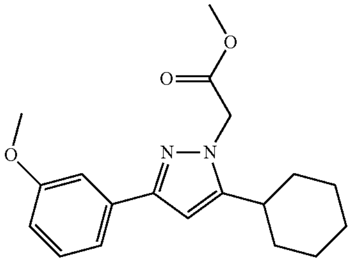 [SMILES: COC(=O)Cn1nc(-c2cccc(OC)c2)cc1C1CCCCC1] | 329 | | |
| 6.02.03.12 | 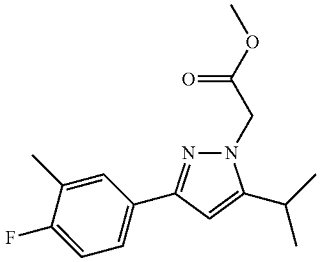 [SMILES: COC(=O)Cn1nc(-c2ccc(F)c(C)c2)cc1C(C)C] | 291 | method J | 1.47 |

-continued
| Examples | Product | MS m/z [M + H]+ | HPLC Method | Rt min |
|---|---|---|---|---|
| 6.02.03.13 | 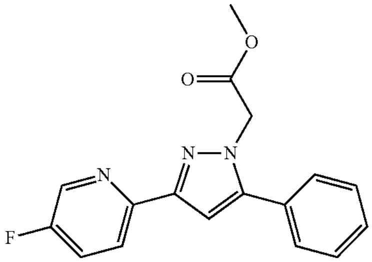 [SMILES: COC(=O)Cn1nc(-c2ccc(F)cn2)cc1-c1ccccc1] | 312 | method D | 0.99 |
| 6.02.03.14 | 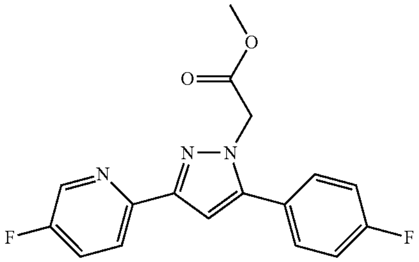 [SMILES: COC(=O)Cn1nc(-c2ccc(F)cn2)cc1-c1ccc(F)cc1] | 330 | method D | 1.01 |
| 6.02.03.15 | 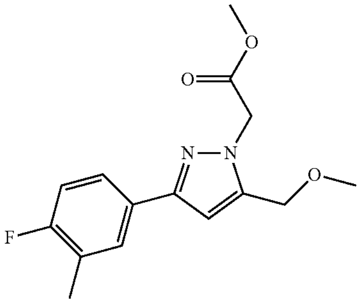 [SMILES: COCc1cc(-c2ccc(F)c(C)c2)nn1CC(=O)OC] | 293 | method S | 1.20 |
| 6.02.03.16 | 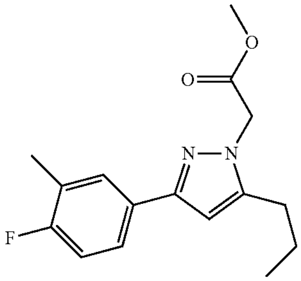 [SMILES: CCCc1cc(-c2ccc(F)c(C)c2)nn1CC(=O)OC] | 291 | method I | 0.97 |
| 6.02.03.17 | 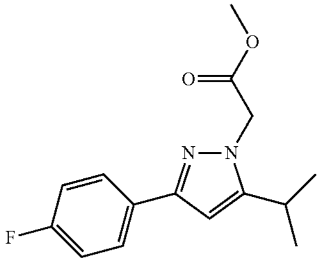 [SMILES: COC(=O)Cn1nc(-c2ccc(F)cc2)cc1C(C)C] | 291 | method T | 1.33 |

-continued
| Examples | Product | MS m/z [M + H]+ | HPLC Method | Rt min |
|---|---|---|---|---|
| 6.02.03.18 | 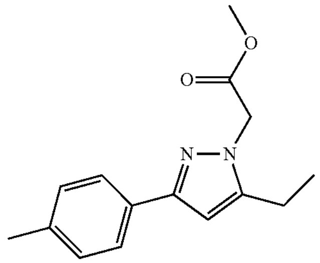 [SMILES: CCc1cc(-c2ccc(C)cc2)nn1CC(=O)OC] | 259 | method U | 0.81 |
| 6.02.03.19 | 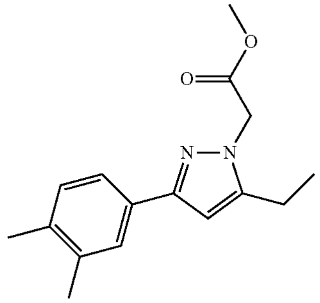 [SMILES: CCc1cc(-c2ccc(C)c(C)c2)nn1CC(=O)OC] | 273 | method T | 1.42 |
| 6.02.03.20 | 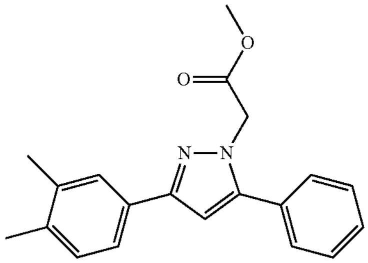 [SMILES: COC(=O)Cn1nc(-c2ccc(C)c(C)c2)cc1-c1ccccc1] | 321 | method I | 1.07 |
| 6.02.03.21 | 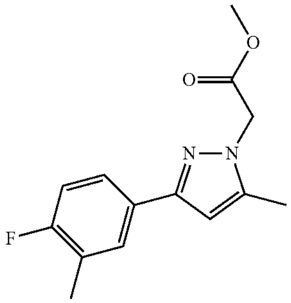 [SMILES: COC(=O)Cn1nc(-c2ccc(F)c(C)c2)cc1C] | 263 | method V | 1.20 |
| 6.02.03.22 | 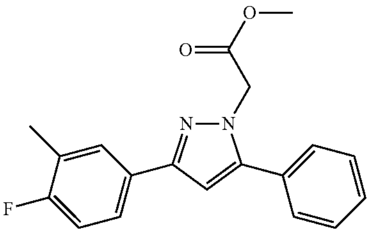 [SMILES: COC(=O)Cn1nc(-c2ccc(F)c(C)c2)cc1-c1ccccc1] | 325 | method I | 0.97 |

-continued
| Examples | Product | MS m/z [M + H]+ | HPLC Method | Rt min |
|---|---|---|---|---|
| 6.02.03.23 | 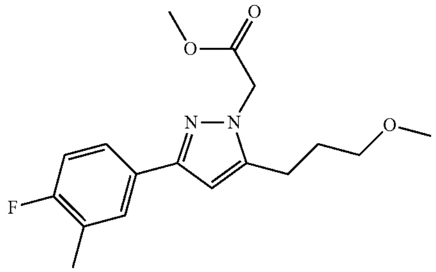 [SMILES: COCCCc1cc(-c2ccc(F)c(C)c2)nn1CC(=O)OC] | 321 | method U | 0.80 |
| 6.02.03.24 | 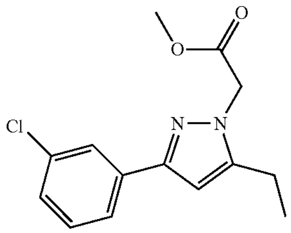 [SMILES: CCc1cc(-c2cccc(Cl)c2)nn1CC(=O)OC] | 279 | method U | 1.44 |
| 6.02.03.25 | 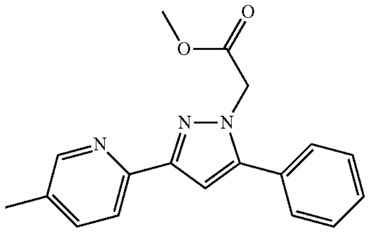 [SMILES: COC(=O)Cn1nc(-c2ccc(C)cn2)cc1-c1ccccc1] | 308 | method I | 0.66 |
| 6.02.03.26 | 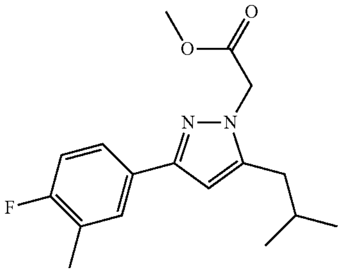 [SMILES: COC(=O)Cn1nc(-c2ccc(F)c(C)c2)cc1CC(C)C] | 305 | method W | 1.56 |
| 6.02.03.27 | 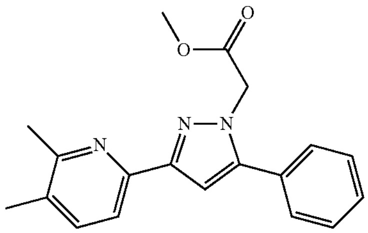 [SMILES: COC(=O)Cn1nc(-c2ccc(C)c(C)n2)cc1-c1ccccc1] | 322 | method I | 0.64 |

-continued
| Examples | Product | MS m/z [M + H]+ | HPLC Method | Rt min |
|---|---|---|---|---|
| 6.02.03.28 | 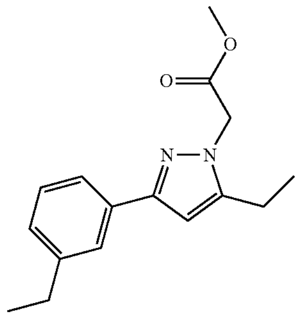 [SMILES: CCc1cccc(-c2cc(CC)n(CC(=O)OC)n2)c1] | 273 | method W | 1.50 |
| 6.02.03.29 | 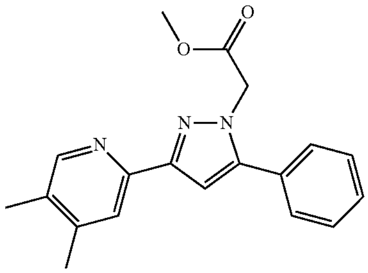 [SMILES: COC(=O)Cn1nc(-c2cc(C)c(C)cn2)cc1-c1ccccc1] | 322 | method I | 0.71 |
| 6.02.03.30 | 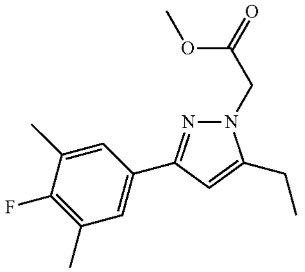 [SMILES: CCc1cc(-c2cc(C)c(F)c(C)c2)nn1CC(=O)OC] | 291 | method W | 1.53 |
| 6.02.03.31 | 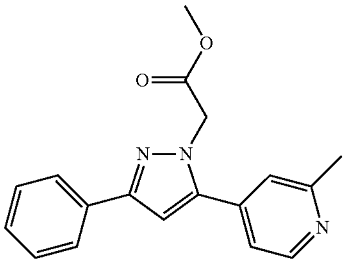 [SMILES: COC(=O)Cn1nc(-c2ccccc2)cc1-c1ccnc(C)c1] | 308 | method V | 0.85 |
| 6.02.03.32 | 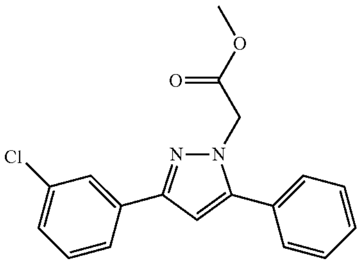 [SMILES: COC(=O)Cn1nc(-c2cccc(Cl)c2)cc1-c1ccccc1] | 327 | method W | 1.55 |

-continued
| Examples | Product | MS m/z [M + H]$^+$ | HPLC Method | Rt min |
|---|---|---|---|---|
| 6.02.03.33 | 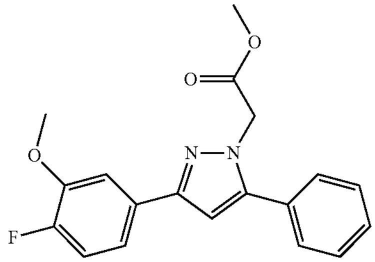 [SMILES: COC(=O)Cn1nc(-c2ccc(F)c(OC)c2)cc1-c1ccccc1] | 341 | method AA | 0.79 |
| 6.02.03.34 | 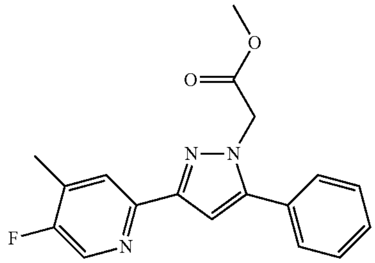 [SMILES: COC(=O)Cn1nc(-c2cc(C)c(F)cn2)cc1-c1ccccc1] | 326 | method W | 1.34 |
| 6.02.03.35 | 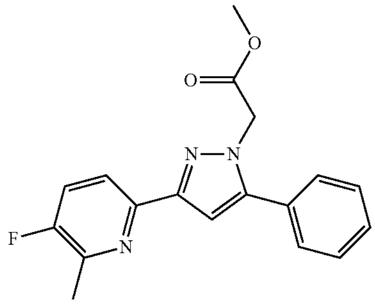 [SMILES: COC(=O)Cn1nc(-c2ccc(F)c(C)n2)cc1-c1ccccc1] | 326 | method W | 1.38 |
| 6.02.03.36 | 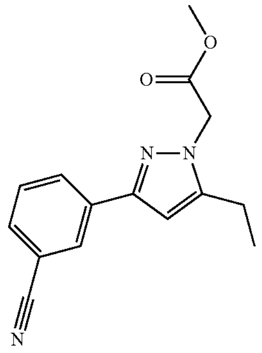 [SMILES: CCc1cc(-c2cccc(C#N)c2)nn1CC(=O)OC] | 270 | method AC | 1.26 |
| 6.02.03.37 | 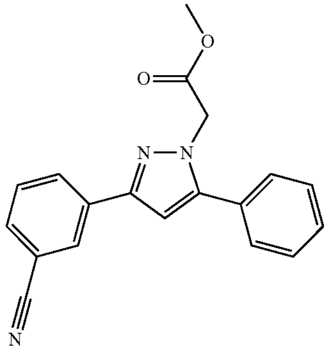 [SMILES: COC(=O)Cn1nc(-c2cccc(C#N)c2)cc1-c1ccccc1] | 318 | method AB | 1.39 |

-continued
| Examples | Product | MS m/z [M + H]+ | HPLC Method | Rt min |
|---|---|---|---|---|
| 6.02.03.38 | 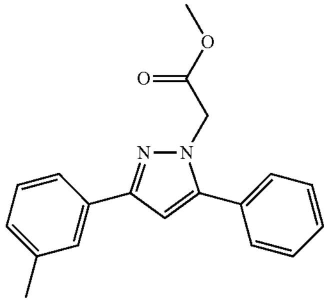 [SMILES: COC(=O)Cn1nc(-c2cccc(C)c2)cc1-c1ccccc1] | 307 | method X | 1.53 |
| 6.02.03.39 | 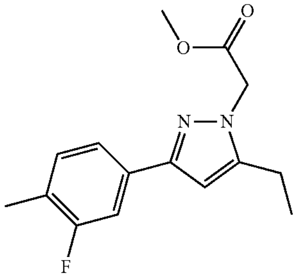 [SMILES: CCc1cc(-c2ccc(C)c(F)c2)nn1CC(=O)OC] | 277 | method AD | 0.90 |
| 6.02.03.40 | 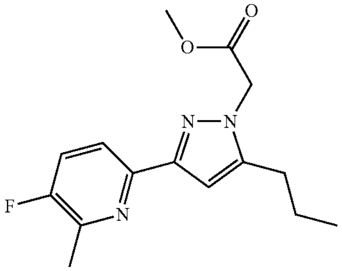 [SMILES: CCCc1cc(-c2ccc(F)c(C)n2)nn1CC(=O)OC] | 292 | method AB | 0.82 |
| 6.02.03.41 | 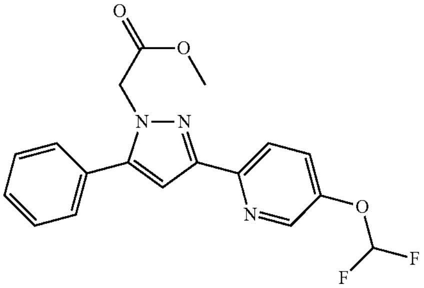 [SMILES: COC(=O)Cn1nc(-c2ccc(OC(F)F)cn2)cc1-c1ccccc1] | 360 | method AB | 0.86 |
| 6.02.03.43 | 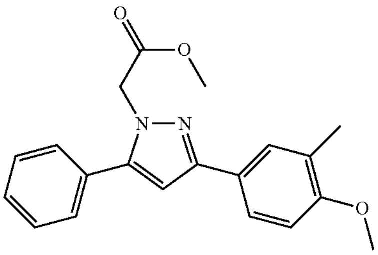 [SMILES: COC(=O)Cn1nc(-c2ccc(OC)c(C)c2)cc1-c1ccccc1] | 337 | method AB | 1.51 |

-continued

| Examples | Product | MS m/z [M + H]+ | HPLC Method | Rt min |
|---|---|---|---|---|
| 6.02.03.44 | 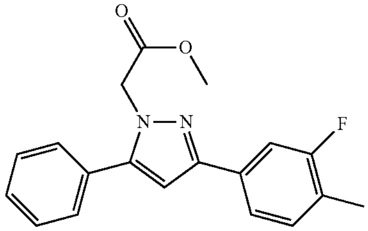 [SMILES: COC(=O)Cn1nc(-c2ccc(C)c(F)c2)cc1-c1ccccc1] | 325 | method AB | 0.98 |
| 6.02.03.45 | 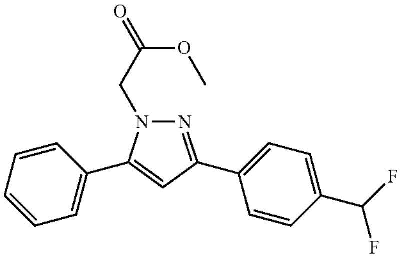 [SMILES: COC(=O)Cn1nc(-c2ccc(C(F)F)cc2)cc1-c1ccccc1] | 343 | | |

6.02.04.01 (3,5-Bis-(4-fluoro-phenyl)-pyrazol-1-yl)-acid

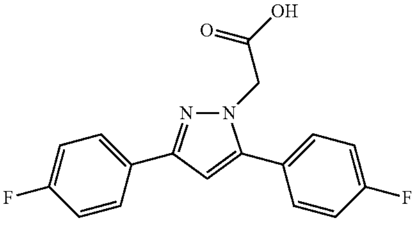 [SMILES: O=C(O)Cn1nc(-c2ccc(F)cc2)cc1-c1ccc(F)cc1]

3.6 g of 3-(4-fluoro-3-methyl-phenyl)-5-phenyl-pyrazol-1-yl-acetic acid methyl ester was dissolved in 20 mL dioxane and a solution of 292 mg LiOH in 3 mL of water was added. The mixture was stirred over the weekend at RT. The solvent was removed and the residue was dissolved in 2M HCl and stirred for 2 h. The solvent was removed to yield 2.4 g of the product.

$R_t$: 1.43 (method E), $(M+H)^+$: 315

By using the same synthesis strategy as for (3,5-Bis-(4-fluoro-phenyl)-pyrazol-1-yl)-acid the following compounds were obtained:

| Examples | Product | MS m/z [M + H]+ | HPLC Method | Rt min |
|---|---|---|---|---|
| 6.02.04.02 | 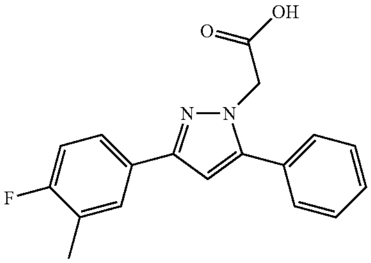 [SMILES: Cc1cc(-c2cc(-c3ccccc3)n(CC(=O)O)n2)ccc1F] | 311 | method D | 1.05 |
| 6.02.04.03 | 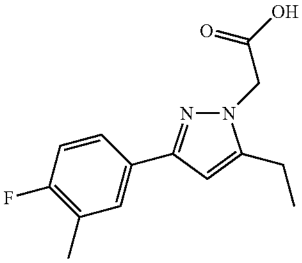 [SMILES: CCc1cc(-c2ccc(F)c(C)c2)nn1CC(=O)O] | 263 | method C | 0.93 |

-continued
| Examples | Product | MS m/z [M + H]+ | HPLC Method | Rt min |
|---|---|---|---|---|
| 6.02.04.04 | 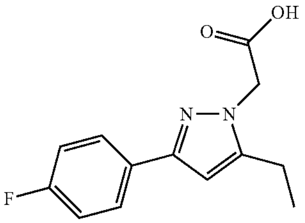 [SMILES: CCc1cc(-c2ccc(F)cc2)nn1CC(=O)O] | 249 | method C | 0.87 |
| 6.02.04.05 | 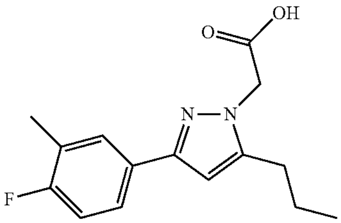 [SMILES: CCCc1cc(-c2ccc(F)c(C)c2)nn1CC(=O)O] | 277 | method I | 0.90 |
| 6.02.04.06 | 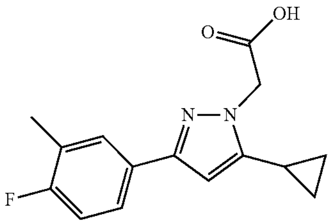 [SMILES: Cc1cc(-c2cc(C3CC3)n(CC(=O)O)n2)ccc1F] | 275 | method J | 1.05 |
| 6.02.04.07 | 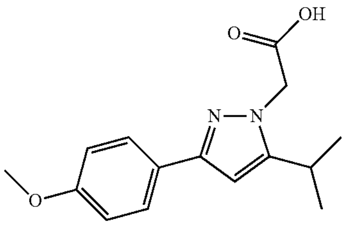 [SMILES: COc1ccc(-c2cc(C(C)C)n(CC(=O)O)n2)cc1] | 275 | method J | 1.30 |
| 6.02.04.08 | 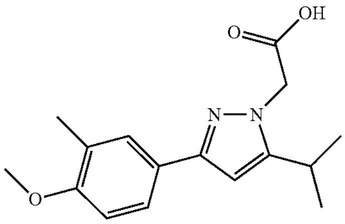 [SMILES: COc1ccc(-c2cc(C(C)C)n(CC(=O)O)n2)cc1C] | 289 | method J | 1.39 |
| 6.02.04.09 | 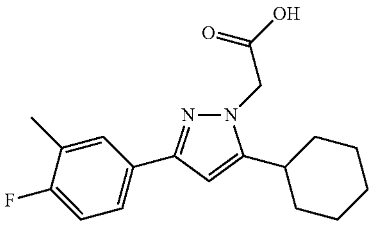 [SMILES: Cc1cc(-c2cc(C3CCCCC3)n(CC(=O)O)n2)ccc1F] | 317 | method J | 1.58 |

-continued
| Examples | Product | MS m/z [M + H]$^+$ | HPLC Method | Rt min |
|---|---|---|---|---|
| 6.02.04.10 | 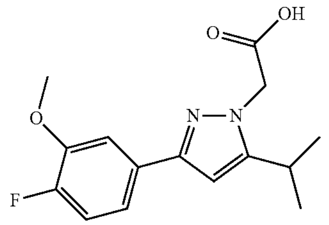 [SMILES: COc1cc(-c2cc(C(C)C)n(CC(=O)O)n2)ccc1F] | 293 | method N | 1.04 |
| 6.02.04.11 | 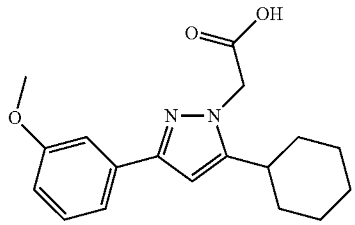 [SMILES: COc1cccc(-c2cc(C3CCCCC3)n(CC(=O)O)n2)c1] | 315 | $^1$H-NMR: 6.57(s, 1H, CH), 4.95(s, 2H, CH2), 3.80(s, 3H, CH3) | |
| 6.02.04.12 | 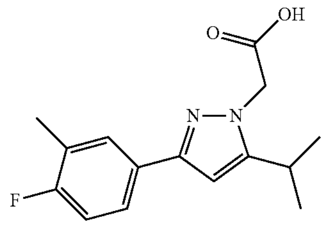 [SMILES: Cc1cc(-c2cc(C(C)C)n(CC(=O)O)n2)ccc1F] | 277 | method J | 1.45 |
| 6.02.04.13 | 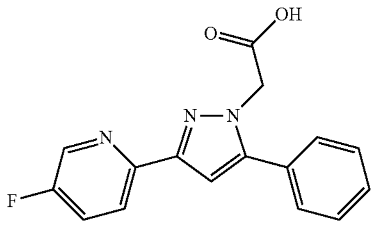 [SMILES: O=C(O)Cn1nc(-c2ccc(F)cn2)cc1-c1ccccc1] | 298 | method D | 0.90 |
| 6.02.04.14 | 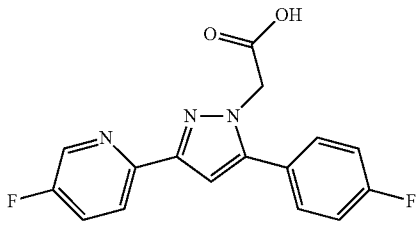 [SMILES: O=C(O)Cn1nc(-c2ccc(F)cn2)cc1-c1ccc(F)cc1] | 316 | method E | 1.33 |
| 6.02.04.15 | 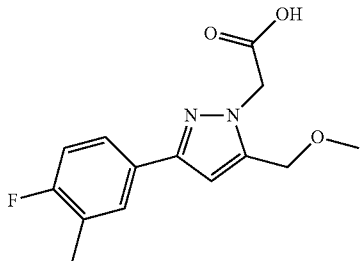 [SMILES: COCc1cc(-c2ccc(F)c(C)c2)nn1CC(=O)O] | 279 | method R | 1.40 |

-continued
| Examples | Product | MS m/z [M + H]+ | HPLC Method | Rt min |
|---|---|---|---|---|
| 6.02.04.16 | 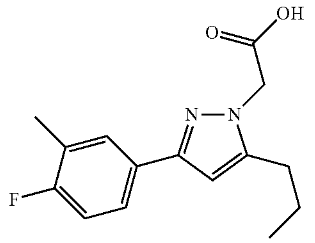 [SMILES: CCCc1cc(-c2ccc(F)c(C)c2)nn1CC(=O)O] | 277 | method I | 0.90 |
| 6.02.04.17 | 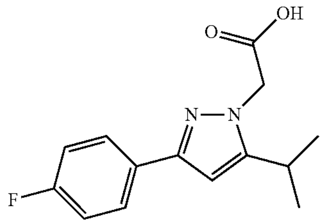 [SMILES: CC(C)c1cc(-c2ccc(F)cc2)nn1CC(=O)O] | 263 | method U | 0.78 |
| 6.02.04.18 | 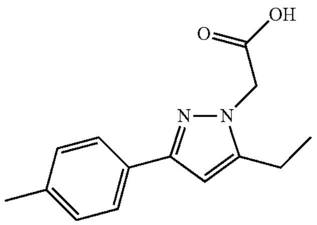 [SMILES: CCc1cc(-c2ccc(C)cc2)nn1CC(=O)O] | 245 | method T | 1.25 |
| 6.02.04.19 | 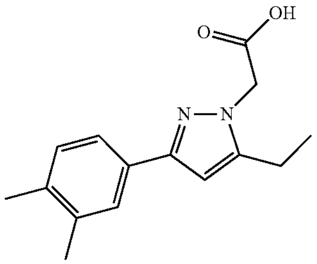 [SMILES: CCc1cc(-c2ccc(C)c(C)c2)nn1CC(=O)O] | 259 | method T | 1.32 |
| 6.02.04.20 | 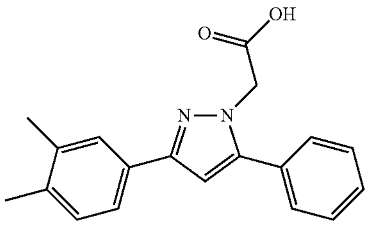 [SMILES: Cc1ccc(-c2cc(-c3ccccc3)n(CC(=O)O)n2)cc1C] | 307 | method I | 0.97 |
| 6.02.04.21 | 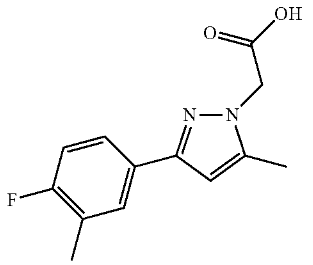 [SMILES: Cc1cc(-c2cc(C)n(CC(=O)O)n2)ccc1F] | 249 | method V | 1.20 |

-continued
| Examples | Product | MS m/z [M + H]+ | HPLC Method | Rt min |
|---|---|---|---|---|
| 6.02.04.22 | 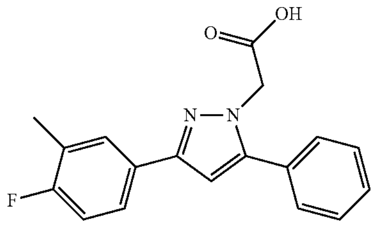 [SMILES: Cc1cc(-c2cc(-c3ccccc3)n(CC(=O)O)n2)ccc1F] | 311 | method I | 0.95 |
| 6.02.04.23 | 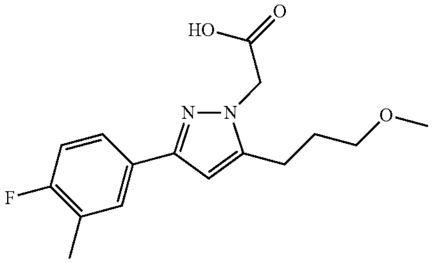 [SMILES: COCCCc1cc(-c2ccc(F)c(C)c2)nn1CC(=O)O] | 307 | method U | 0.75 |
| 6.02.04.24 | 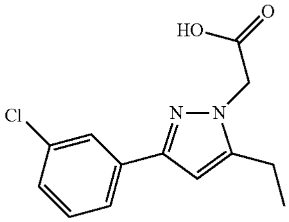 [SMILES: CCc1cc(-c2cccc(Cl)c2)nn1CC(=O)O] | 265 | method W | 1.38 |
| 6.02.04.25 | 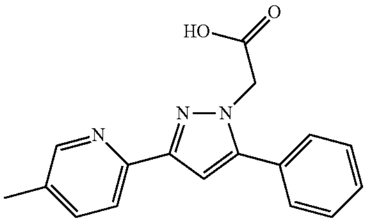 [SMILES: Cc1ccc(-c2cc(-c3ccccc3)n(CC(=O)O)n2)nc1] | 294 | method I | 0.65 |
| 6.02.04.26 | 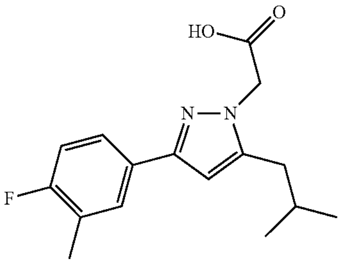 [SMILES: Cc1cc(-c2cc(CC(C)C)n(CC(=O)O)n2)ccc1F] | 291 | method U | 0.85 |
| 6.02.04.27 | 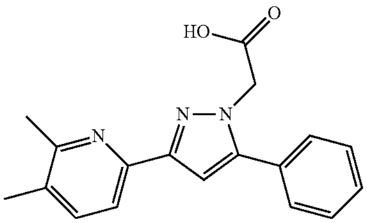 [SMILES: Cc1ccc(-c2cc(-c3ccccc3)n(CC(=O)O)n2)nc1C] | 308 | method I | 0.65 |

-continued
| Examples | Product | MS m/z [M + H]$^+$ | HPLC Method | Rt min |
|---|---|---|---|---|
| 6.02.04.28 | 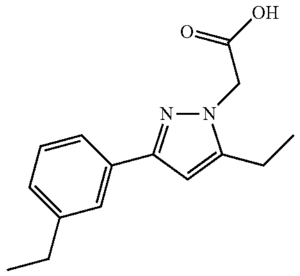 [SMILES: CCc1cccc(-c2cc(CC)n(CC(=O)O)n2)c1] | 259 | method W | 1.41 |
| 6.02.04.29 | 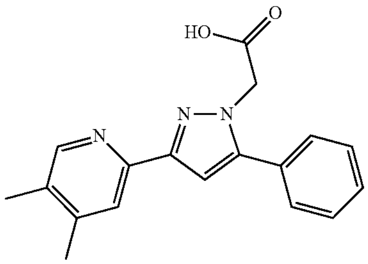 [SMILES: Cc1cnc(-c2cc(-c3ccccc3)n(CC(=O)O)n2)cc1C] | 308 | method Y | 0.91 |
| 6.02.04.30 | 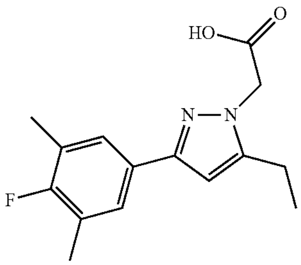 [SMILES: CCc1cc(-c2cc(C)c(F)c(C)c2)nn1CC(=O)O] | 277 | method W | 1.45 |
| 6.02.04.31 | 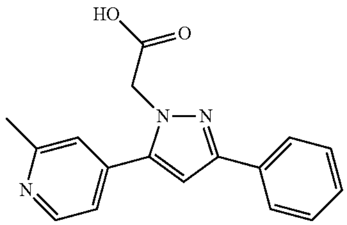 [SMILES: Cc1cc(-c2cc(-c3ccccc3)nn2CC(=O)O)ccn1] | 294 | method S | 0.80 |
| 6.02.04.32 | 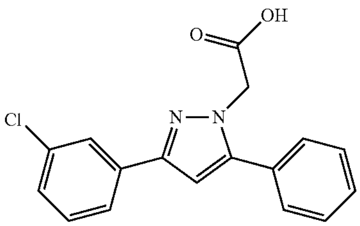 [SMILES: O=C(O)Cn1nc(-c2cccc(Cl)c2)cc1-c1ccccc1] | 313 | method W | 1.51 |
| 6.02.04.33 | 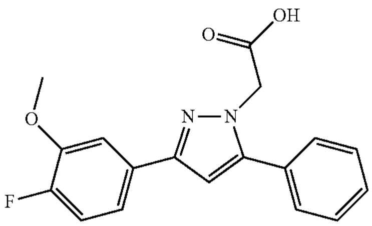 [SMILES: COc1cc(-c2cc(-c3ccccc3)n(CC(=O)O)n2)ccc1F] | 327 | method I | 0.87 |

-continued
| Examples | Product | MS m/z $[M + H]^+$ | HPLC Method | Rt min |
|---|---|---|---|---|
| 6.02.04.34 | 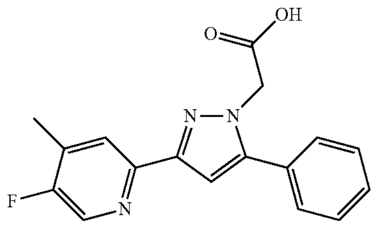 [SMILES: Cc1cc(-c2cc(-c3ccccc3)n(CC(=O)O)n2)ncc1F] | 312 | method W | 1.26 |
| 6.02.04.35 | 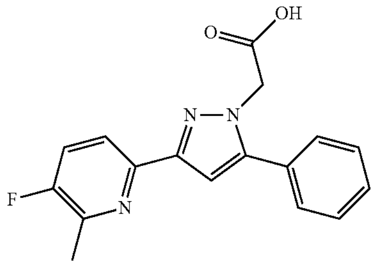 [SMILES: Cc1nc(-c2cc(-c3ccccc3)n(CC(=O)O)n2)ccc1F] | 312 | method W | 1.30 |
| 6.02.04.36 | 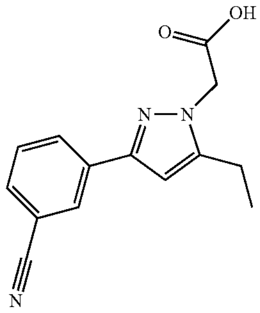 [SMILES: CCc1cc(-c2cccc(C#N)c2)nn1CC(=O)O] | 256 | method AB | 0.88 |
| 6.02.04.37 | 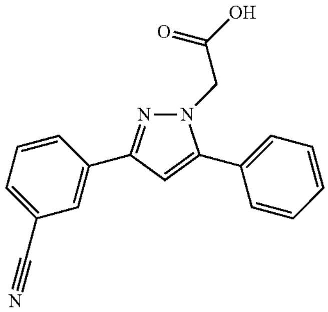 [SMILES: N#Cc1cccc(-c2cc(-c3ccccc3)n(CC(=O)O)n2)c1] | 304 | method AB | 1.02 |
| 6.02.04.38 | 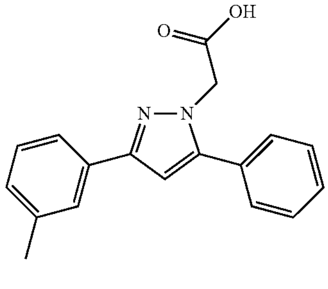 [SMILES: Cc1cccc(-c2cc(-c3ccccc3)n(CC(=O)O)n2)c1] | 293 | method U | 0.97 |

-continued
| Examples | Product | MS m/z [M + H]+ | HPLC Method | Rt min |
|---|---|---|---|---|
| 6.02.04.39 | 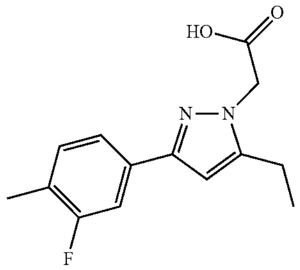 [SMILES: CCc1cc(-c2ccc(C)c(F)c2)nn1CC(=O)O] | 263 | method Y | 0.86 |
| 6.02.04.40 | 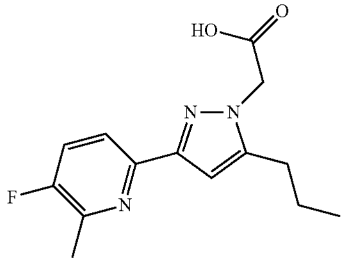 [SMILES: CCCc1cc(-c2ccc(F)c(C)n2)nn1CC(=O)O] | 278 | method AB | 0.76 |
| 6.02.04.41 | 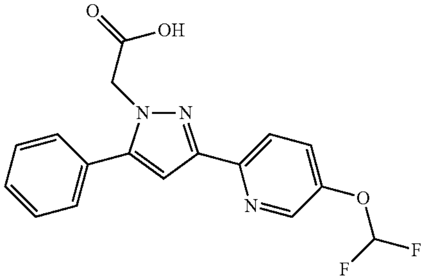 [SMILES: O=C(O)Cn1nc(-c2ccc(OC(F)F)cn2)cc1-c1ccccc1] | 346 | method AB | 0.81 |
| 6.02.04.42 | 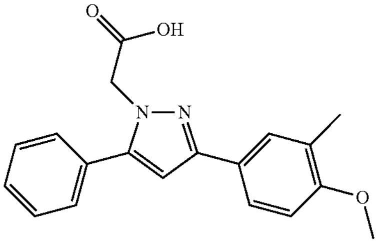 [SMILES: COc1ccc(-c2cc(-c3ccccc3)n(CC(=O)O)n2)cc1C] | 323 | method M | 1.46 |
| 6.02.04.43 | 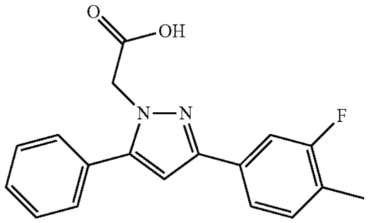 [SMILES: Cc1ccc(-c2cc(-c3ccccc3)n(CC(=O)O)n2)cc1F] | 311 | method M | 0.95 |
| 6.02.04.44 | 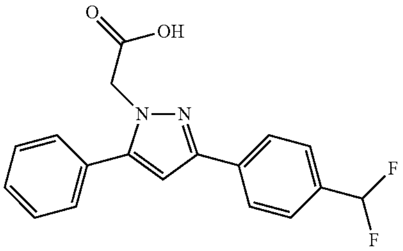 [SMILES: O=C(O)Cn1nc(-c2ccc(C(F)F)cc2)cc1-c1ccccc1] | 329 | method M | 0.68 |

7. Synthesis of Target Compounds 7.01.001 2-(3,5-diphenyl-pyrazol-1-yl)-1-(4-(5-chloro-pyrimidin-2-yl)-1-piperidinyl)-ethanon

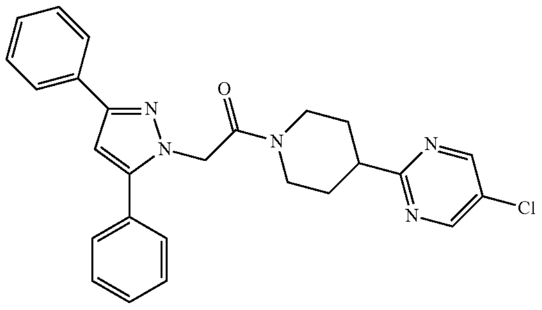 [SMILES: O=C(Cn1nc(-c2ccccc2)cc1-c1ccccc1)N1CCC(c2ncc(Cl)cn2)CC1]

28 mg (3,5-diphenyl-pyrazol-1-yl)-acetic acid was dissolved in 2 mL DMF and 26 mg DIPEA and 32 mg TBTU were added to this solution and the reaction was stirred for 5 minutes at RT. The mixture was added to 20 mg 5-chloro-2-piperidin-4-ylpyrimidine and stirred for 2 h. The reaction was cleaned by RP-chromatographie (methanol/water, 0.1% $NH_3$) to yield 11 mg of the desired compound. $R_t$: 2.38 (method A), $(M+H)^+$: 458

By using the same synthetic strategy as for 2-(3,5-diphenyl-pyrazol-1-yl)-1-(4-(5-chloro-pyrimidin-2-yl)-1-piperidinyl)-ethanon the following compounds were obtained:

| Examples | Product | MS m/z $[M + H]^+$ | HPLC Method | Rt min |
|---|---|---|---|---|
| 7.01.002 | 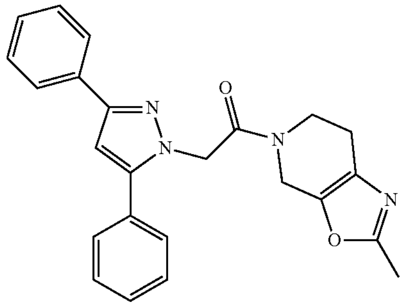 [SMILES: Cc1nc2c(o1)CN(C(=O)Cn1nc(-c3ccccc3)cc1-c1ccccc1)CC2] | 399 | method B | 2.15 |
| 7.01.003 | 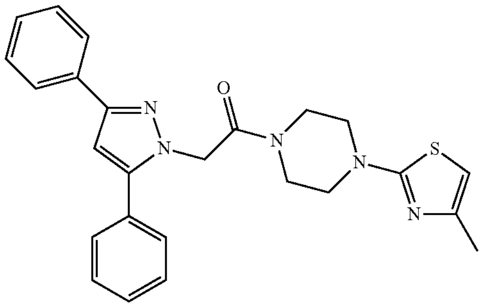 [SMILES: Cc1csc(N2CCN(C(=O)Cn3nc(-c4ccccc4)cc3-c3ccccc3)CC2)n1] | 444 | method A | 2.09 |
| 7.01.004 | 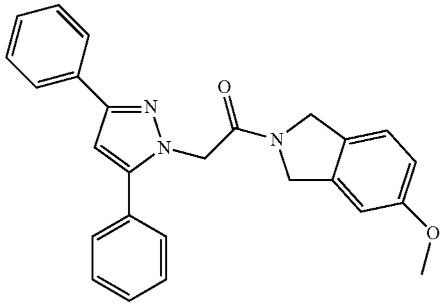 [SMILES: COc1ccc2c(c1)CN(C(=O)Cn1nc(-c3ccccc3)cc1-c1ccccc1)C2] | 410 | method B | 2.33 |

-continued
| Examples | Product | MS m/z [M + H]+ | HPLC Method | Rt min |
|---|---|---|---|---|
| 7.01.005 | 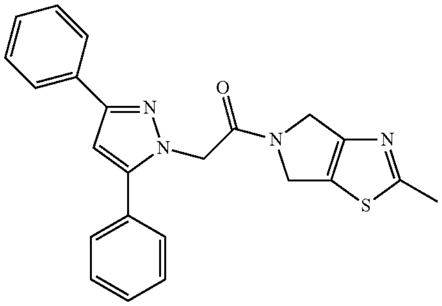 [SMILES: Cc1nc2c(s1)CN(C(=O)Cn1nc(-c3ccccc3)cc1-c1ccccc1)C2] | 401 | method A | 2.35 |
| 7.01.006 | 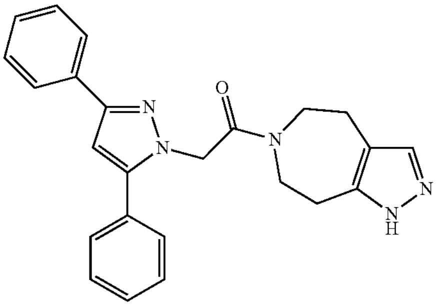 [SMILES: O=C(Cn1nc(-c2ccccc2)cc1-c1ccccc1)N1CCc2cn[nH]c2CC1] | 398 | method A | 2.19 |
| 7.01.007 | 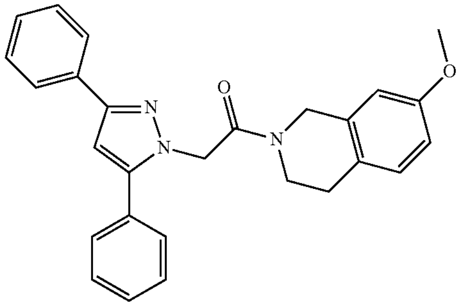 [SMILES: COc1ccc2c(c1)CN(C(=O)Cn1nc(-c3ccccc3)cc1-c1ccccc1)CC2] | 424 | method B | 2.37 |
| 7.01.008 | 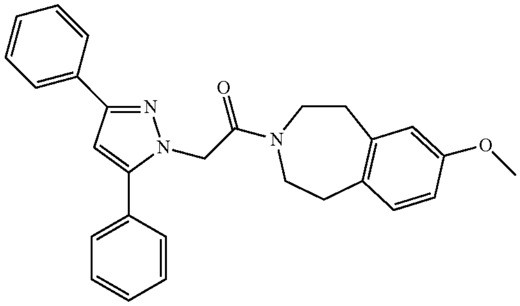 [SMILES: COc1ccc2c(c1)CCN(C(=O)Cn1nc(-c3ccccc3)cc1-c1ccccc1)CC2] | 438 | method B | 2.39 |
| 7.01.009 | 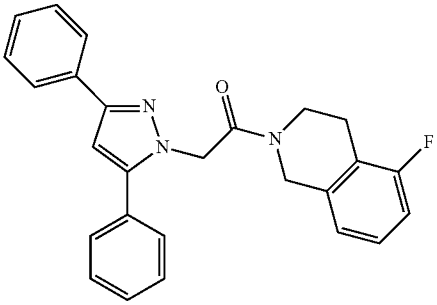 [SMILES: O=C(Cn1nc(-c2ccccc2)cc1-c1ccccc1)N1CCc2c(F)cccc2C1] | 412 | method A | 2.41 |

-continued
| Examples | Product | MS m/z $[M + H]^+$ | HPLC Method | Rt min |
|---|---|---|---|---|
| 7.01.010 | 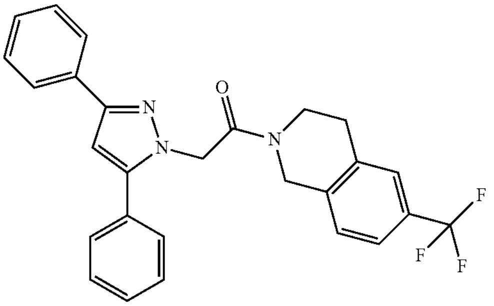 [SMILES: O=C(Cn1nc(-c2ccccc2)cc1-c1ccccc1)N1CCc2cc(C(F)(F)F)ccc2C1] | 462 | method B | 2.46 |
| 7.01.011 | 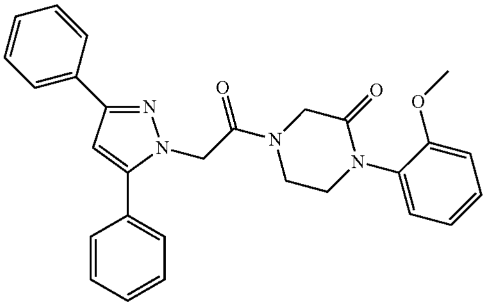 [SMILES: COc1ccccc1N1CCN(C(=O)Cn2nc(-c3ccccc3)cc2-c2ccccc2)CC1=O] | 467 | method A | 2.31 |
| 7.01.012 | 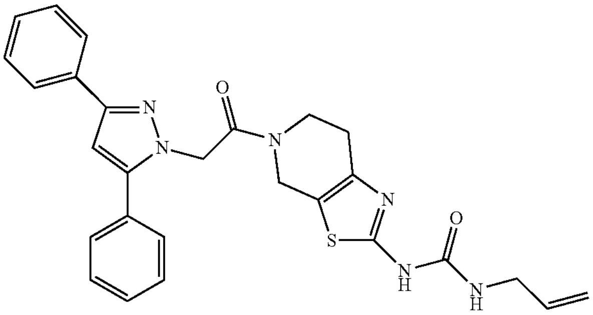 [SMILES: C=CCNC(=O)Nc1nc2c(s1)CN(C(=O)Cn1nc(-c3ccccc3)cc1-c1ccccc1)CC2] | 499 | method A | 2.33 |
| 7.01.013 | 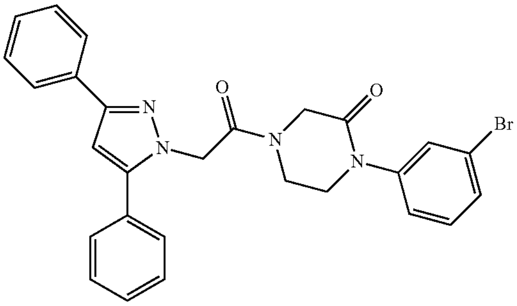 [SMILES: O=C(Cn1nc(-c2ccccc2)cc1-c1ccccc1)N1CCN(c2cccc(Br)c2)C(=O)C1] | 515 | method A | 2.36 |
| 7.01.014 | 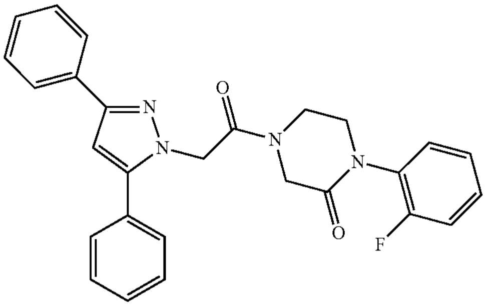 [SMILES: O=C(Cn1nc(-c2ccccc2)cc1-c1ccccc1)N1CCN(c2ccccc2F)C(=O)C1] | 455 | method A | 2.32 |

-continued
| Examples | Product | MS m/z $[M + H]^+$ | HPLC Method | Rt min |
|---|---|---|---|---|
| 7.01.015 | 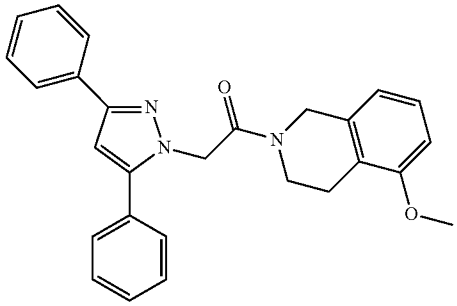 [SMILES: COc1cccc2c1CCN(C(=O)Cn1nc(-c3ccccc3)cc1-c1ccccc1)C2] | 424 | method A | 2.44 |
| 7.01.016 | 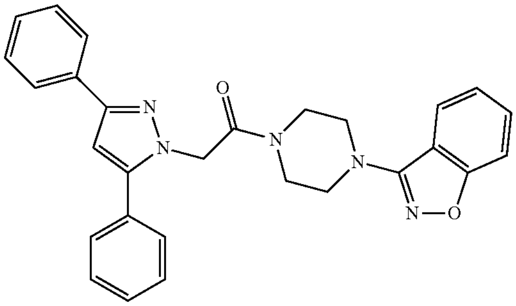 [SMILES: O=C(Cn1nc(-c2ccccc2)cc1-c1ccccc1)N1CCN(c2noc3ccccc23)CC1] | 464 | method A | 2.40 |
| 7.01.017 | 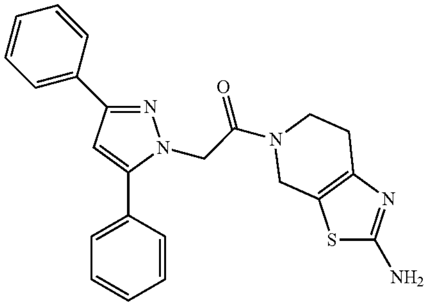 [SMILES: Nc1nc2c(s1)CN(C(=O)Cn1nc(-c3ccccc3)cc1-c1ccccc1)CC2] | 415 | method B | 1.69 |
| 7.01.018 | 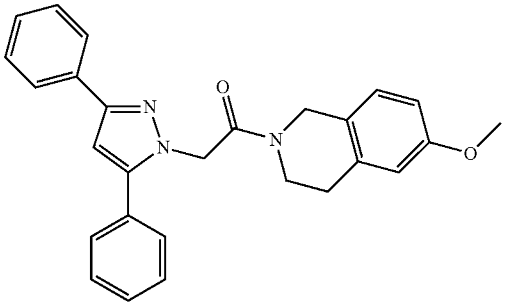 [SMILES: COc1ccc2c(c1)CCN(C(=O)Cn1nc(-c3ccccc3)cc1-c1ccccc1)C2] | 424 | method B | 2.35 |
| 7.01.019 | 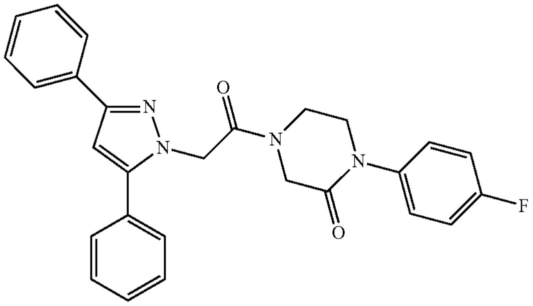 [SMILES: O=C(Cn1nc(-c2ccccc2)cc1-c1ccccc1)N1CCN(c2ccc(F)cc2)C(=O)C1] | 455 | method A | 2.31 |

-continued
| Examples | Product | MS m/z [M + H]+ | HPLC Method | Rt min |
|---|---|---|---|---|
| 7.01.020 | 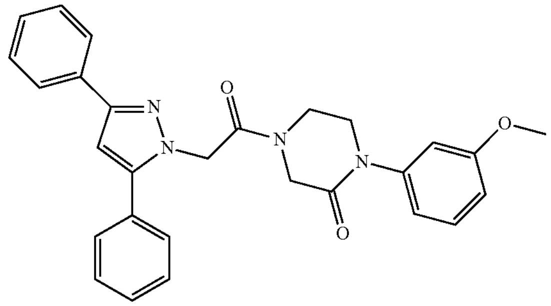 [SMILES: COc1cccc(N2CCN(C(=O)Cn3nc(-c4ccccc4)cc3-c3ccccc3)CC2=O)c1] | 467 | method A | 2.27 |
| 7.01.021 | 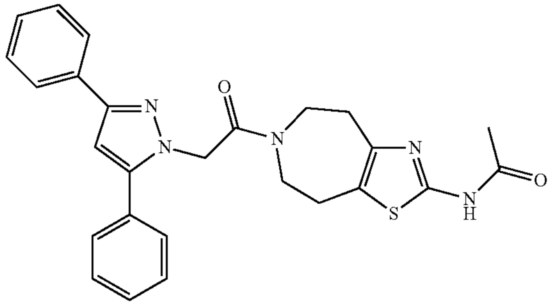 [SMILES: CC(=O)Nc1nc2c(s1)CCN(C(=O)Cn1nc(-c3ccccc3)cc1-c1ccccc1)CC2] | 472 | method A | 2.31 |
| 7.01.022 | 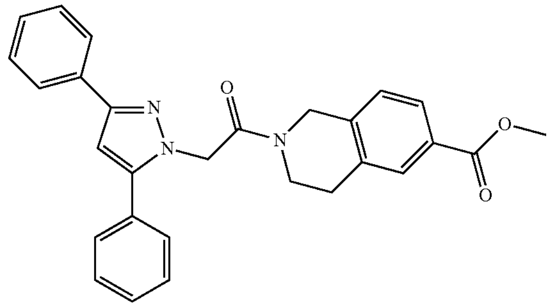 [SMILES: COC(=O)c1ccc2c(c1)CCN(C(=O)Cn1nc(-c3ccccc3)cc1-c1ccccc1)C2] | 452 | method A | 2.39 |
| 7.01.23 | 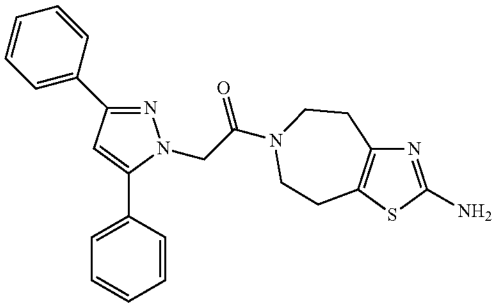 [SMILES: Nc1nc2c(s1)CCN(C(=O)Cn1nc(-c3ccccc3)cc1-c1ccccc1)CC2] | 430 | method G | 1.86 |
| 7.01.024 | 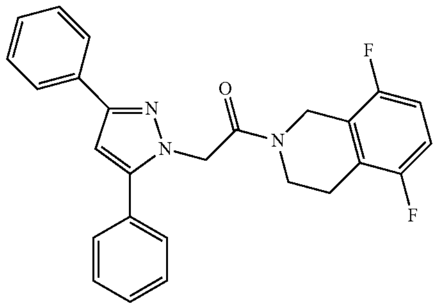 [SMILES: O=C(Cn1nc(-c2ccccc2)cc1-c1ccccc1)N1CCc2c(F)ccc(F)c2C1] | 430 | method A | 2.40 |

-continued
| Examples | Product | MS m/z [M + H]+ | HPLC Method | Rt min |
|---|---|---|---|---|
| 7.01.025 | 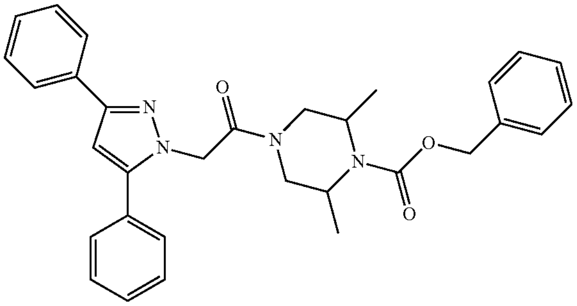 [SMILES: CC1CN(C(=O)Cn2nc(-c3ccccc3)cc2-c2ccccc2)CC(C)N1C(=O)OCc1ccccc1] | 509 | method B | 2.42 |
| 7.01.026 | 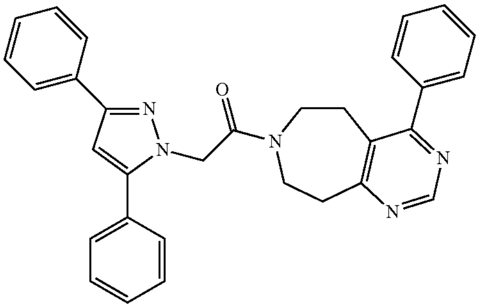 [SMILES: O=C(Cn1nc(-c2ccccc2)cc1-c1ccccc1)N1CCc2ncnc(-c3ccccc3)c2CC1] | 486 | method A | 2.37 |
| 7.01.027 | 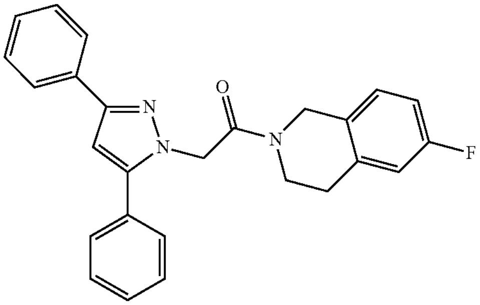 [SMILES: O=C(Cn1nc(-c2ccccc2)cc1-c1ccccc1)N1CCc2cc(F)ccc2C1] | 412 | method A | 2.39 |
| 7.01.028 | 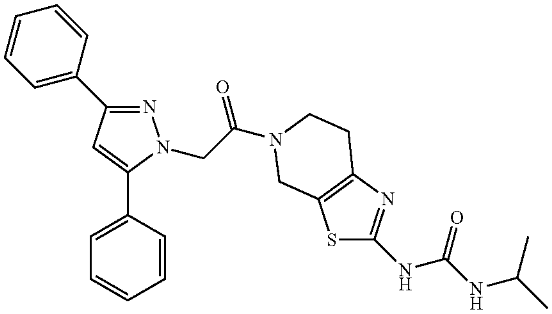 [SMILES: CC(C)NC(=O)Nc1nc2c(s1)CN(C(=O)Cn1nc(-c3ccccc3)cc1-c1ccccc1)CC2] | 501 | method A | 2.34 |
| 7.01.029 | 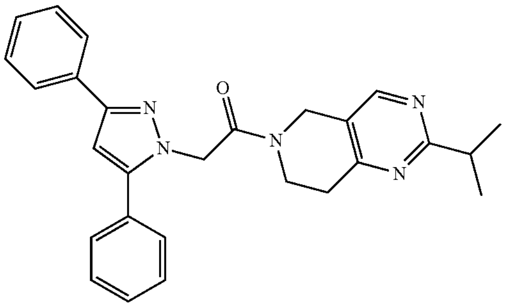 [SMILES: CC(C)c1ncc2c(n1)CCN(C(=O)Cn1nc(-c3ccccc3)cc1-c1ccccc1)C2] | 438 | method A | 2.37 |

-continued
| Examples | Product | MS m/z [M + H]+ | HPLC Method | Rt min |
|---|---|---|---|---|
| 7.01.030 | 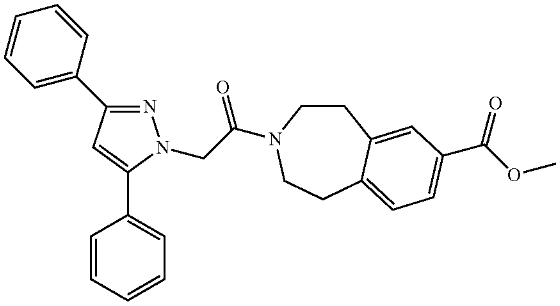 [SMILES: COC(=O)c1ccc2c(c1)CCN(C(=O)Cn1nc(-c3ccccc3)cc1-c1ccccc1)CC2] | 466 | method A | 2.40 |
| 7.01.031 | 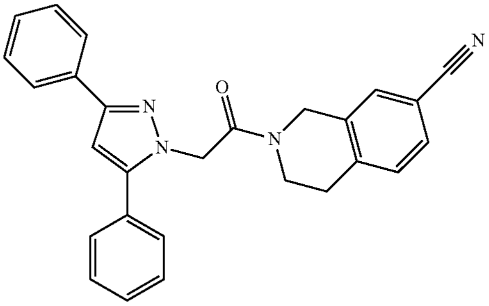 [SMILES: N#Cc1ccc2c(c1)CN(C(=O)Cn1nc(-c3ccccc3)cc1-c1ccccc1)CC2] | 419 | method B | 2.29 |
| 7.01.032 | 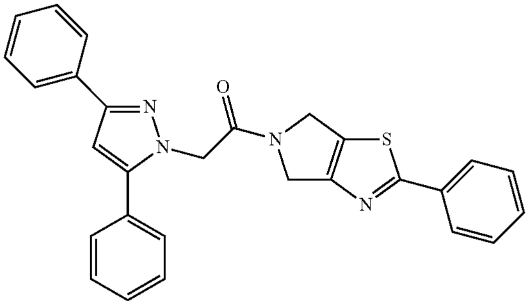 [SMILES: O=C(Cn1nc(-c2ccccc2)cc1-c1ccccc1)N1Cc2nc(-c3ccccc3)sc2C1] | 463 | method B | 2.45 |
| 7.01.033 | 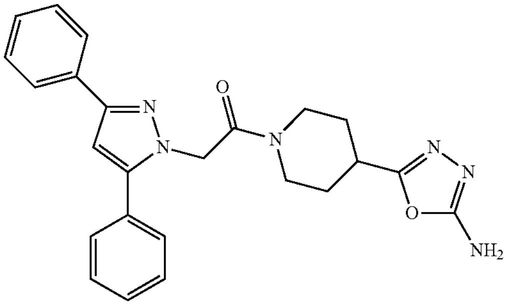 [SMILES: Nc1nnc(C2CCN(C(=O)Cn3nc(-c4ccccc4)cc3-c3ccccc3)CC2)o1] | 429 | method B | 1.83 |
| 7.01.034 | 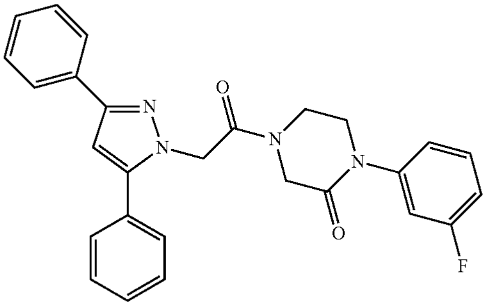 [SMILES: O=C(Cn1nc(-c2ccccc2)cc1-c1ccccc1)N1CCN(c2cccc(F)c2)C(=O)C1] | 455 | method A | 2.31 |

-continued
| Examples | Product | MS m/z [M + H]+ | HPLC Method | Rt min |
|---|---|---|---|---|
| 7.01.035 | 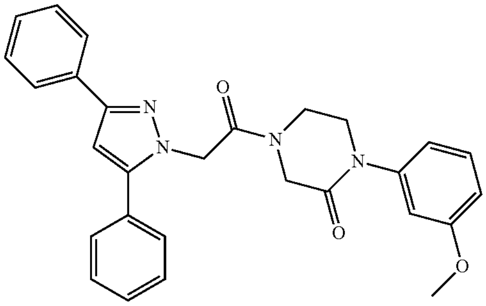 [SMILES: COc1cccc(N2CCN(C(=O)Cn3nc(-c4ccccc4)cc3-c3ccccc3)CC2=O)c1] | 467 | method A | 2.34 |
| 7.01.036 | 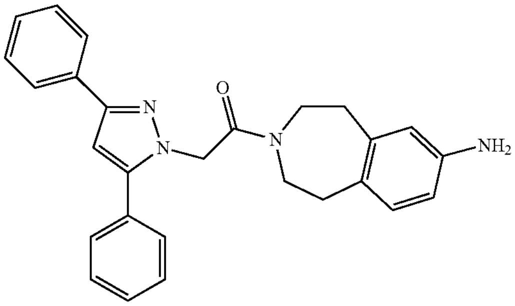 [SMILES: Nc1ccc2c(c1)CCN(C(=O)Cn1nc(-c3ccccc3)cc1-c1ccccc1)CC2] | 423 | method A | 1.99 |
| 7.01.037 | 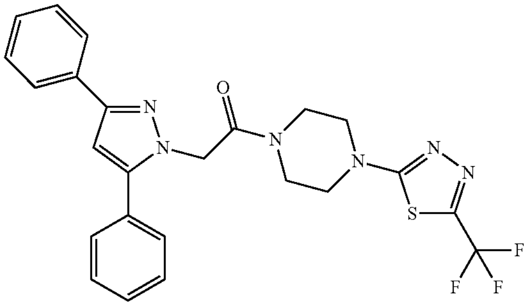 [SMILES: O=C(Cn1nc(-c2ccccc2)cc1-c1ccccc1)N1CCN(c2nnc(C(F)(F)F)s2)CC1] | 499 | method A | 2.33 |
| 7.01.038 | 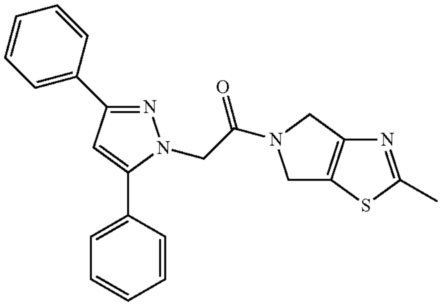 [SMILES: Cc1nc2c(s1)CN(C(=O)Cn1nc(-c3ccccc3)cc1-c1ccccc1)C2] | 401 | method A | 2.32 |
| 7.01.039 | 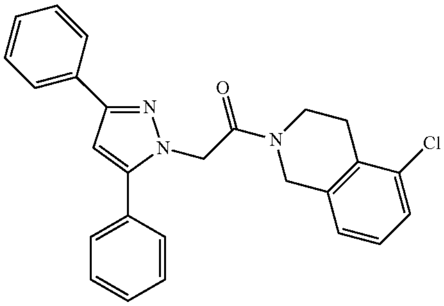 [SMILES: O=C(Cn1nc(-c2ccccc2)cc1-c1ccccc1)N1CCc2c(Cl)cccc2C1] | 428 | method A | 2.46 |

-continued
| Examples | Product | MS m/z [M + H]+ | HPLC Method | Rt min |
|---|---|---|---|---|
| 7.01.040 | 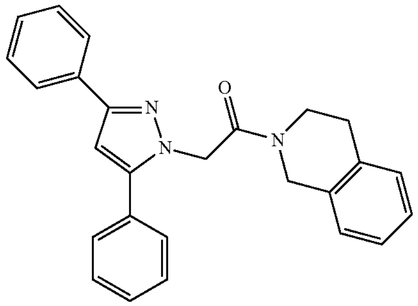 [SMILES: O=C(Cn1nc(-c2ccccc2)cc1-c1ccccc1)N1CCc2ccccc2C1] | 394 | method A | 2.40 |
| 7.01.041 | 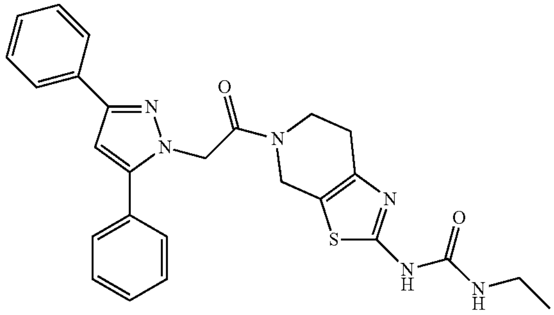 [SMILES: CCNC(=O)Nc1nc2c(s1)CN(C(=O)Cn1nc(-c3ccccc3)cc1-c1ccccc1)CC2] | 487 | method A | 2.31 |
| 7.01.042 | 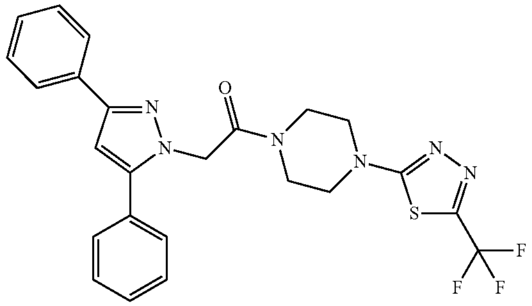 [SMILES: O=C(Cn1nc(-c2ccccc2)cc1-c1ccccc1)N1CCN(c2nnc(C(F)(F)F)s2)CC1] | 499 | method A | 2.36 |
| 7.01.043 | 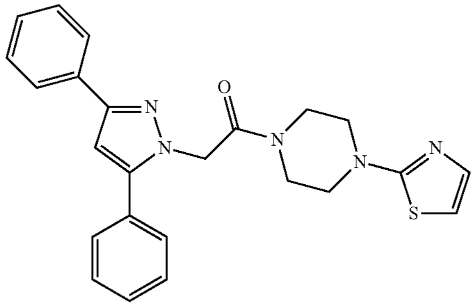 [SMILES: O=C(Cn1nc(-c2ccccc2)cc1-c1ccccc1)N1CCN(c2nccs2)CC1] | 430 | method K | 1.27 |
| 7.01.044 | 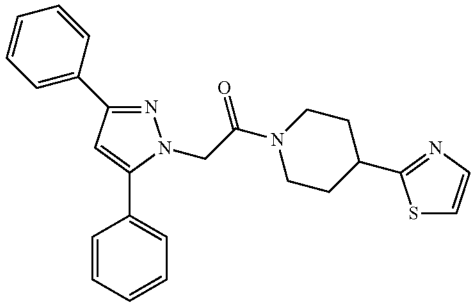 [SMILES: O=C(Cn1nc(-c2ccccc2)cc1-c1ccccc1)N1CCC(c2nccs2)CC1] | 429 | method A | 2.34 |

-continued
| Examples | Product | MS m/z [M + H]+ | HPLC Method | Rt min |
|---|---|---|---|---|
| 7.01.045 | 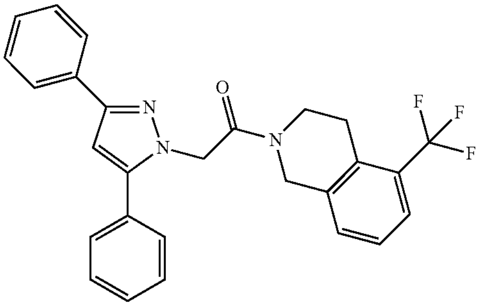 [SMILES: O=C(Cn1nc(-c2ccccc2)cc1-c1ccccc1)N1CCc2c(cccc2C(F)(F)F)C1] | 462 | method A | 2.44 |
| 7.01.046 | 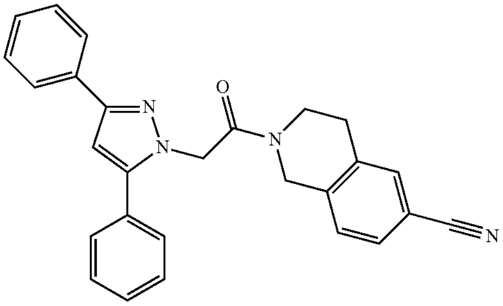 [SMILES: N#Cc1ccc2c(c1)CCN(C(=O)Cn1nc(-c3ccccc3)cc1-c1ccccc1)C2] | 420 | method B | 2.29 |
| 7.01.047 | 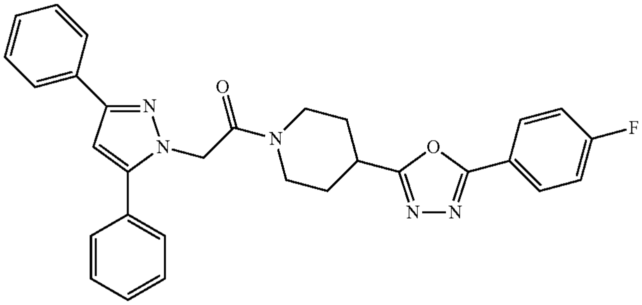 [SMILES: O=C(Cn1nc(-c2ccccc2)cc1-c1ccccc1)N1CCC(c2nnc(-c3ccc(F)cc3)o2)CC1] | 508 | method A | 2.39 |
| 7.01.048 | 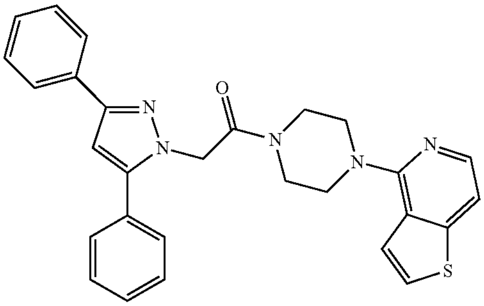 [SMILES: O=C(Cn1nc(-c2ccccc2)cc1-c1ccccc1)N1CCN(c2nccc3sccc23)CC1] | 480 | method A | 2.03 |
| 7.01.049 | 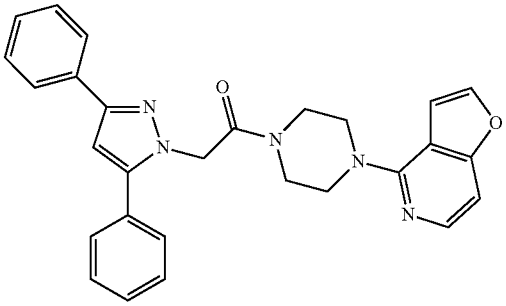 [SMILES: O=C(Cn1nc(-c2ccccc2)cc1-c1ccccc1)N1CCN(c2nccc3occc23)CC1] | 464 | method A | 2.02 |

-continued
| Examples | Product | MS m/z $[M + H]^+$ | HPLC Method | Rt min |
|---|---|---|---|---|
| 7.01.50 | 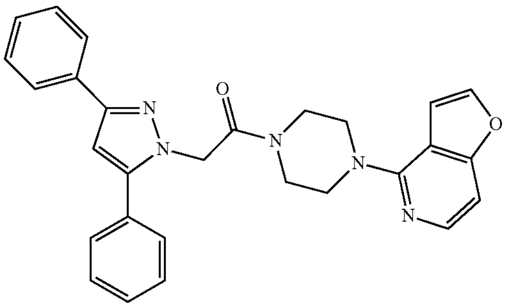 [SMILES: O=C(Cn1nc(-c2ccccc2)cc1-c1ccccc1)N1CCN(c2nccc3occc23)CC1] | 464 | method AH | 2.02 |
| 7.01.051 | 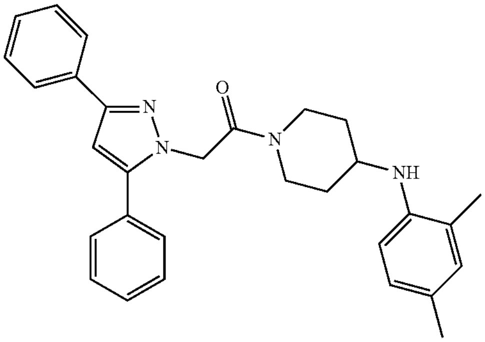 [SMILES: Cc1ccc(NC2CCN(C(=O)Cn3nc(-c4ccccc4)cc3-c3ccccc3)CC2)c(C)c1] | 465 | method A | 2.17 |
| 7.01.52 | 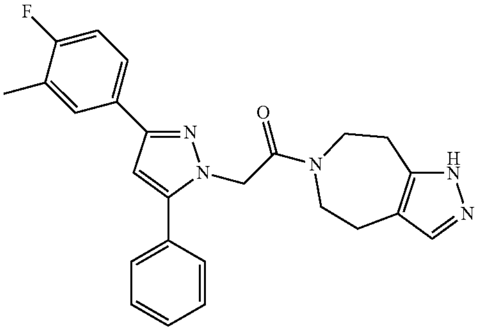 [SMILES: Cc1cc(-c2cc(-c3ccccc3)n(CC(=O)N3CCc4cn[nH]c4CC3)n2)ccc1F] | 430 | method AD | 0.74 |
| 7.01.053 | 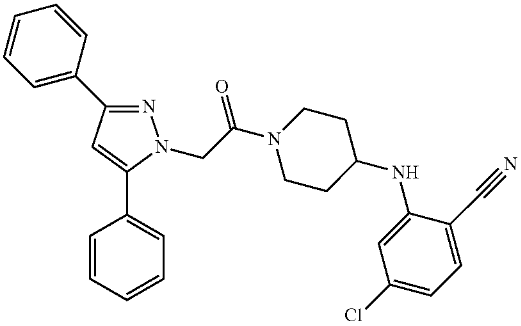 [SMILES: N#Cc1ccc(Cl)cc1NC1CCN(C(=O)Cn2nc(-c3ccccc3)cc2-c2ccccc2)CC1] | 497 | method A | 2.44 |

-continued
| Examples | Product | MS m/z [M + H]+ | HPLC Method | Rt min |
|---|---|---|---|---|
| 7.01.054 | 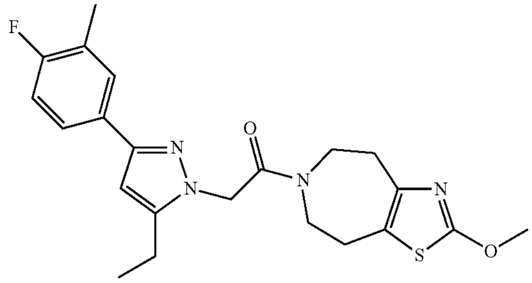 [SMILES: CCc1cc(-c2ccc(F)c(C)c2)nn1CC(=O)N1CCc2nc(OC)sc2CC1] | 429 | method AD | 0.75 |
| 7.01.055 | 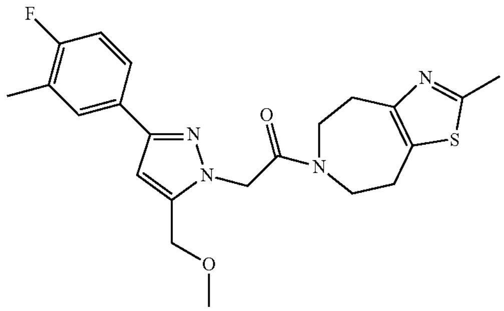 | 429 | method Q | 1.40 |
| 7.01.056 | 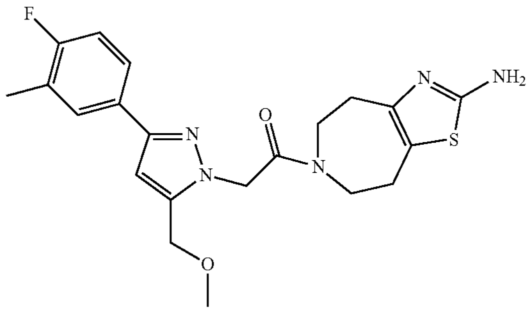 [SMILES: COCc1cc(-c2ccc(F)c(C)c2)nn1CC(=O)N1CCc2nc(N)sc2CC1] | 430 | method Q | 1.27 |
| 7.01.057 | 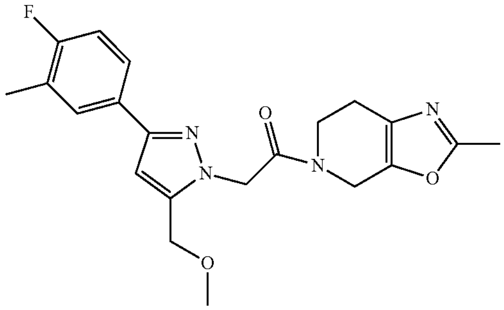 | 399 | method Q | 1.46 |
| 7.01.058 | 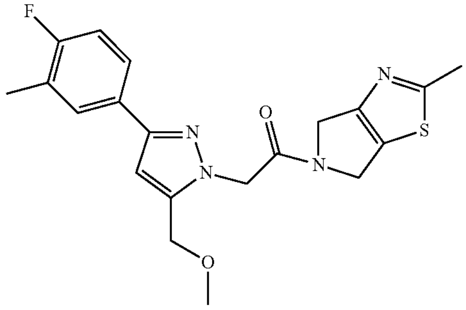 | 401 | method S | 1.47 |

-continued
| Examples | Product | MS m/z $[M + H]^+$ | HPLC Method | Rt min |
|---|---|---|---|---|
| 7.01.059 | 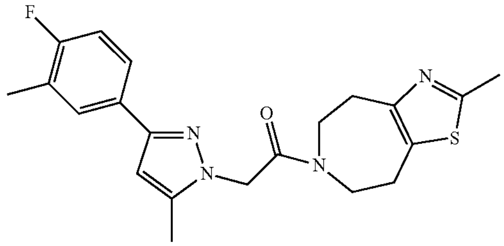 | 399 | method S | 1.10 |
| 7.01.060 | 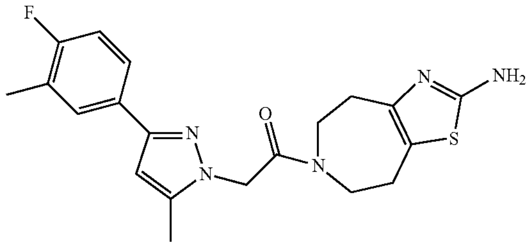 [SMILES: Cc1cc(-c2cc(C)n(CC(=O)N3CCc4nc(N)sc4CC3)n2)ccc1F] | 400 | method S | 1.00 |
| 7.01.061 | 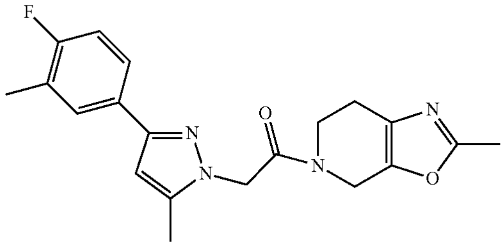 | 369 | method S | 1.20 |
| 7.01.062 | 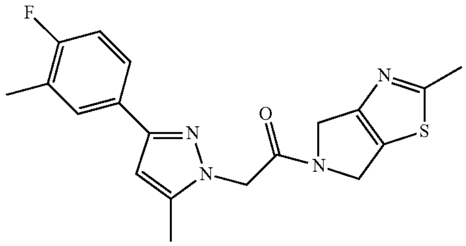 | 371 | method S | 1.20 |
| 7.01.063 | 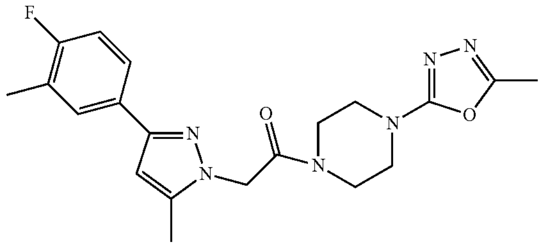 | 399 | method S | 1.40 |

-continued
| Examples | Product | MS m/z $[M + H]^+$ | HPLC Method | Rt min |
|---|---|---|---|---|
| 7.01.064 | 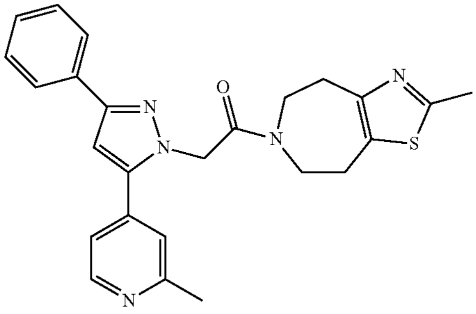 [SMILES: Cc1cc(-c2cc(-c3ccccc3)nn2CC(=O)N2CCc3nc(C)sc3CC2)ccn1] | 444 | method V | 0.88 |
| 7.01.065 | 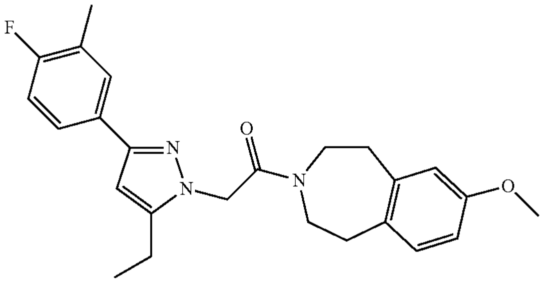 [SMILES: CCc1cc(-c2ccc(F)c(C)c2)nn1CC(=O)N1CCc2ccc(OC)cc2CC1] | 422 | method AD | 0.73 |
| 7.01.066 | 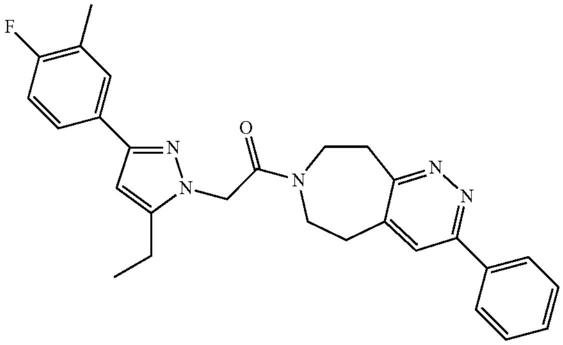 [SMILES: CCc1cc(-c2ccc(F)c(C)c2)nn1CC(=O)N1CCc2cc(-c3ccccc3)nnc2CC1] | 470 | method AD | 0.70 |
| 7.01.067 | 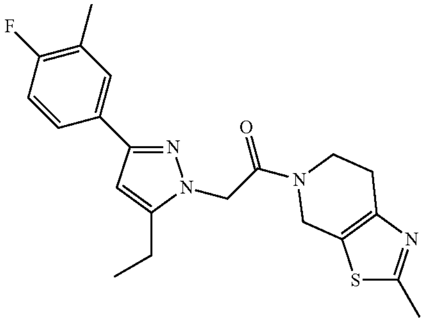 | 399 | method AD | 0.70 |

-continued
| Examples | Product | MS m/z [M + H]+ | HPLC Method | Rt min |
|---|---|---|---|---|
| 7.01.068 | 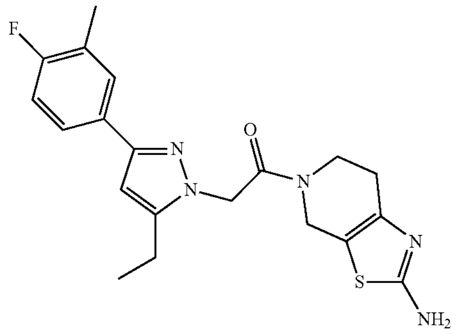 [SMILES: CCc1cc(-c2ccc(F)c(C)c2)nn1CC(=O)N1CCc2nc(N)sc2C1] | 400 | method AD | 0.68 |
| 7.01.069 | 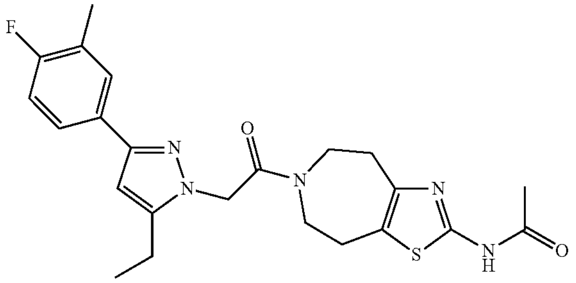 [SMILES: CCc1cc(-c2ccc(F)c(C)c2)nn1CC(=O)N1CCc2nc(NC(C)=O)sc2CC1] | 456 | method AD | 0.69 |
| 7.01.070 | 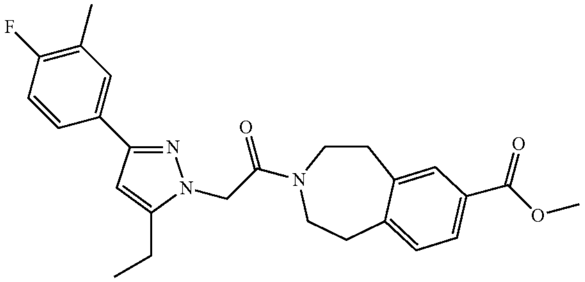 [SMILES: CCc1cc(-c2ccc(F)c(C)c2)nn1CC(=O)N1CCc2ccc(C(=O)OC)cc2CC1] | 450 | method AD | 0.71 |
| 7.01.071 | 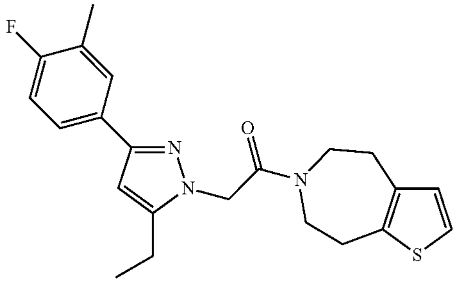 [SMILES: CCc1cc(-c2ccc(F)c(C)c2)nn1CC(=O)N1CCc2ccsc2CC1] | 398 | method AD | 0.71 |
| 7.01.072 | 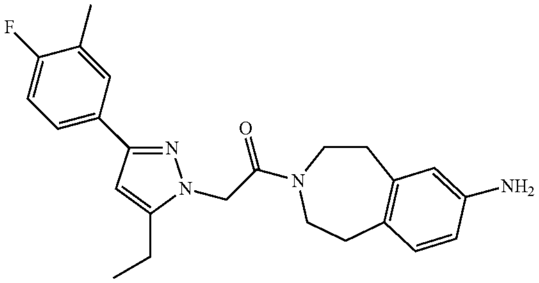 [SMILES: CCc1cc(-c2ccc(F)c(C)c2)nn1CC(=O)N1CCc2ccc(N)cc2CC1] | 407 | method AD | 0.66 |

-continued
| Examples | Product | MS m/z [M + H]+ | HPLC Method | Rt min |
|---|---|---|---|---|
| 7.01.073 | 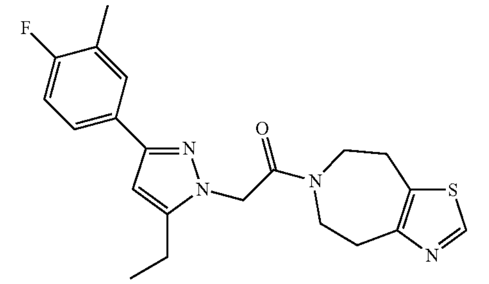 [SMILES: CCc1cc(-c2ccc(F)c(C)c2)nn1CC(=O)N1CCc2ncsc2CC1] | 399 | method AD | 0.74 |
| 7.01.074 | 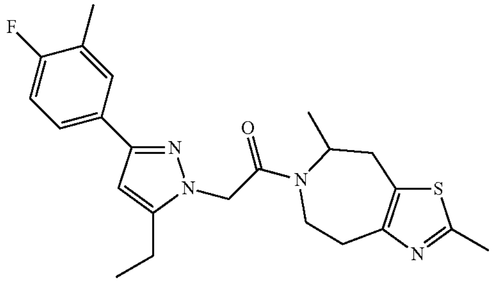 [SMILES: CCc1cc(-c2ccc(F)c(C)c2)nn1CC(=O)N1CCc2nc(C)sc2CC1C] | 427 | method AD | 0.74 |
| 7.01.075 | 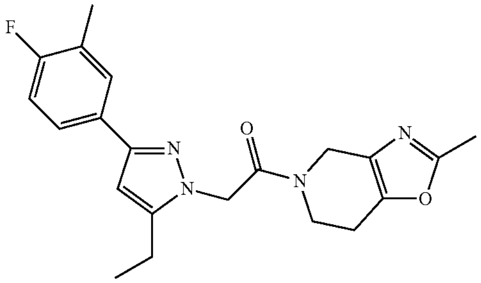 [SMILES: CCc1cc(-c2ccc(F)c(C)c2)nn1CC(=O)N1CCc2oc(C)nc2C1] | 383 | method AD | 0.71 |
| 7.01.076 | 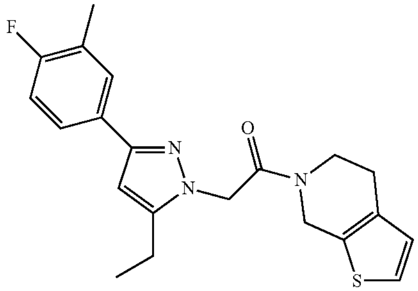 [SMILES: CCc1cc(-c2ccc(F)c(C)c2)nn1CC(=O)N1CCc2ccsc2C1] | 384 | method AD | 0.73 |
| 7.01.077 | 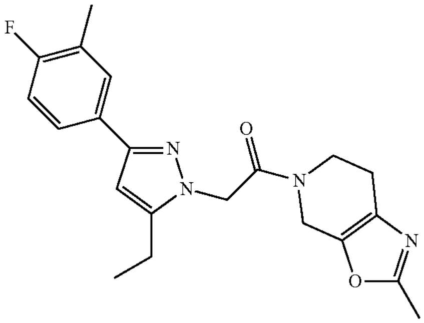 [SMILES: CCc1cc(-c2ccc(F)c(C)c2)nn1CC(=O)N1CCc2nc(C)oc2C1] | 383 | method AD | 0.71 |

-continued
| Examples | Product | MS m/z [M + H]+ | HPLC Method | Rt min |
|---|---|---|---|---|
| 7.01.078 | 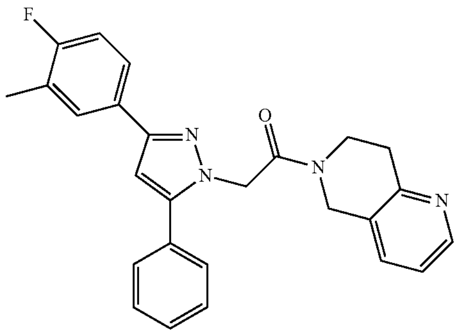 [SMILES: Cc1cc(-c2cc(-c3ccccc3)n(CC(=O)N3CCc4ncccc4C3)n2)ccc1F] | 427 | method AD | 0.75 |
| 7.01.079 | 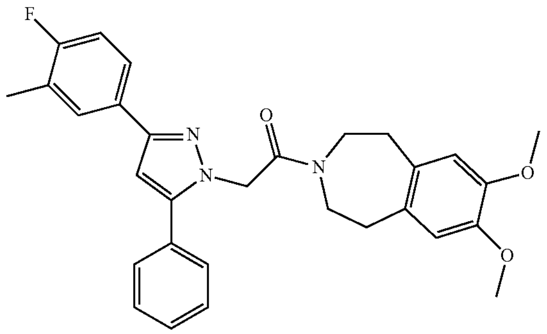 | 500 | method AD | 0.79 |
| 7.01.080 | 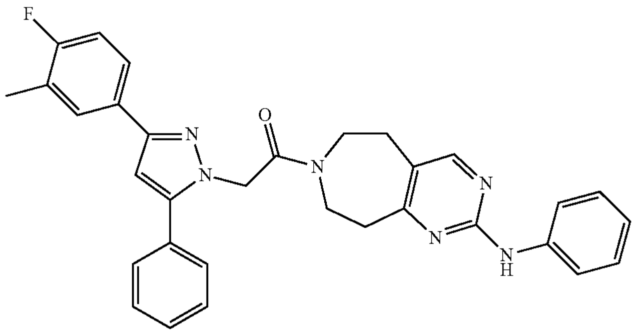 [SMILES: Cc1cc(-c2cc(-c3ccccc3)n(CC(=O)N3CCc4cnc(Nc5ccccc5)nc4CC3)n2)ccc1F] | 533 | method AD | 0.77 |
| 7.01.081 | 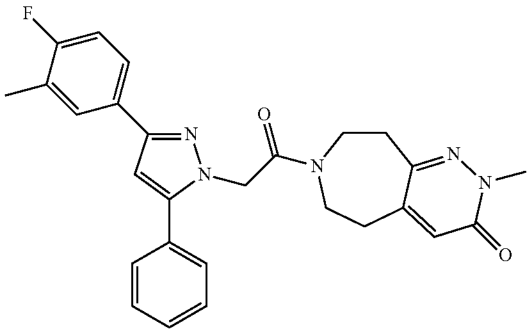 | 472 | method AF | 1.50 |

-continued
| Examples | Product | MS m/z [M + H]+ | HPLC Method | Rt min |
|---|---|---|---|---|
| 7.01.082 | 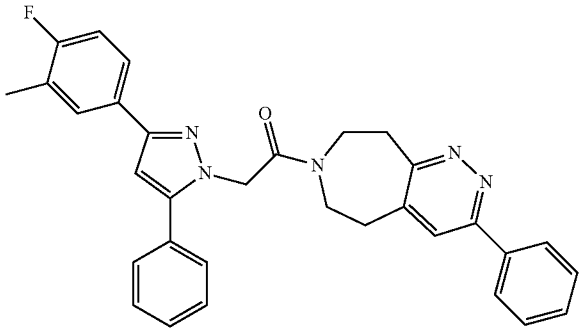 [SMILES: Cc1cc(-c2cc(-c3ccccc3)n(CC(=O)N3CCc4cc(-c5ccccc5)nnc4CC3)n2)ccc1F] | 518 | method AD | 0.76 |
| 7.01.083 | 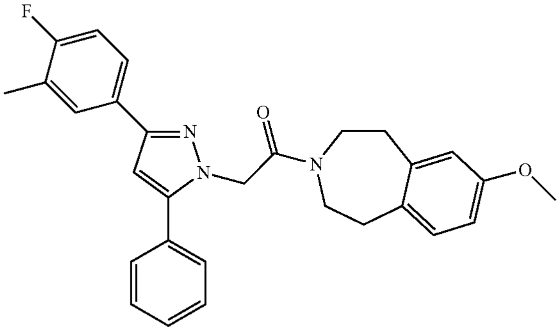 | 470 | method AD | 0.79 |
| 7.01.084 | 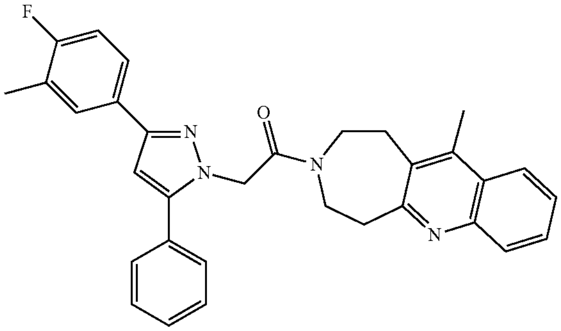 [SMILES: Cc1cc(-c2cc(-c3ccccc3)n(CC(=O)N3CCc4nc5ccccc5c(C)c4CC3)n2)ccc1F] | 505 | method AD | 0.75 |
| 7.01.085 | 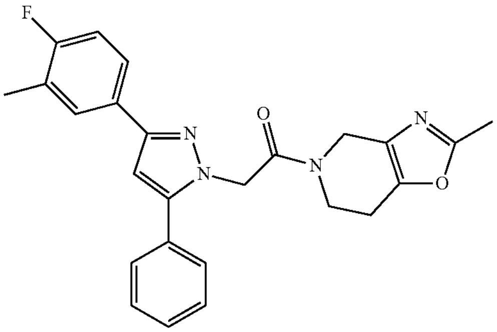 | 431 | method AD | 0.78 |

-continued
| Examples | Product | MS m/z [M + H]+ | HPLC Method | Rt min |
|---|---|---|---|---|
| 7.01.086 | 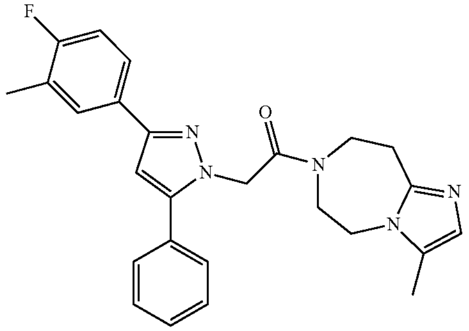 [SMILES: Cc1cc(-c2cc(-c3ccccc3)n(CC(=O)N3CCc4ncc(C)n4CC3)n2)ccc1F] | 444 | method AD | 0.76 |
| 7.01.087 | 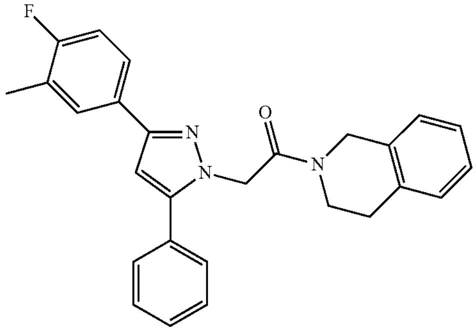 [SMILES: Cc1cc(-c2cc(-c3ccccc3)n(CC(=O)N3CCc4ccccc4C3)n2)ccc1F] | 426 | method AD | 0.80 |
| 7.01.088 | 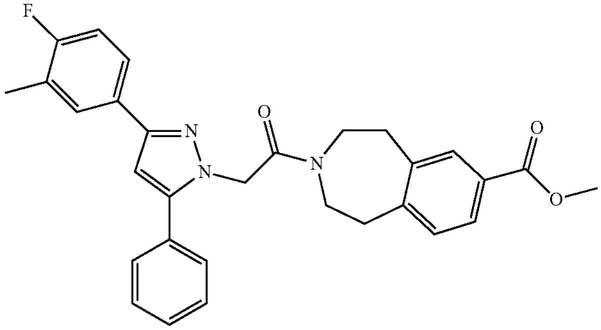 | 498 | method AD | 0.79 |
| 7.010.089 | 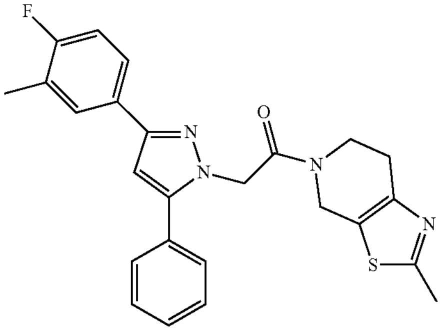 | 447 | method AD | 0.77 |

-continued
| Examples | Product | MS m/z $[M + H]^+$ | HPLC Method | Rt min |
|---|---|---|---|---|
| 7.01.090 | 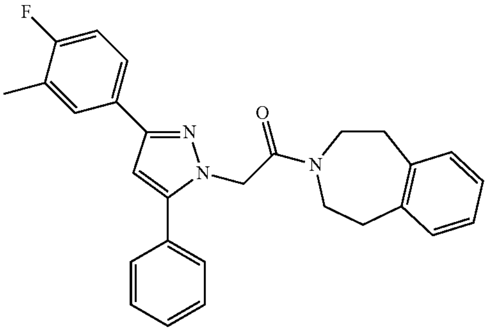 [SMILES: Cc1cc(-c2cc(-c3ccccc3)n(CC(=O)N3CCc4ccccc4CC3)n2)ccc1F] | 440 | method AD | 0.79 |
| 7.01.091 | 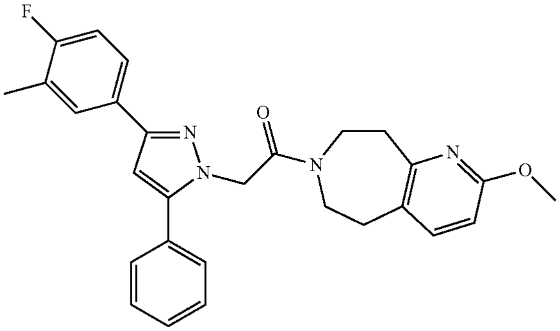 | 471 | method AD | 0.77 |
| 7.01.092 | 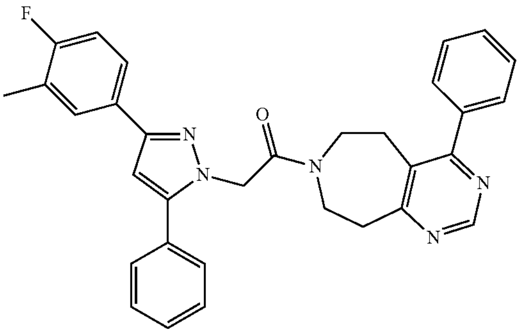 [SMILES: Cc1cc(-c2cc(-c3ccccc3)n(CC(=O)N3CCc4ncnc(-c5ccccc5)c4CC3)n2)ccc1F] | 518 | method AD | 0.78 |
| 7.01.093 | 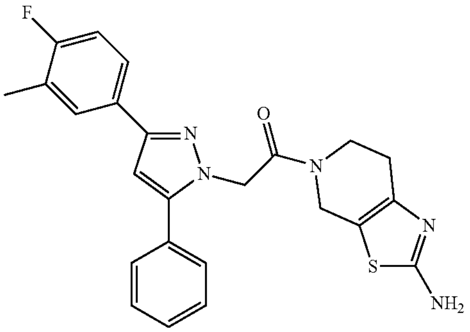 [SMILES: Cc1cc(-c2cc(-c3ccccc3)n(CC(=O)N3CCc4nc(N)sc4C3)n2)ccc1F] | 448 | method AD | 0.74 |

-continued
| Examples | Product | MS m/z [M + H]+ | HPLC Method | Rt min |
|---|---|---|---|---|
| 7.01.094 | 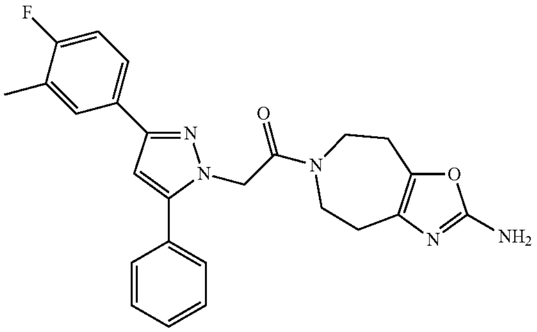 [SMILES: Cc1cc(-c2cc(-c3ccccc3)n(CC(=O)N3CCc4nc(N)oc4CC3)n2)ccc1F] | 446 | method AD | 0.75 |
| 7.01.095 | 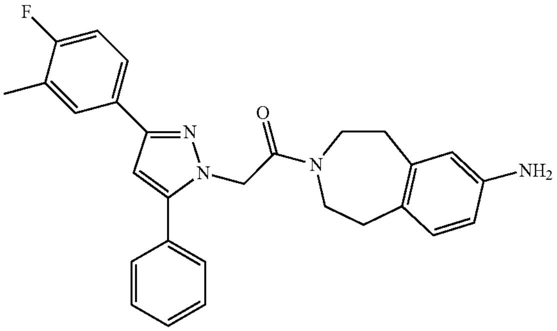 [SMILES: Cc1cc(-c2cc(-c3ccccc3)n(CC(=O)N3CCc4ccc(N)cc4CC3)n2)ccc1F] | 455 | method AD | 0.74 |
| 7.01.096 | 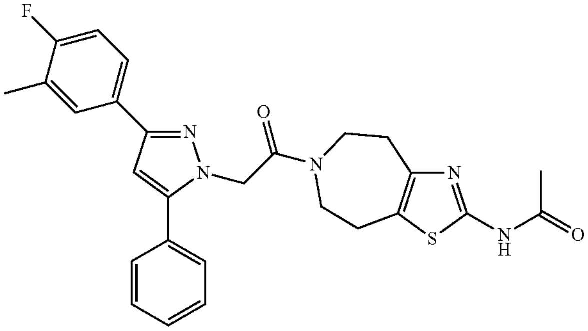 [SMILES: CC(=O)Nc1nc2c(s1)CCN(C(=O)Cn1nc(-c3ccc(F)c(C)c3)cc1-c1ccccc1)CC2] | 448 | method AD | 0.74 |
| 7.01.097 | 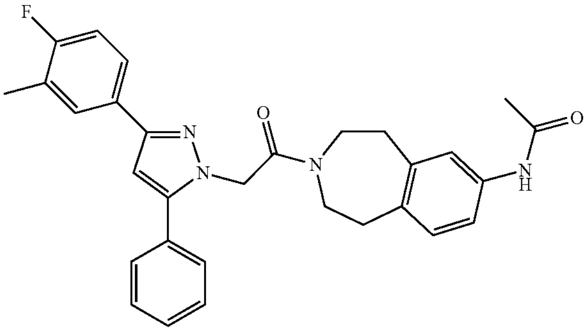 [SMILES: CC(=O)Nc1ccc2c(c1)CCN(C(=O)Cn1nc(-c3ccc(F)c(C)c3)cc1-c1ccccc1)CC2] | 497 | method AD | 0.77 |

-continued

| Examples | Product | MS m/z [M + H]+ | HPLC Method | Rt min |
|---|---|---|---|---|
| 7.01.098 | 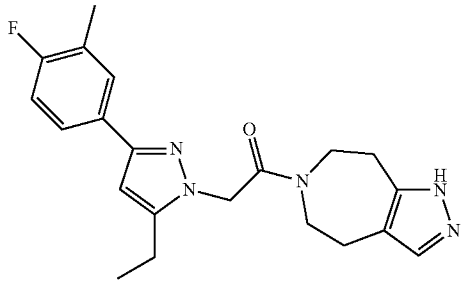 [SMILES: CCc1cc(-c2ccc(F)c(C)c2)nn1CC(=O)N1CCc2cn[nH]c2CC1] | 382 | method AD | 0.67 |

7.02.001 1-(2-Amino-4,5,7,8-tetrahydro-thiazolo (4,5-d) azepin-6-yl)-2-[3,5-bis-(4-fluoro-phenyl)-pyrazol-1-yl]-ethanone

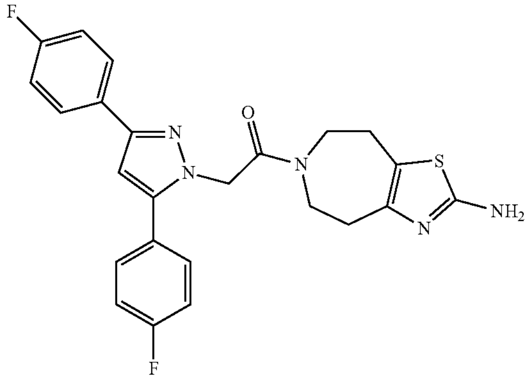 [SMILES: Nc1nc2c(s1)CCN(C(=O)Cn1nc(-c3ccc(F)cc3)cc1-c1ccc(F)cc1)CC2]

100 mg (3,5-bis-(4-fluoro-phenyl)-pyrazol-1-yl)-acetic acid was dissolved in 2 mL DMF. 165 mg PFTU and 170 μL DIPEA were added to this solution and the mixture was stirred for 15 min at RT. Then, 160 mg 5,6,7,8-Tetrahydro-4H-thiazolo (4,5-d) azepin-2-ylamine hydrobromide was added and the reaction was stirred over night. Then, $K_2CO_3$ solution (5%) and $CH_2Cl_2$ were added, the organic phase was separated and washed two times with water. The solvent was removed and the residue was purified by HPLC (method 1) to give 78 mg of the desired compound. $R_t$: 0.80 min (method C), $(M+H)^+$: 466

By using the same synthesis strategy as for 1-(2-Amino-4,5,7,8-tetrahydro-thiazolo (4,5-d) azepin-6-yl)-2-[3,5-bis-(4-fluoro-phenyl)-pyrazol-1-yl]-ethanone the following compounds were obtained:

| | | | | |
|---|---|---|---|---|
| 7.02.002 | 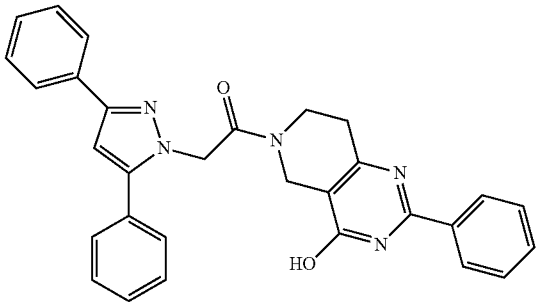 [SMILES: O=C(Cn1nc(-c2ccccc2)cc1-c1ccccc1)N1CCc2nc(-c3ccccc3)nc(O)c2C1] | 488 | method A | 2.09 |
| 7.02.003 | 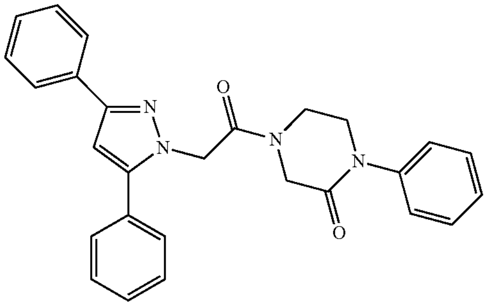 [SMILES: O=C(Cn1nc(-c2ccccc2)cc1-c1ccccc1)N1CCN(c2ccccc2)C(=O)C1] | 437 | method A | 2.06 |

-continued
| | | | | |
|---|---|---|---|---|
| 7.02.004 | 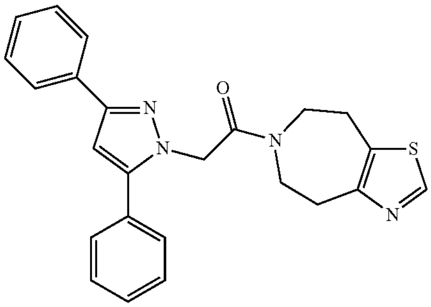 [SMILES: O=C(Cn1nc(-c2ccccc2)cc1-c1ccccc1)N1CCc2ncsc2CC1] | 415 | method A | 2.04 |
| 7.02.005 | 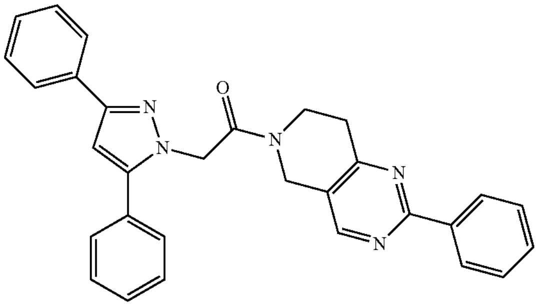 [SMILES: O=C(Cn1nc(-c2ccccc2)cc1-c1ccccc1)N1CCc2nc(-c3ccccc3)ncc2C1] | 472 | method A | 2.16 |
| 7.02.006 | 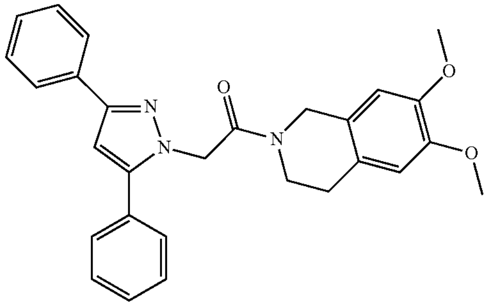 [SMILES: COc1cc2c(cc1OC)CN(C(=O)Cn1nc(-c3ccccc3)cc1-c1ccccc1)CC2] | 454 | method A | 2.10 |
| 7.02.007 | 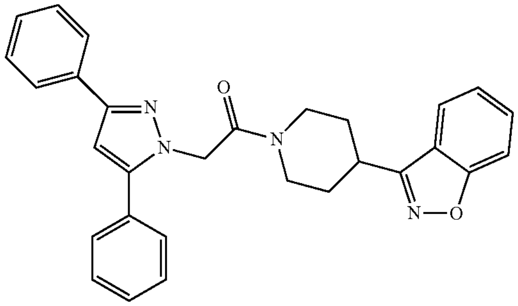 [SMILES: O=C(Cn1nc(-c2ccccc2)cc1-c1ccccc1)N1CCC(c2noc3ccccc23)CC1] | 463 | method A | 2.13 |
| 7.02.008 | 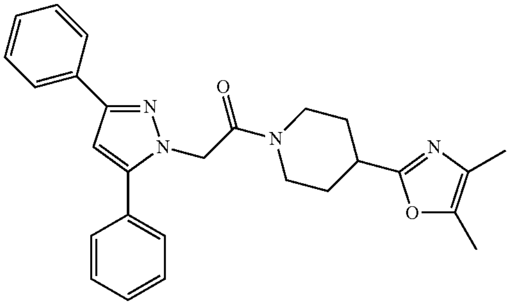 [SMILES: Cc1nc(C2CCN(C(=O)Cn3nc(-c4ccccc4)cc3-c3ccccc3)CC2)oc1C] | 441 | method A | 2.11 |

-continued
| | | | | |
|---|---|---|---|---|
| 7.02.009 | 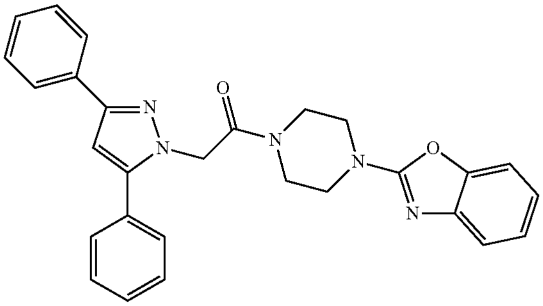 [SMILES: O=C(Cn1nc(-c2ccccc2)cc1-c1ccccc1)N1CCN(c2nc3ccccc3o2)CC1] | 464 | method A | 2.13 |
| 7.02.010 | 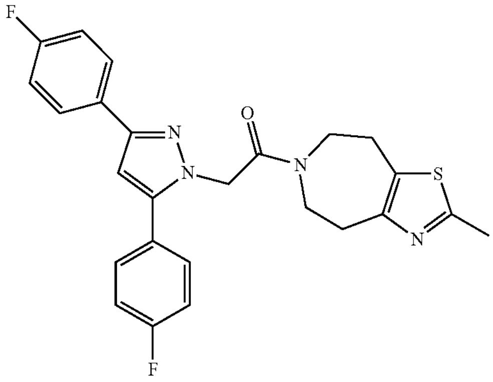 [SMILES: Cc1nc2c(s1)CCN(C(=O)Cn1nc(-c3ccc(F)cc3)cc1-c1ccc(F)cc1)CC2] | 465 | method C | 0.95 |
| 7.02.011 | 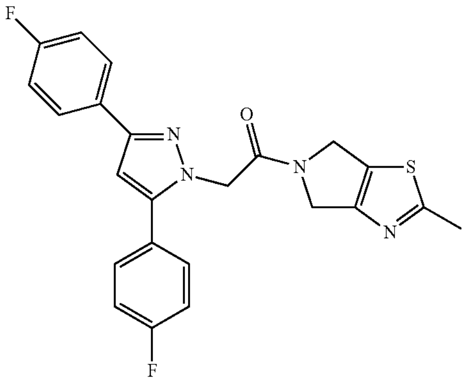 [SMILES: Cc1nc2c(s1)CN(C(=O)Cn1nc(-c3ccc(F)cc3)cc1-c1ccc(F)cc1)C2] | 437 | method C | 0.99 |
| 7.02.012 | 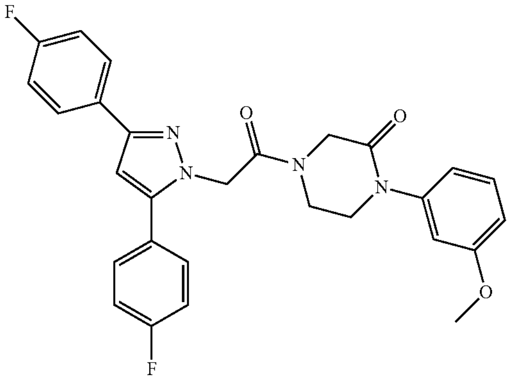 [SMILES: COc1cccc(N2CCN(C(=O)Cn3nc(-c4ccc(F)cc4)cc3-c3ccc(F)cc3)CC2=O)c1] | 503 | method C | 0.98 |

-continued
| | | | | |
|---|---|---|---|---|
| 7.02.013 | 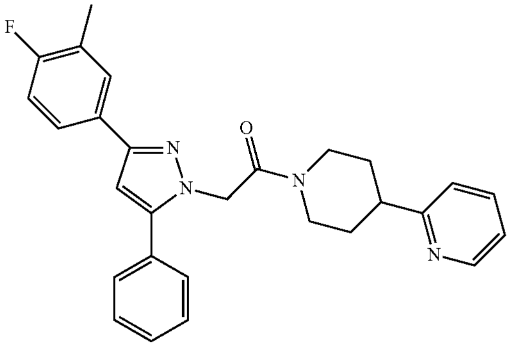 [SMILES: Cc1cc(-c2cc(-c3ccccc3)n(CC(=O)N3CCC(c4ccccn4)CC3)n2)ccc1F] | 455 | method I | 0.83 |
| 7.02.014 | 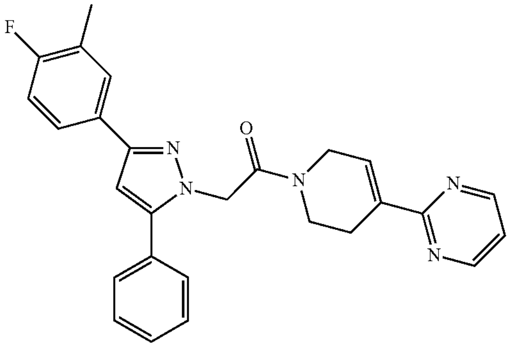 [SMILES: Cc1cc(-c2cc(-c3ccccc3)n(CC(=O)N3CC=C(c4ncccn4)CC3)n2)ccc1F] | 454 | method I | 0.98 |
| 7.02.015 | 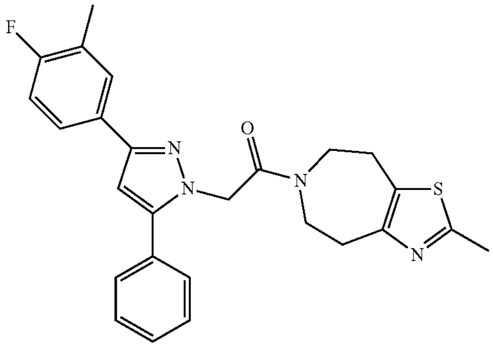 [SMILES: Cc1nc2c(s1)CCN(C(=O)Cn1nc(-c3ccc(F)c(C)c3)cc1-c1ccccc1)CC2] | 461 | method I | 0.95 |
| 7.02.016 | 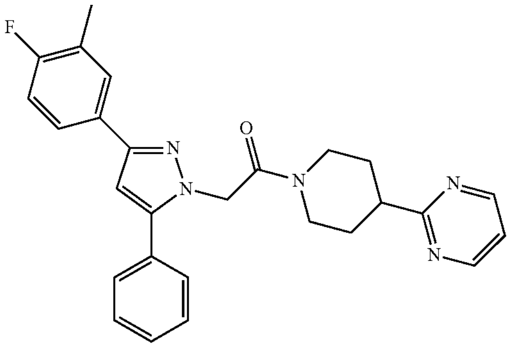 [SMILES: Cc1cc(-c2cc(-c3ccccc3)n(CC(=O)N3CCC(c4ncccn4)CC3)n2)ccc1F] | 456 | method I | 0.97 |

-continued
| | | | | |
|---|---|---|---|---|
| 7.02.017 | 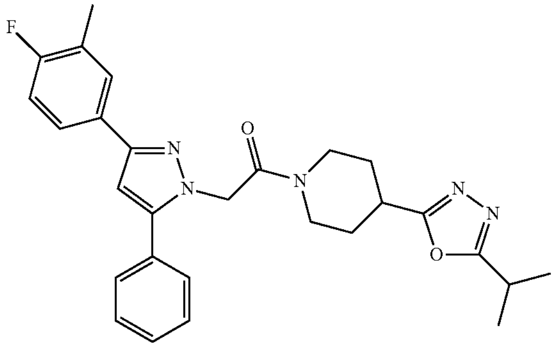 [SMILES: Cc1cc(-c2cc(-c3ccccc3)n(CC(=O)N3CCC(c4nnc(C(C)C)o4)CC3)n2)ccc1F] | 488 | method I | 0.99 |
| 7.02.018 | 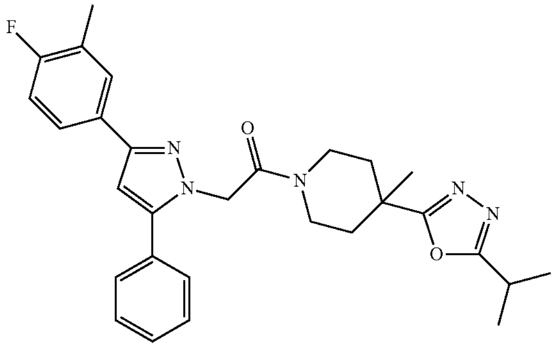 | 502 | method I | 1.00 |
| 7.02.019 | 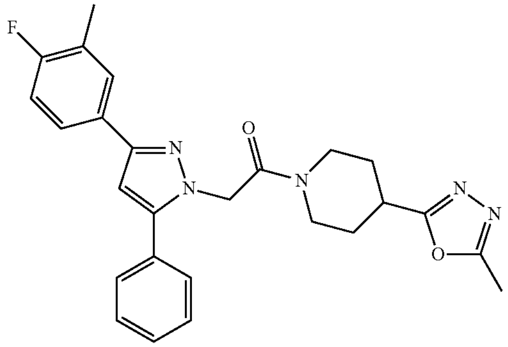 [SMILES: Cc1nnc(C2CCN(C(=O)Cn3nc(-c4ccc(F)c(C)c4)cc3-c3ccccc3)CC2)o1] | 460 | method I | 0.94 |
| 7.02.020 | 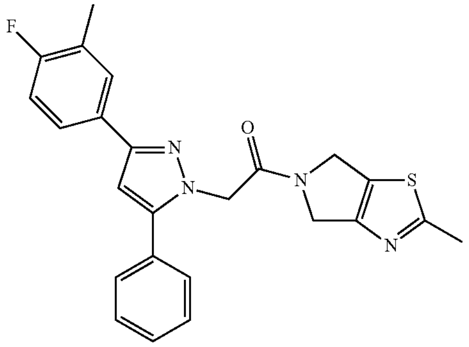 [SMILES: Cc1nc2c(s1)CN(C(=O)Cn1nc(-c3ccc(F)c(C)c3)cc1-c1ccccc1)C2] | 433 | method I | 0.98 |

-continued
| | | | | |
|---|---|---|---|---|
| 7.02.021 | 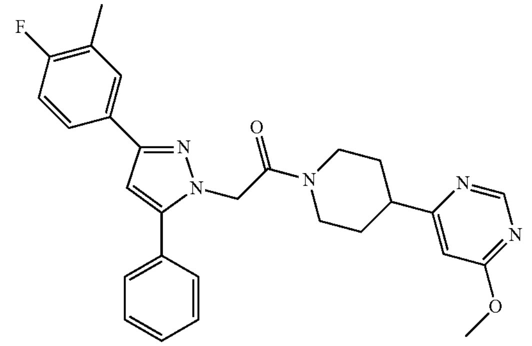 | 486 | method I | 0.99 |
| 7.02.022 | 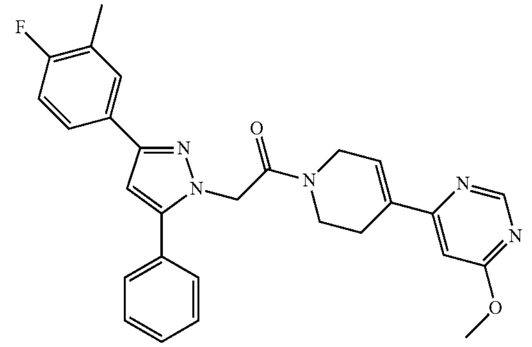 [SMILES: COc1cc(C2=CCN(C(=O)Cn3nc(-c4ccc(F)c(C)c4)cc3-c3ccccc3)CC2)ncn1] | 484 | method I | 1.00 |
| 7.02.023 | 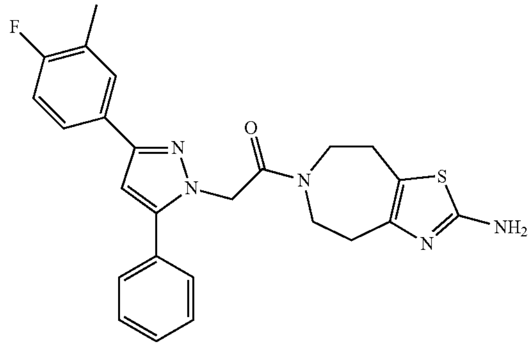 [SMILES: Cc1cc(-c2cc(-c3ccccc3)n(CC(=O)N3CCc4nc(N)sc4CC3)n2)ccc1F] | 462 | method I | 0.80 |
| 7.02.024 | 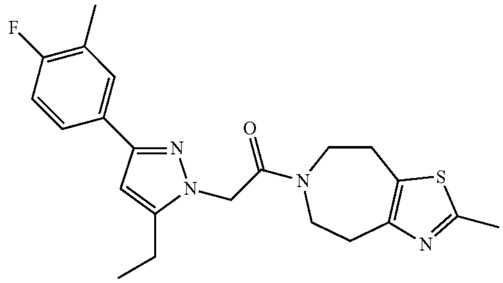 [SMILES: CCc1cc(-c2ccc(F)c(C)c2)nn1CC(=O)N1CCc2nc(C)sc2CC1] | 413 | method C | 0.83 |
| 7.02.025 | 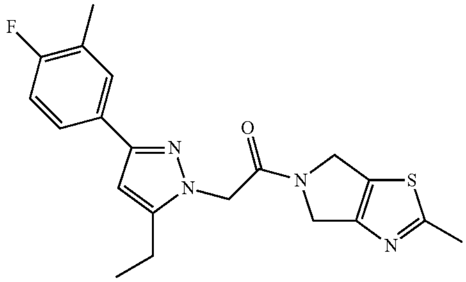 [SMILES: CCc1cc(-c2ccc(F)c(C)c2)nn1CC(=O)N1Cc2nc(C)sc2C1] | 385 | method C | 0.87 |

-continued
| | | | | |
|---|---|---|---|---|
| 7.02.026 | 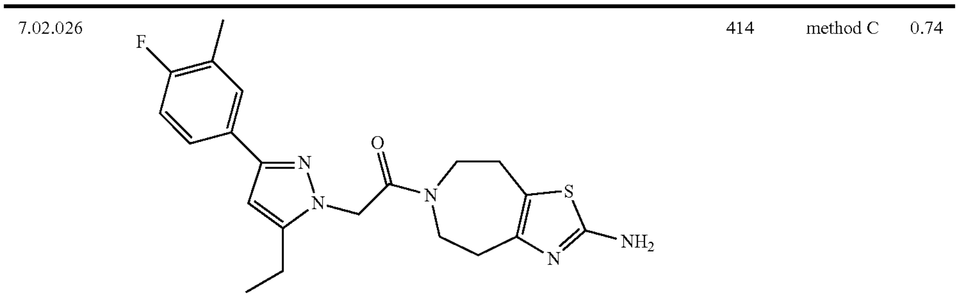 | 414 | method C | 0.74 |
| 7.02.027 | 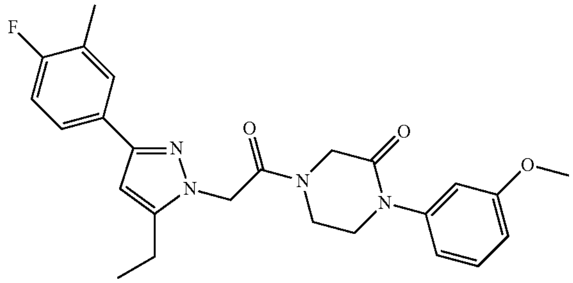 [SMILES: CCc1cc(-c2ccc(F)c(C)c2)nn1CC(=O)N1CCN(c2cccc(OC)c2)C(=O)C1] | 451 | method C | 0.96 |
| 7.02.028 | 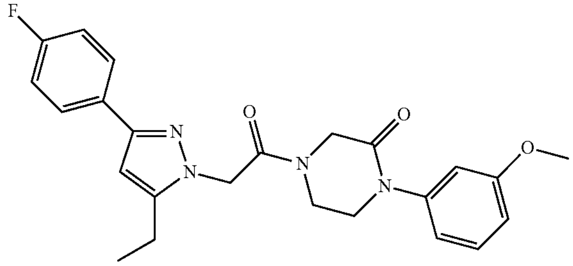 [SMILES: CCc1cc(-c2ccc(F)cc2)nn1CC(=O)N1CCN(c2cccc(OC)c2)C(=O)C1] | 437 | method C | 0.92 |
| 7.02.029 | 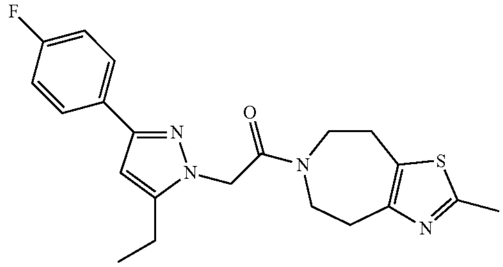 [SMILES: CCc1cc(-c2ccc(F)cc2)nn1CC(=O)N1CCc2nc(C)sc2CC1] | 399 | method I | 0.81 |
| 7.02.030 | 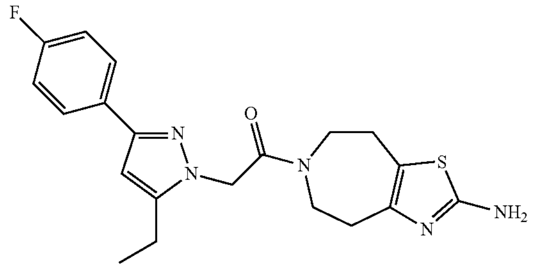 [SMILES: CCc1cc(-c2ccc(F)cc2)nn1CC(=O)N1CCc2nc(N)sc2CC1] | 400 | method I | 0.68 |

-continued
| | | | | |
|---|---|---|---|---|
| 7.02.031 | 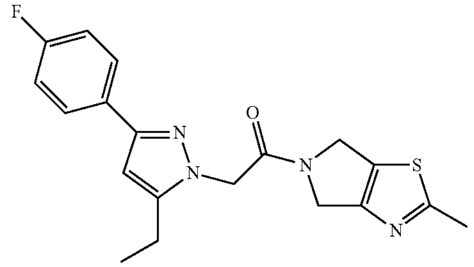 [SMILES: CCc1cc(-c2ccc(F)cc2)nn1CC(=O)N1Cc2nc(C)sc2C1] | 371 | method C | 0.81 |
| 7.02.032 | 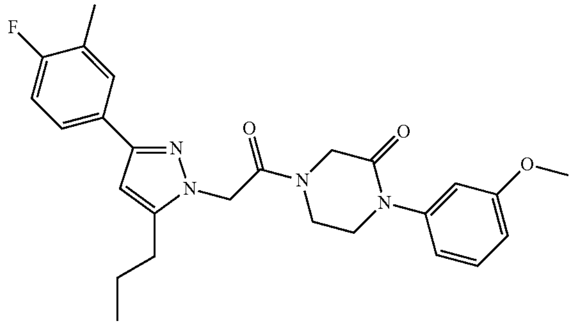 [SMILES: CCCc1cc(-c2ccc(F)c(C)c2)nn1CC(=O)N1CCN(c2cccc(OC)c2)C(=O)C1] | 465 | method I | 1.01 |
| 7.02.033 | 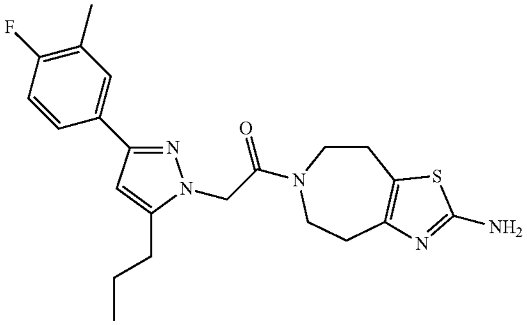 [SMILES: CCCc1cc(-c2ccc(F)c(C)c2)nn1CC(=O)N1CCc2nc(N)sc2CC1] | 428 | method I | 0.85 |
| 7.02.034 | 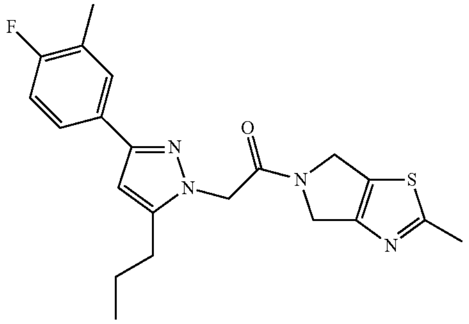 [SMILES: CCCc1cc(-c2ccc(F)c(C)c2)nn1CC(=O)N1Cc2nc(C)sc2C1] | 399 | method I | 1.01 |
| 7.02.035 | 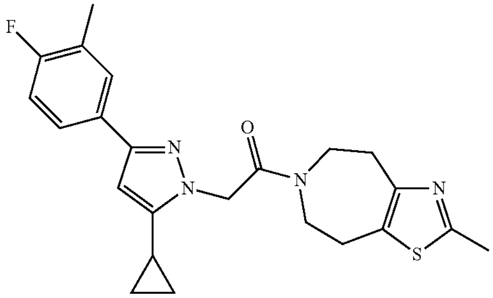 [SMILES: Cc1nc2c(s1)CCN(C(=O)Cn1nc(-c3ccc(F)c(C)c3)cc1C1CC1)CC2] | 425 | method M | 0.54 |

-continued
| | | | | |
|---|---|---|---|---|
| 7.02.036 | 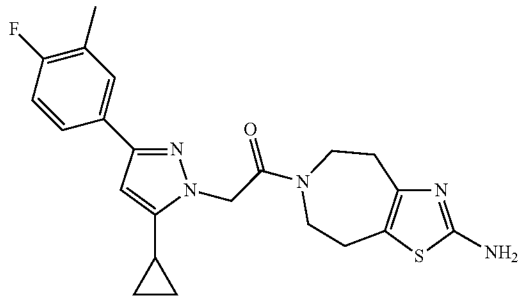 [SMILES: Cc1cc(-c2cc(C3CC3)n(CC(=O)N3CCc4nc(N)sc4CC3)n2)ccc1F] | 426 | method M | 0.50 |
| 7.02.037 | 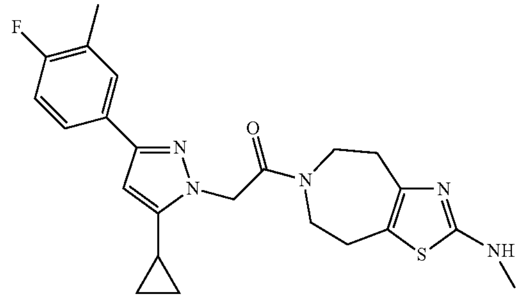 [SMILES: CNc1nc2c(s1)CCN(C(=O)Cn1nc(-c3ccc(F)c(C)c3)cc1C1CC1)CC2] | 440 | method L | 1.30 |
| 7.02.038 | 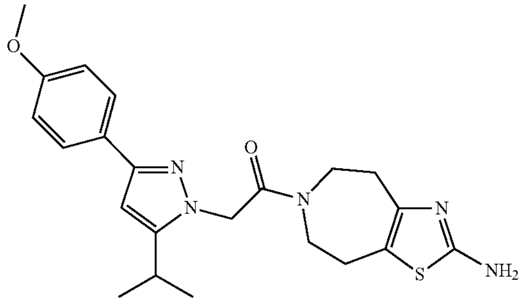 [SMILES: COc1ccc(-c2cc(C(C)C)n(CC(=O)N3CCc4nc(N)sc4CC3)n2)cc1] | 425 | method J | 1.30 |
| 7.02.039 | 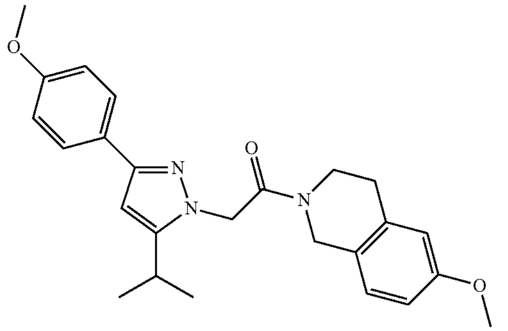 [SMILES: COc1ccc(-c2cc(C(C)C)n(CC(=O)N3CCc4cc(OC)ccc4C3)n2)cc1] | 420 | method J | 1.45 |
| 7.02.040 | 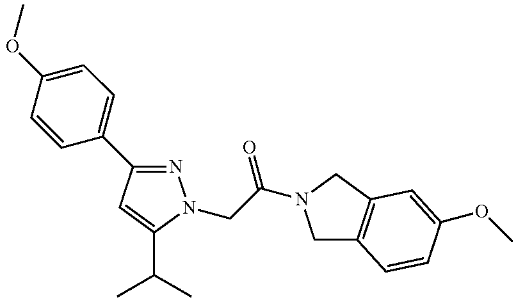 [SMILES: COc1ccc(-c2cc(C(C)C)n(CC(=O)N3Cc4ccc(OC)cc4C3)n2)cc1] | 406 | method J | 1.44 |

-continued
| | | | | |
|---|---|---|---|---|
| 7.02.041 | 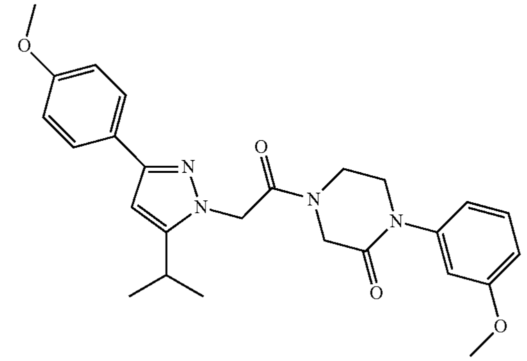 [SMILES: COc1ccc(-c2cc(C(C)C)n(CC(=O)N3CCN(c4cccc(OC)c4)C(=O)C3)n2)cc1] | 463 | method J | 1.35 |
| 7.02.042 | 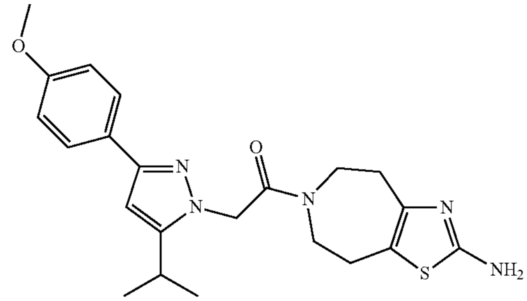 [SMILES: COc1ccc(-c2cc(C(C)C)n(CC(=O)N3CCc4nc(N)sc4CC3)n2)cc1] | 426 | method J | 1.20 |
| 7.02.043 | 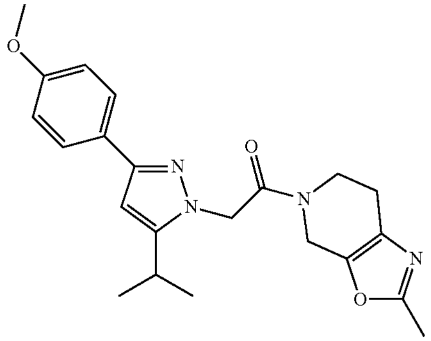 [SMILES: COc1ccc(-c2cc(C(C)C)n(CC(=O)N3CCc4nc(C)oc4C3)n2)cc1] | 395 | method J | 1.35 |
| 7.02.044 | 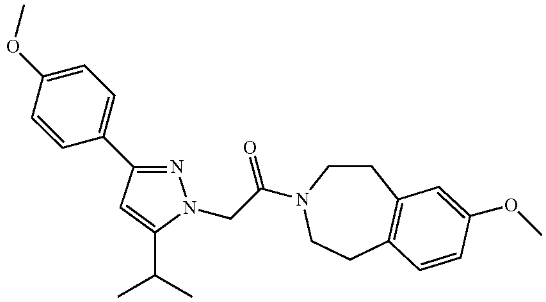 [SMILES: COc1ccc(-c2cc(C(C)C)n(CC(=O)N3CCc4ccc(OC)cc4CC3)n2)cc1] | 434 | method J | 1.48 |
| 7.02.045 | 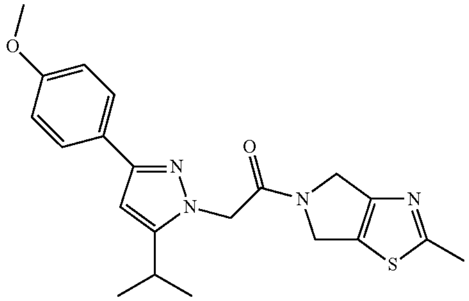 [SMILES: COc1ccc(-c2cc(C(C)C)n(CC(=O)N3Cc4nc(C)sc4C3)n2)cc1] | 397 | method J | 1.35 |

-continued
| | | | | |
|---|---|---|---|---|
| 7.02.046 | 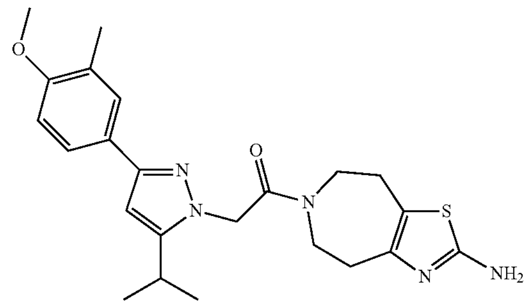 [SMILES: COc1ccc(-c2cc(C(C)C)n(CC(=O)N3CCc4nc(N)sc4CC3)n2)cc1C] | 440 | method J | 1.31 |
| 7.02.047 | 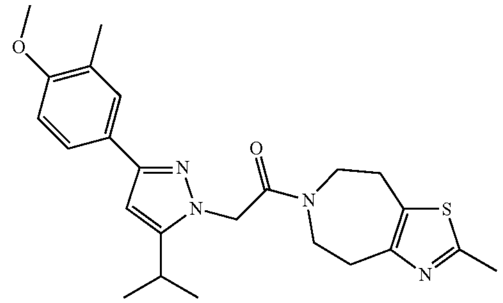 [SMILES: COc1ccc(-c2cc(C(C)C)n(CC(=O)N3CCc4nc(C)sc4CC3)n2)cc1C] | 439 | method J | 1.38 |
| 7.02.048 | 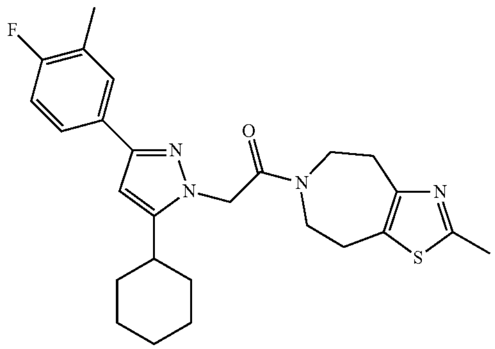 [SMILES: Cc1nc2c(s1)CCN(C(=O)Cn1nc(-c3ccc(F)c(C)c3)cc1C1CCCCC1)CC2] | 467 | method J | 1.57 |
| 7.02.049 | 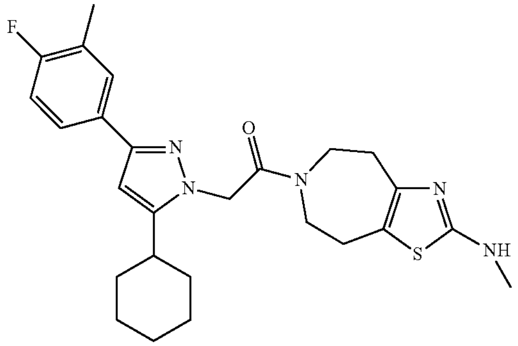 [SMILES: CNc1nc2c(s1)CCN(C(=O)Cn1nc(-c3ccc(F)c(C)c3)cc1C1CCCCC1)CC2] | 482 | method L | 1.46 |

-continued
| | | | | |
|---|---|---|---|---|
| 7.02.050 | 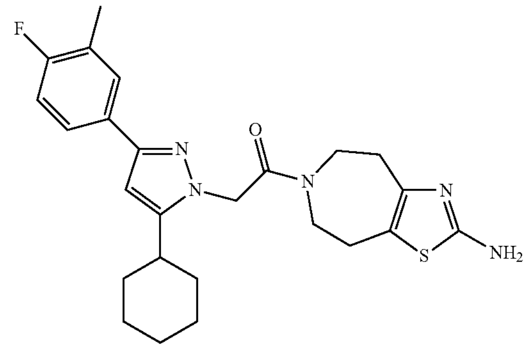 [SMILES: Cc1cc(-c2cc(C3CCCCC3)n(CC(=O)N3CCc4nc(N)sc4CC3)n2)ccc1F] | 468 | method J | 1.47 |
| 7.02.051 | 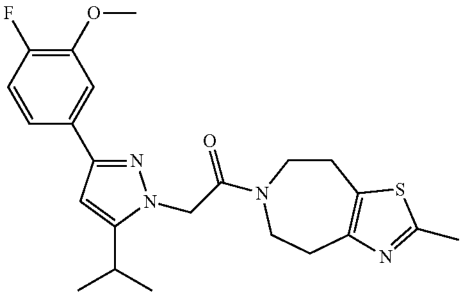 [SMILES: COc1cc(-c2cc(C(C)C)n(CC(=O)N3CCc4nc(C)sc4CC3)n2)ccc1F] | 443 | method L | 1.33 |
| 7.02.052 | 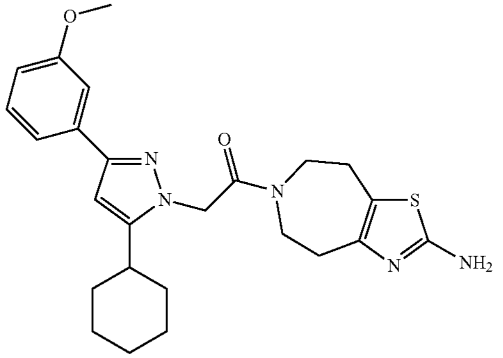 [SMILES: COc1cccc(-c2cc(C3CCCCC3)n(CC(=O)N3CCc4nc(N)sc4CC3)n2)c1] | 466 | method J | 1.37 |
| 7.02.053 | 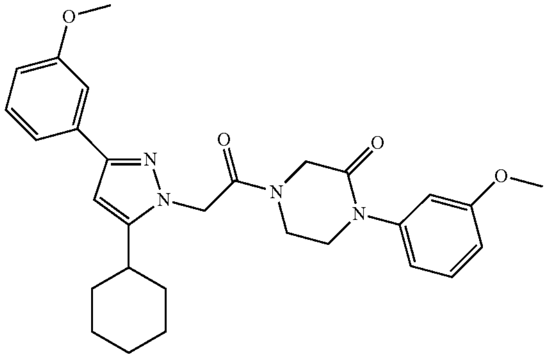 [SMILES: COc1cccc(-c2cc(C3CCCCC3)n(CC(=O)N3CCN(c4cccc(OC)c4)C(=O)C3)n2)c1] | 503 | method J | 1.50 |
| 7.02.054 | 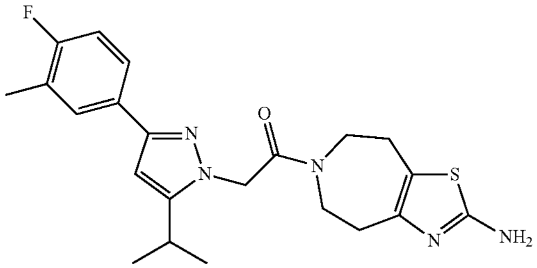 [SMILES: Cc1cc(-c2cc(C(C)C)n(CC(=O)N3CCc4nc(N)sc4CC3)n2)ccc1F] | 428 | method J | 1.34 |

-continued
| | | | | |
|---|---|---|---|---|
| 7.02.055 | 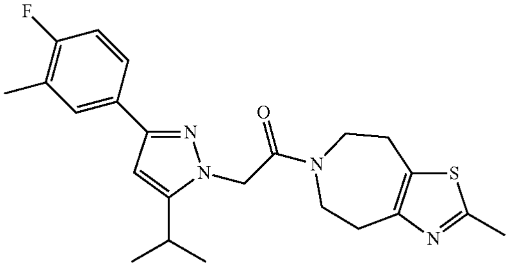 | 427 | method J | 1.44 |
| 7.02.056 | 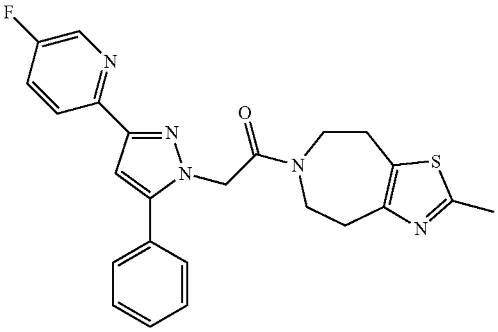 [SMILES: Cc1nc2c(s1)CCN(C(=O)Cn1nc(-c3ccc(F)cn3)cc1-c1ccccc1)CC2] | 448 | method C | 0.75 |
| 7.02.057 | 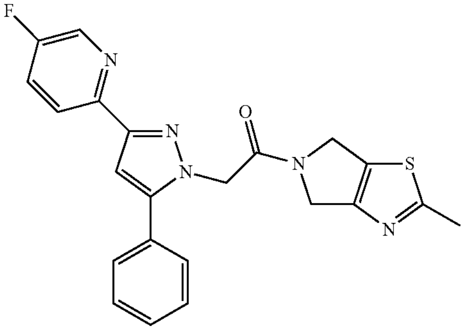 [SMILES: Cc1nc2c(s1)CN(C(=O)Cn1nc(-c3ccc(F)cn3)cc1-c1ccccc1)C2] | 421 | method C | 0.90 |
| 7.02.058 | 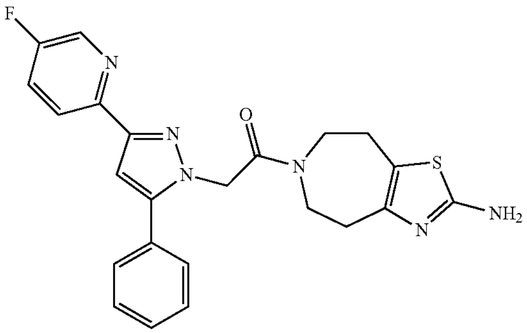 [SMILES: Nc1nc2c(s1)CCN(C(=O)Cn1nc(-c3ccc(F)cn3)cc1-c1ccccc1)CC2] | 449 | method C | 0.67 |

-continued
| | | | | |
|---|---|---|---|---|
| 7.02.059 | 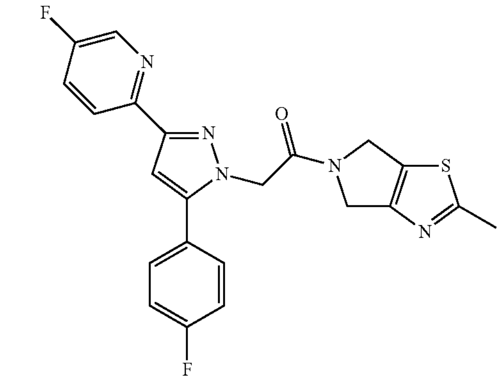 | 439 | method C | 0.92 |
| 7.02.060 | 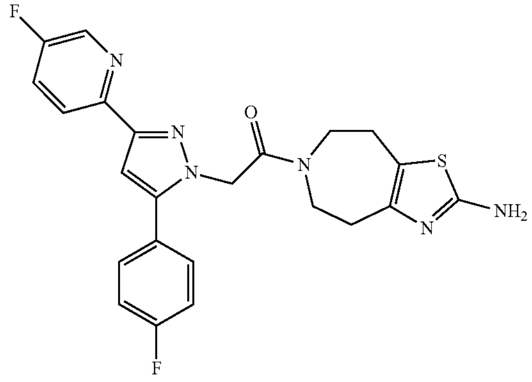 [SMILES: Nc1nc2c(s1)CCN(C(=O)Cn1nc(-c3ccc(F)cn3)cc1-c1ccc(F)cc1)CC2] | 467 | method C | 0.72 |
| 7.02.061 | 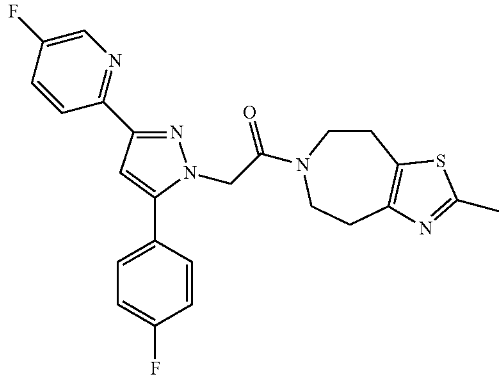 [SMILES: Cc1nc2c(s1)CCN(C(=O)Cn1nc(-c3ccc(F)cn3)cc1-c1ccc(F)cc1)CC2] | 466 | method I | 0.82 |
| 7.02.062 | 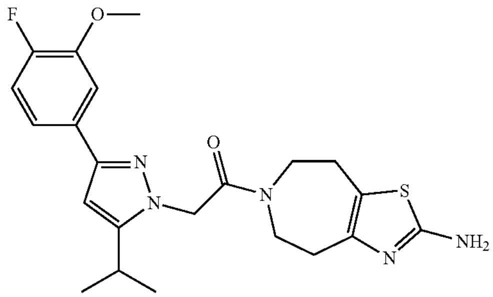 [SMILES: COc1cc(-c2cc(C(C)C)n(CC(=O)N3CCc4nc(N)sc4CC3)n2)ccc1F] | 444 | method L | 1.25 |

-continued
| | | | | |
|---|---|---|---|---|
| 7.02.063 | 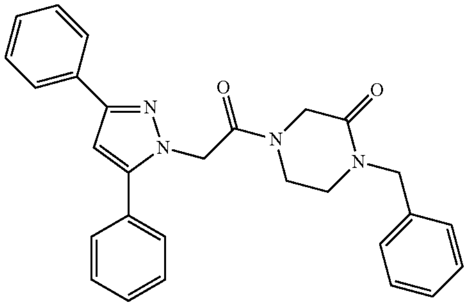 [SMILES: O=C(Cn1nc(-c2ccccc2)cc1-c1ccccc1)N1CCN(Cc2ccccc2)C(=O)C1] | 451 | method A | 2.08 |
| 7.02.064 | 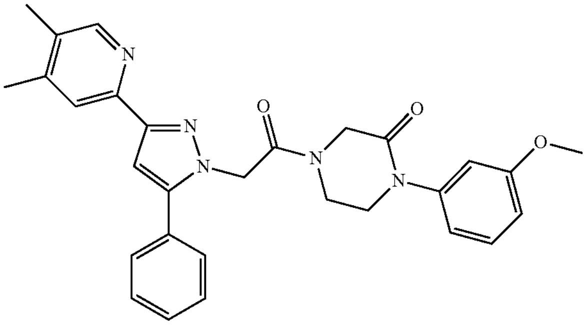 | 496 | method I | 0.73 |
| 7.02.065 | 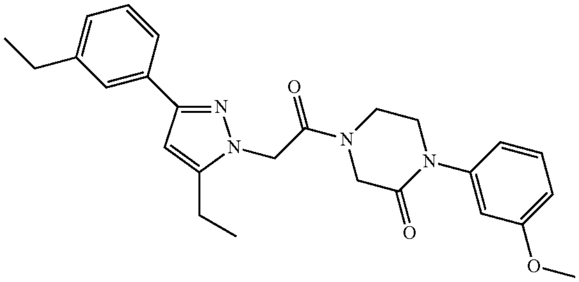 [SMILES: CCc1cccc(-c2cc(CC)n(CC(=O)N3CCN(c4cccc(OC)c4)C(=O)C3)n2)c1] | 447 | method U | 0.81 |
| 7.02.066 | 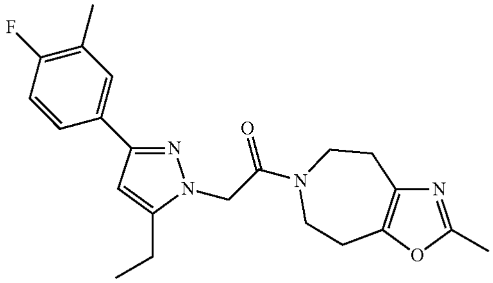 [SMILES: CCc1cc(-c2ccc(F)c(C)c2)nn1CC(=O)N1CCc2nc(C)oc2CC1] | 397 | method U | 0.74 |
| 7.02.067 | 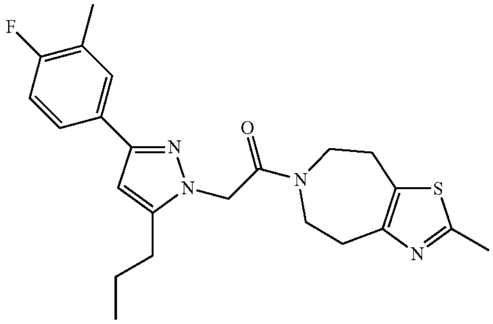 [SMILES: CCCc1cc(-c2ccc(F)c(C)c2)nn1CC(=O)N1CCc2nc(C)sc2CC1] | 427 | method I | 1.00 |

-continued
| | | | | |
|---|---|---|---|---|
| 7.02.068 | 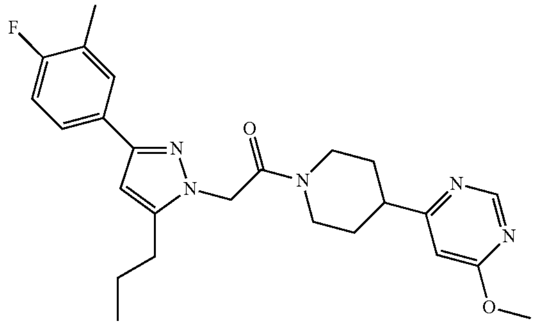 [SMILES: CCCc1cc(-c2ccc(F)c(C)c2)nn1CC(=O)N1CCC(c2cc(OC)ncn2)CC1] | 452 | method I | 1.04 |
| 7.02.069 | 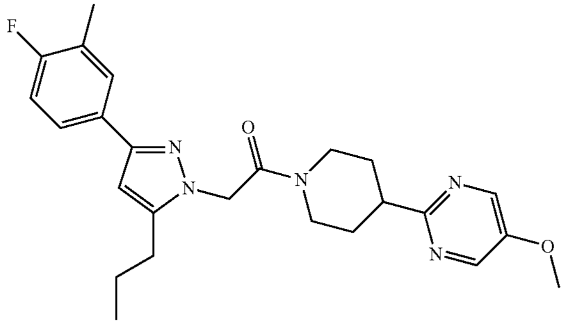 [SMILES: CCCc1cc(-c2ccc(F)c(C)c2)nn1CC(=O)N1CCC(c2ncc(OC)cn2)CC1] | 452 | method I | 1.04 |
| 7.02.070 | 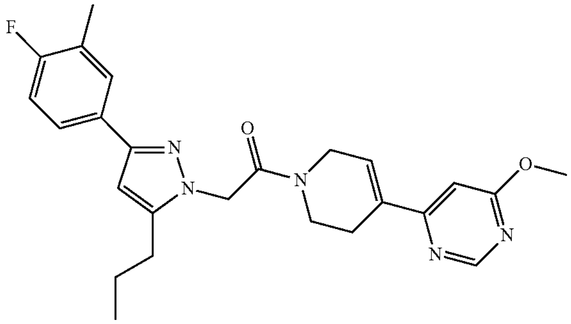 [SMILES: CCCc1cc(-c2ccc(F)c(C)c2)nn1CC(=O)N1CC=C(c2cc(OC)ncn2)CC1] | 450 | method I | 1.06 |
| 7.02.071 | 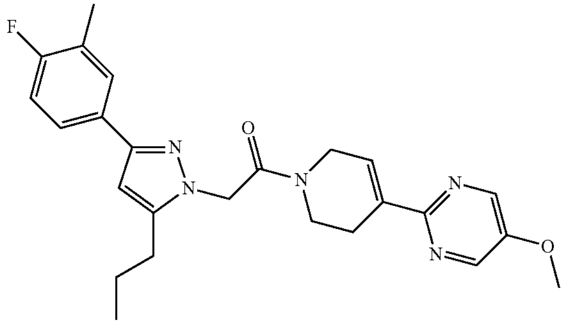 [SMILES: CCCc1cc(-c2ccc(F)c(C)c2)nn1CC(=O)N1CC=C(c2ncc(OC)cn2)CC1] | 450 | method I | 1.06 |
| 7.02.072 | 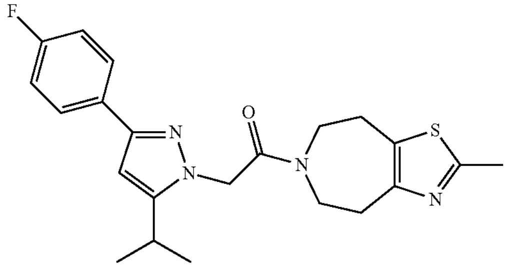 [SMILES: Cc1nc2c(s1)CCN(C(=O)Cn1nc(-c3ccc(F)cc3)cc1C(C)C)CC2] | 413 | method U | 0.79 |

-continued
| | | | | |
|---|---|---|---|---|
| 7.02.073 | 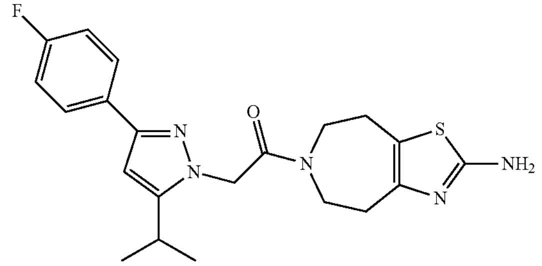 [SMILES: CC(C)c1cc(-c2ccc(F)cc2)nn1CC(=O)N1CCc2nc(N)sc2CC1] | 414 | method U | 0.72 |
| 7.02.074 | 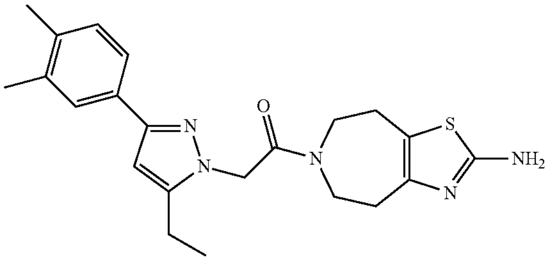 [SMILES: CCc1cc(-c2ccc(C)c(C)c2)nn1CC(=O)N1CCc2nc(N)sc2CC1] | 410 | method U | 0.75 |
| 7.02.075 | 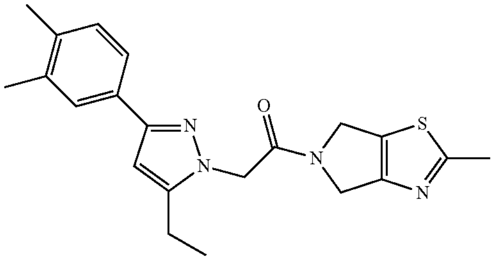 | 381 | method U | 0.85 |
| 7.02.076 | 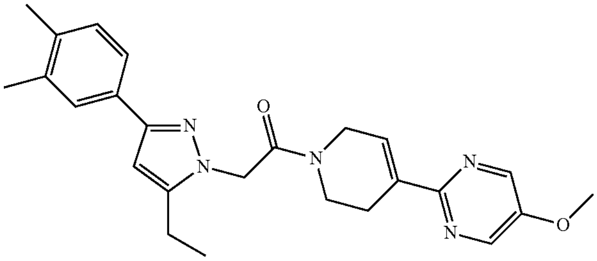 | 432 | method U | 0.88 |
| 7.02.077 | 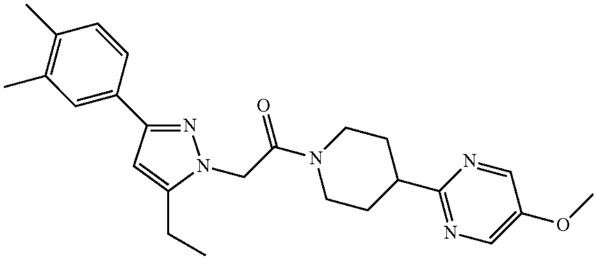 | 434 | method U | 0.85 |
| 7.02.078 | 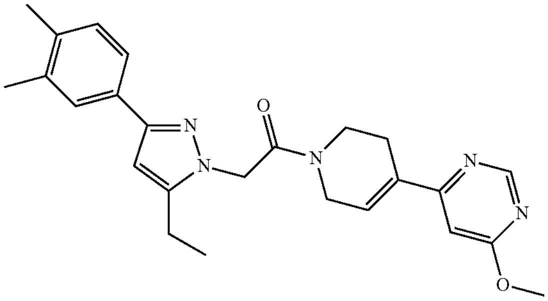 | 432 | method U | 0.88 |

-continued
| | | | | |
|---|---|---|---|---|
| 7.02.079 | 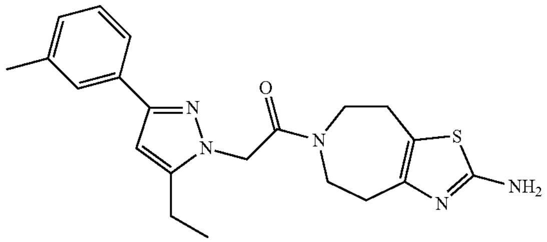 [SMILES: CCc1cc(-c2cccc(C)c2)nn1CC(=O)N1CCc2nc(N)sc2CC1] | 396 | method U | 0.70 |
| 7.02.080 | 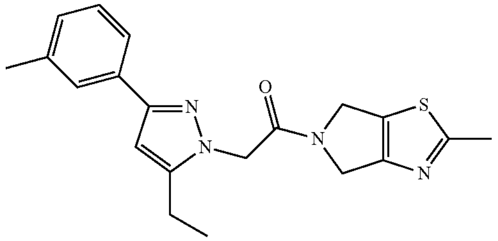 | 367 | method U | 0.80 |
| 7.02.081 | 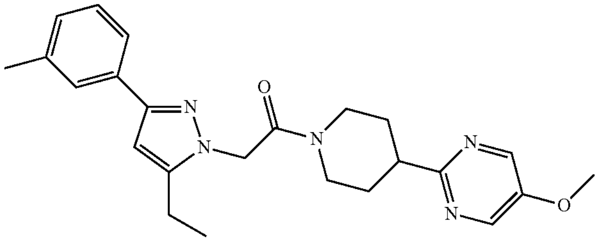 | 420 | method U | 0.82 |
| 7.02.082 | 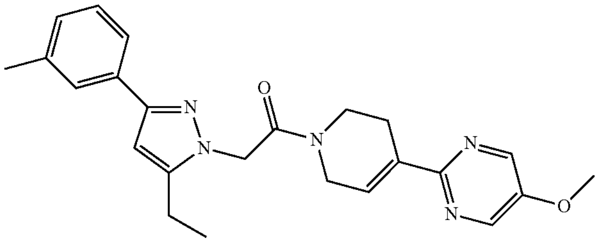 | 418 | method U | 0.84 |
| 7.02.083 | 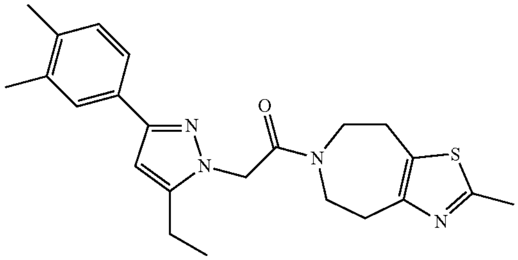 | 409 | method U | 0.81 |
| 7.02.084 | 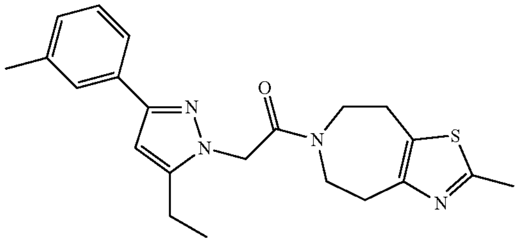 | 395 | method U | 0.77 |

-continued
| | | | | |
|---|---|---|---|---|
| 7.02.085 | 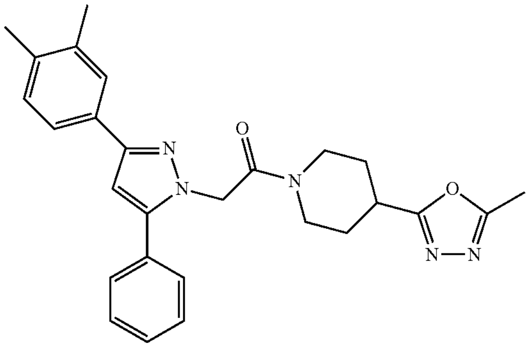 | 456 | method I | 1.00 |
| 7.02.086 | 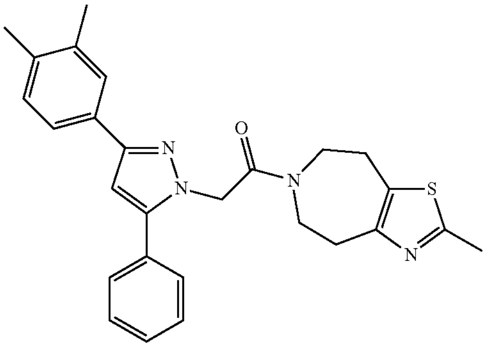 | 457 | method I | 1.00 |
| 7.02.087 | 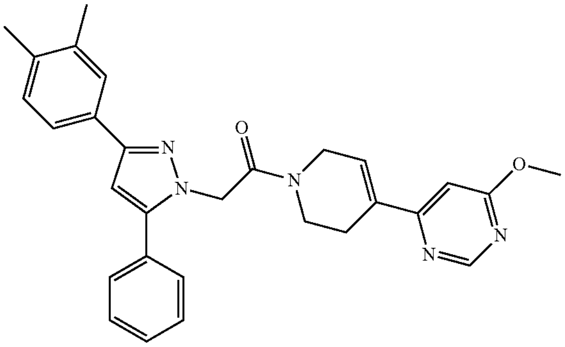 | 480 | method I | 1.06 |
| 7.02.088 | 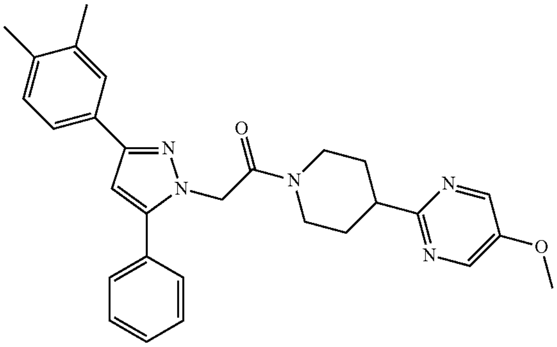 | 482 | method I | 1.04 |

-continued
| | | | | |
|---|---|---|---|---|
| 7.02.089 | 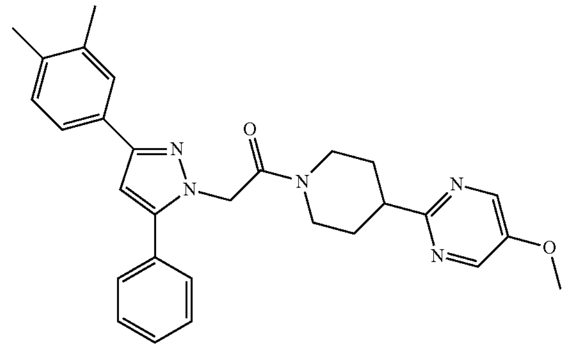 | 480 | method I | 1.05 |
| 7.02.090 | 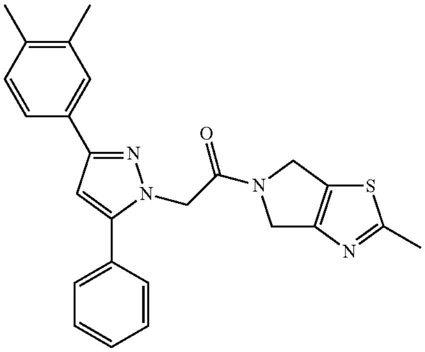 [SMILES: Cc1nc2c(s1)CN(C(=O)Cn1nc(-c3ccc(C)c(C)c3)cc1-c1ccccc1)C2] | 429 | method F | 1.53 |
| 7.02.091 | 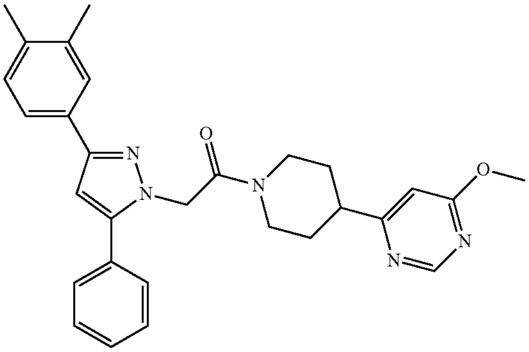 [SMILES: COc1cc(C2CCN(C(=O)Cn3nc(-c4ccc(C)c(C)c4)cc3-c3ccccc3)CC2)ncn1] | 482 | method I | 1.04 |
| 7.02.092 | 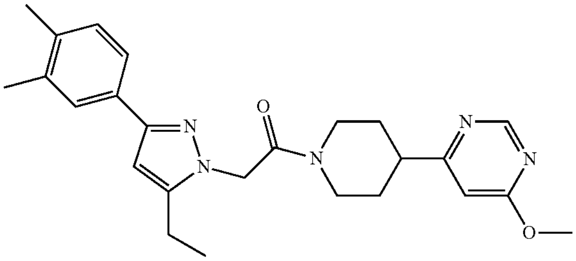 | 434 | method U | 0.84 |
| 7.02.093 | 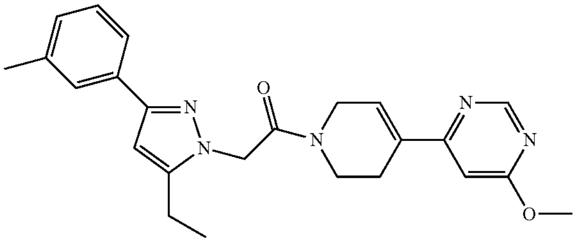 | 418 | method U | 0.83 |

-continued
| | | | | |
|---|---|---|---|---|
| 7.02.094 | 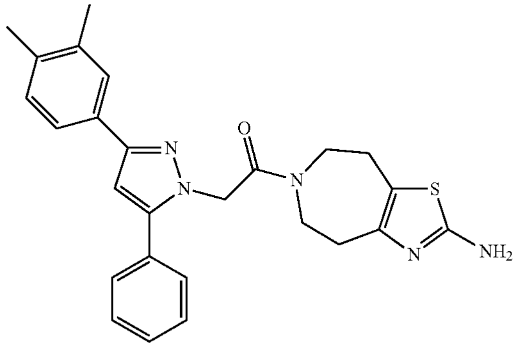 [SMILES: Cc1ccc(-c2cc(-c3ccccc3)n(CC(=O)N3CCc4nc(N)sc4CC3)n2)cc1C] | 458 | method I | 0.86 |
| 7.02.095 | 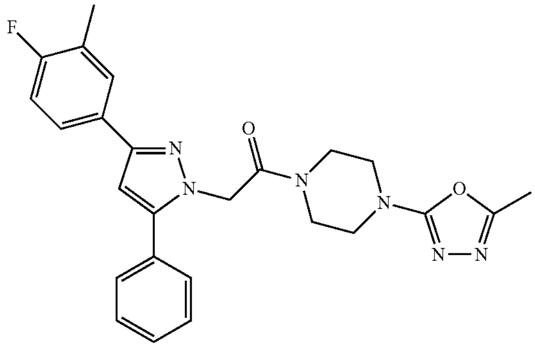 [SMILES: Cc1nnc(N2CCN(C(=O)Cn3nc(-c4ccc(F)c(C)c4)cc3-c3ccccc3)CC2)o1] | 461 | method I | 0.96 |
| 7.02.096 | 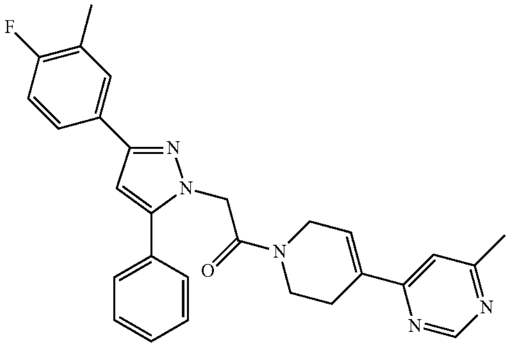 [SMILES: Cc1cc(C2=CCN(C(=O)Cn3nc(-c4ccc(F)c(C)c4)cc3-c3ccccc3)CC2)ncn1] | 468 | method I | 0.99 |
| 7.02.097 | 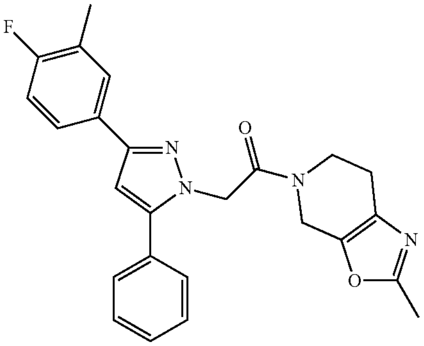 [SMILES: Cc1nc2c(o1)CN(C(=O)Cn1nc(-c3ccc(F)c(C)c3)cc1-c1ccccc1)CC2] | 431 | method I | 0.99 |

-continued
| | | | | |
|---|---|---|---|---|
| 7.02.098 | 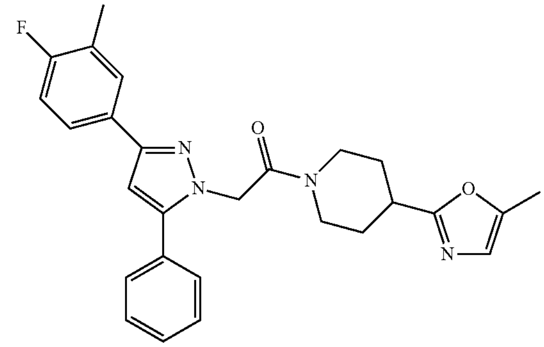 | 459 | method I | 1.01 |
| 7.02.099 | 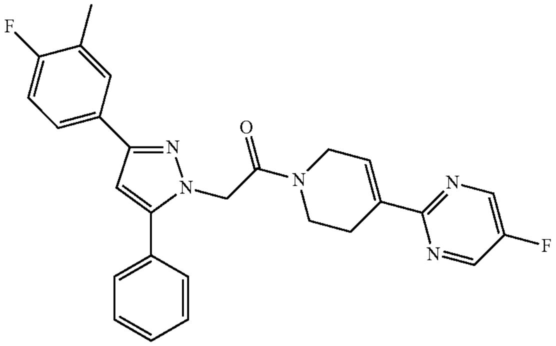 [SMILES: Cc1cc(-c2cc(-c3ccccc3)n(CC(=O)N3CC=C(c4ncc(F)cn4)CC3)n2)ccc1F] | 472 | method I | 1.04 |
| 7.02.100 | 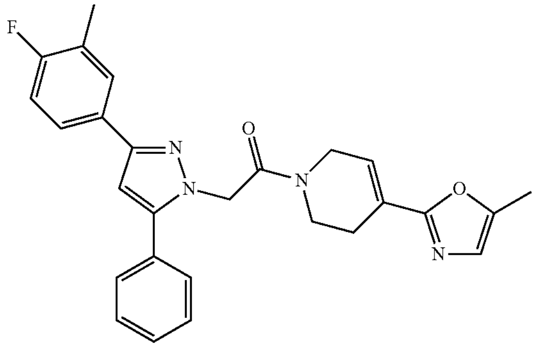 | 457 | method I | 1.02 |
| 7.02.101 | 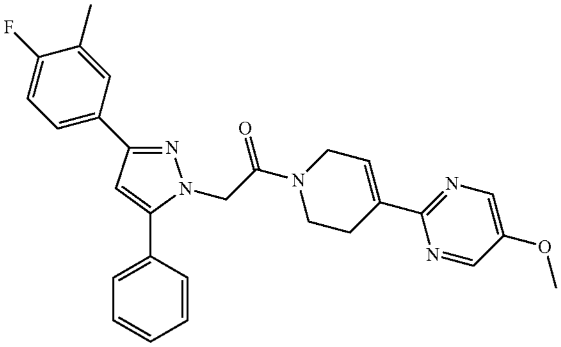 [SMILES: COc1cnc(C2=CCN(C(=O)Cn3nc(-c4ccc(F)c(C)c4)cc3-c3ccccc3)CC2)nc1] | 484 | method I | 1.03 |

-continued
| | | | | |
|---|---|---|---|---|
| 7.02.102 | 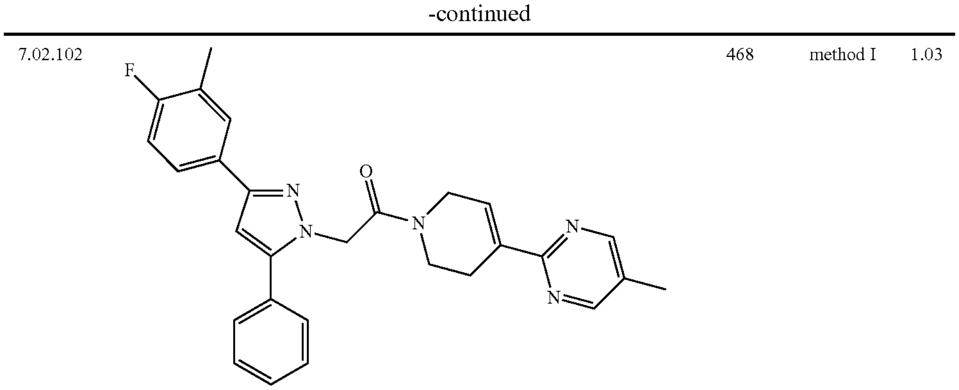 | 468 | method I | 1.03 |
| 7.02.103 | 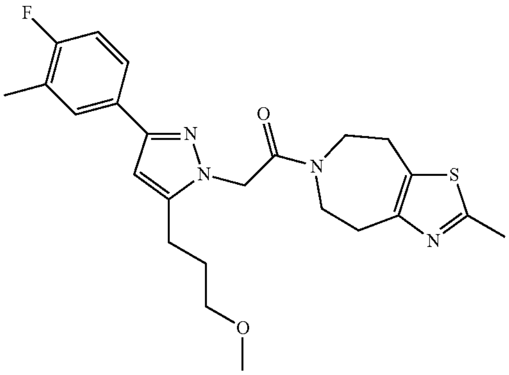 | 457 | method U | 0.77 |
| 7.02.104 | 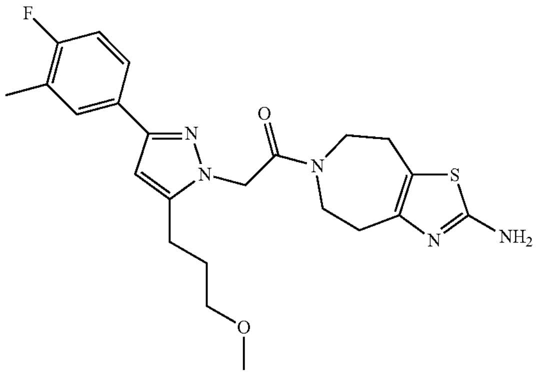 [SMILES: COCCCc1cc(-c2ccc(F)c(C)c2)nn1CC(=O)N1CCc2nc(N)sc2CC1] | 458 | method U | 0.69 |
| 7.02.105 | 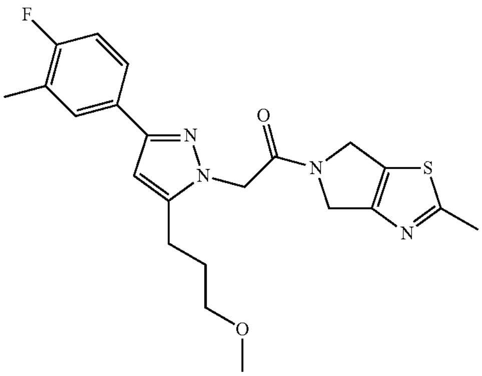 | 429 | method U | 0.79 |

-continued
| | | | | |
|---|---|---|---|---|
| 7.02.106 | 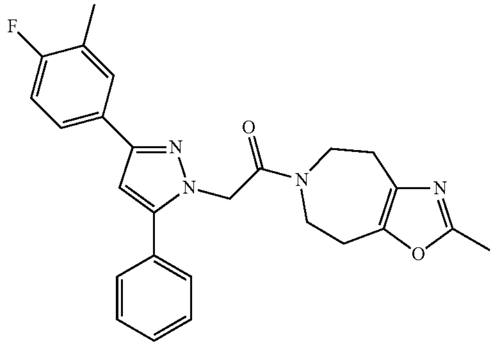 [SMILES: Cc1nc2c(o1)CCN(C(=O)Cn1nc(-c3ccc(F)c(C)c3)cc1-c1ccccc1)CC2] | 445 | method X | 0.85 |
| 7.02.107 | 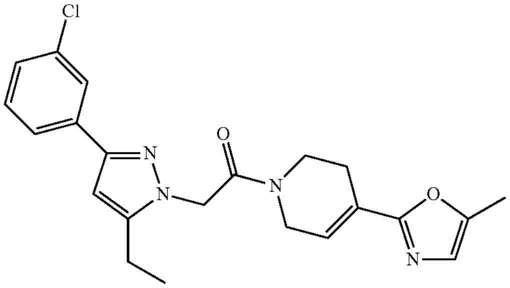 [SMILES: CCc1cc(-c2cccc(Cl)c2)nn1CC(=O)N1CC=C(c2ncc(C)o2)CC1] | 411 | method X | 0.84 |
| 7.02.108 | 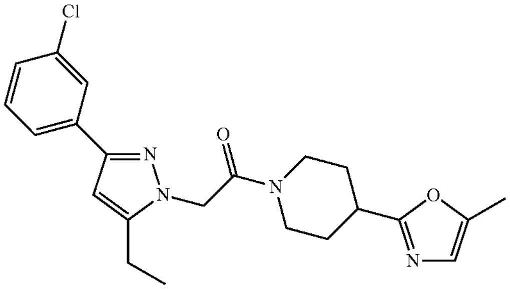 | 413 | method X | 0.83 |
| 7.02.109 | 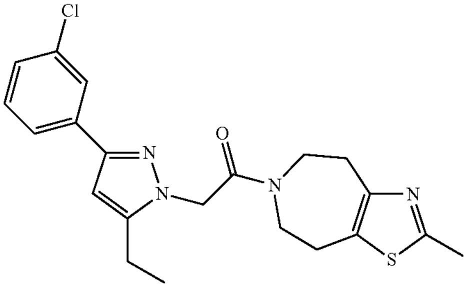 [SMILES: CCc1cc(-c2cccc(Cl)c2)nn1CC(=O)N1CCc2nc(C)sc2CC1] | 415 | method X | 0.77 |
| 7.02.110 | 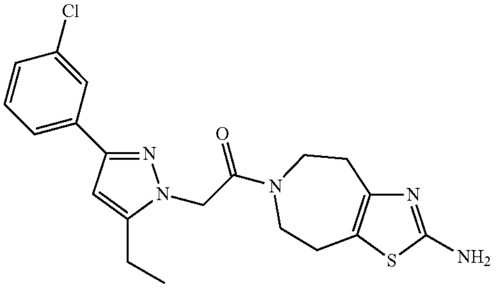 [SMILES: CCc1cc(-c2cccc(Cl)c2)nn1CC(=O)N1CCc2nc(N)sc2CC1] | 416 | method X | 0.69 |

-continued
| | | | | |
|---|---|---|---|---|
| 7.02.111 | 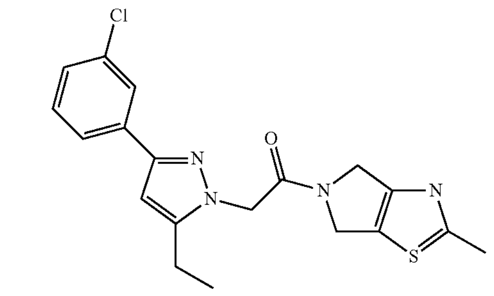 | 387 | method X | 0.81 |
| 7.02.112 | 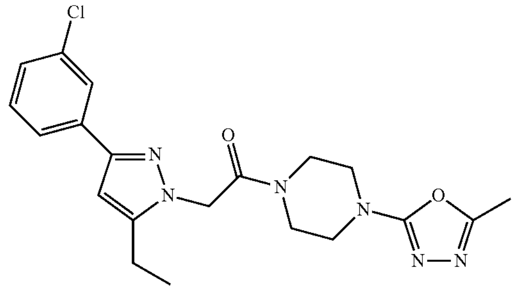 [SMILES: CCc1cc(-c2cccc(Cl)c2)nn1CC(=O)N1CCN(c2nnc(C)o2)CC1] | 415 | method X | 0.73 |
| 7.02.113 | 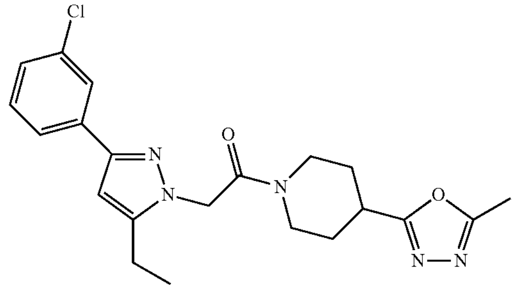 | 415 | method X | 0.73 |
| 7.02.114 | 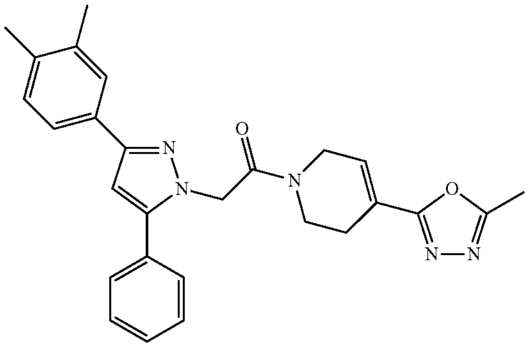 | 454 | method I | 1.00 |
| 7.02.115 | 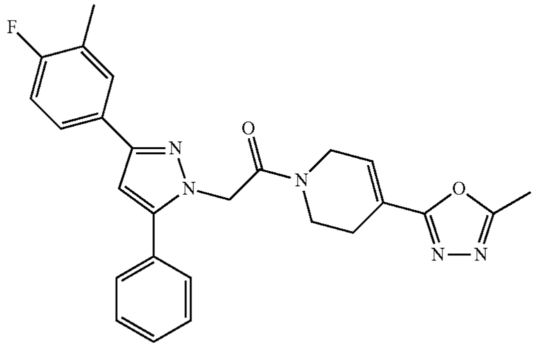 [SMILES: Cc1nnc(C2=CCN(C(=O)Cn3nc(-c4ccc(F)c(C)c4)cc3-c3ccccc3)CC2)o1] | 454 | method I | 0.97 |

-continued
| | | | | |
|---|---|---|---|---|
| 7.02.116 | 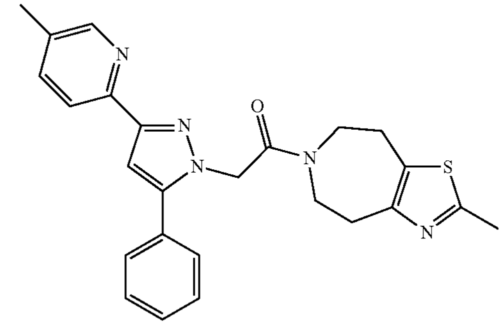 | 444 | method I | 0.70 |
| 7.02.117 | 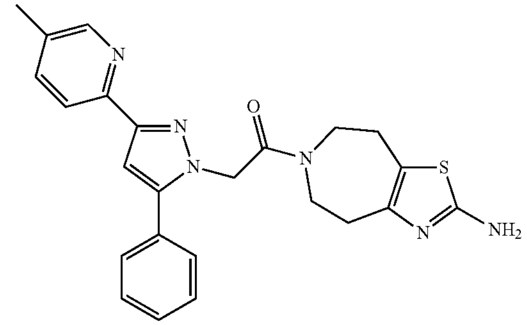 [SMILES: Cc1ccc(-c2cc(-c3ccccc3)n(CC(=O)N3CCc4nc(N)sc4CC3)n2)nc1] | 445 | method I | 0.59 |
| 7.02.118 | 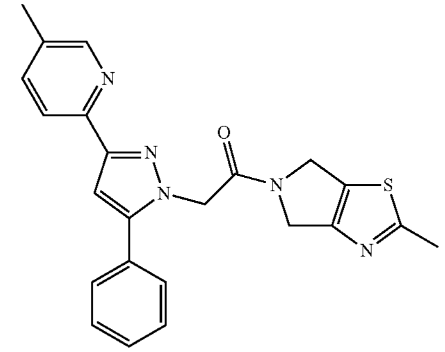 [SMILES: Cc1ccc(-c2cc(-c3ccccc3)n(CC(=O)N3Cc4nc(C)sc4C3)n2)nc1] | 416 | method I | 0.72 |
| 7.02.119 | 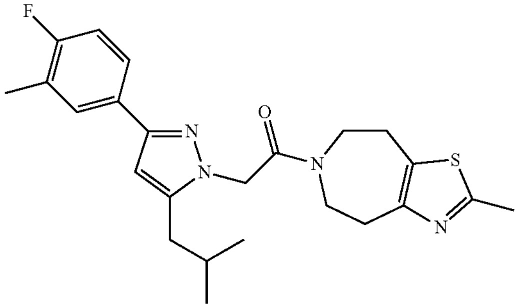 | 441 | method U | 0.86 |
| 7.02.120 | 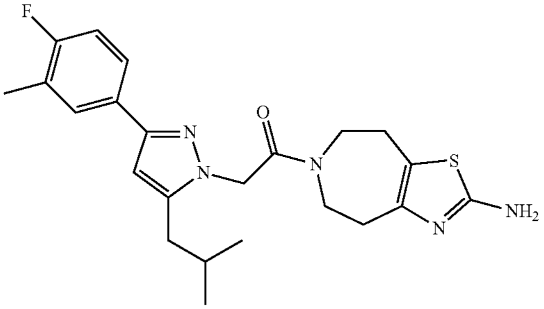 [SMILES: Cc1cc(-c2cc(CC(C)C)n(CC(=O)N3CCc4nc(N)sc4CC3)n2)ccc1F] | 442 | method U | 0.77 |

-continued
| | | | | |
|---|---|---|---|---|
| 7.02.121 | 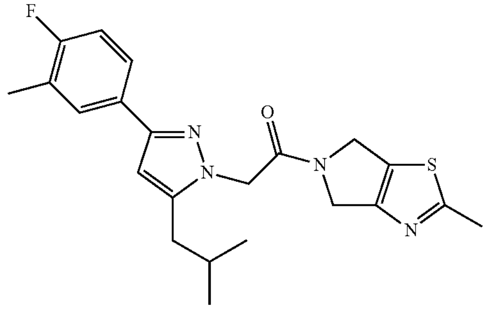 | 413 | method U | 0.88 |
| 7.02.122 | 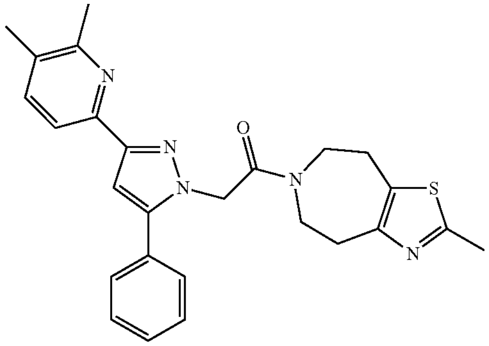 | 458 | method I | 0.68 |
| 7.02.123 | 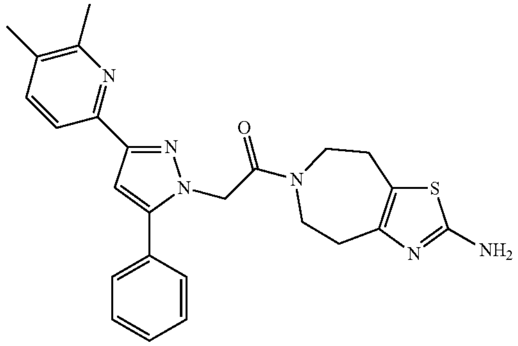 | 459 | method I | 0.58 |
| 7.02.124 | 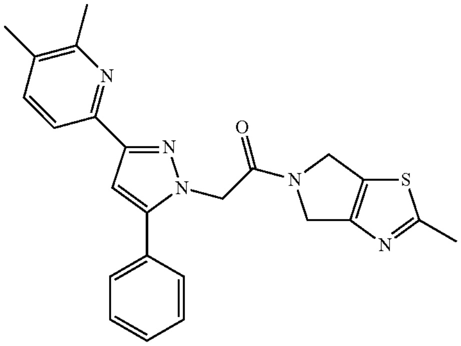 | 430 | method I | 0.71 |
| 7.02.125 | 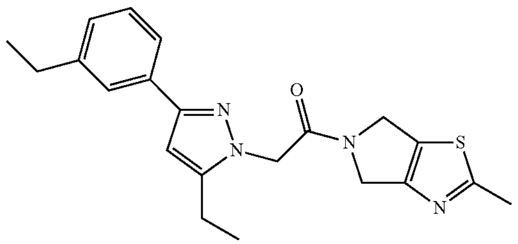 [SMILES: CCc1cccc(-c2cc(CC)n(CC(=O)N3Cc4nc(C)sc4C3)n2)c1] | 381 | method U | 0.82 |

-continued
| | | | | |
|---|---|---|---|---|
| 7.02.126 | 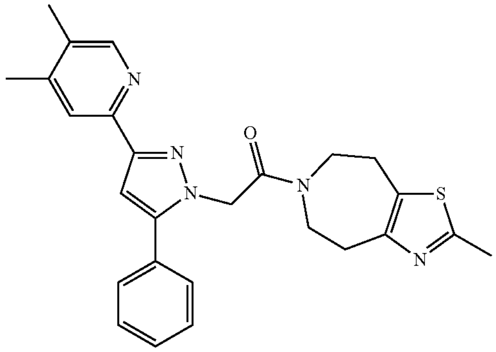 | 458 | method I | 0.70 |
| 7.02.127 | 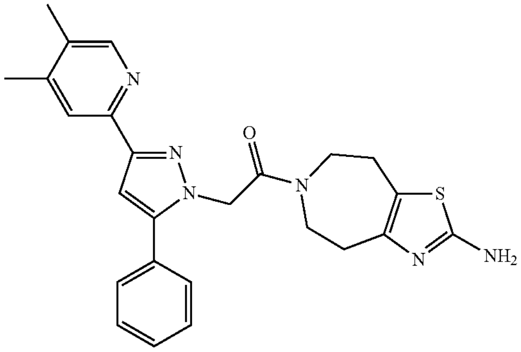 [SMILES: Cc1cnc(-c2cc(-c3ccccc3)n(CC(=O)N3CCc4nc(N)sc4CC3)n2)cc1C] | 459 | method I | 0.61 |
| 7.02.128 | 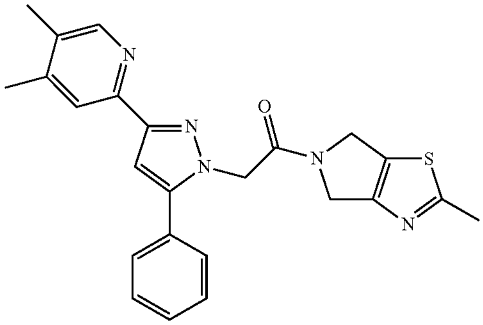 | 430 | method I | 0.73 |
| 7.02.129 | 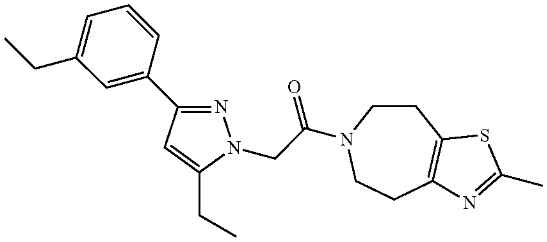 [SMILES: CCc1cccc(-c2cc(CC)n(CC(=O)N3CCc4nc(C)sc4CC3)n2)c1] | 409 | method U | 0.80 |
| 7.02.130 | 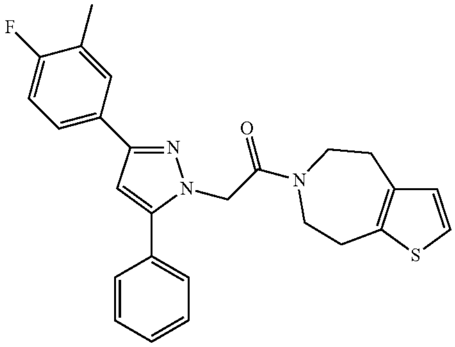 [SMILES: Cc1cc(-c2cc(-c3ccccc3)n(CC(=O)N3CCc4ccsc4CC3)n2)ccc1F] | 446 | method U | 0.90 |

-continued
| | | | | |
|---|---|---|---|---|
| 7.02.131 | 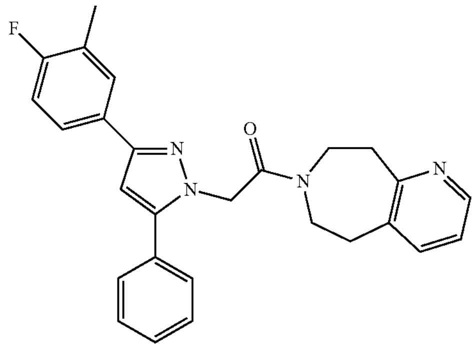 [SMILES: Cc1cc(-c2cc(-c3ccccc3)n(CC(=O)N3CCc4cccnc4CC3)n2)ccc1F] | 441 | method U | 0.86 |
| 7.02.132 | 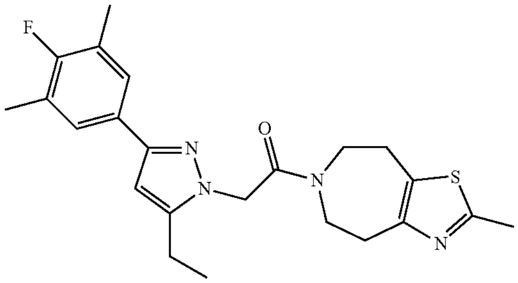 | 427 | method U | 0.80 |
| 7.02.133 | 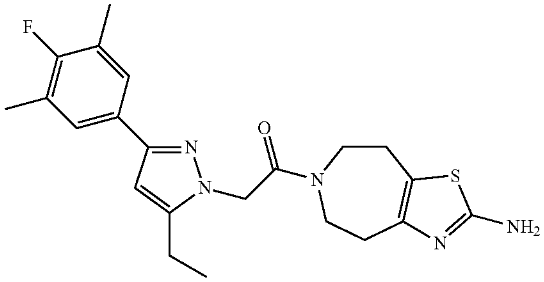 [SMILES: CCc1cc(-c2cc(C)c(F)c(C)c2)nn1CC(=O)N1CCc2nc(N)sc2CC1] | 428 | method U | 0.71 |
| 7.02.134 | 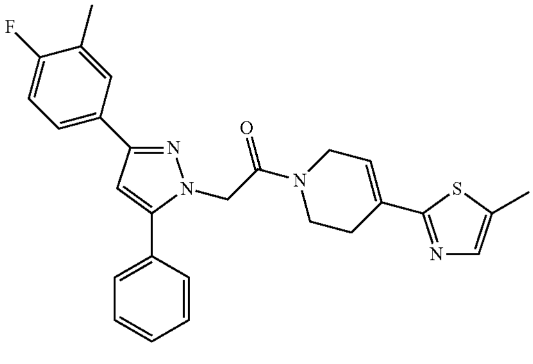 [SMILES: Cc1cnc(C2=CCN(C(=O)Cn3nc(-c4ccc(F)c(C)c4)cc3-c3ccccc3)CC2)s1] | 473 | method I | 1.00 |
| 7.02.135 | 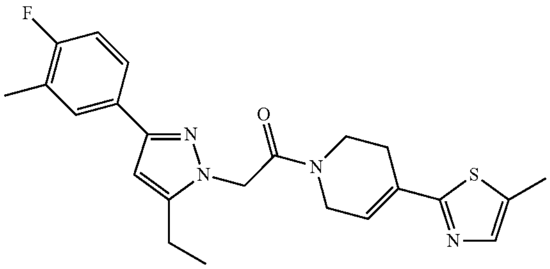 | 425 | method I | 0.95 |

-continued
| | | | | |
|---|---|---|---|---|
| 7.02.136 | 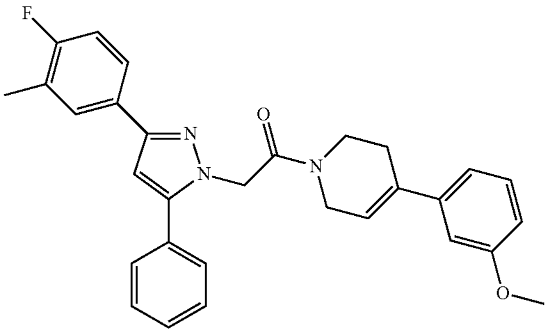 | 482 | method I | 1.04 |
| 7.02.137 | 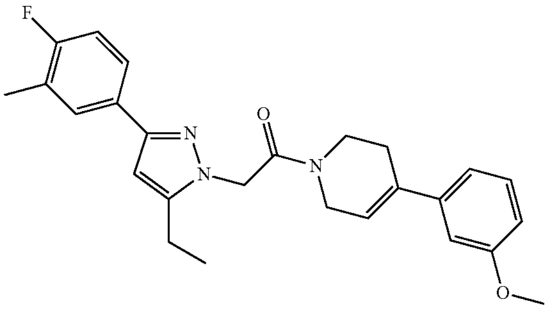 | 434 | method I | 1.00 |
| 7.02.138 | 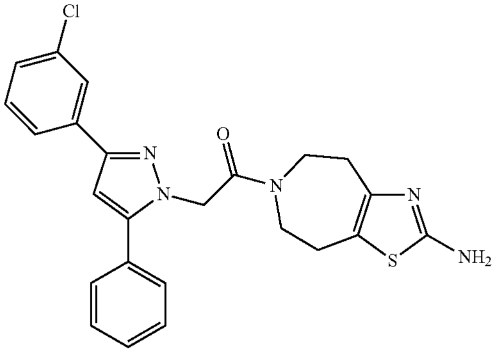 [SMILES: Nc1nc2c(s1)CCN(C(=O)Cn1nc(-c3cccc(Cl)c3)cc1-c1ccccc1)CC2] | 464/466 | method X | 0.70 |
| 7.02.139 | 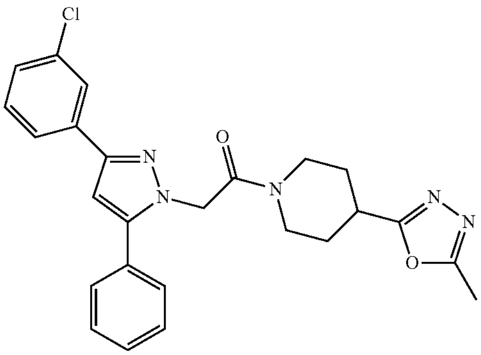 [SMILES: Cc1nnc(C2CCN(C(=O)Cn3nc(-c4cccc(Cl)c4)cc3-c3ccccc3)CC2)o1] | 462 | method X | 0.78 |

-continued
| | | | | |
|---|---|---|---|---|
| 7.02.140 | 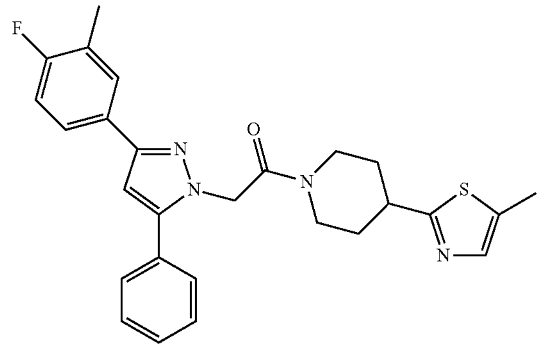 [SMILES: Cc1cnc(C2CCN(C(=O)Cn3nc(-c4ccc(F)c(C)c4)cc3-c3ccccc3)CC2)s1] | 475 | method I | 0.98 |
| 7.02.141 | 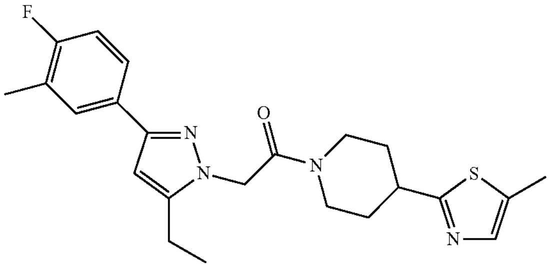 | 427 | method I | 0.93 |
| 7.02.142 | 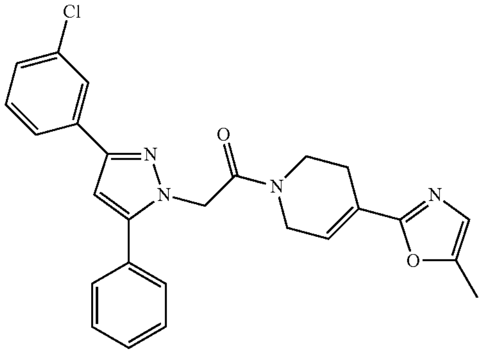 [SMILES: Cc1cnc(C2=CCN(C(=O)Cn3nc(-c4cccc(Cl)c4)cc3-c3ccccc3)CC2)o1] | 459 | method X | 0.84 |
| 7.02.143 | 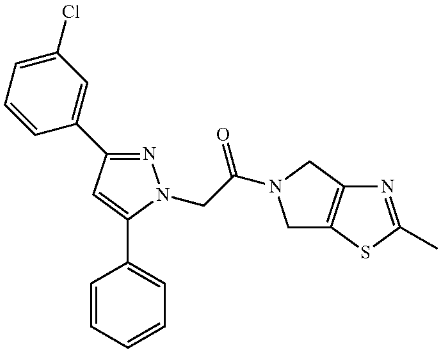 [SMILES: Cc1nc2c(s1)CN(C(=O)Cn1nc(-c3cccc(Cl)c3)cc1-c1ccccc1)C2] | 435 | method X | 0.82 |

-continued
| | | | | |
|---|---|---|---|---|
| 7.02.144 | 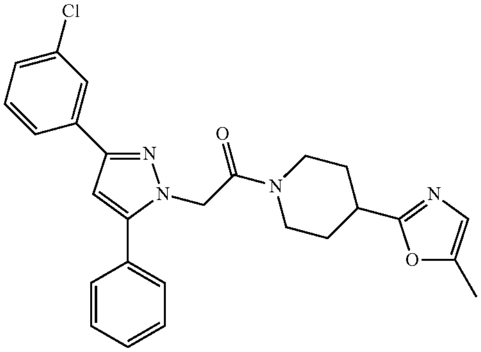 [SMILES: Cc1cnc(C2CCN(C(=O)Cn3nc(-c4cccc(Cl)c4)cc3-c3ccccc3)CC2)o1] | 461 | method X | 0.83 |
| 7.02.145 | 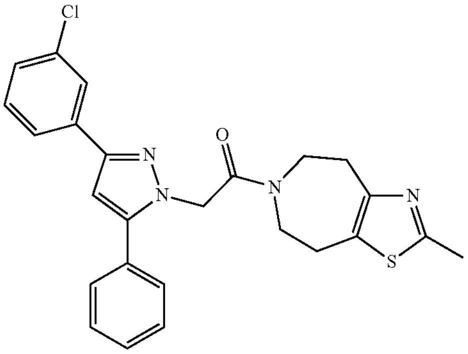 [SMILES: Cc1nc2c(s1)CCN(C(=O)Cn1nc(-c3cccc(Cl)c3)cc1-c1ccccc1)CC2] | 463/465 | method X | 0.80 |
| 7.02.146 | 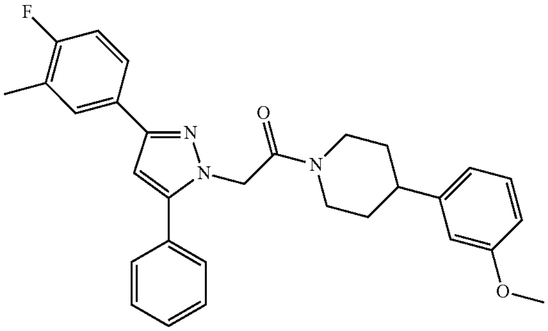 | 484 | method I | 1.03 |
| 7.02.147 | 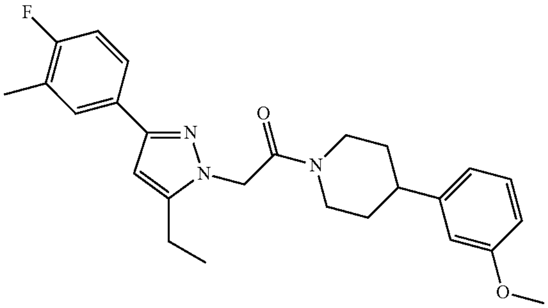 | 436 | method I | 0.99 |

-continued
| | | | | |
|---|---|---|---|---|
| 7.02.148 | 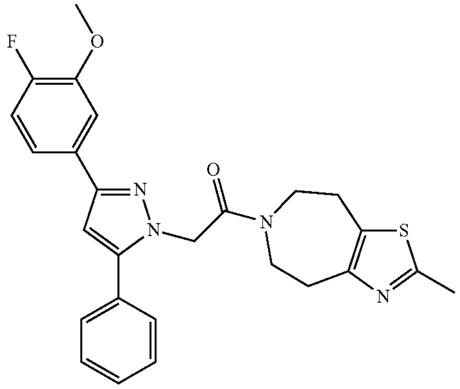 [SMILES: COc1cc(-c2cc(-c3ccccc3)n(CC(=O)N3CCc4nc(C)sc4CC3)n2)ccc1F] | 477 | method I | 0.86 |
| 7.02.149 | 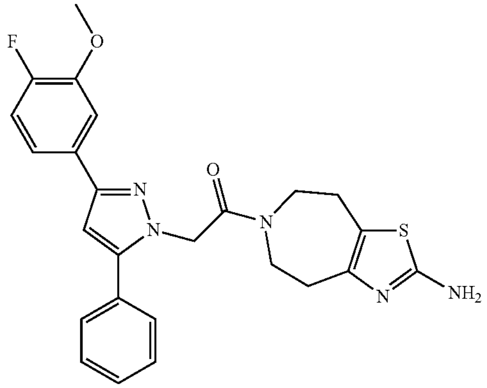 [SMILES: COc1cc(-c2cc(-c3ccccc3)n(CC(=O)N3CCc4nc(N)sc4CC3)n2)ccc1F] | 478 | method I | 0.74 |
| 7.02.150 | 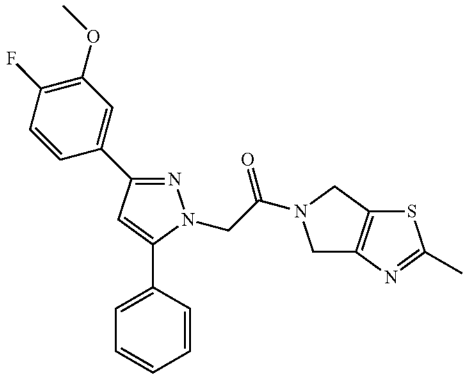 [SMILES: COc1cc(-c2cc(-c3ccccc3)n(CC(=O)N3Cc4nc(C)sc4C3)n2)ccc1F] | 449 | method I | 0.91 |
| 7.02.151 | 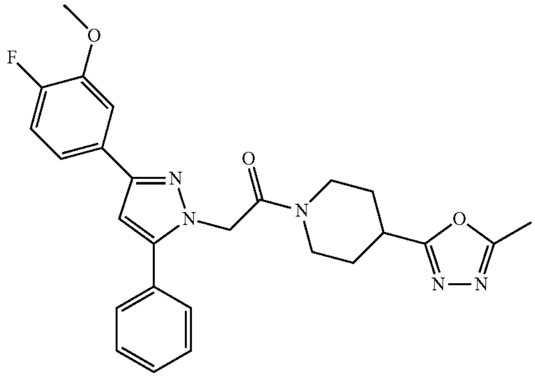 [SMILES: COc1cc(-c2cc(-c3ccccc3)n(CC(=O)N3CCC(c4nnc(C)o4)CC3)n2)ccc1F] | 476 | method I | 0.87 |

-continued
| | | | | |
|---|---|---|---|---|
| 7.02.152 | 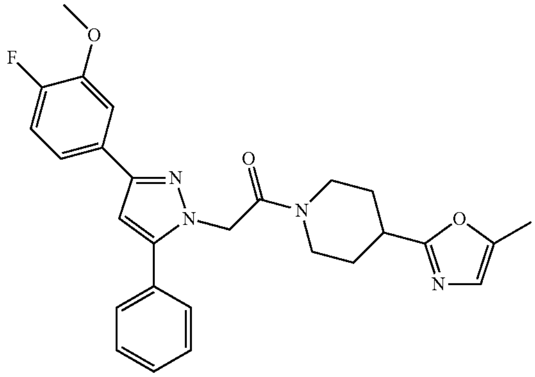 [SMILES: COc1cc(-c2cc(-c3ccccc3)n(CC(=O)N3CCC(c4ncc(C)o4)CC3)n2)ccc1F] | 475 | method I | 0.92 |
| 7.02.153 | 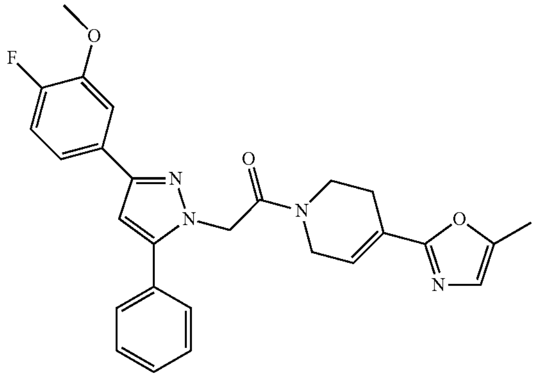 [SMILES: COc1cc(-c2cc(-c3ccccc3)n(CC(=O)N3CC=C(c4ncc(C)o4)CC3)n2)ccc1F] | 473 | method I | 0.93 |
| 7.02.154 | 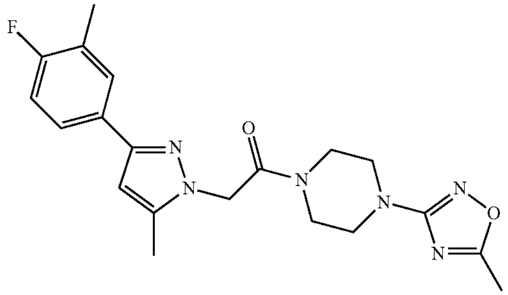 [SMILES: Cc1nc(N2CCN(C(=O)Cn3nc(-c4ccc(F)c(C)c4)cc3C)CC2)no1] | 399 | method I | 0.84 |
| 7.02.155 | 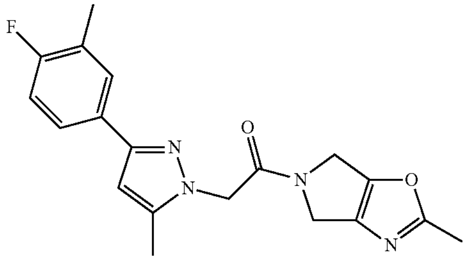 [SMILES: Cc1nc2c(o1)CN(C(=O)Cn1nc(-c3ccc(F)c(C)c3)cc1C)C2] | 355 | method I | 0.85 |

-continued
| | | | | |
|---|---|---|---|---|
| 7.02.156 | 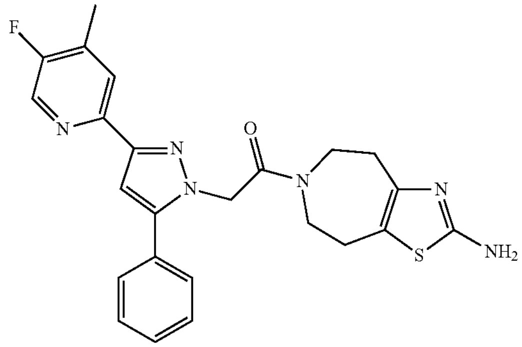 [SMILES: Cc1cc(-c2cc(-c3ccccc3)n(CC(=O)N3CCc4nc(N)sc4CC3)n2)ncc1F] | 355 | method I | 0.85 |
| 7.02.157 | 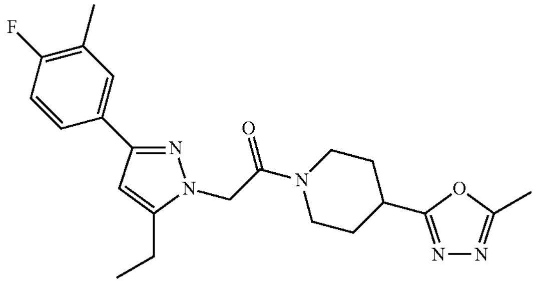 [SMILES: CCc1cc(-c2ccc(F)c(C)c2)nn1CC(=O)N1CCC(c2nnc(C)o2)CC1] | 412 | method U | 0.71 |
| 7.02.158 | 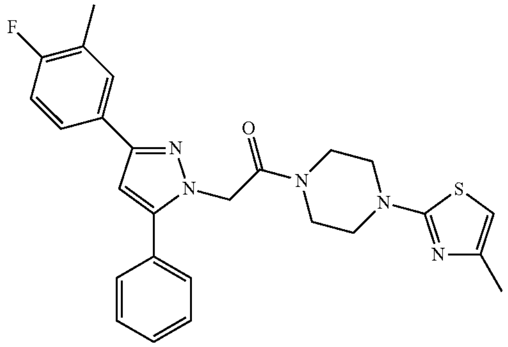 [SMILES: Cc1csc(N2CCN(C(=O)Cn3nc(-c4ccc(F)c(C)c4)cc3-c3ccccc3)CC2)n1] | 476 | method U | 0.73 |
| 7.02.159 | 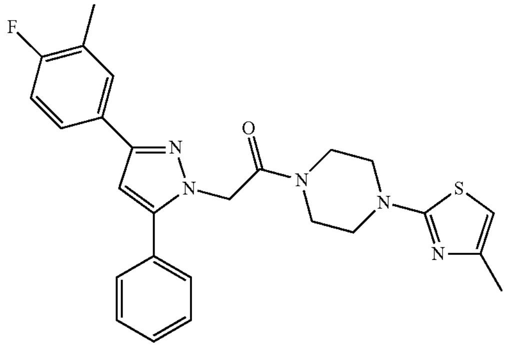 [SMILES: Cc1csc(N2CCN(C(=O)Cn3nc(-c4ccc(F)c(C)c4)cc3-c3ccccc3)CC2)n1] | 531 | method U | 0.84 |

-continued
| | | | | |
|---|---|---|---|---|
| 7.02.160 | 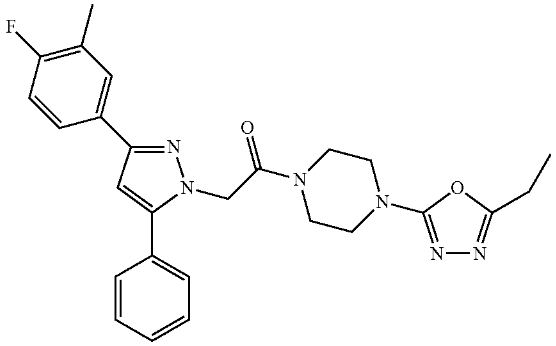 [SMILES: CCc1nnc(N2CCN(C(=O)Cn3nc(-c4ccc(F)c(C)c4)cc3-c3ccccc3)CC2)o1] | 475 | method U | 0.79 |
| 7.02.161 | 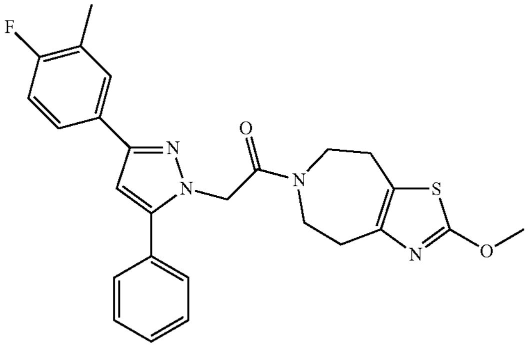 [SMILES: COc1nc2c(s1)CCN(C(=O)Cn1nc(-c3ccc(F)c(C)c3)cc1-c1ccccc1)CC2] | 477 | method U | 0.84 |
| 7.02.162 | 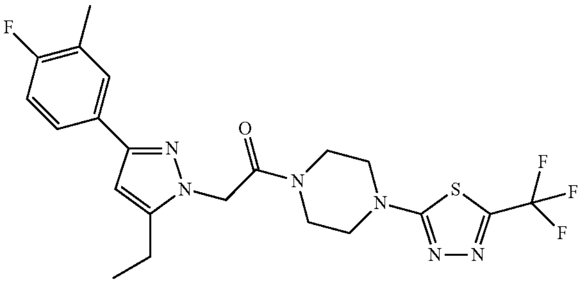 [SMILES: CCc1cc(-c2ccc(F)c(C)c2)nn1CC(=O)N1CCN(c2nnc(C(F)(F)F)s2)CC1] | 483 | method U | 0.80 |
| 7.02.163 | 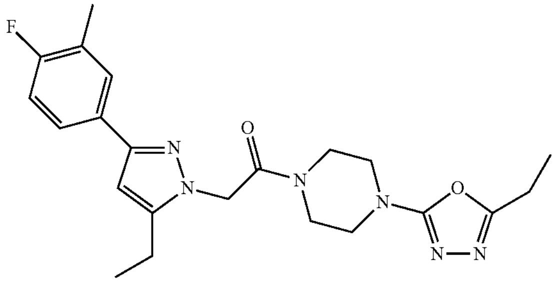 [SMILES: CCc1nnc(N2CCN(C(=O)Cn3nc(-c4ccc(F)c(C)c4)cc3CC)CC2)o1] | 427 | method U | 0.73 |
| 7.02.164 | 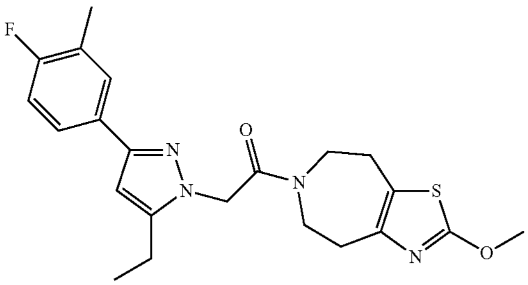 [SMILES: CCc1cc(-c2ccc(F)c(C)c2)nn1CC(=O)N1CCc2nc(OC)sc2CC1] | 428 | method U | 0.93 |

-continued
| | | | | |
|---|---|---|---|---|
| 7.02.165 | 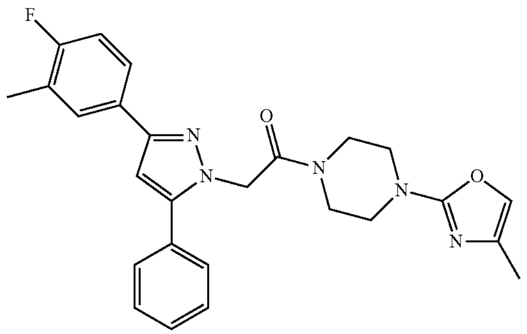 | 460 | method AB | 1.51 |
| 7.02.166 | 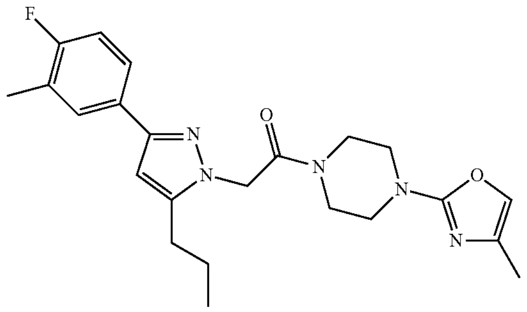 | 426 | method AB | 1.49 |
| 7.02.167 | 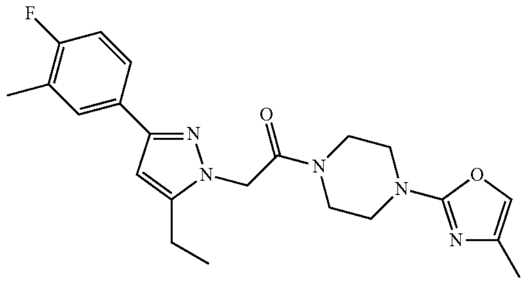 | 412 | method AB | 1.45 |
| 7.02.168 | 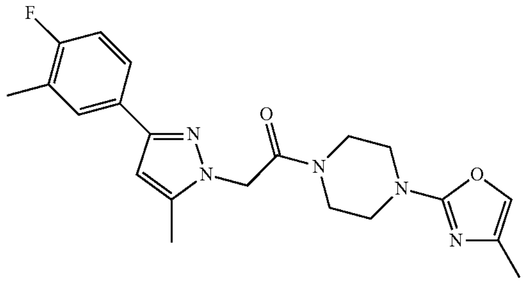 | 398 | method AB | 1.39 |
| 7.02.169 | 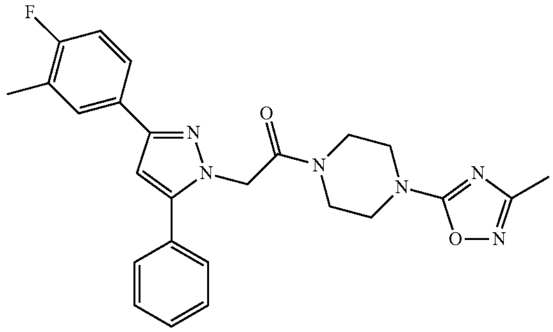 | 461 | method I | 0.97 |

-continued
| | | | | |
|---|---|---|---|---|
| 7.02.170 | 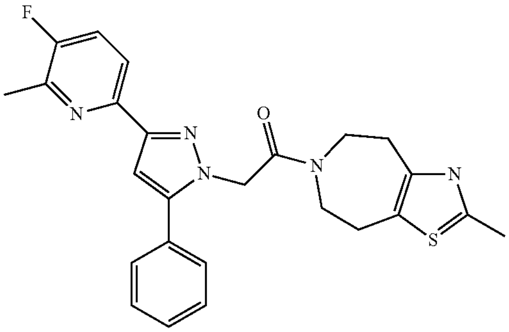 | 462 | method U | 0.68 |
| 7.02.171 | 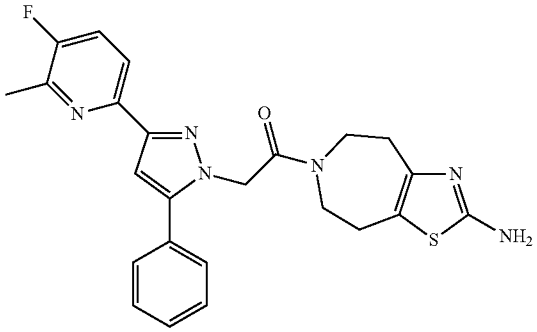 [SMILES: Cc1nc(-c2cc(-c3ccccc3)n(CC(=O)N3CCc4nc(N)sc4CC3)n2)ccc1F] | 463 | method U | 0.60 |
| 7.02.172 | 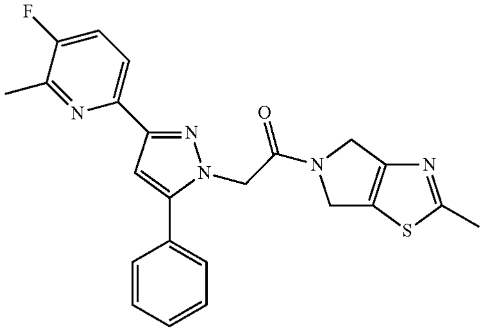 | 434 | method U | 0.72 |
| 7.02.173 | 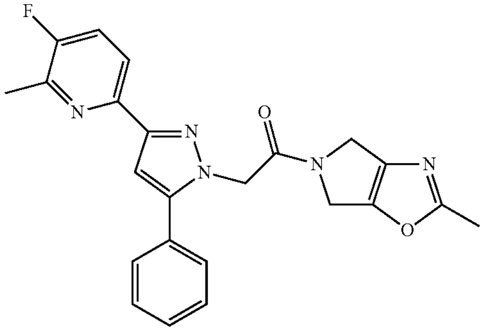 | 418 | method U | 0.70 |

-continued
| | | | | |
|---|---|---|---|---|
| 7.02.174 | 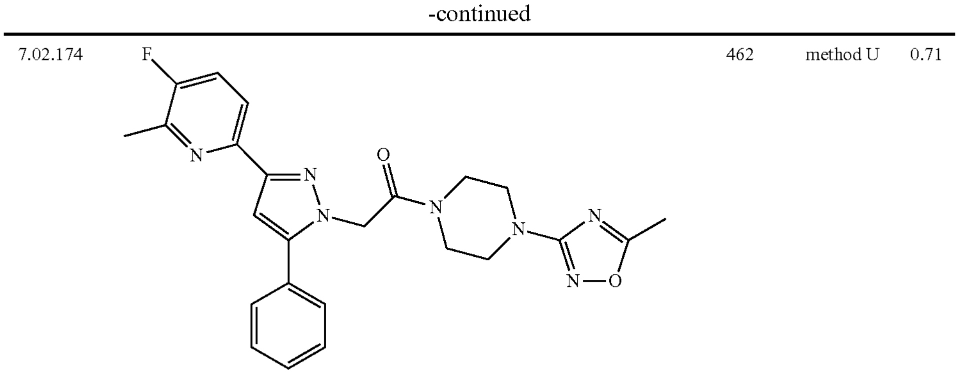 | 462 | method U | 0.71 |
| 7.02.175 | 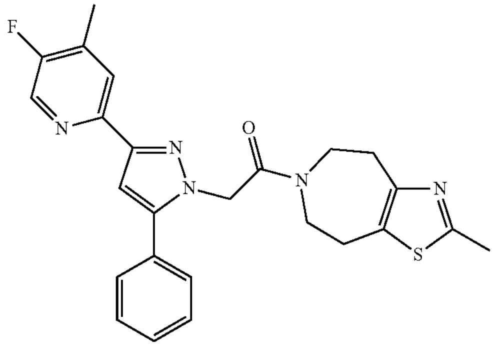 [SMILES: Cc1nc2c(s1)CCN(C(=O)Cn1nc(-c3cc(C)c(F)cn3)cc1-c1ccccc1)CC2] | 462 | method U | 0.66 |
| 7.02.176 | 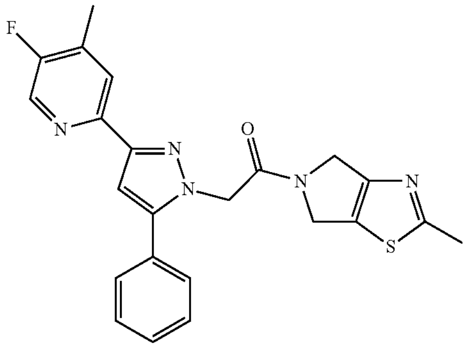 [SMILES: Cc1nc2c(s1)CN(C(=O)Cn1nc(-c3cc(C)c(F)cn3)cc1-c1ccccc1)C2] | 434 | method U | 0.69 |
| 7.02.177 | 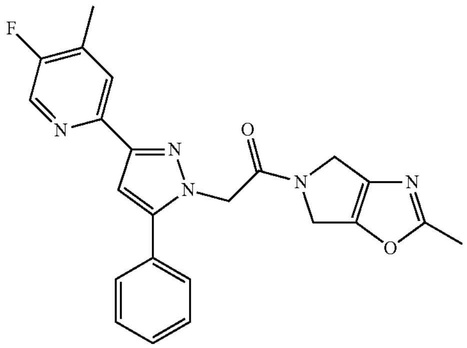 [SMILES: Cc1nc2c(o1)CN(C(=O)Cn1nc(-c3cc(C)c(F)cn3)cc1-c1ccccc1)C2] | 418 | method U | 0.67 |

-continued
| | | | | |
|---|---|---|---|---|
| 7.02.178 | 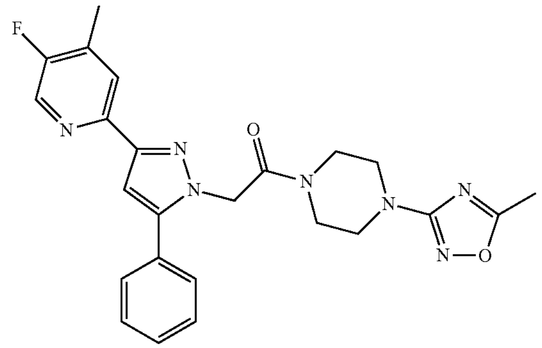 [SMILES: Cc1nc(N2CCN(C(=O)Cn3nc(-c4cc(C)c(F)cn4)cc3-c3ccccc3)CC2)no1] | 462 | method U | 0.68 |
| 7.02.179 | 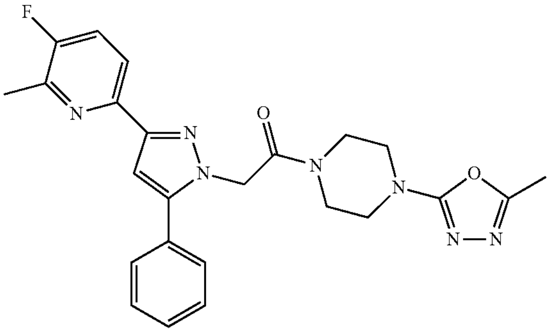 | 462 | method U | 0.68 |
| 7.02.180 | 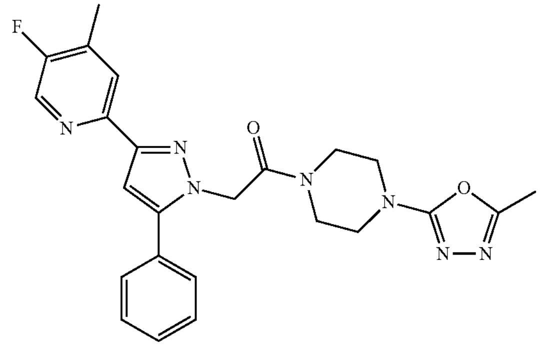 [SMILES: Cc1nnc(N2CCN(C(=O)Cn3nc(-c4cc(C)c(F)cn4)cc3-c3ccccc3)CC2)o1] | 462 | method U | 0.65 |
| 7.02.181 | 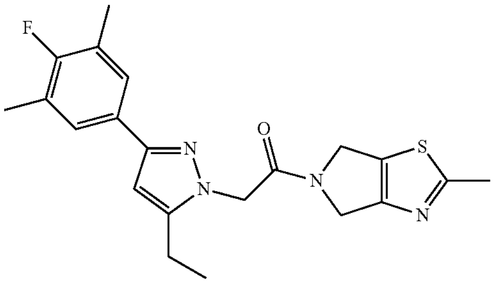 | 399 | method U | 0.81 |
| 7.02.182 | 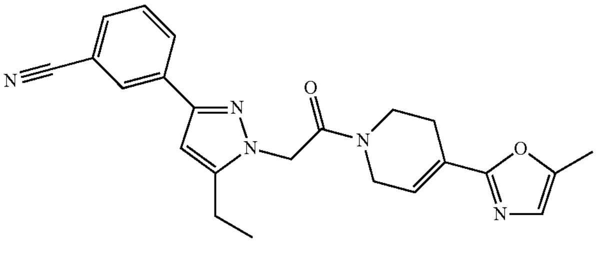 [SMILES: CCc1cc(-c2cccc(C#N)c2)nn1CC(=O)N1CC=C(c2ncc(C)o2)CC1] | 402 | method I | 0.95 |

-continued
| | | | | |
|---|---|---|---|---|
| 7.02.183 | 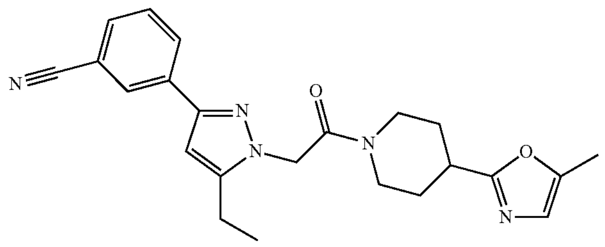 [SMILES: CCc1cc(-c2cccc(C#N)c2)nn1CC(=O)N1CCC(c2ncc(C)o2)CC1] | 404 | method I | 0.85 |
| 7.02.184 | 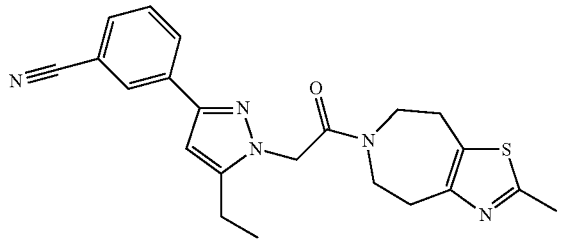 [SMILES: CCc1cc(-c2cccc(C#N)c2)nn1CC(=O)N1CCc2nc(C)sc2CC1] | 406 | method I | 0.77 |
| 7.02.185 | 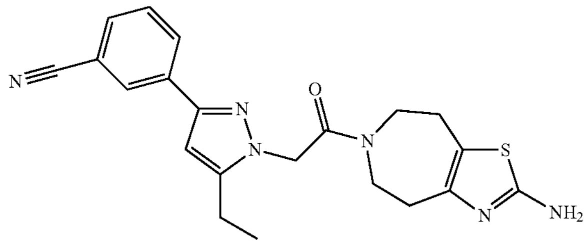 [SMILES: CCc1cc(-c2cccc(C#N)c2)nn1CC(=O)N1CCc2nc(N)sc2CC1] | 407 | method I | 0.65 |
| 7.02.186 | 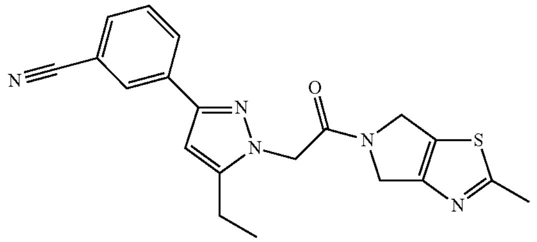 [SMILES: CCc1cc(-c2cccc(C#N)c2)nn1CC(=O)N1Cc2nc(C)sc2C1] | 378 | method I | 0.82 |
| 7.02.187 | 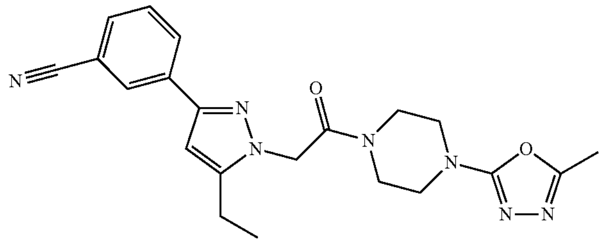 [SMILES: CCc1cc(-c2cccc(C#N)c2)nn1CC(=O)N1CCN(c2nnc(C)o2)CC1] | 406 | method I | 0.76 |
| 7.02.188 | 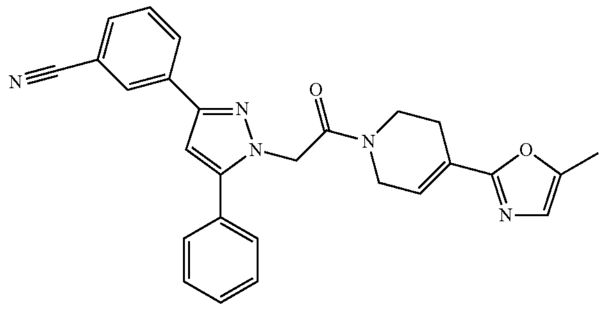 [SMILES: Cc1cnc(C2=CCN(C(=O)Cn3nc(-c4cccc(C#N)c4)cc3-c3ccccc3)CC2)o1] | 450 | method I | 0.91 |

-continued
| | | | | |
|---|---|---|---|---|
| 7.02.189 | 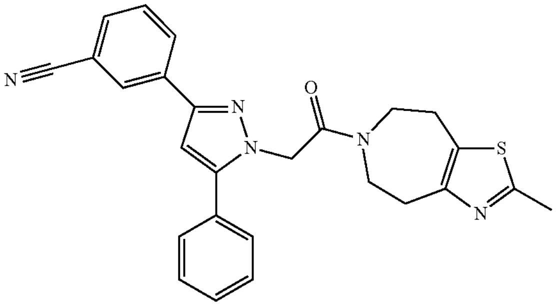 [SMILES: Cc1nc2c(s1)CCN(C(=O)Cn1nc(-c3cccc(C#N)c3)cc1-c1ccccc1)CC2] | 454 | method I | 0.85 |
| 7.02.190 | 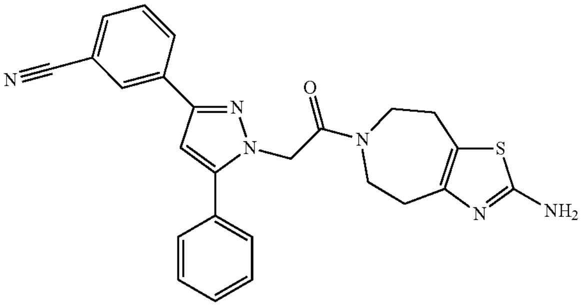 [SMILES: N#Cc1cccc(-c2cc(-c3ccccc3)n(CC(=O)N3CCc4nc(N)sc4CC3)n2)c1] | 455 | method I | 0.71 |
| 7.02.191 | 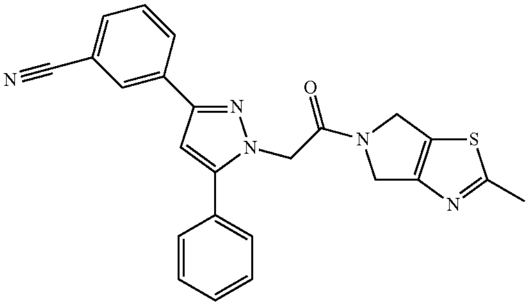 [SMILES: Cc1nc2c(s1)CN(C(=O)Cn1nc(-c3cccc(C#N)c3)cc1-c1ccccc1)C2] | 426 | method I | 0.89 |
| 7.02.192 | 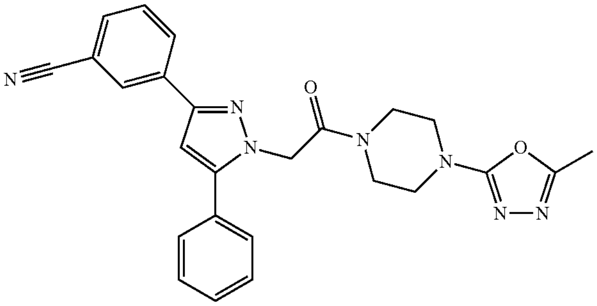 | 454 | method I | 0.83 |
| 7.02.193 | 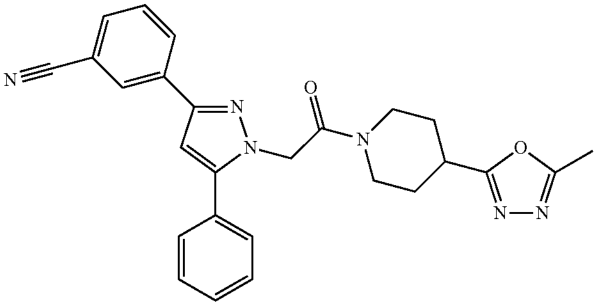 [SMILES: Cc1nnc(C2CCN(C(=O)Cn3nc(-c4cccc(C#N)c4)cc3-c3ccccc3)CC2)o1] | 453 | method I | 0.84 |

-continued
| | | | | |
|---|---|---|---|---|
| 7.02.194 | 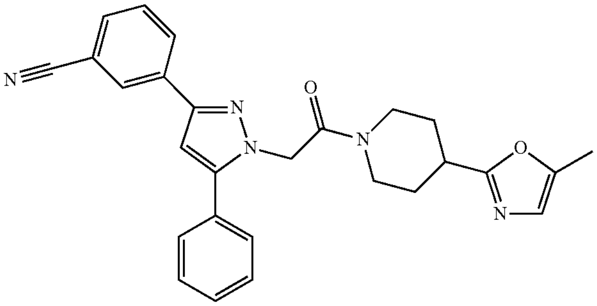 [SMILES: Cc1cnc(C2CCN(C(=O)Cn3nc(-c4cccc(C#N)c4)cc3-c3ccccc3)CC2)o1] | 452 | method I | 0.89 |
| 7.02.195 | 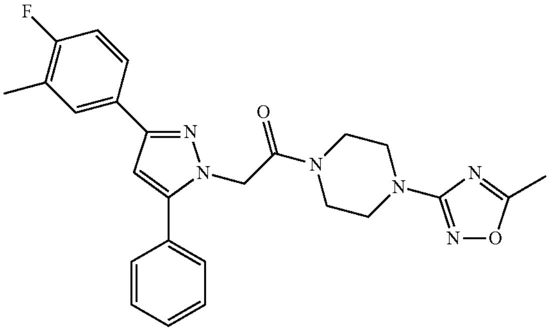 | 461 | method I | 0.95 |
| 7.02.196 | 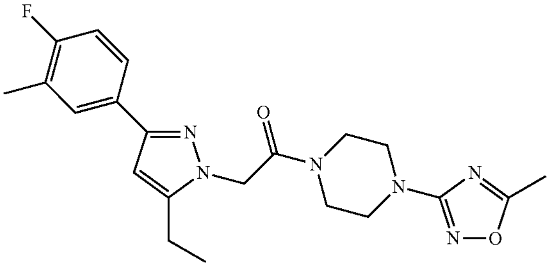 | 413 | method I | 0.90 |
| 7.02.197 | 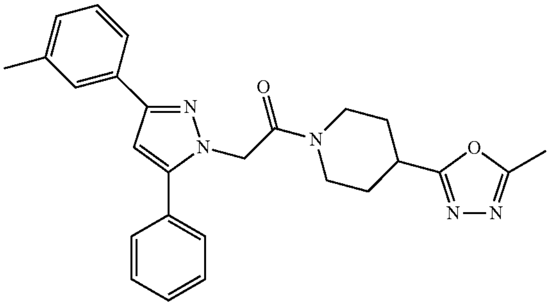 | 442 | method U | 0.78 |
| 7.02.198 | 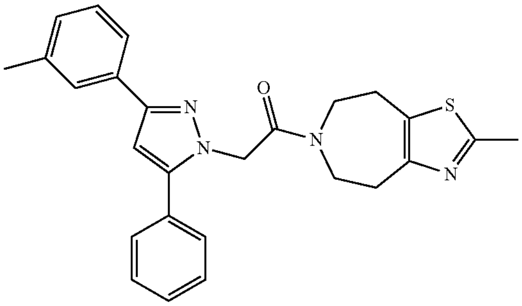 | 443 | method U | 0.78 |

-continued
| | | | | |
|---|---|---|---|---|
| 7.02.199 | 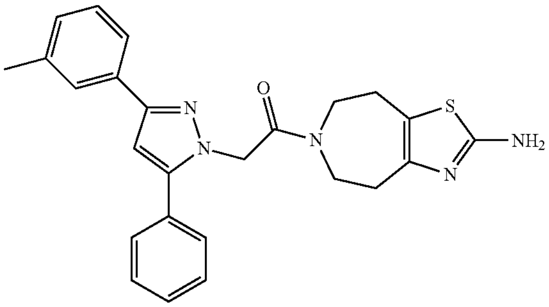 [SMILES: Cc1cccc(-c2cc(-c3ccccc3)n(CC(=O)N3CCc4nc(N)sc4CC3)n2)c1] | 444 | method U | 0.70 |
| 7.02.200 | 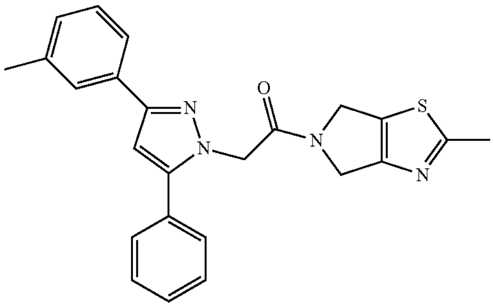 | 415 | method U | 0.81 |
| 7.02.201 | 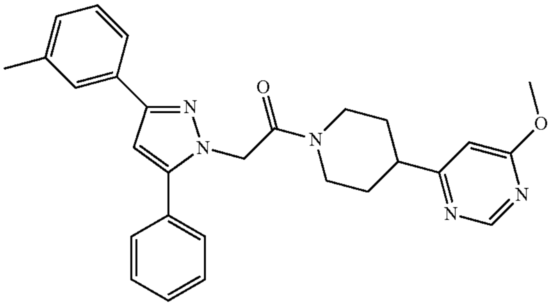 [SMILES: COc1cc(C2CCN(C(=O)Cn3nc(-c4cccc(C)c4)cc3-c3ccccc3)CC2)ncn1] | 468 | method U | 0.83 |
| 7.02.202 | 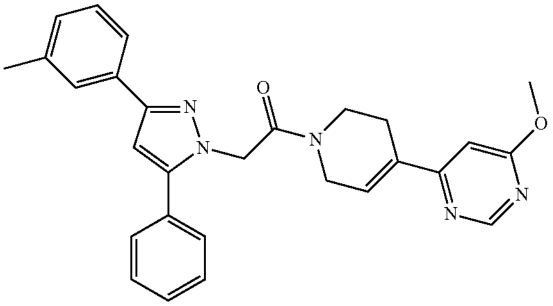 [SMILES: COc1cc(C2=CCN(C(=O)Cn3nc(-c4cccc(C)c4)cc3-c3ccccc3)CC2)ncn1] | 466 | method U | 0.84 |
| 7.02.203 | 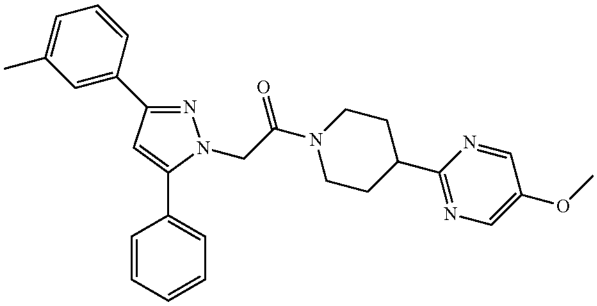 | 468 | method U | 0.83 |

-continued
| | | | | |
|---|---|---|---|---|
| 7.02.204 | 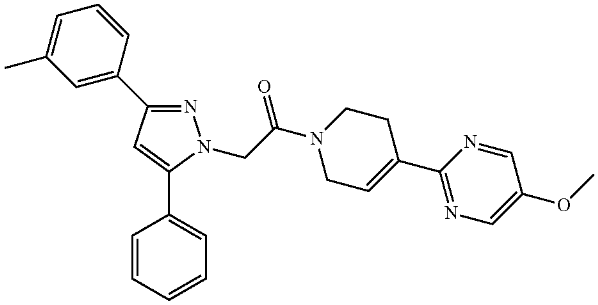 | 466 | method U | 0.83 |
| 7.02.205 | 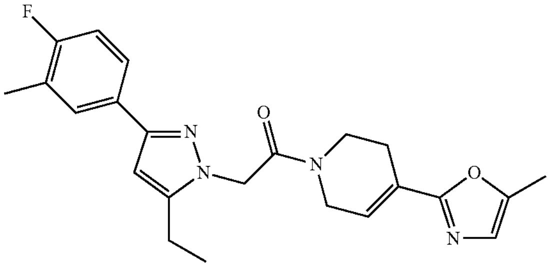 | 409 | method U | 0.78 |
| 7.02.206 | 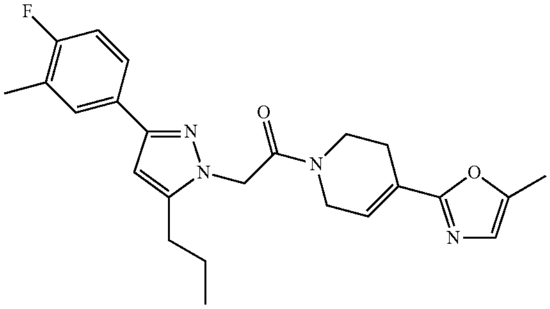 | 422 | method U | 0.82 |
| 7.02.207 | 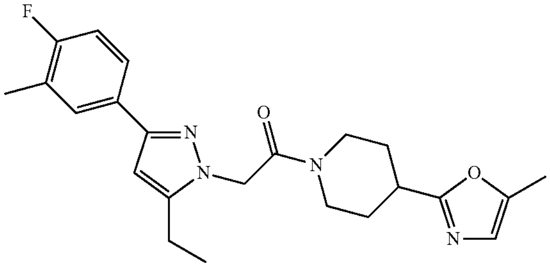 | 411 | method U | 0.78 |
| 7.02.208 | 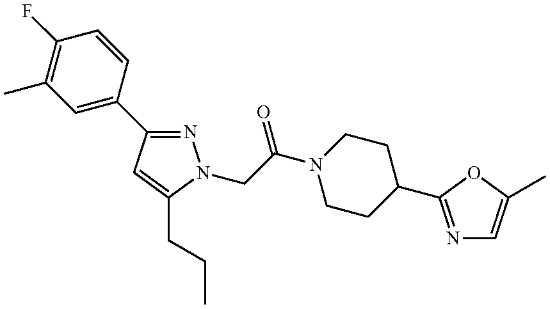 | 425 | method U | 0.81 |

-continued
| | | | | |
|---|---|---|---|---|
| 7.02.209 | 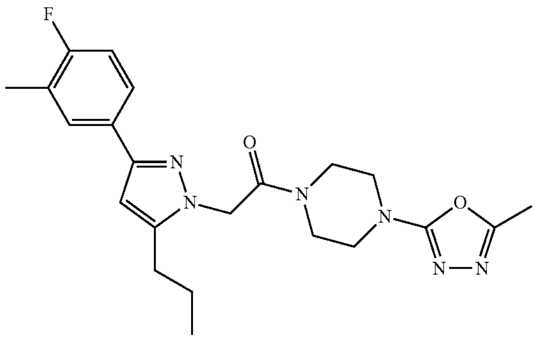 | 427 | method U | 0.76 |
| 7.02.210 | 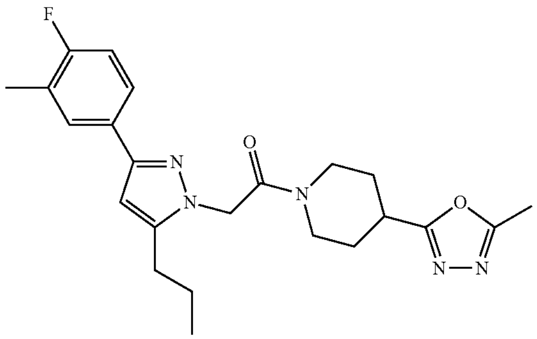 | 426 | method U | 0.76 |
| 7.02.211 | 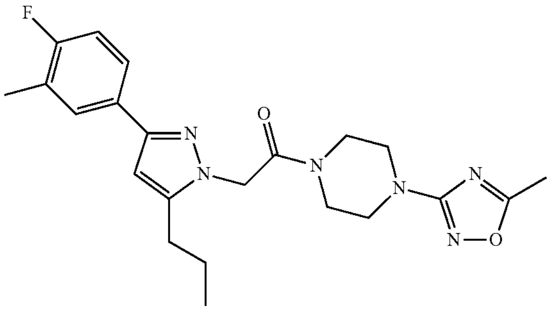 | 427 | method U | 0.79 |
| 7.02.212 | 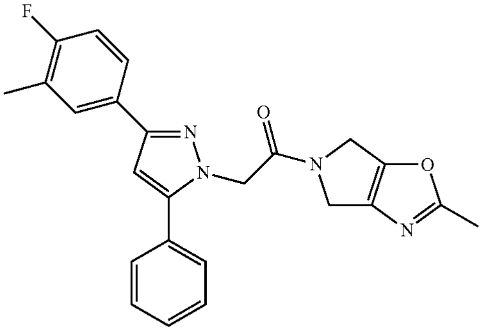 | 417 | method AB | 1.48 |
| 7.02.213 | 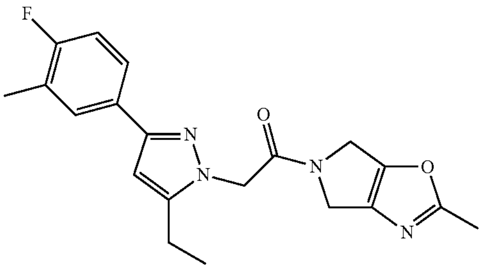 | 369 | method AB | 0.91 |

-continued
| | | | | |
|---|---|---|---|---|
| 7.02.214 | 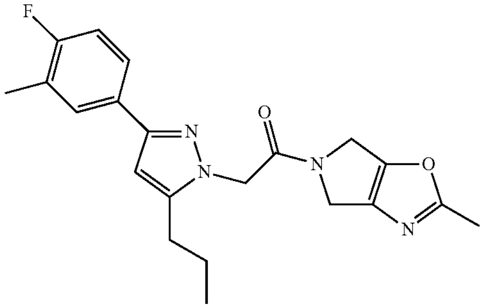 | 383 | method AB | 1.45 |
| 7.02.215 | 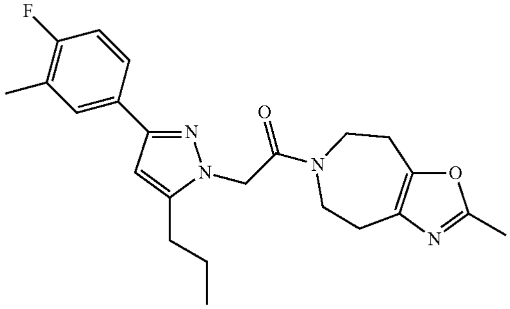 | 411 | method U | 0.78 |
| 7.02.216 | 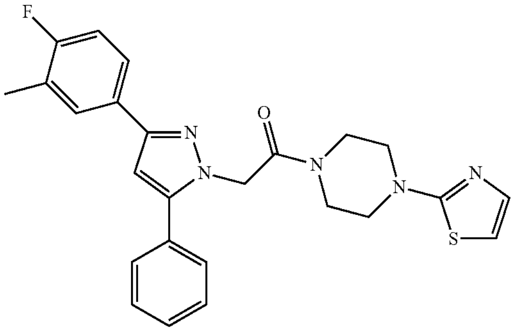 [SMILES: Cc1cc(-c2cc(-c3ccccc3)n(CC(=O)N3CCN(c4nccs4)CC3)n2)ccc1F] | 462 | method U | 0.74 |
| 7.02.217 | 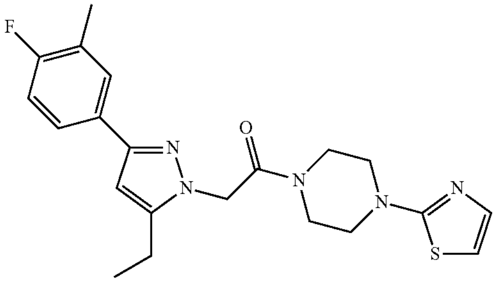 [SMILES: CCc1cc(-c2ccc(F)c(C)c2)nn1CC(=O)N1CCN(c2nccs2)CC1] | 414 | method U | 0.67 |
| 7.02.218 | 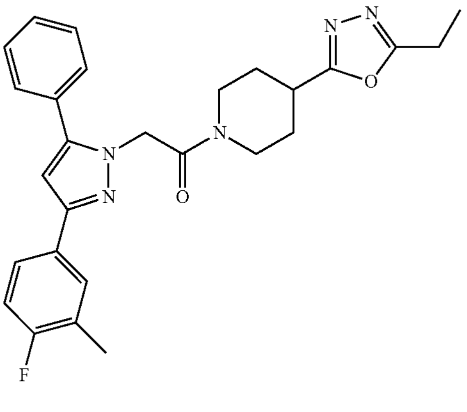 [SMILES: CCc1nnc(C2CCN(C(=O)Cn3nc(-c4ccc(F)c(C)c4)cc3-c3ccccc3)CC2)o1] | 474 | method L 1.47 | |

-continued
| | | | | |
|---|---|---|---|---|
| 7.02.219 | 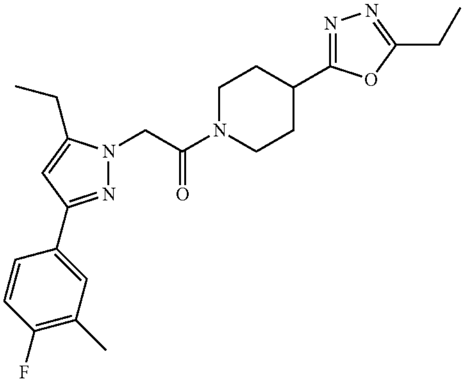 [SMILES: CCc1nnc(C2CCN(C(=O)Cn3nc(-c4ccc(F)c(C)c4)cc3CC)CC2)o1] | 426 | method L | 1.37 |
| 7.02.220 | 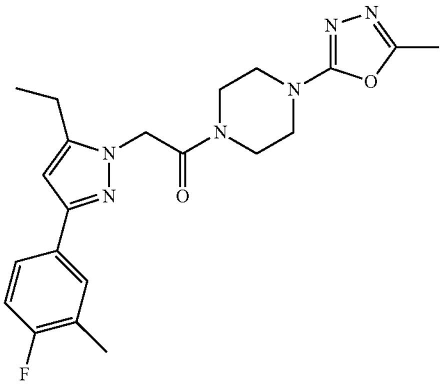 [SMILES: CCc1cc(-c2ccc(F)c(C)c2)nn1CC(=O)N1CCN(c2nnc(C)o2)CC1] | 413 | method L | 1.33 |
| 7.02.221 | 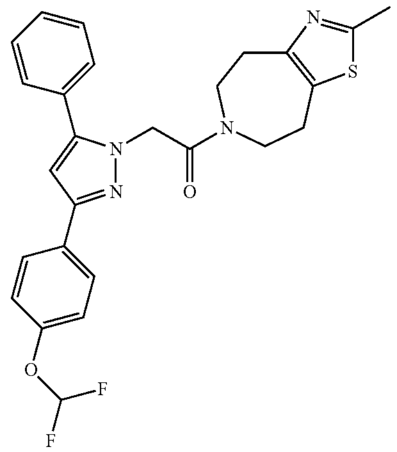 [SMILES: Cc1nc2c(s1)CCN(C(=O)Cn1nc(-c3ccc(OC(F)F)cc3)cc1-c1ccccc1)CC2] | 495 | method L | 1.36 |

-continued
| | | | | |
|---|---|---|---|---|
| 7.02.222 | 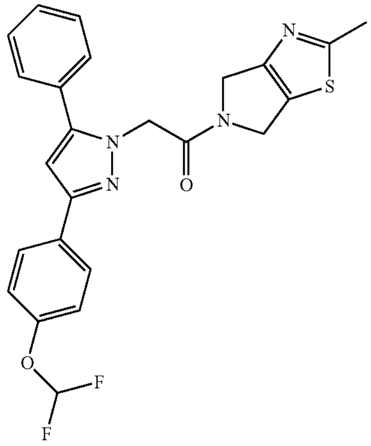 [SMILES: Cc1nc2c(s1)CN(C(=O)Cn1nc(-c3ccc(OC(F)F)cc3)cc1-c1ccccc1)C2] | 467 | method L | 1.42 |
| 7.02.223 | 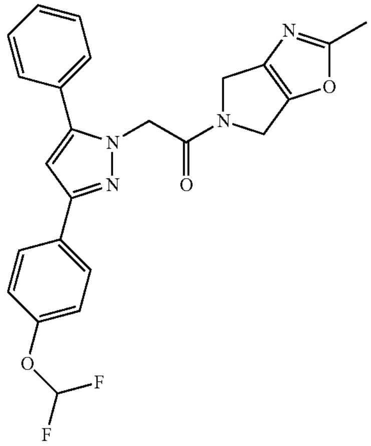 [SMILES: Cc1nc2c(o1)CN(C(=O)Cn1nc(-c3ccc(OC(F)F)cc3)cc1-c1ccccc1)C2] | 451 | method L | 1.40 |
| 7.02.224 | 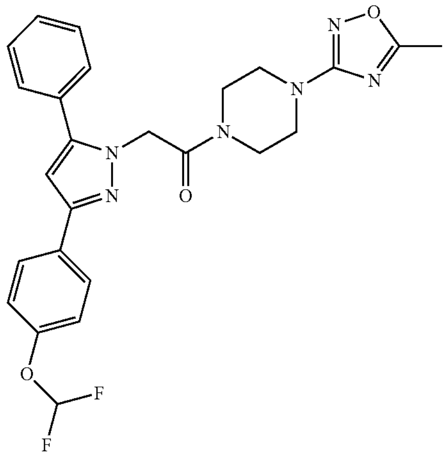 [SMILES: Cc1nc(N2CCN(C(=O)Cn3nc(-c4ccc(OC(F)F)cc4)cc3-c3ccccc3)CC2)no1] | 495 | method L | 1.41 |

-continued
| | | | | |
|---|---|---|---|---|
| 7.02.225 | 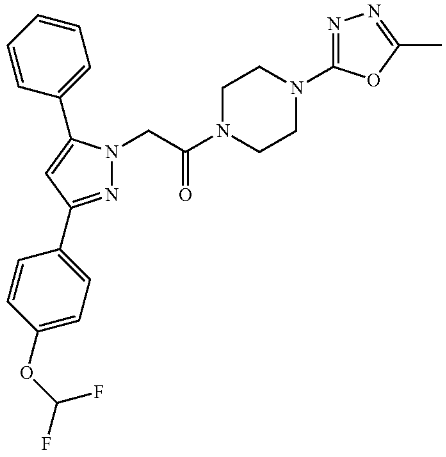 [SMILES: Cc1nnc(N2CCN(C(=O)Cn3nc(-c4ccc(OC(F)F)cc4)cc3-c3ccccc3)CC2)o1] | 495 | method L | 1.35 |
| 7.02.226 | 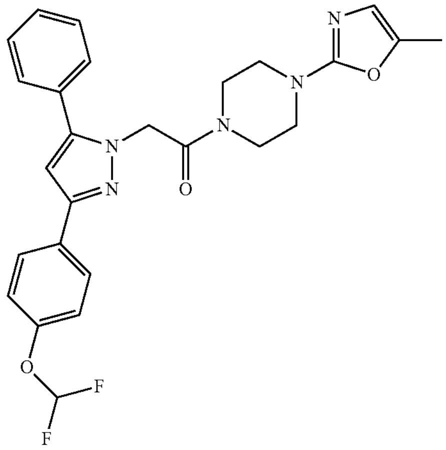 [SMILES: Cc1cnc(N2CCN(C(=O)Cn3nc(-c4ccc(OC(F)F)cc4)cc3-c3ccccc3)CC2)o1] | 494 | method L | 1.29 |
| 7.02.227 | 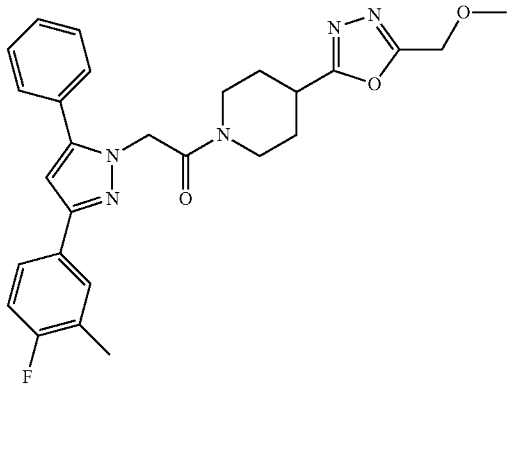 [SMILES: COCc1nnc(C2CCN(C(=O)Cn3nc(-c4ccc(F)c(C)c4)cc3-c3ccccc3)CC2)o1] | 490 | method L | 1.43 |

-continued
| | | | | |
|---|---|---|---|---|
| 7.02.228 | 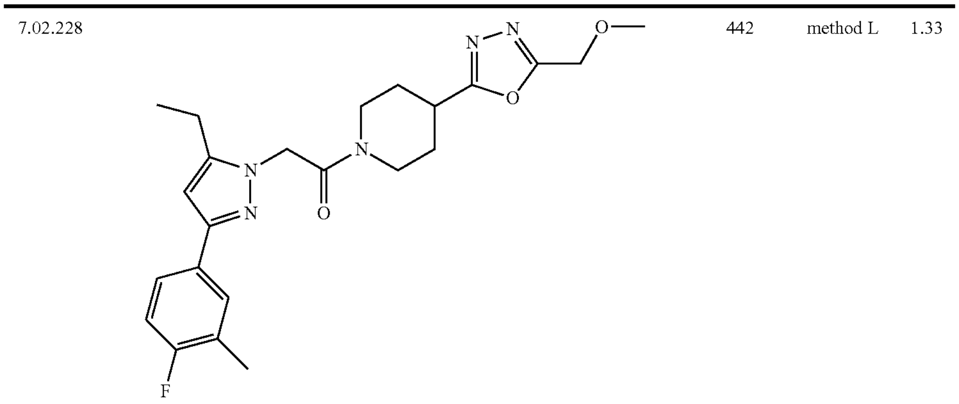 | 442 | method L | 1.33 |
| 7.02.229 | 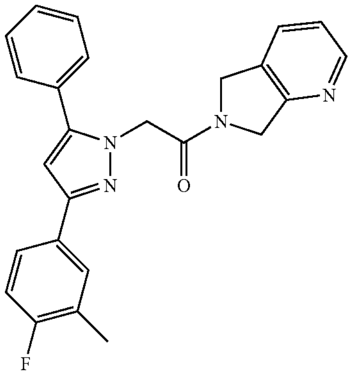 [SMILES: Cc1cc(-c2cc(-c3ccccc3)n(CC(=O)N3Cc4cccnc4C3)n2)ccc1F] | 413 | method L | 1.44 |
| 7.02.230 | 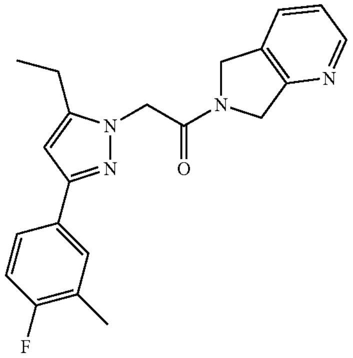 [SMILES: CCc1cc(-c2ccc(F)c(C)c2)nn1CC(=O)N1Cc2cccnc2C1] | 365 | method L | 1.32 |
| 7.02.231 | 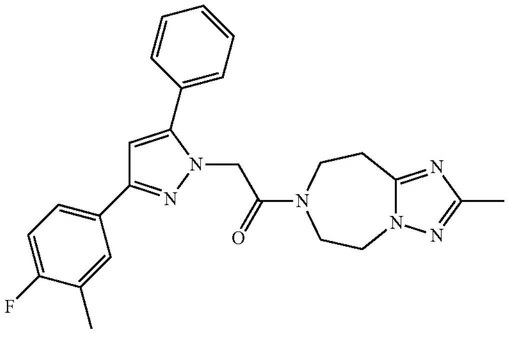 [SMILES: Cc1nc2n(n1)CCN(C(=O)Cn1nc(-c3ccc(F)c(C)c3)cc1-c1ccccc1)CC2] | 445 | method I | 0.89 |

-continued
| | | | | |
|---|---|---|---|---|
| 7.02.232 | 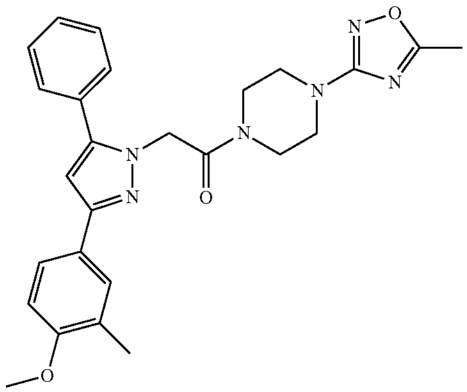 | 473 | method U | 0.83 |
| 7.02.233 | 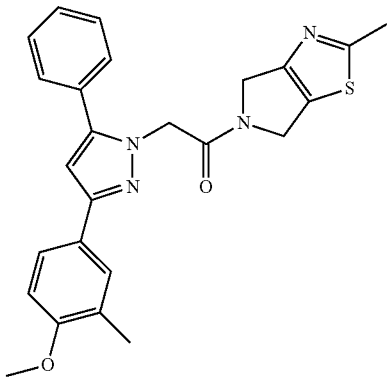 | 445 | method U | 0.84 |
| 7.02.234 | 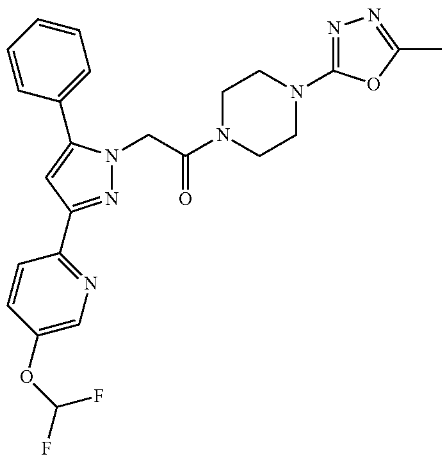 | 496 | method I | 0.80 |

-continued
| | | | | |
|---|---|---|---|---|
| 7.02.235 | 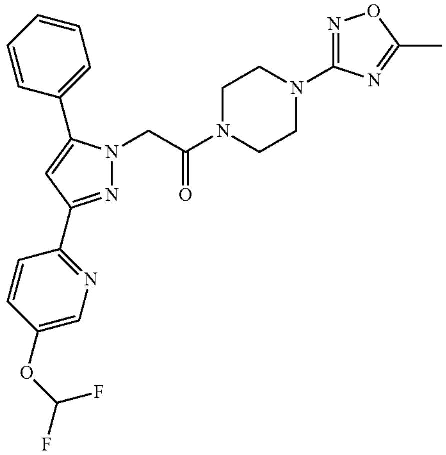 | 496 | method I | 0.84 |
| 7.02.236 | 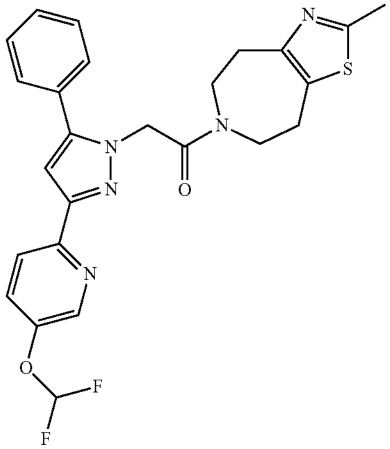 [SMILES: Cc1nc2c(s1)CCN(C(=O)Cn1nc(-c3ccc(OC(F)F)cn3)cc1-c1ccccc1)CC2] | 496 | method I | 0.79 |
| 7.02.237 | 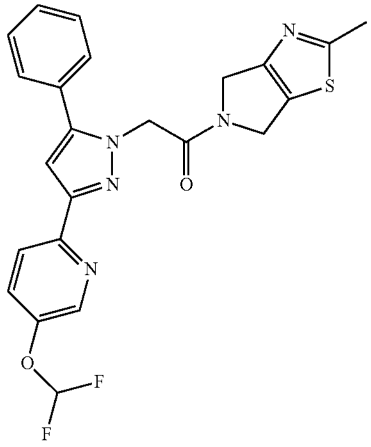 [SMILES: Cc1nc2c(s1)CN(C(=O)Cn1nc(-c3ccc(OC(F)F)cn3)cc1-c1ccccc1)C2] | 468 | method I | 0.85 |
| 7.02.238 | 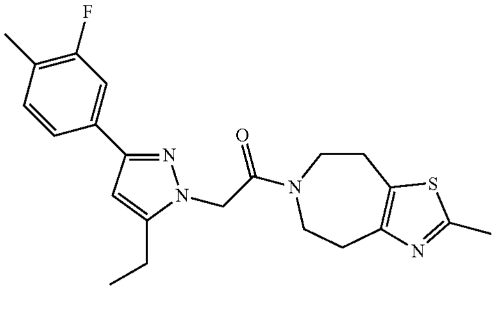 | 413 | method I | 0.85 |

-continued
| | | | | |
|---|---|---|---|---|
| 7.02.239 | 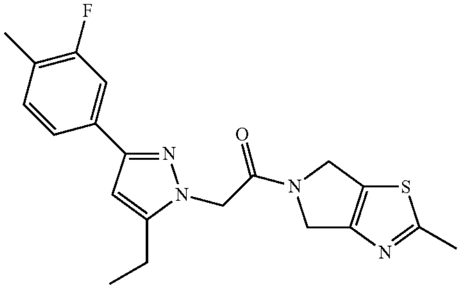 | 385 | method I | 0.90 |
| 7.02.240 | 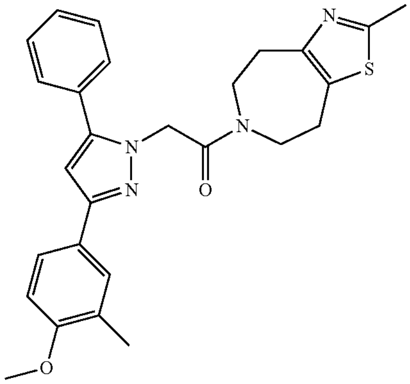 | 473 | method U | 0.79 |
| 7.02.241 | 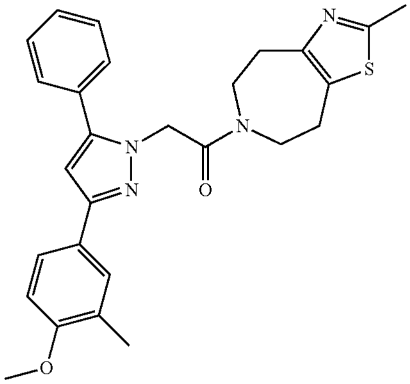 | 472 | method U | 0.74 |
| 7.02.242 | 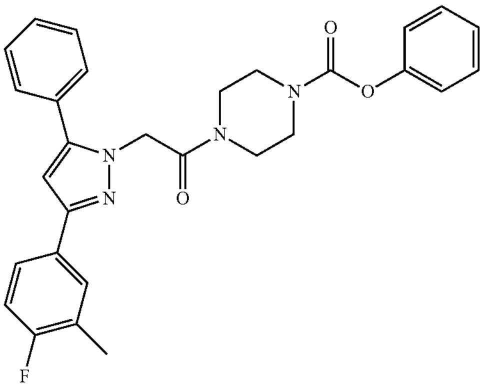 [SMILES: Cc1cc(-c2cc(-c3ccccc3)n(CC(=O)N3CCN(C(=O)Oc4ccccc4)CC3)n2)ccc1F] | 499 | method L | 1.55 |

-continued
| | | | | |
|---|---|---|---|---|
| 7.02.243 | 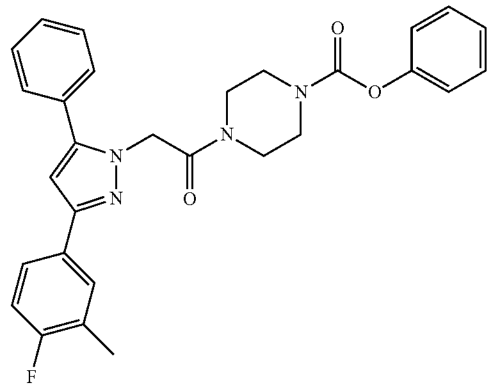 [SMILES: Cc1cc(-c2cc(-c3ccccc3)n(CC(=O)N3CCN(C(=O)Oc4ccccc4)CC3)n2)ccc1F] | 451 | method L | 1.48 |
| 7.02.244 | 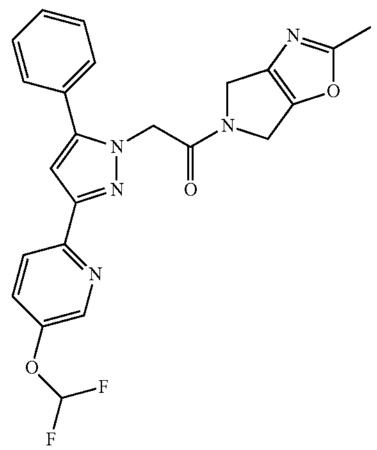 | 452 | method I | 0.81 |
| 7.02.245 | 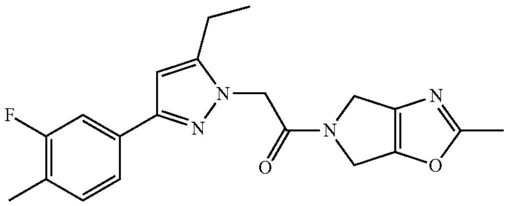 | 369 | method L | |
| 7.02.246 | 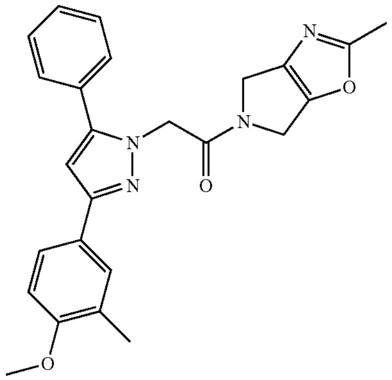 | 429 | method L | 1.45 |

-continued
| | | | | |
|---|---|---|---|---|
| 7.02.247 | 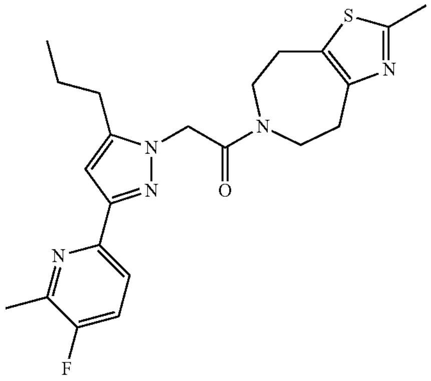 | 428 | method I | 0.79 |
| 7.02.248 | 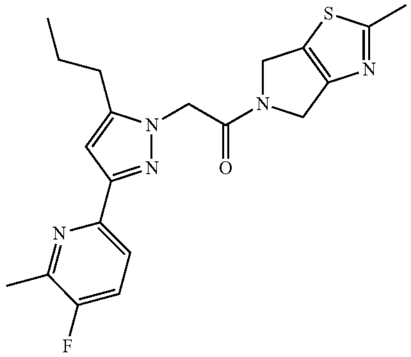 | 400 | method I | 0.83 |
| 7.02.249 | 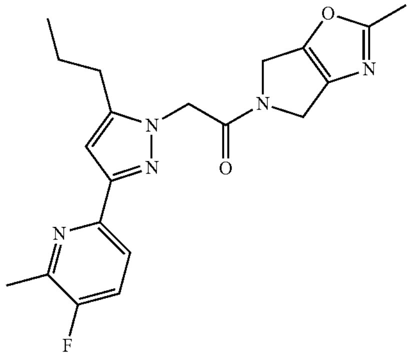 | 384 | method I | 0.81 |
| 7.02.250 | 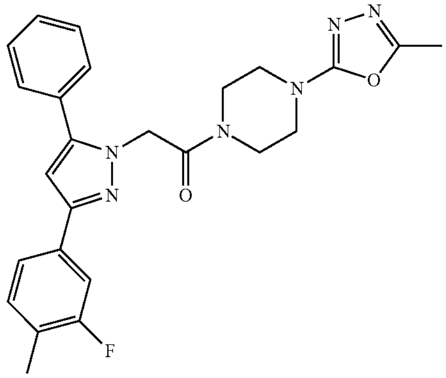 [SMILES: Cc1nnc(N2CCN(C(=O)Cn3nc(-c4ccc(C)c(F)c4)cc3-c3ccccc3)CC2)o1] | 461 | method I | 0.92 |

-continued
| | | | | |
|---|---|---|---|---|
| 7.02.251 | 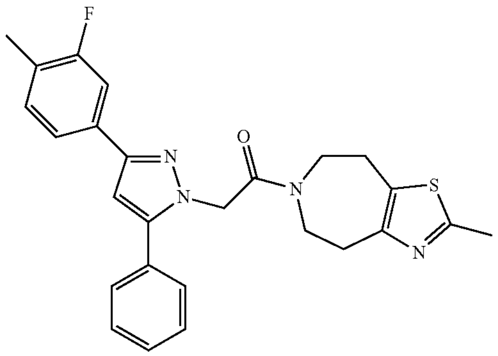 | 461 | method I | 0.94 |
| 7.02.252 | 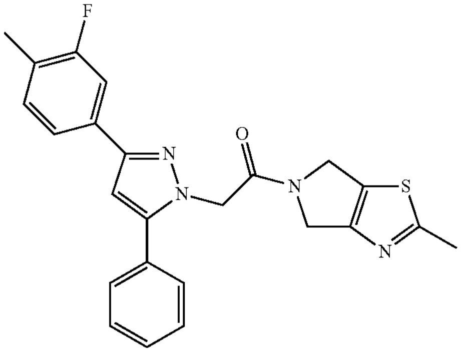 | 433 | method I | 0.97 |
| 7.02.253 | 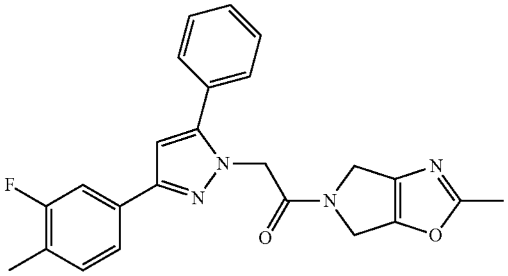 | 417 | method I | 0.95 |
| 7.02.255 | 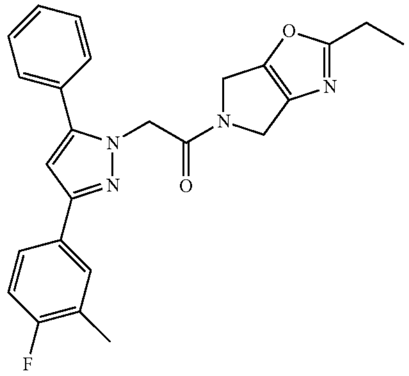 [SMILES: CCc1nc2c(o1)CN(C(=O)Cn1nc(-c3ccc(F)c(C)c3)cc1-c1ccccc1)C2] | 431.12 | method K | 0.81 |

-continued
| | | | | |
|---|---|---|---|---|
| 7.02.256 | 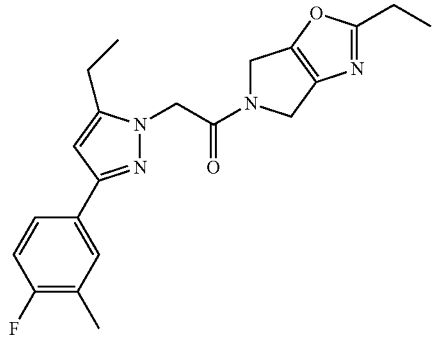 [SMILES: CCc1nc2c(o1)CN(C(=O)Cn1nc(-c3ccc(F)c(C)c3)cc1CC)C2] | 383.1 | method K | 0.73 |
| 7.02.257 | 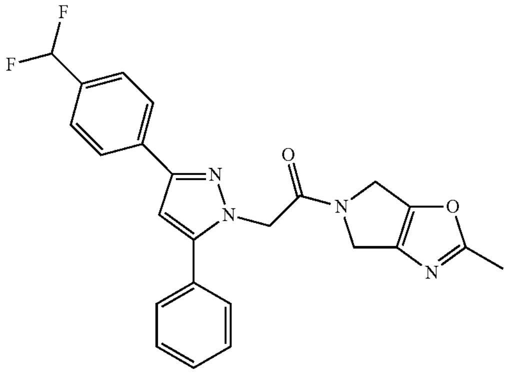 [SMILES: Cc1nc2c(o1)CN(C(=O)Cn1nc(-c3ccc(C(F)F)cc3)cc1-c1ccccc1)C2] | 435.12 | method K | 0.74 |
| 7.02.258 | 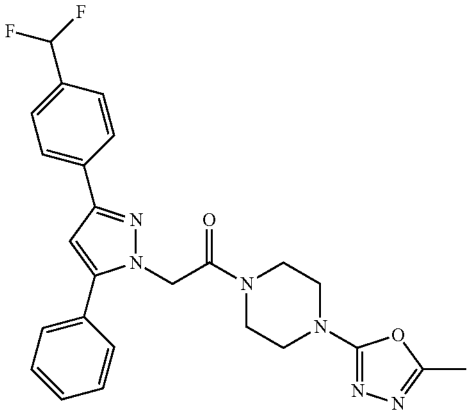 [SMILES: Cc1nnc(N2CCN(C(=O)Cn3nc(-c4ccc(C(F)F)cc4)cc3-c3ccccc3)CC2)o1] | 479.15 | method K | 0.70 |
| 7.02.259 | 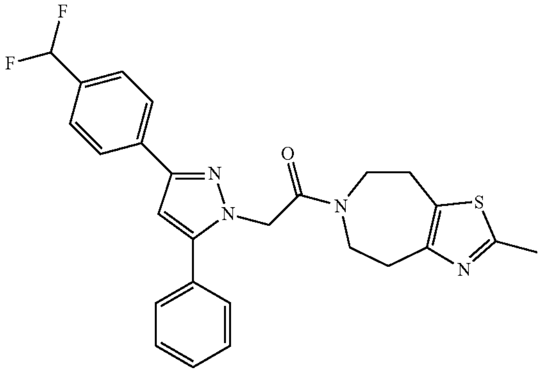 [SMILES: Cc1nc2c(s1)CCN(C(=O)Cn1nc(-c3ccc(C(F)F)cc3)cc1-c1ccccc1)CC2] | 479.13 | method K | 0.77 |

-continued
| | | | | |
|---|---|---|---|---|
| 7.02.260 | 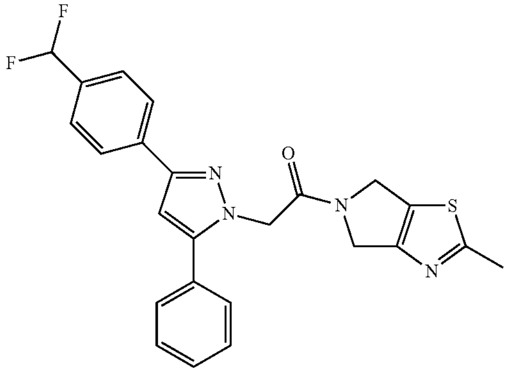 | 451.1 | method K | 0.77 |
The invention claimed is:
1. A compound of formula I
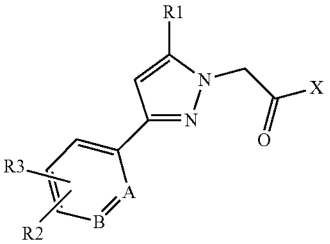
I
in which
A represents CH;
B represents CH;
$R^1$ represents phenyl, methyl, ethyl, propyl, iso-propyl, cyclopropyl, cyclohexyl,
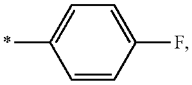,
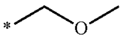,
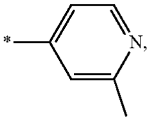
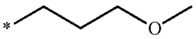 or 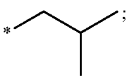;
X represents
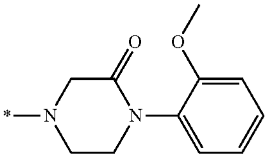,
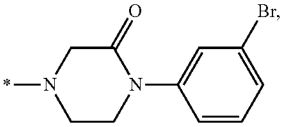
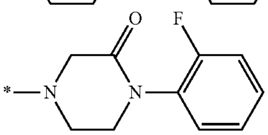,
-continued
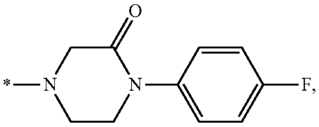
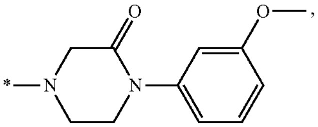
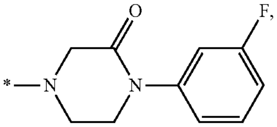
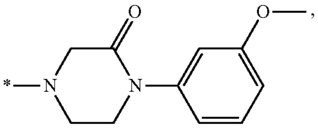
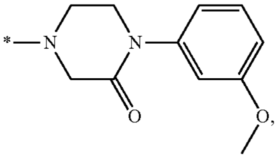
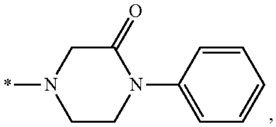,
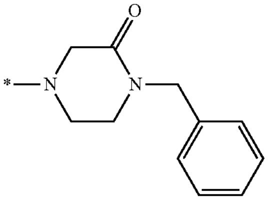,
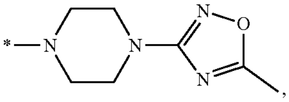,
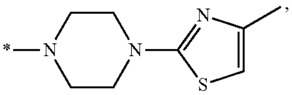,
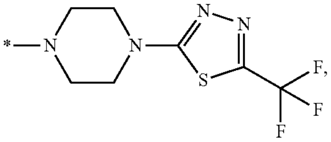

-continued
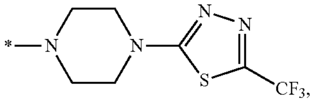
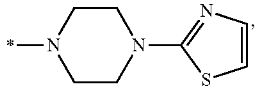
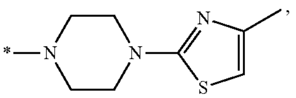
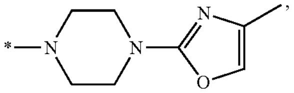
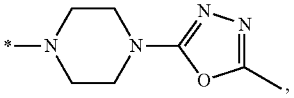
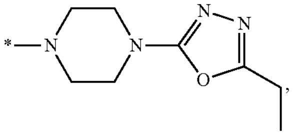
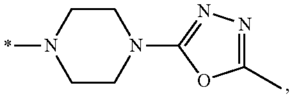
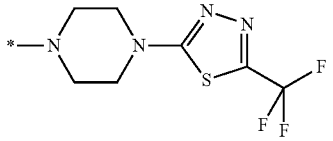
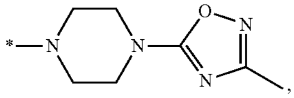
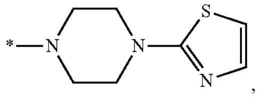
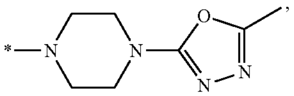
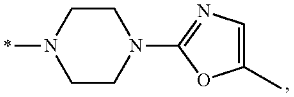
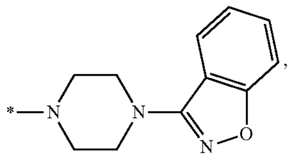
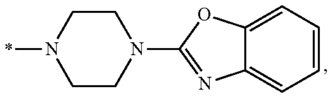
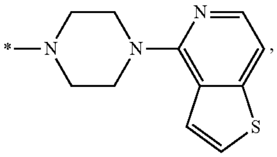
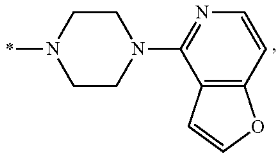
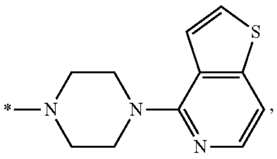
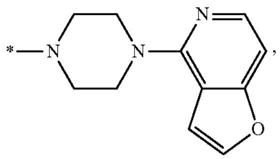
-continued
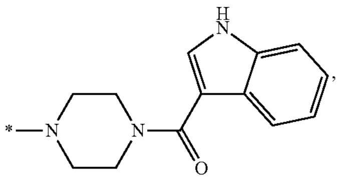
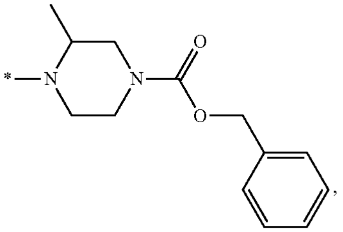
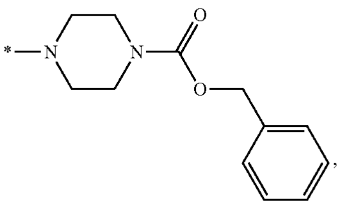
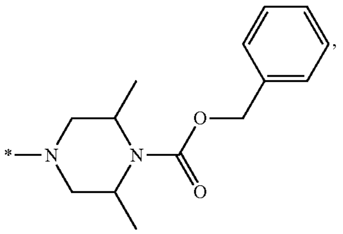
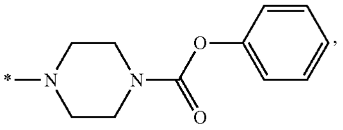
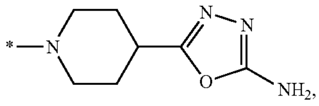
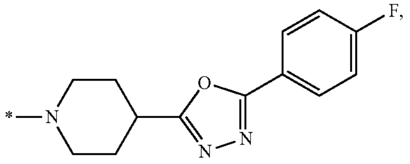
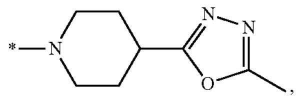
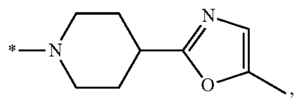
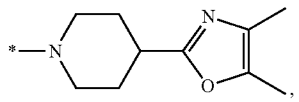
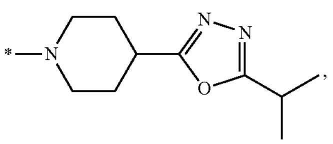

-continued
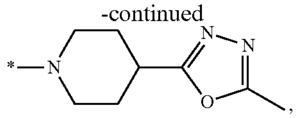
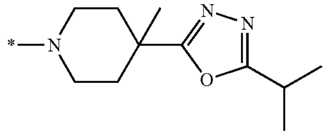
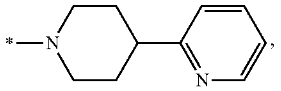
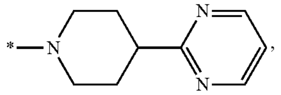
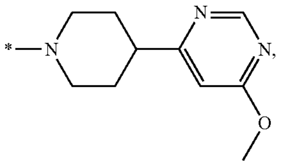
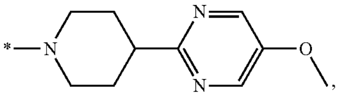
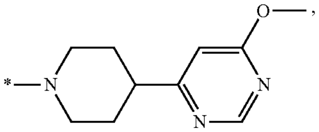
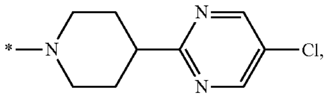
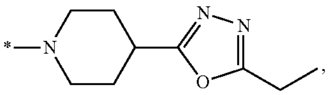
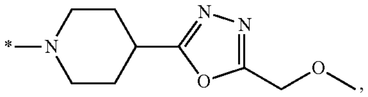
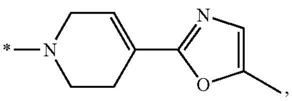
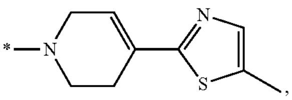
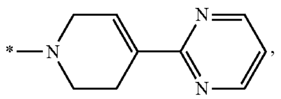
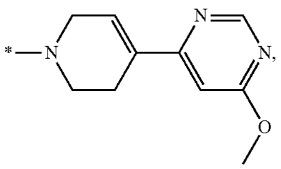
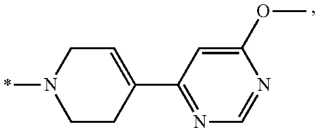
-continued
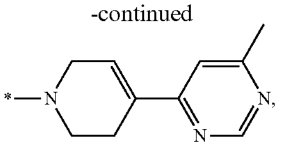
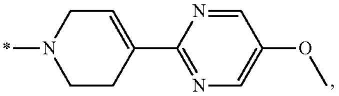
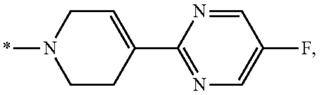
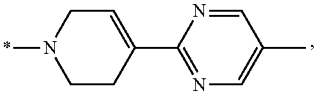
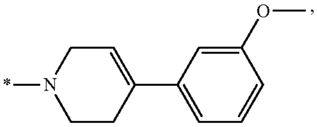
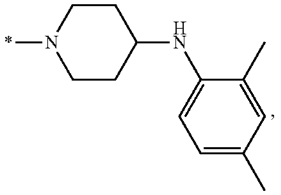
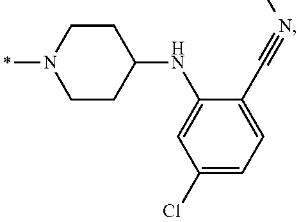
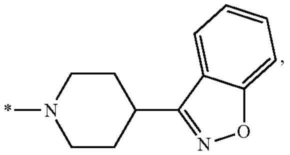
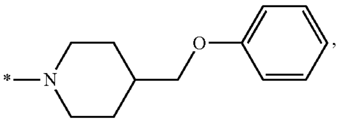
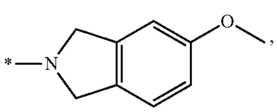
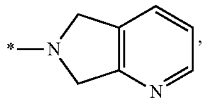
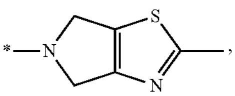
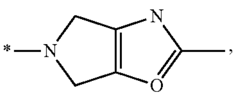
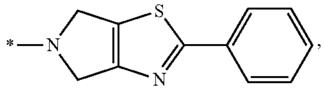
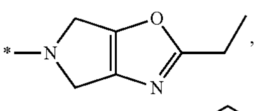
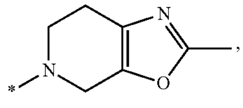
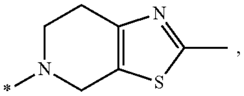

-continued
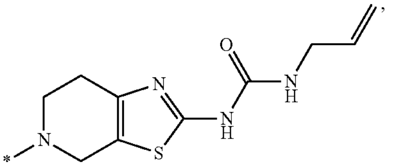
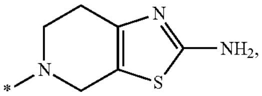
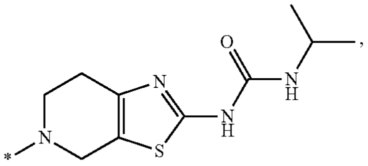
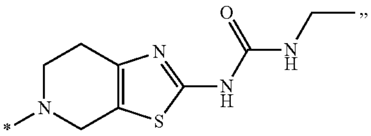
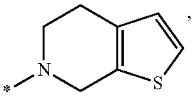
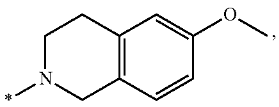
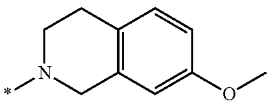
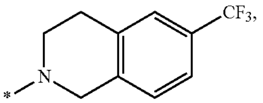
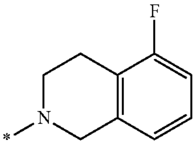
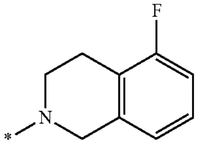
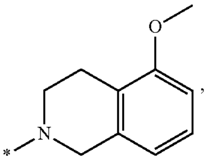
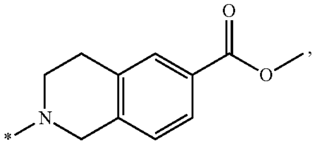
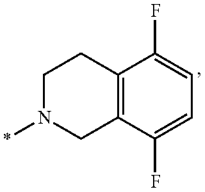
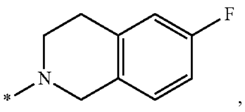
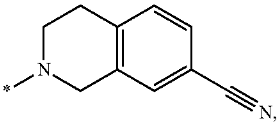
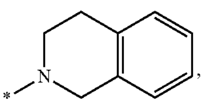
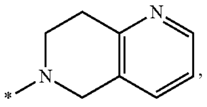
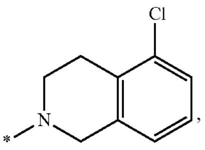
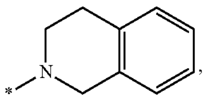
-continued
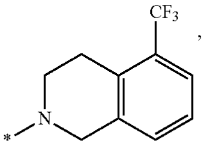
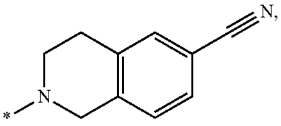
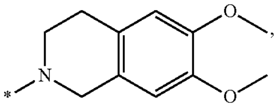
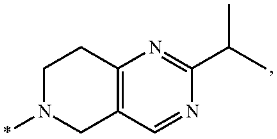
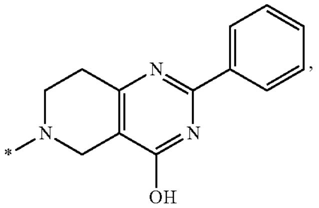
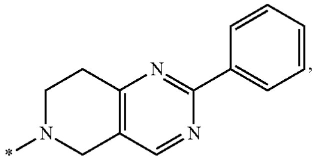
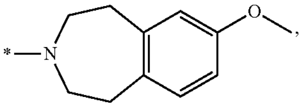
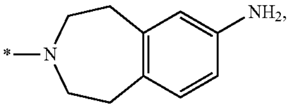
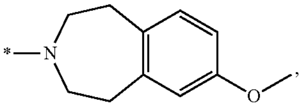
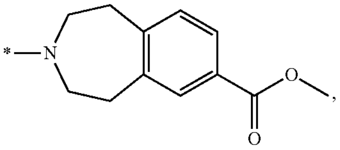
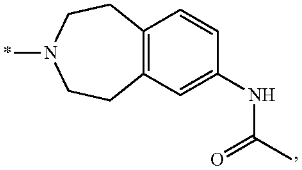
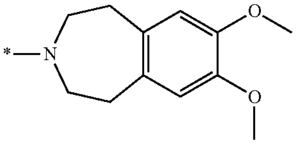
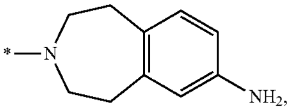
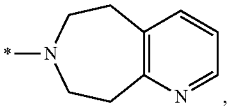
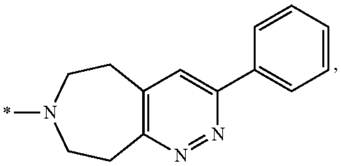

-continued
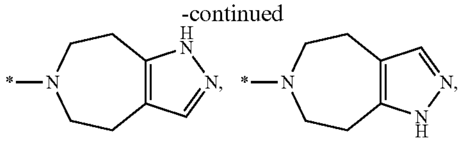
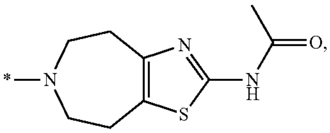
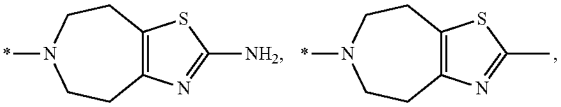
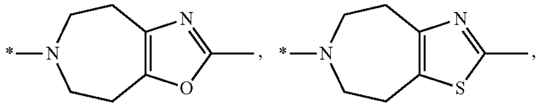
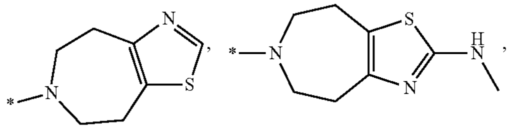
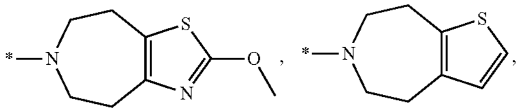
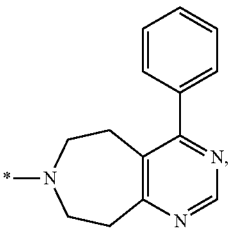
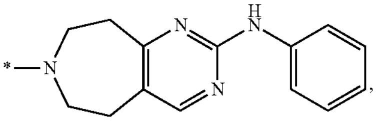
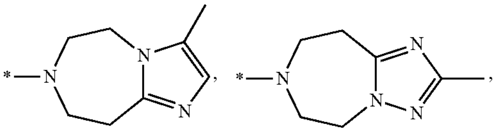
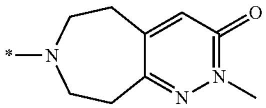
or
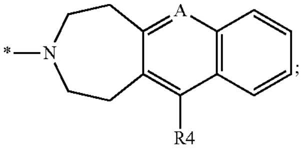
the group
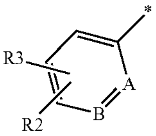
represents
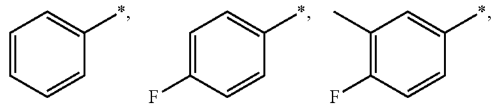
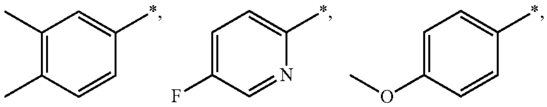
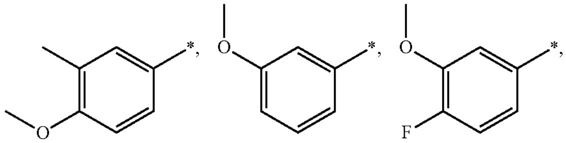
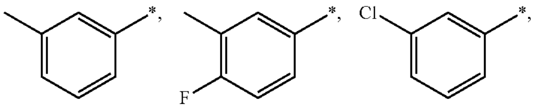
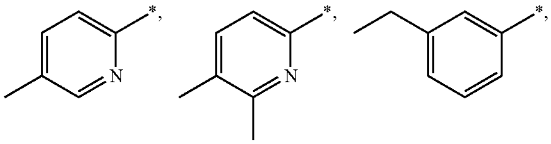
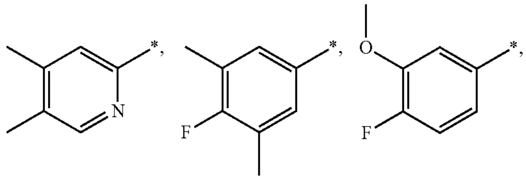
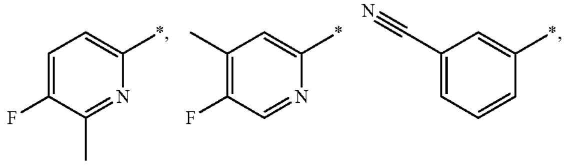
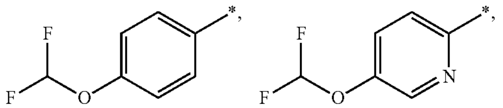
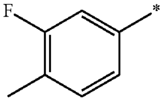
or
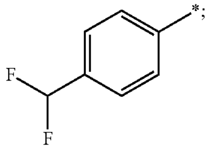
or a physiologically acceptable salt thereof.
2. The compound according to claim 1 selected from the group consisting of
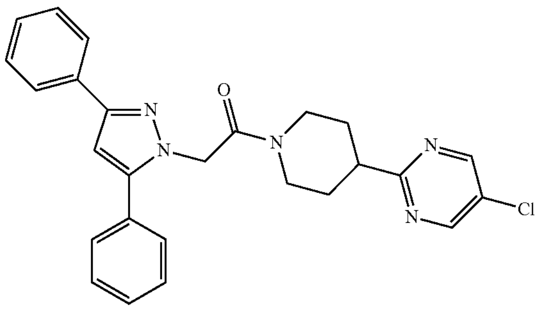

-continued
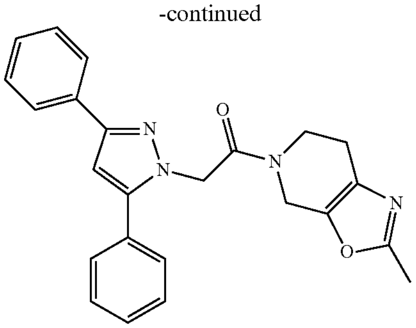
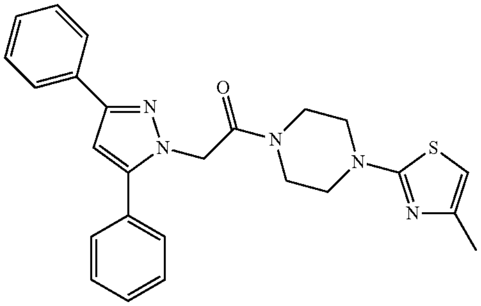
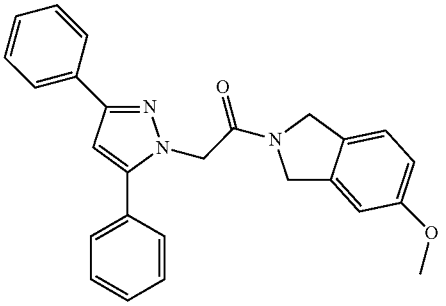
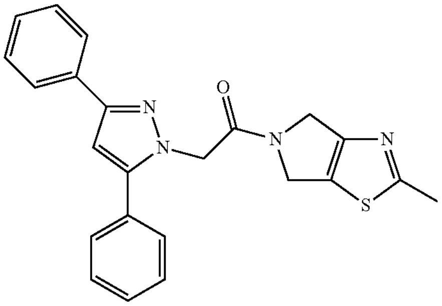
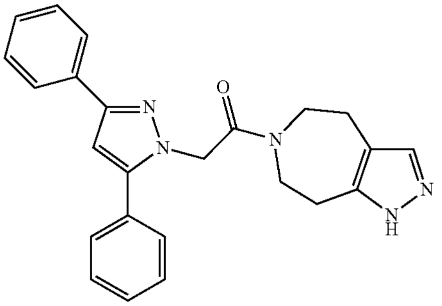
-continued
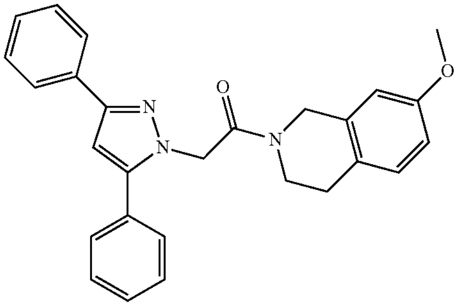
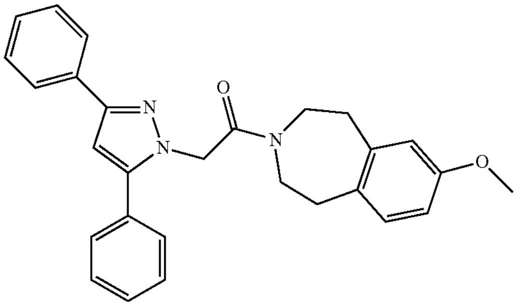
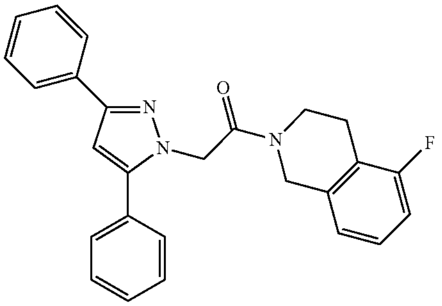
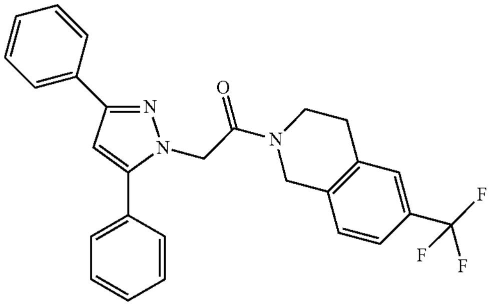
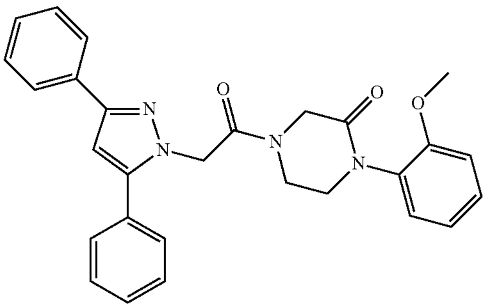

-continued
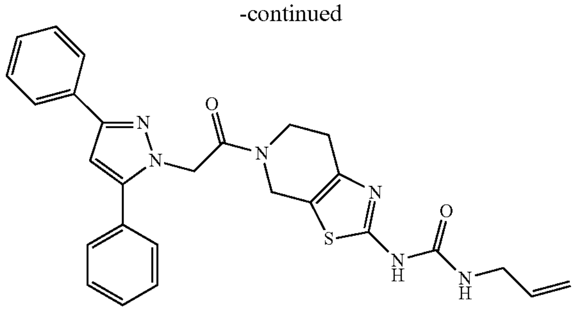
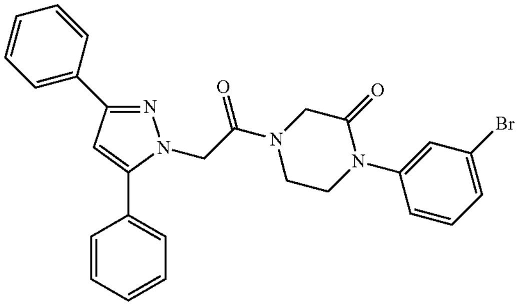
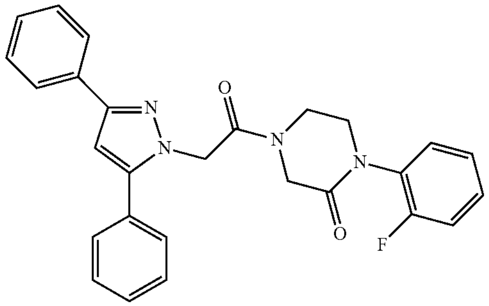
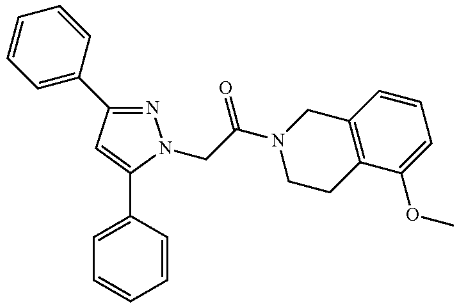
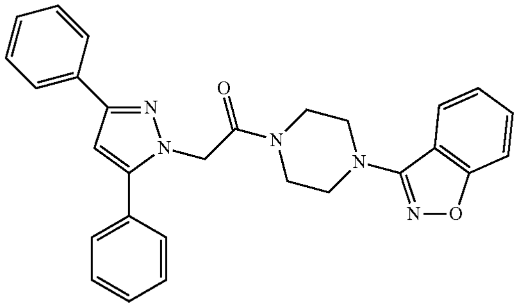
-continued
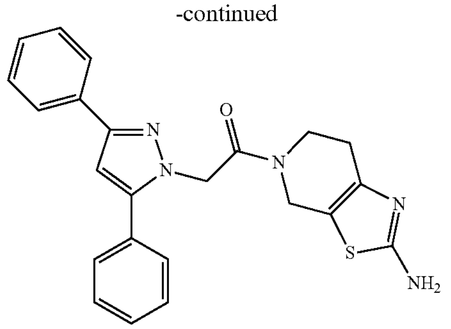
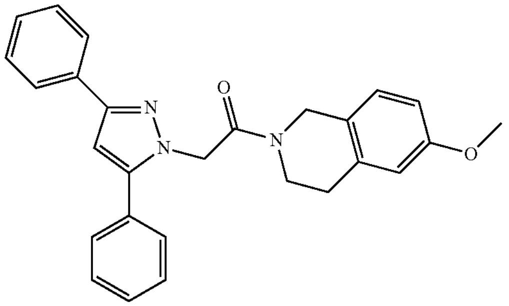
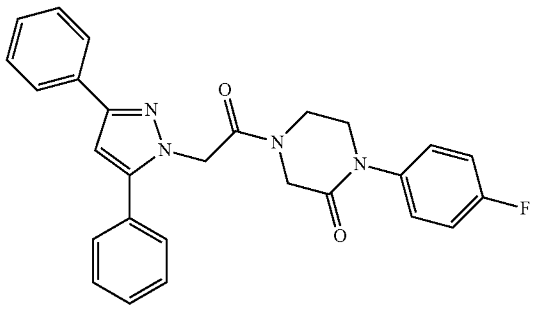
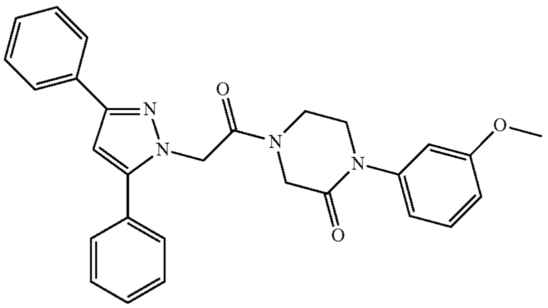
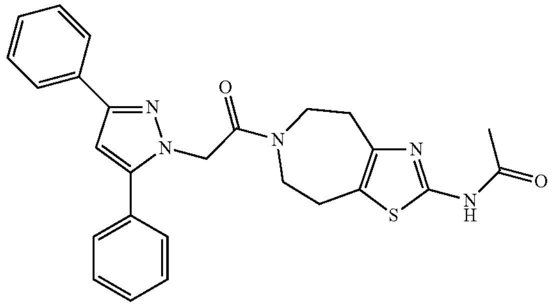

-continued
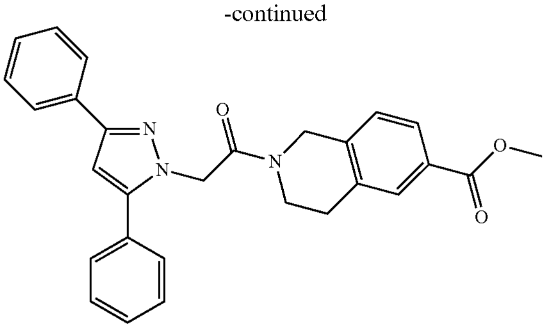
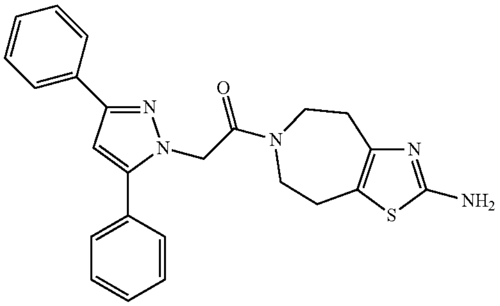
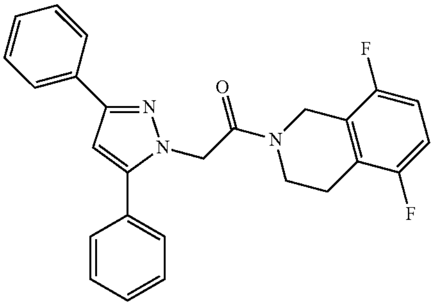
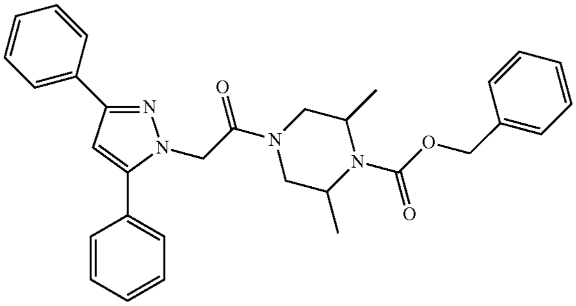
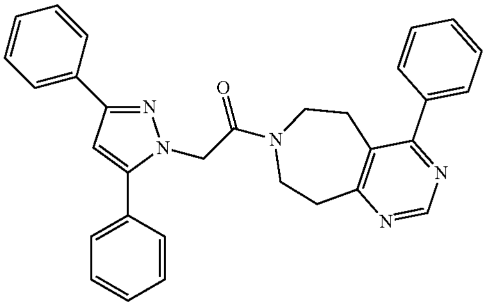
-continued
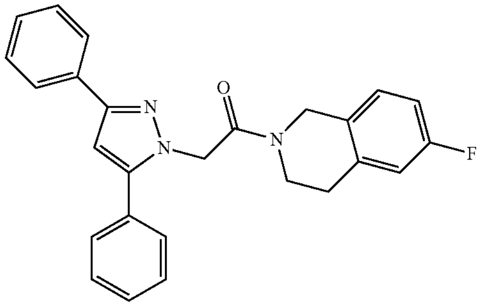
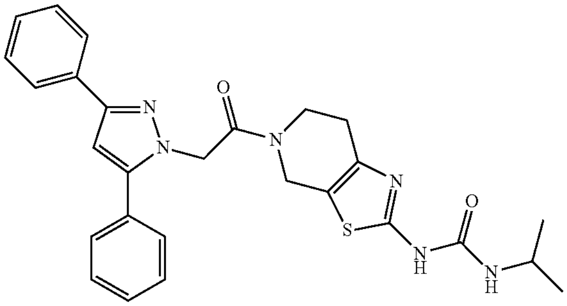
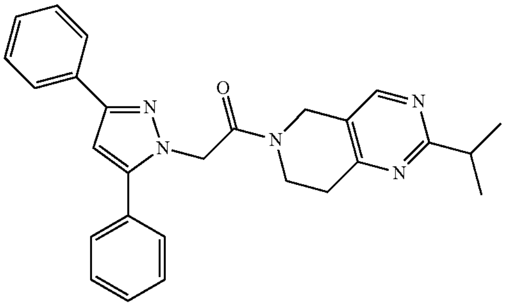
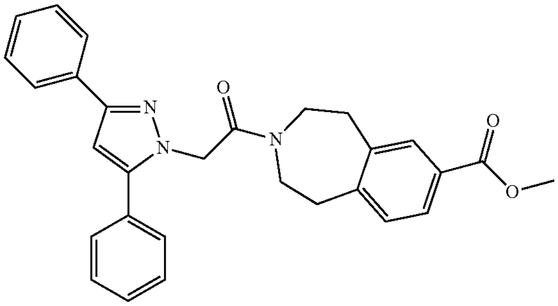
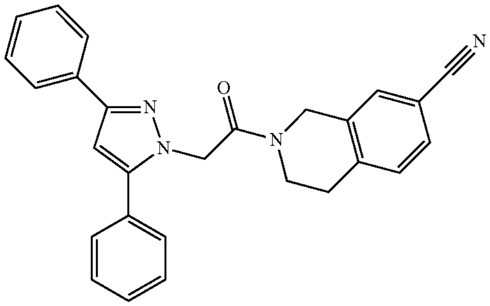

-continued
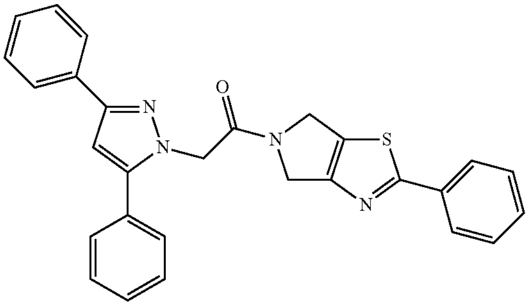
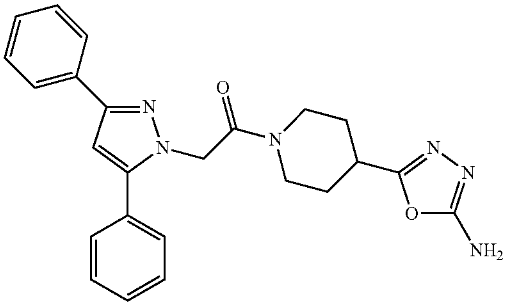
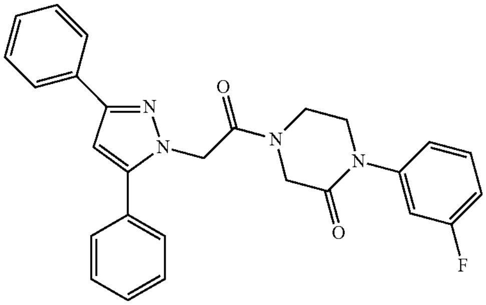
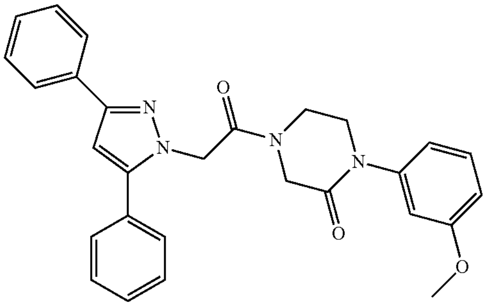
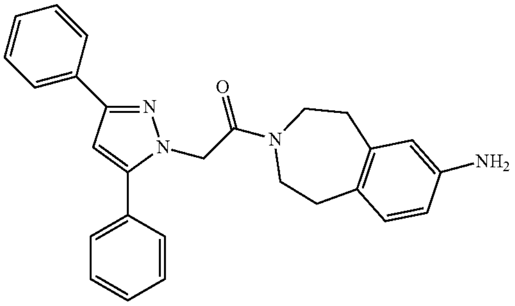
-continued
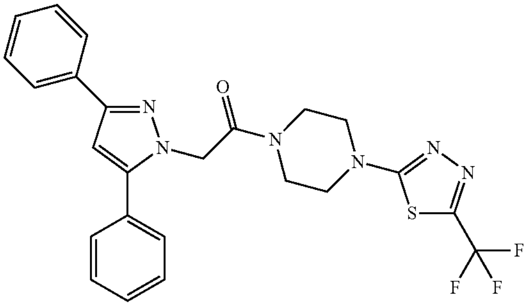
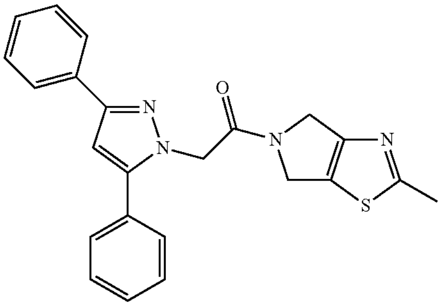
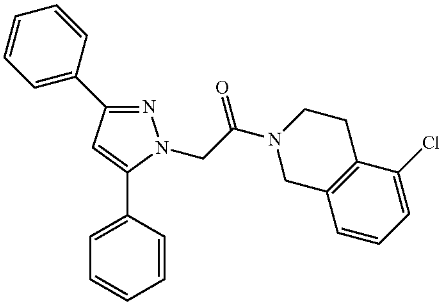
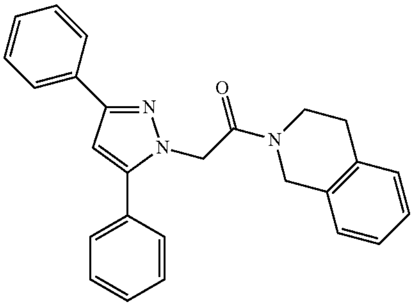
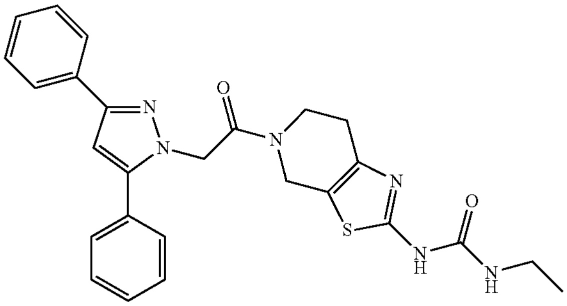

-continued
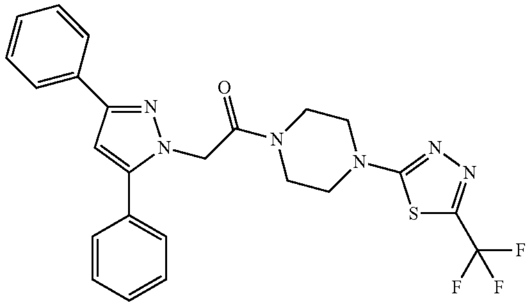
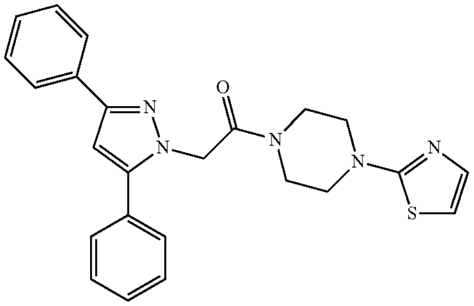
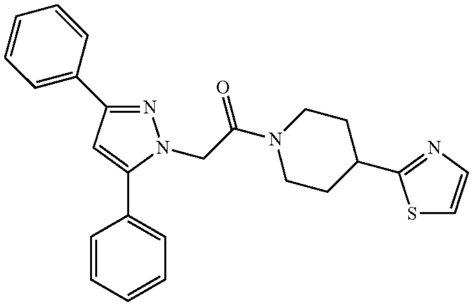
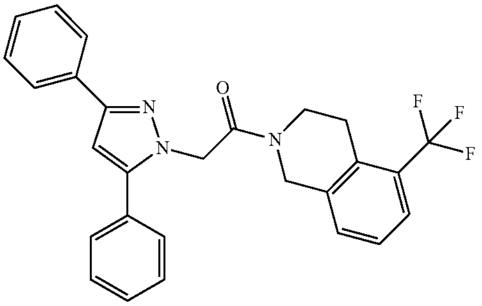
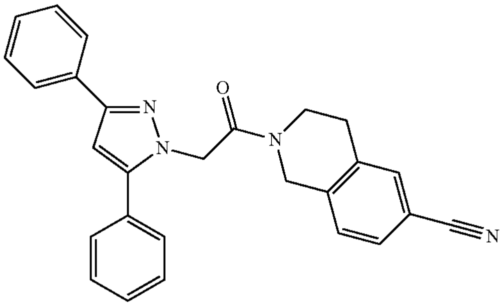
-continued
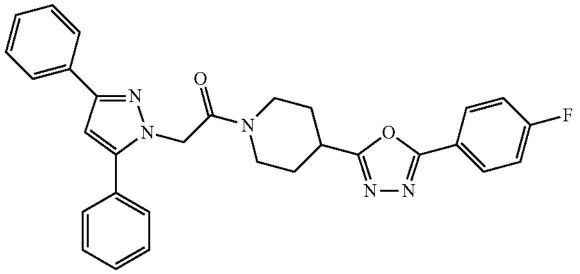
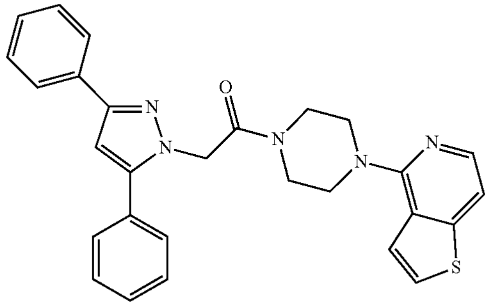
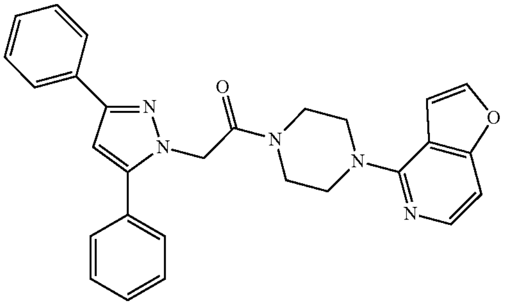
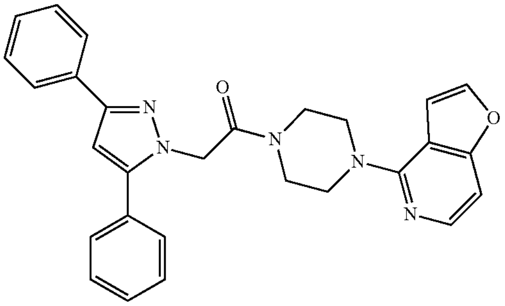
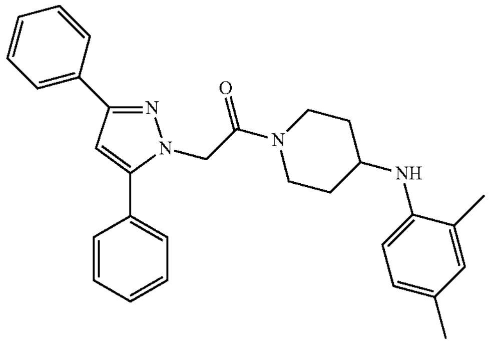

-continued
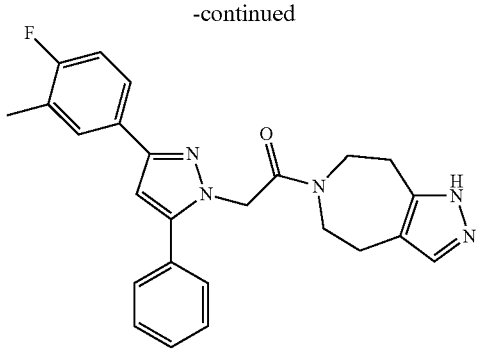
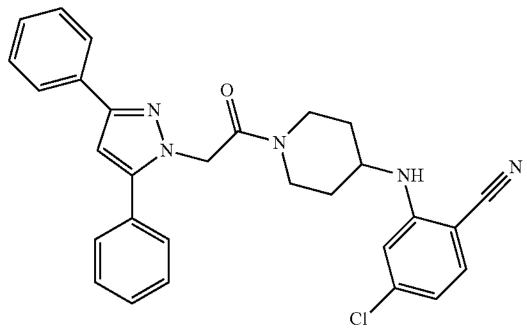
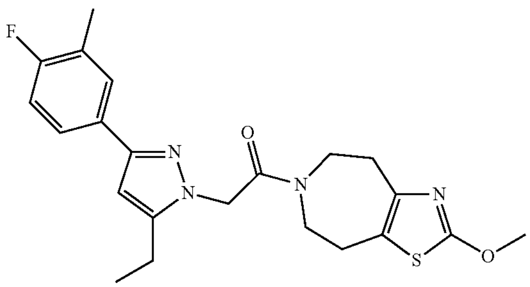
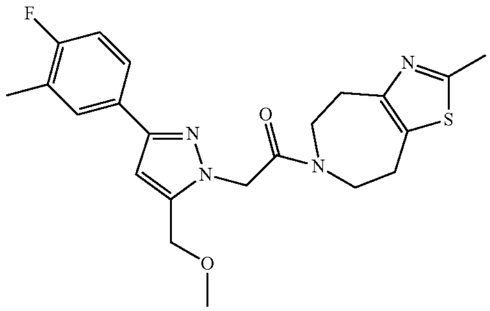
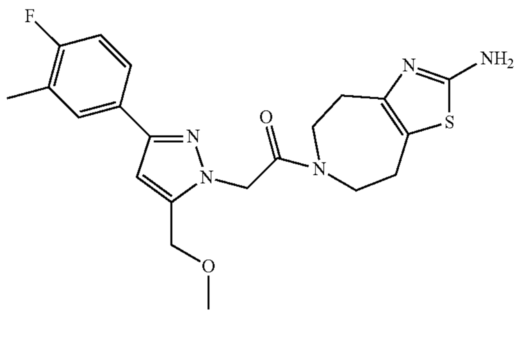
-continued
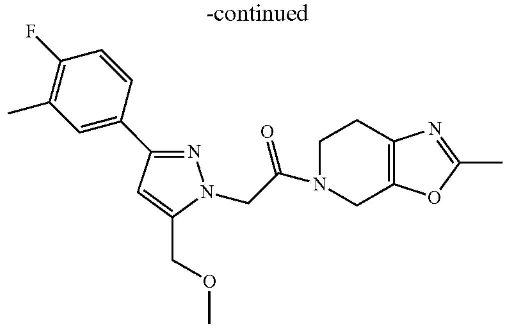
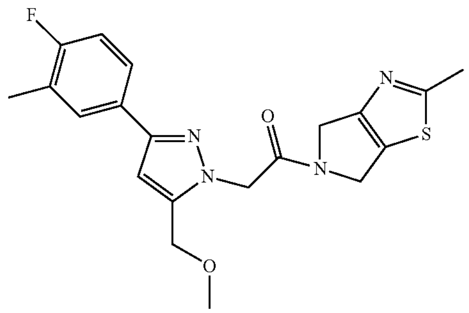
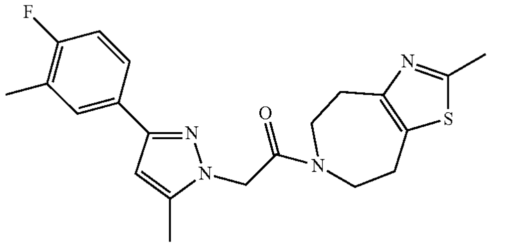
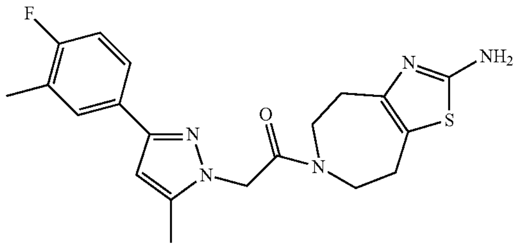
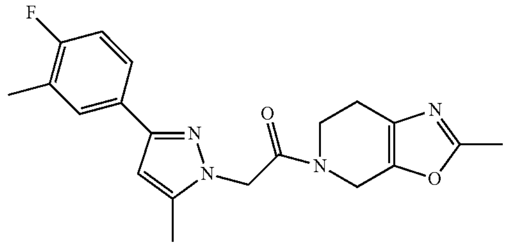
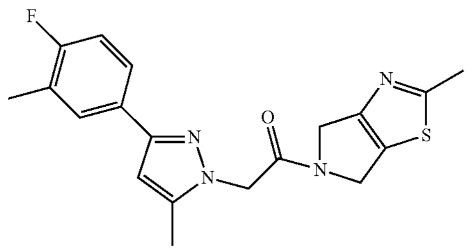

-continued
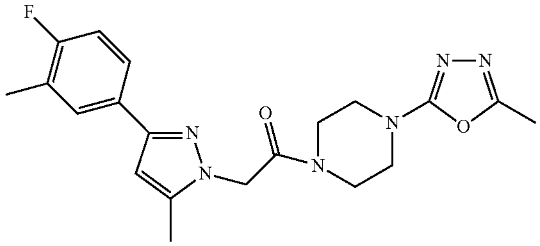
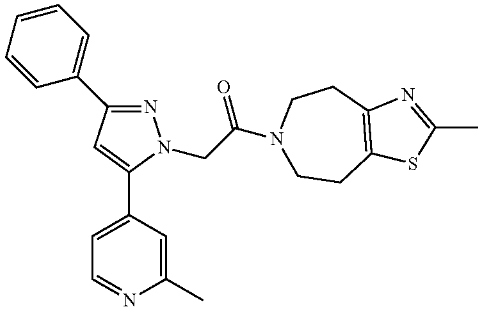
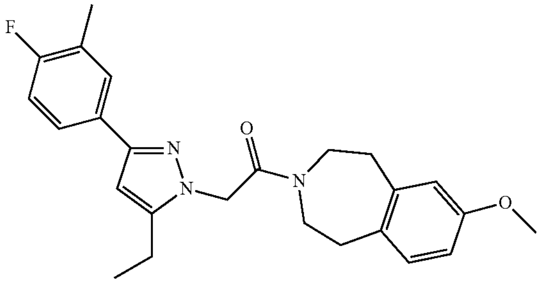
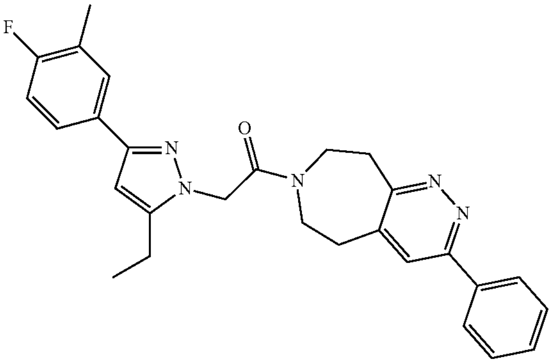
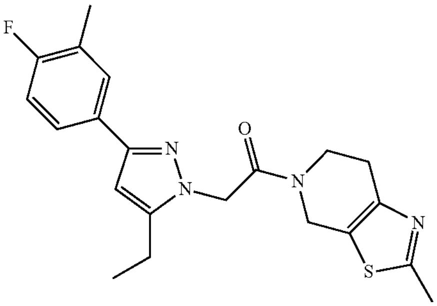
-continued
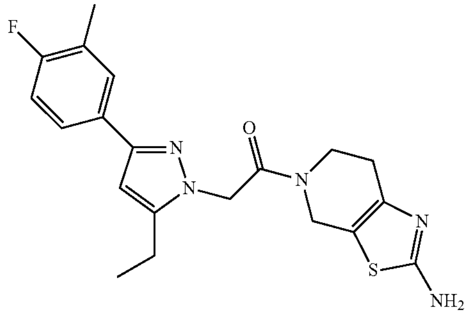
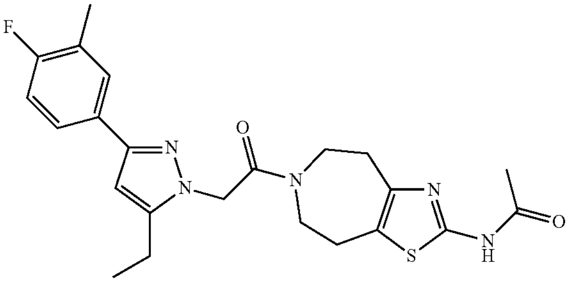
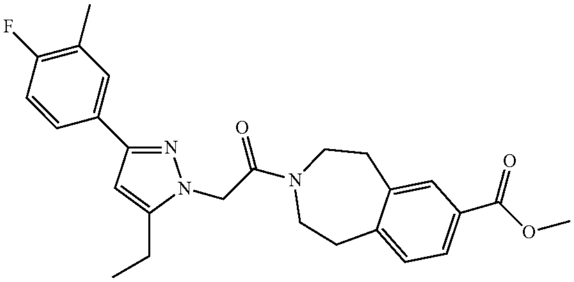
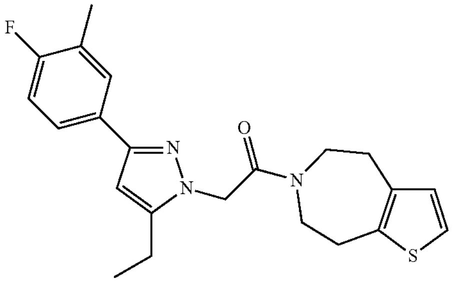
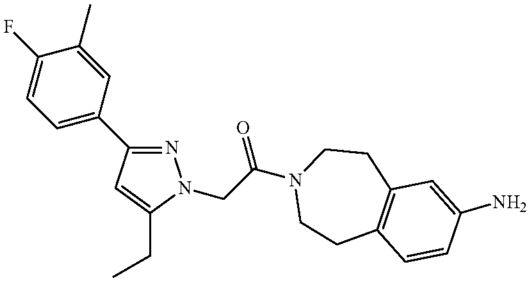
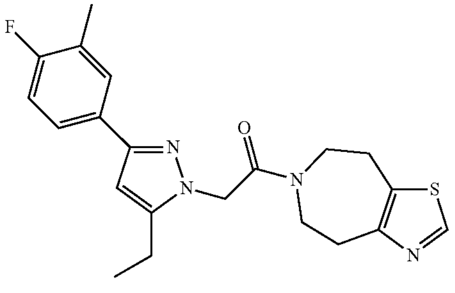

-continued
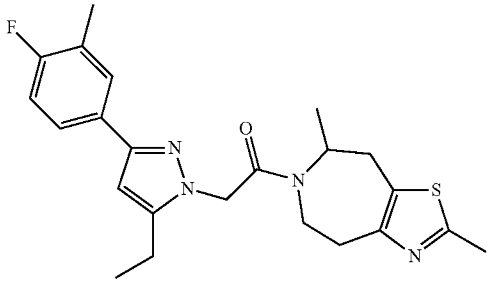
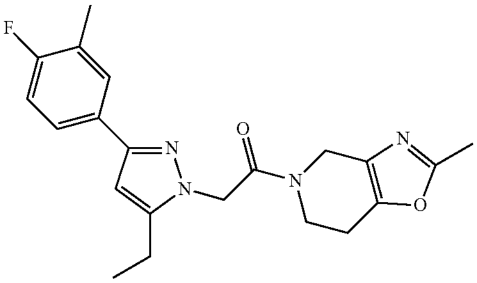
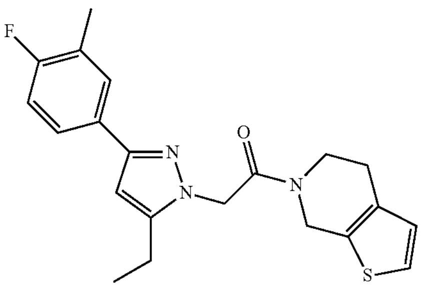
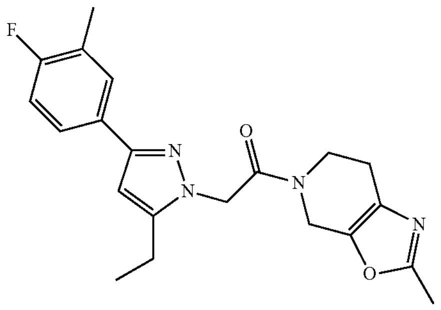
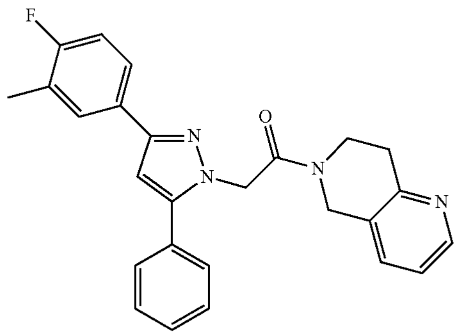
-continued
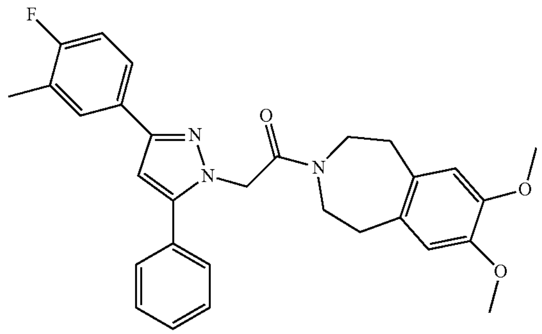
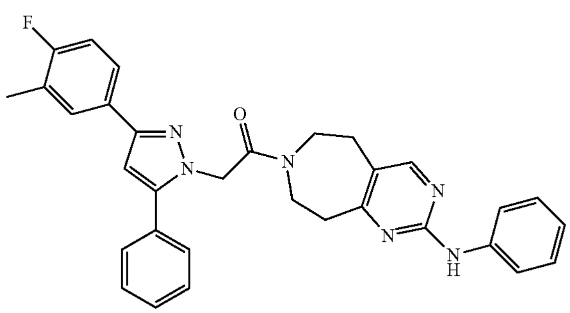
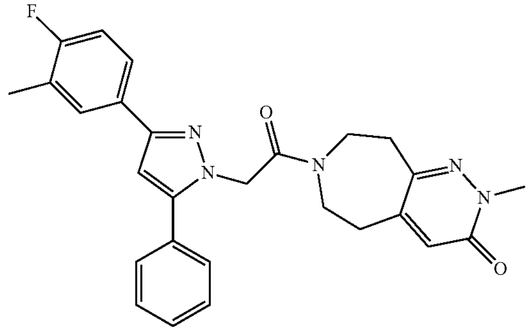
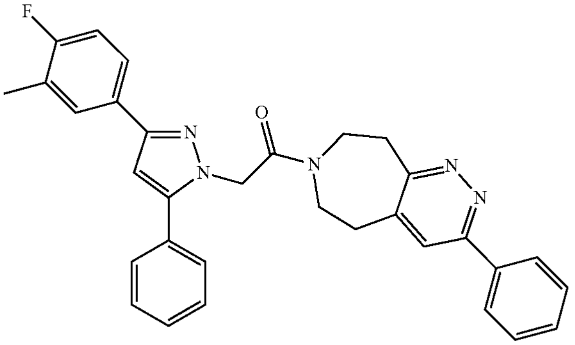
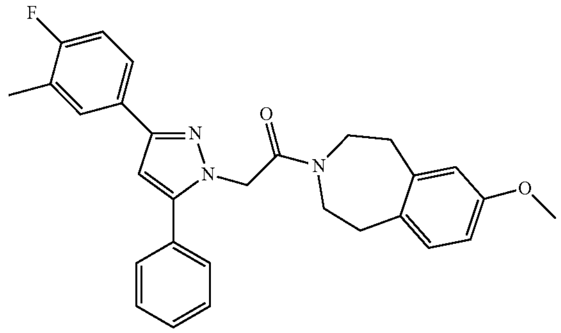

-continued
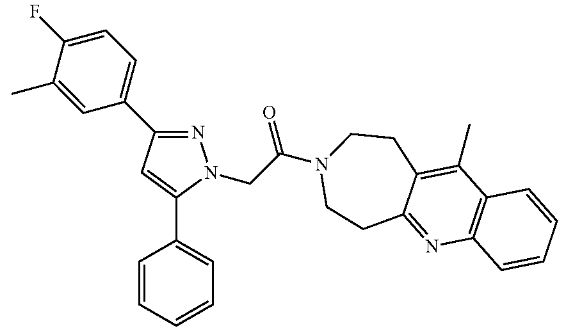
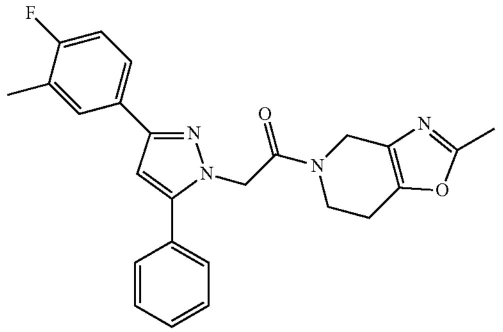
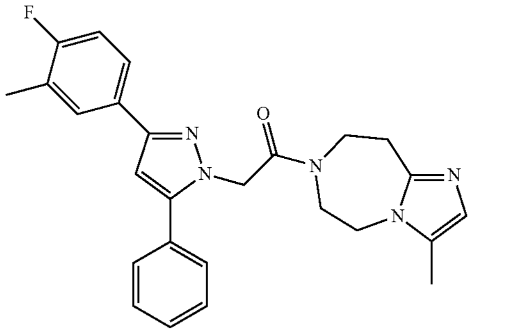
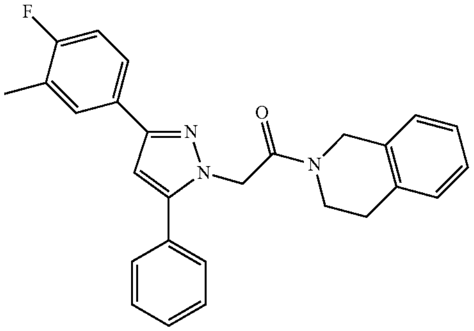
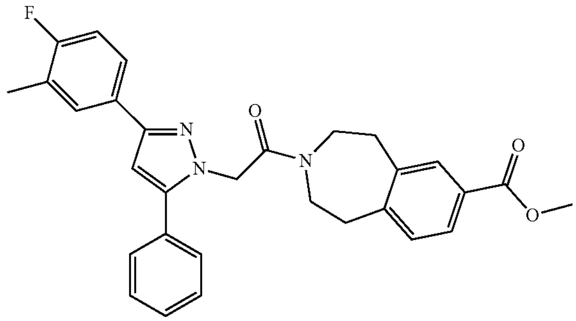
-continued
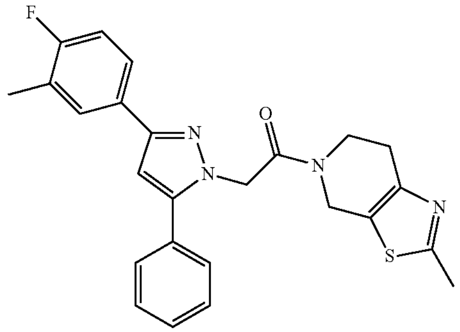
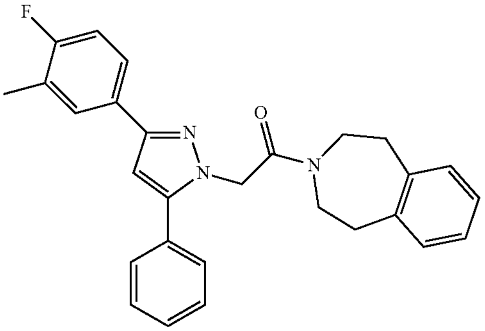
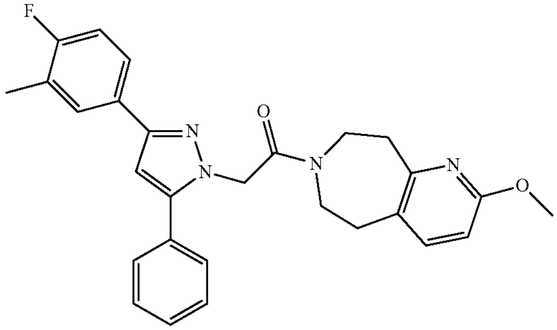
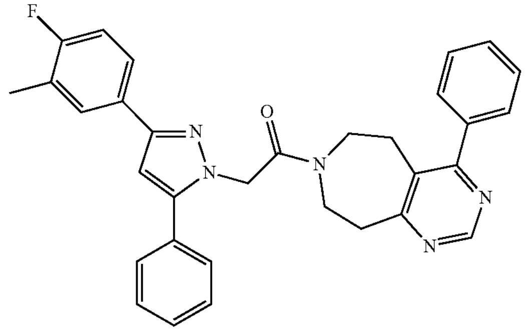
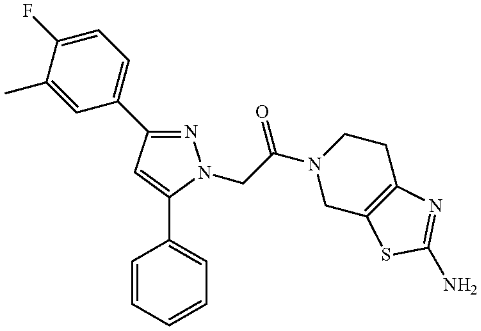

-continued
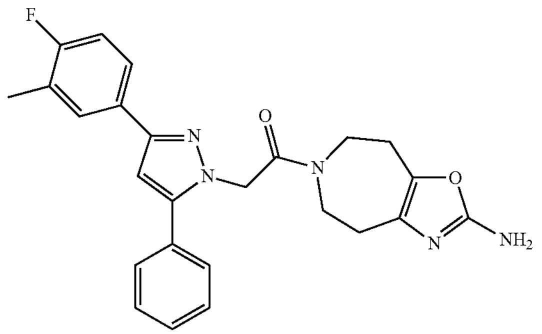
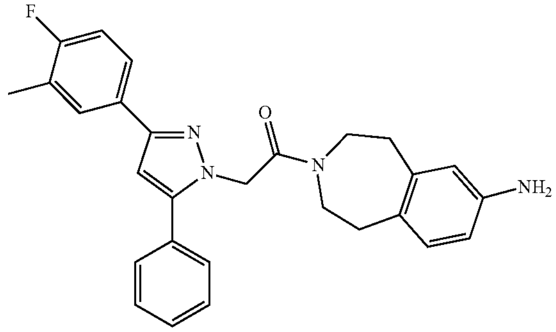
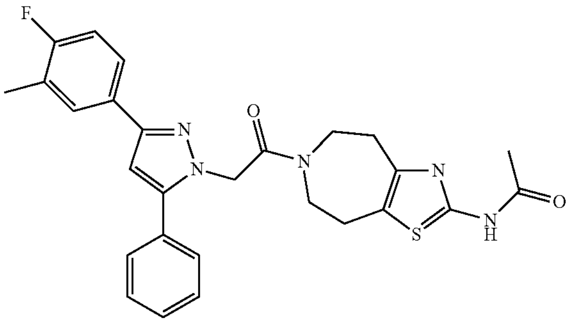
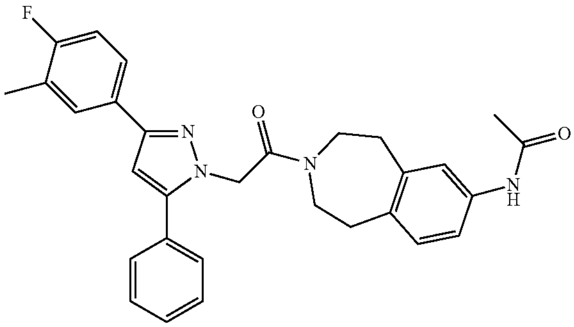
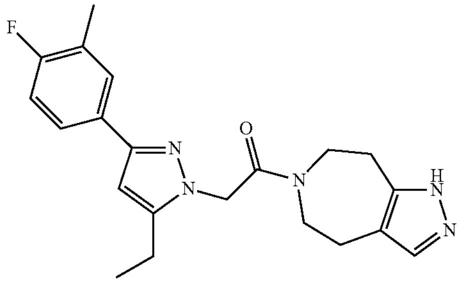
-continued
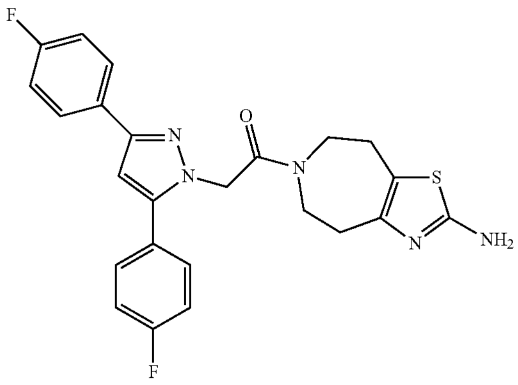
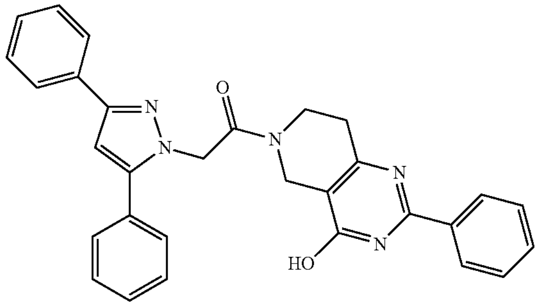
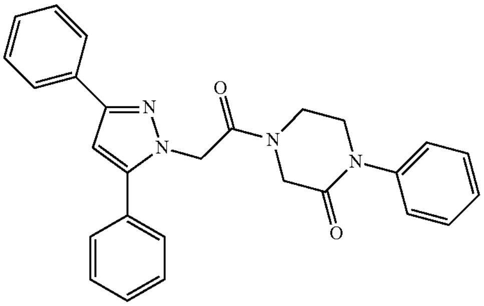
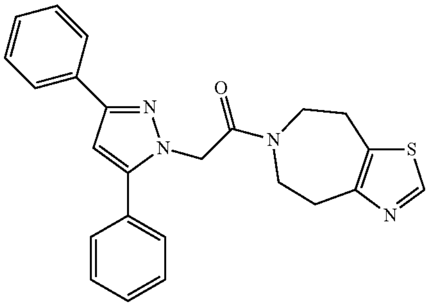
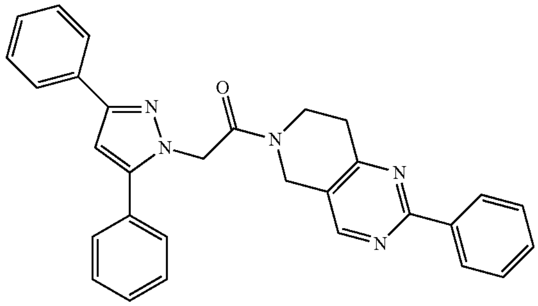

-continued
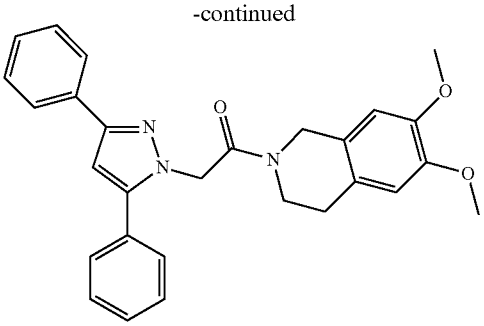
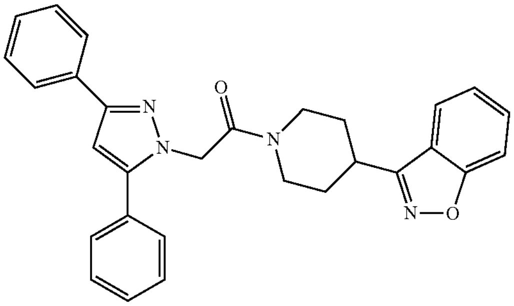
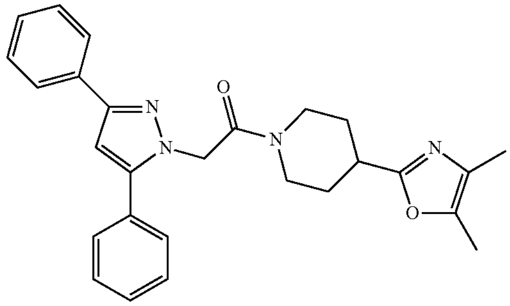
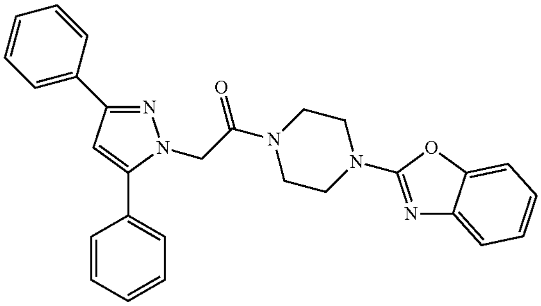
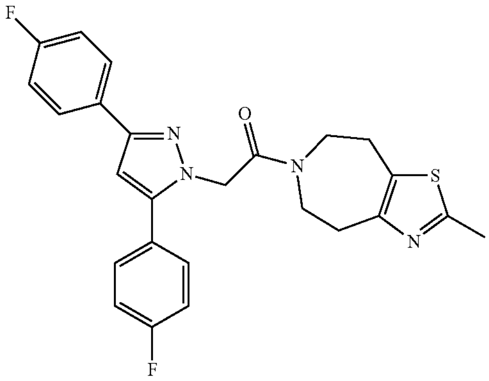
-continued
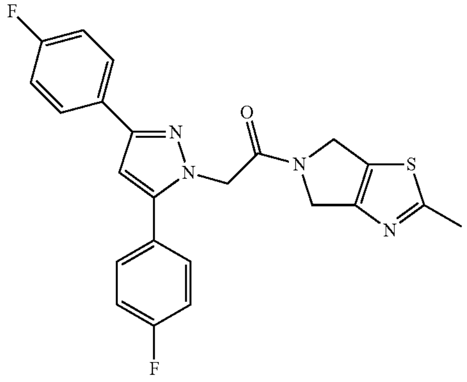
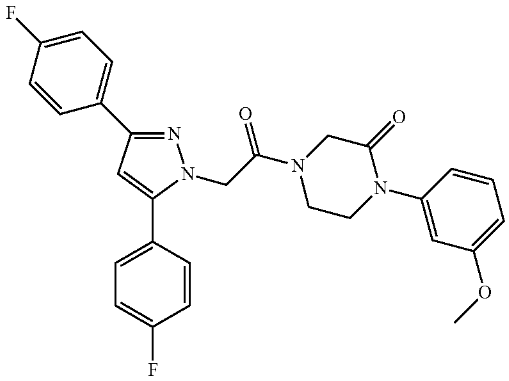
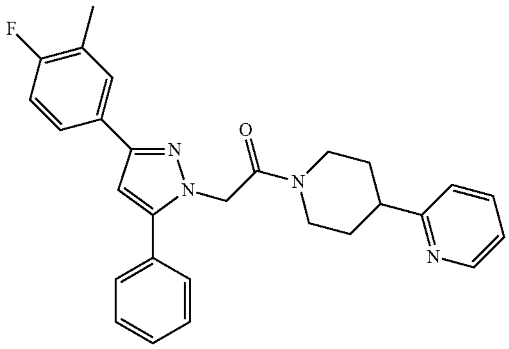
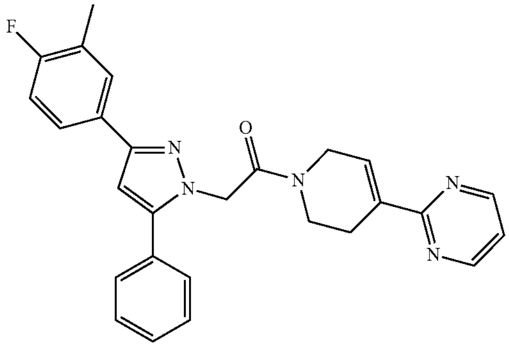

-continued
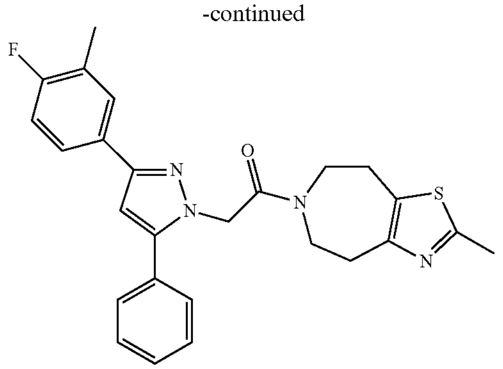
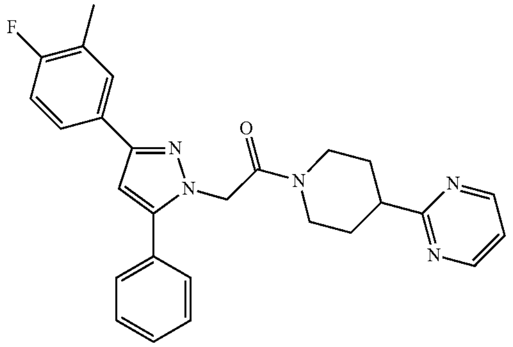
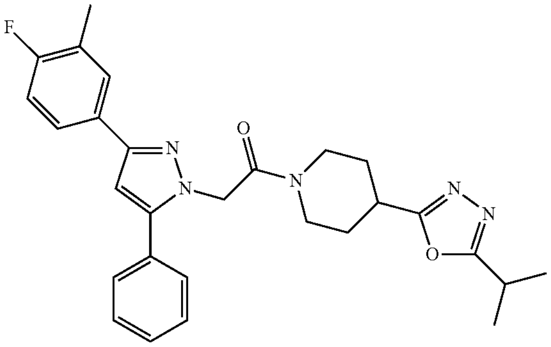
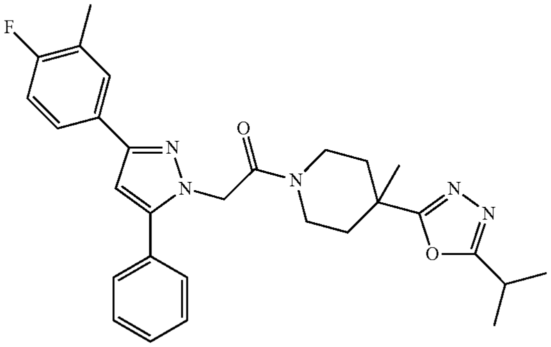
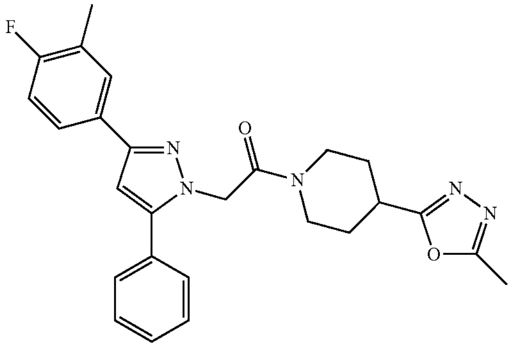
-continued
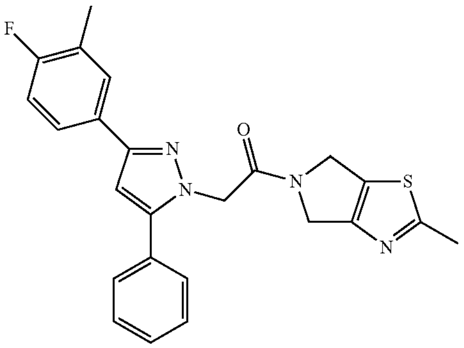
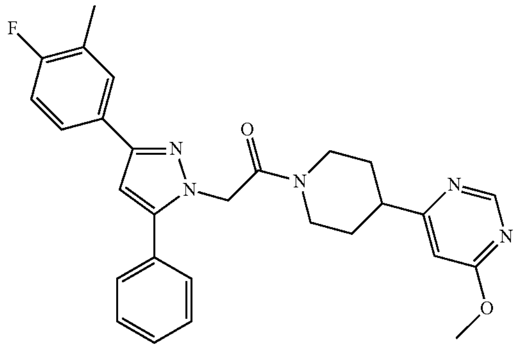
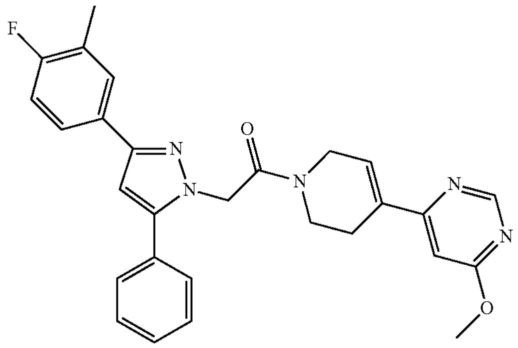
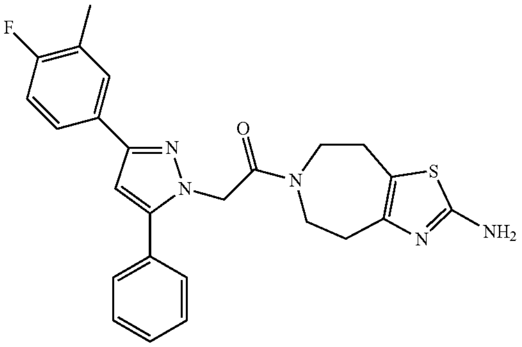
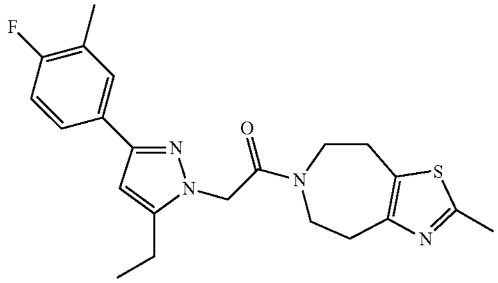

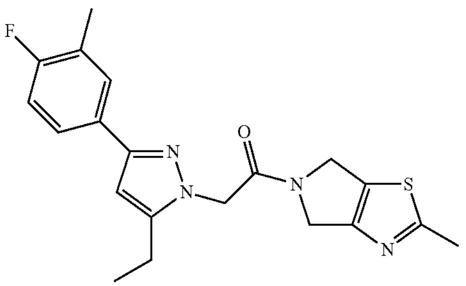
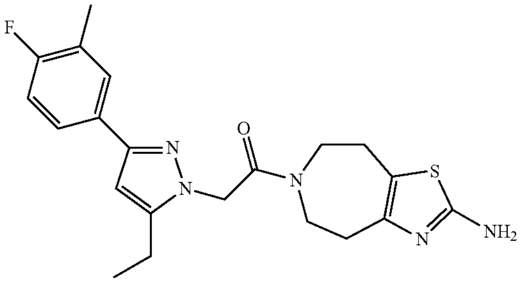
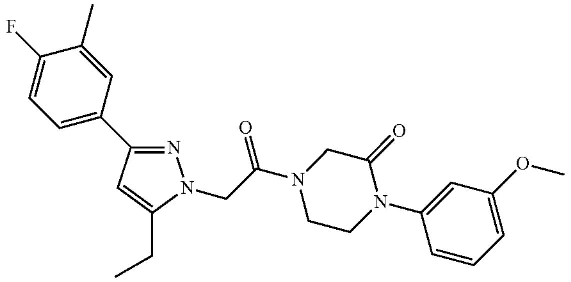
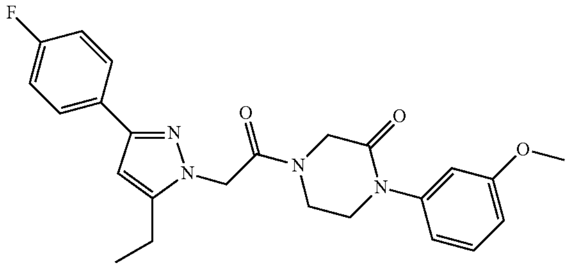
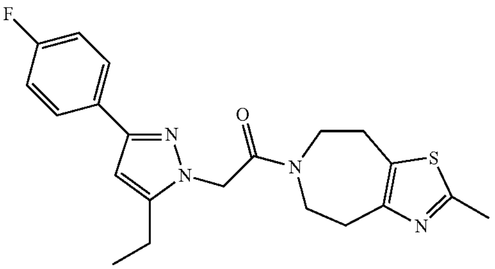
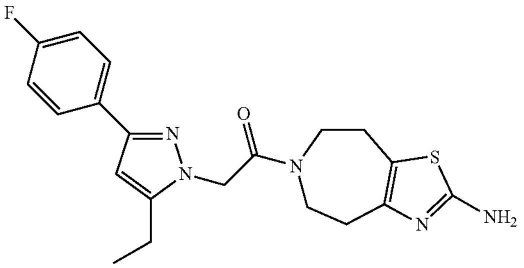
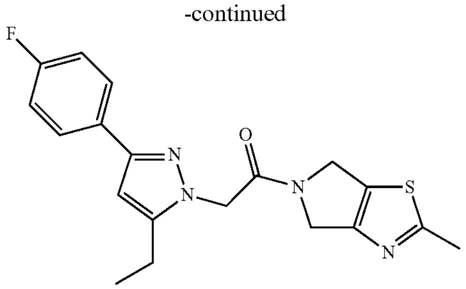
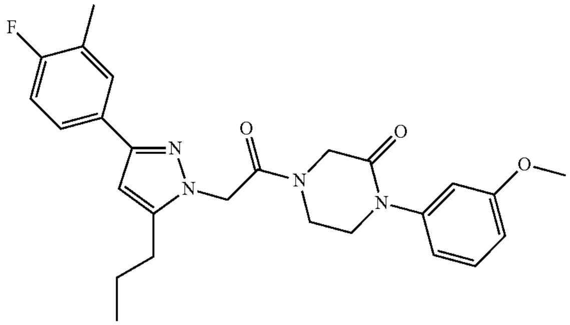
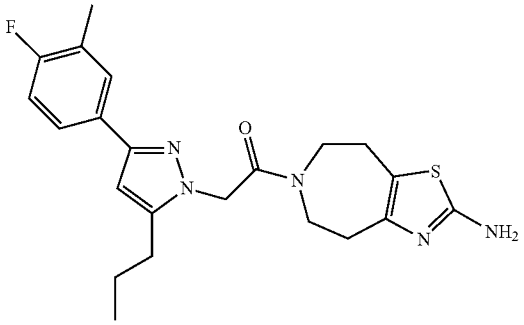
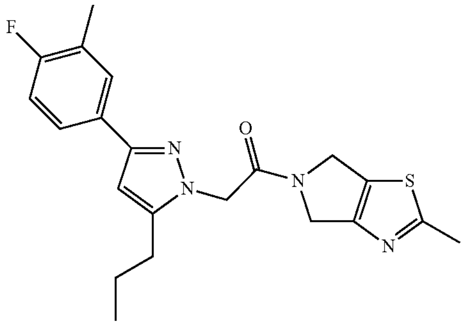
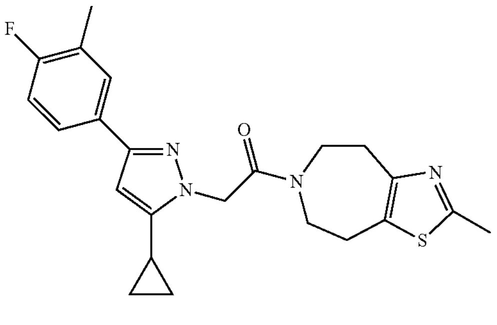

-continued
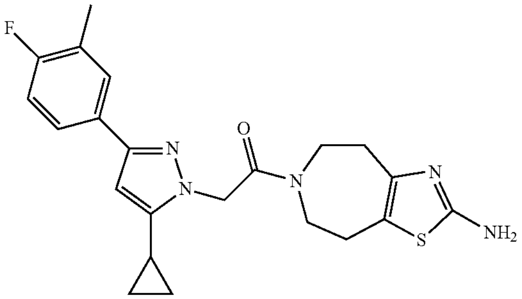
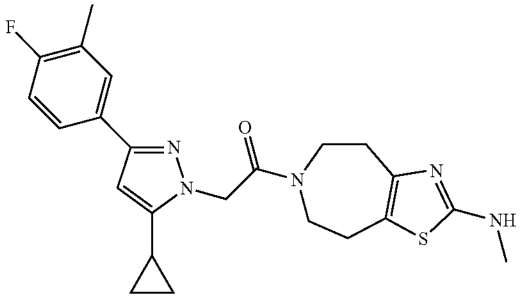
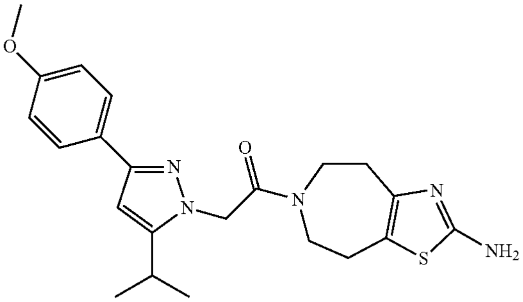
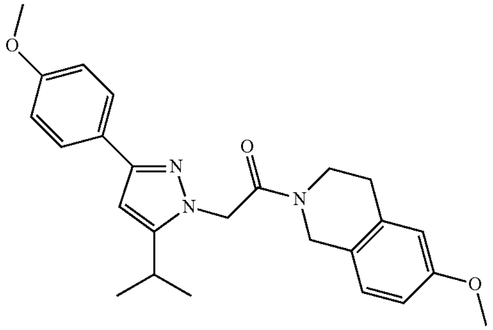
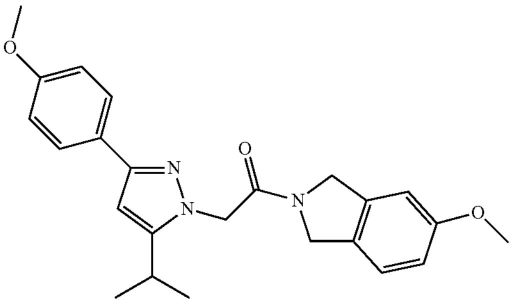
-continued
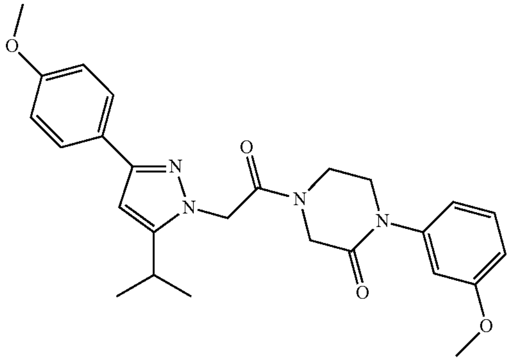
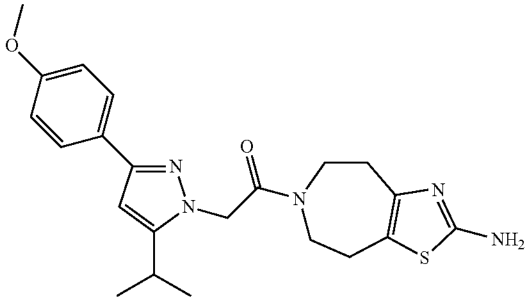
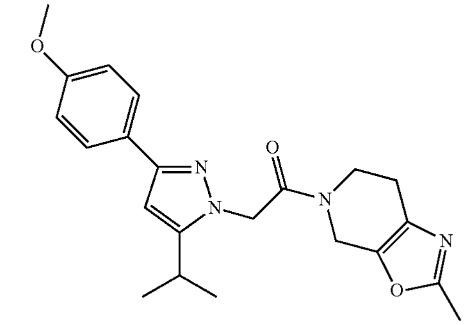
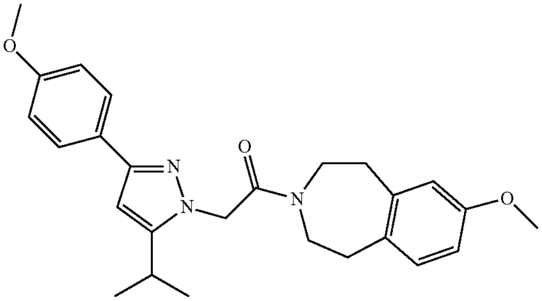
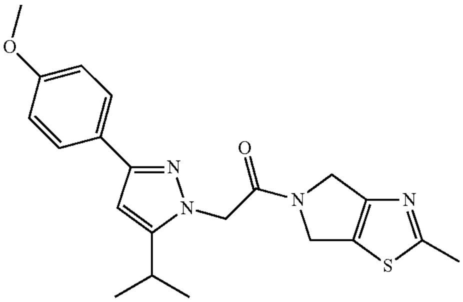

-continued
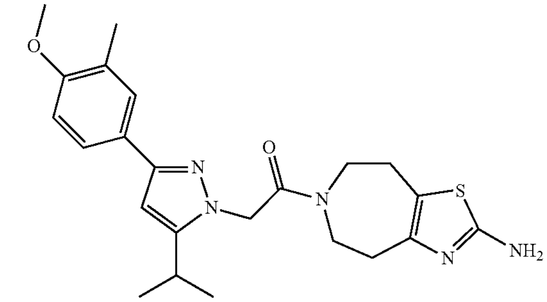
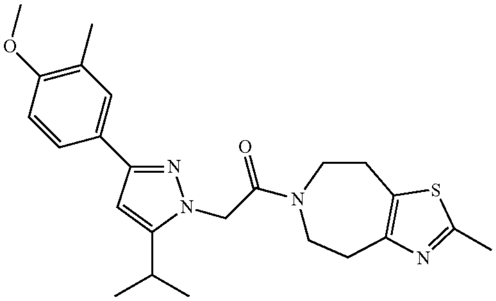
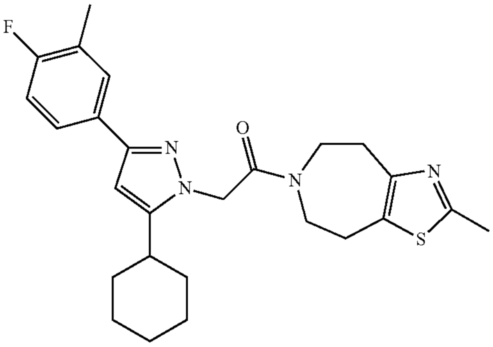
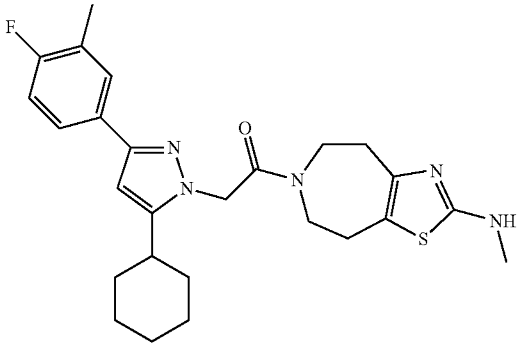
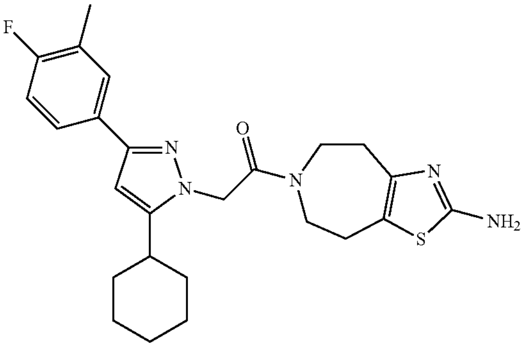
-continued
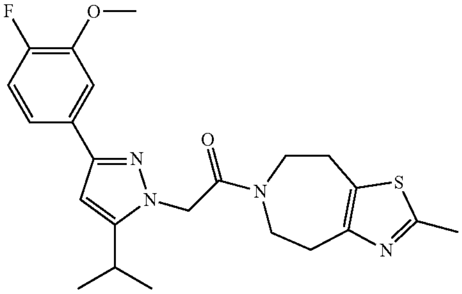
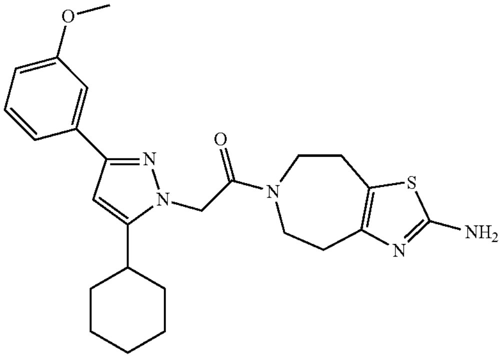
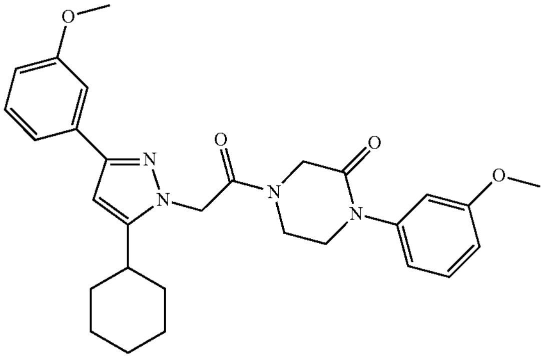
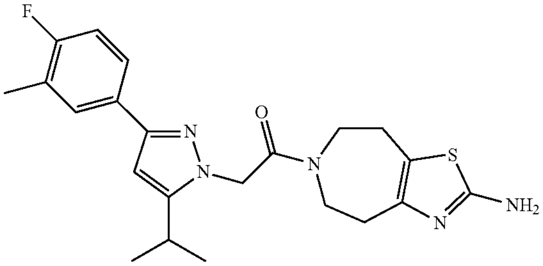
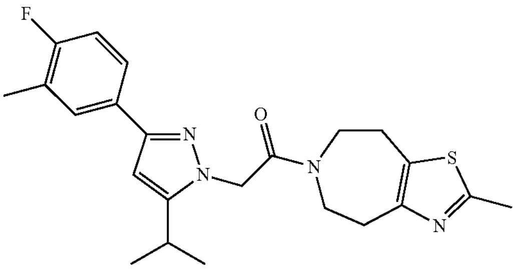

-continued
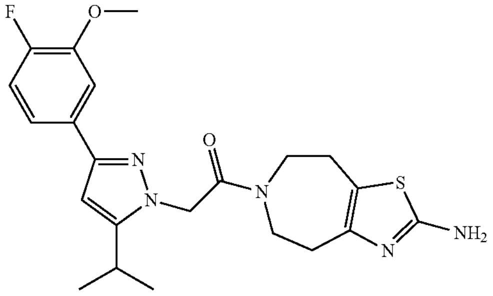
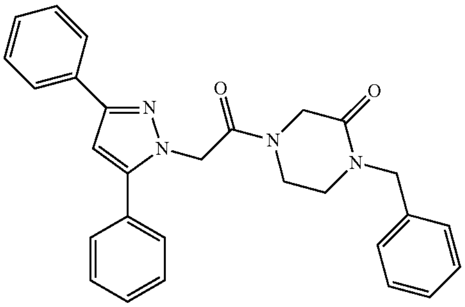
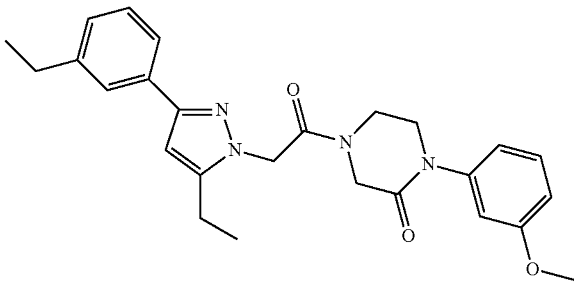
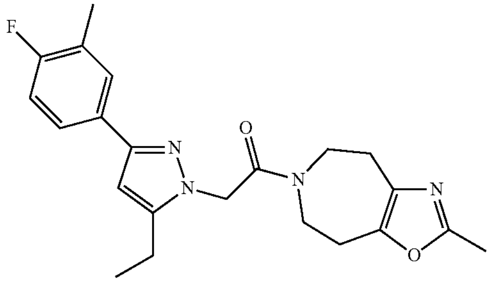
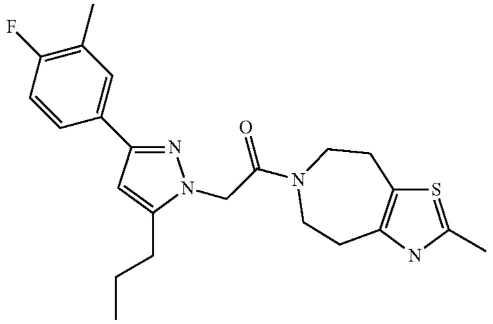
-continued
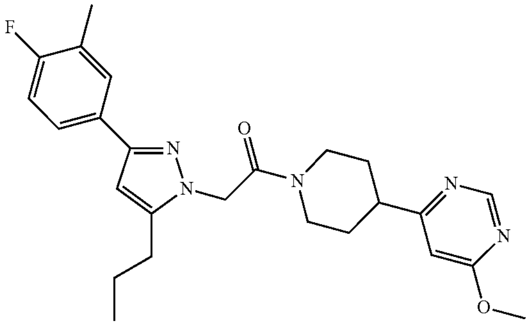
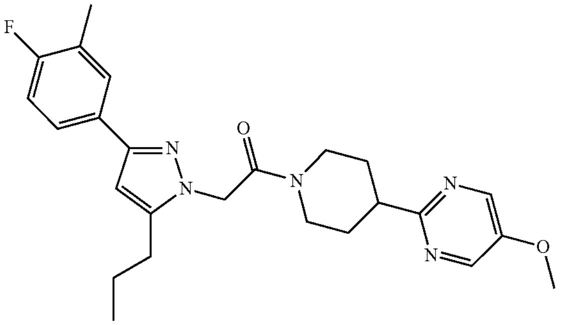
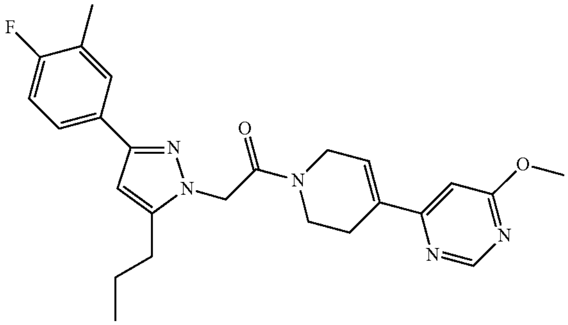
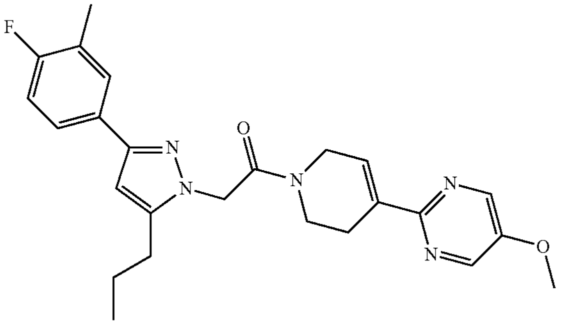
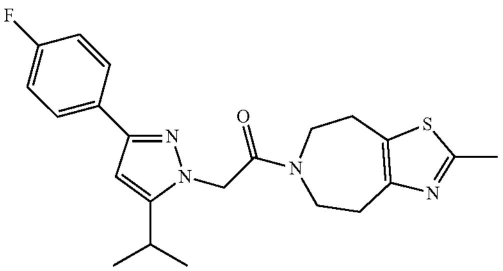

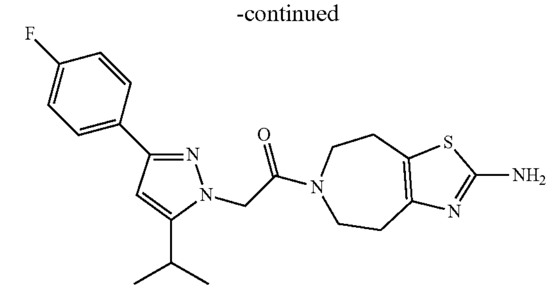
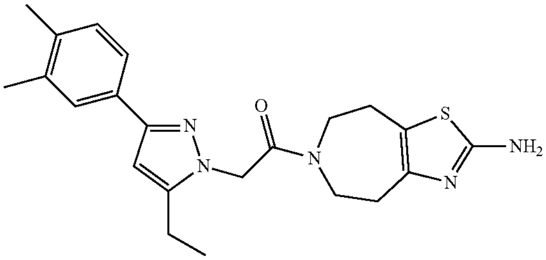
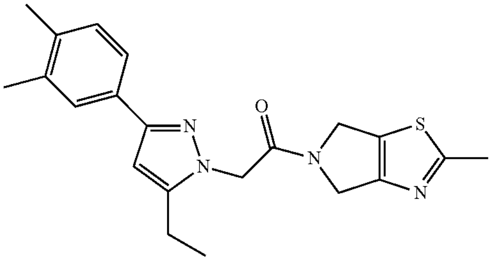
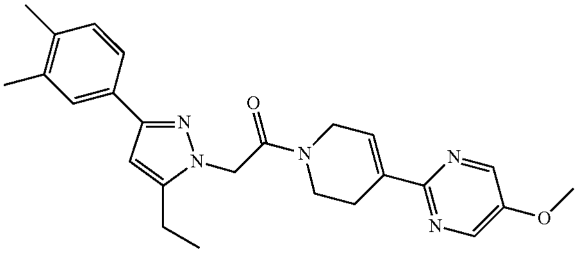
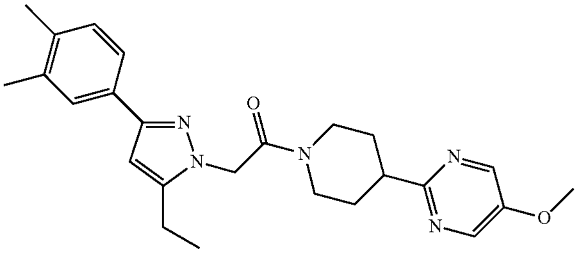
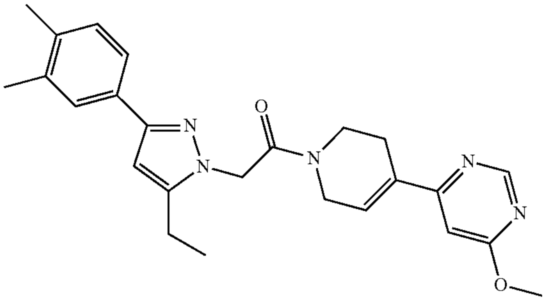
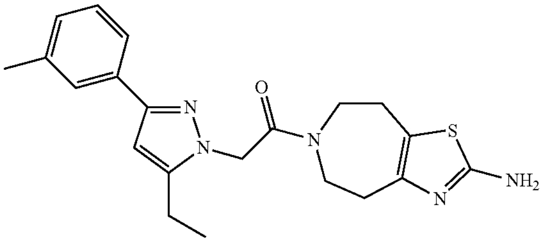
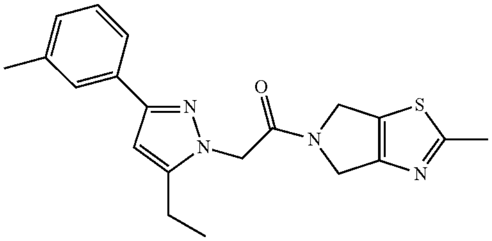
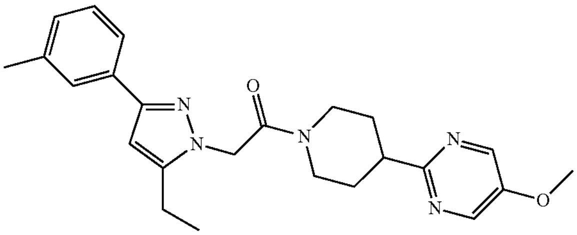
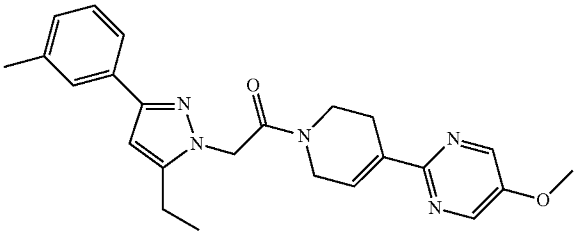
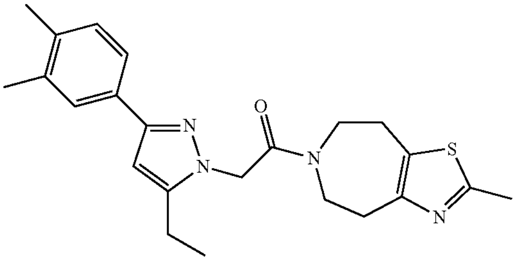
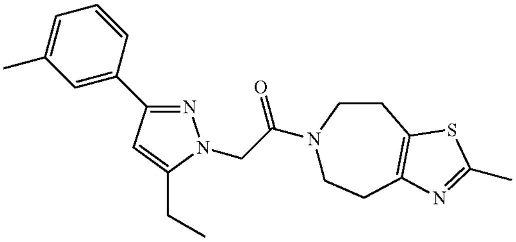

-continued
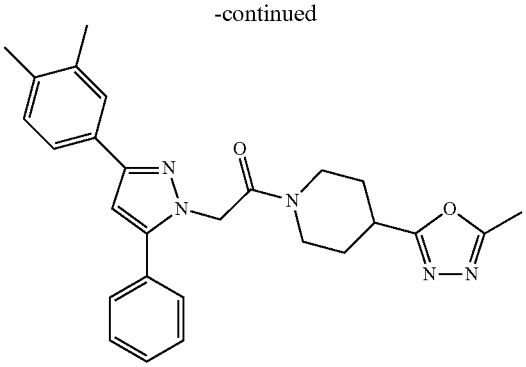
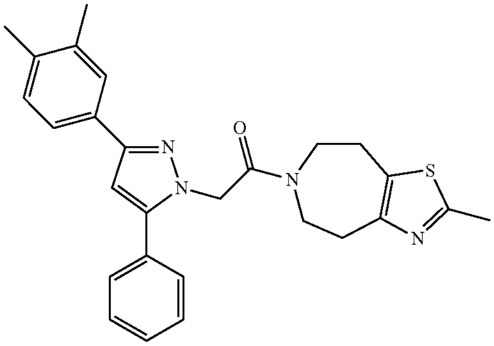
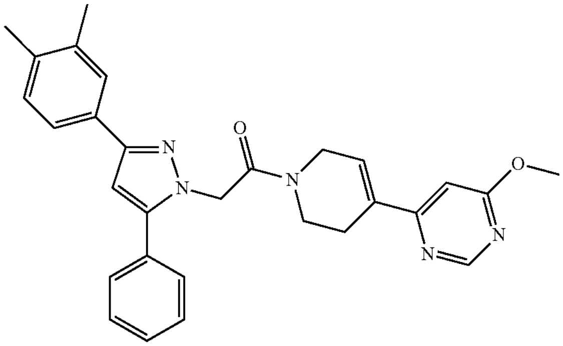
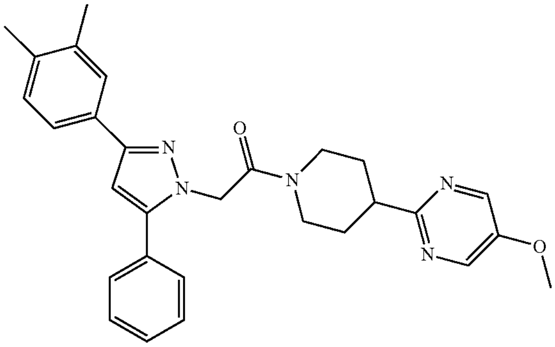
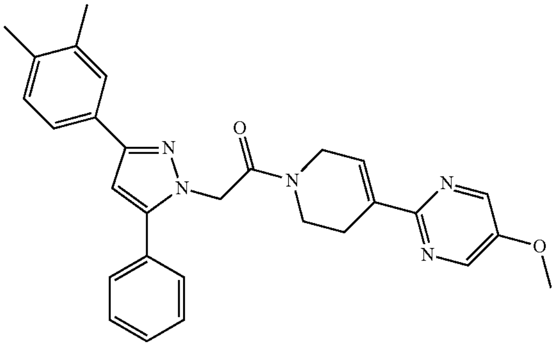
-continued
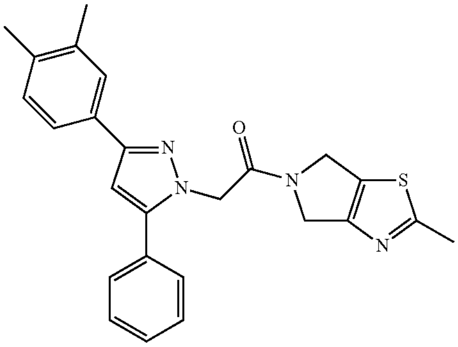
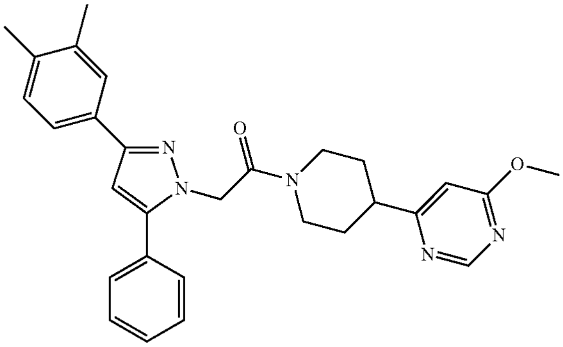
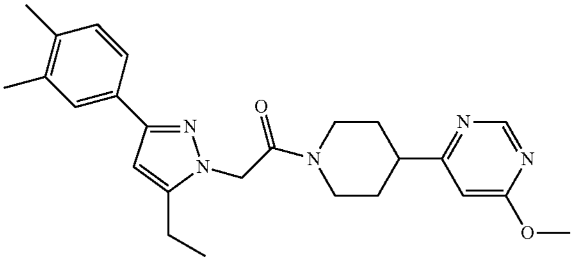
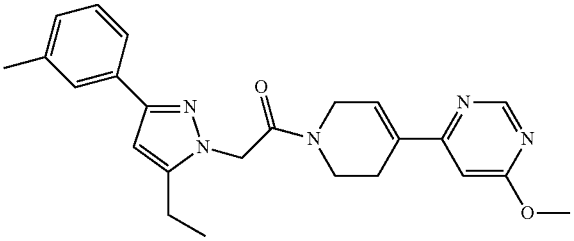
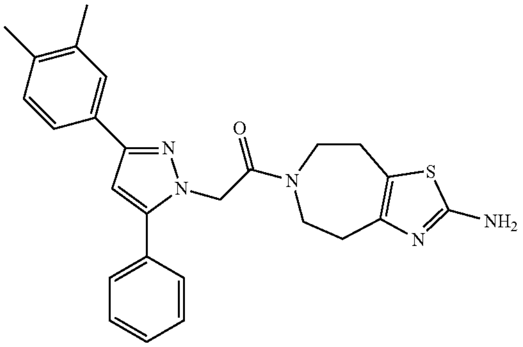

-continued
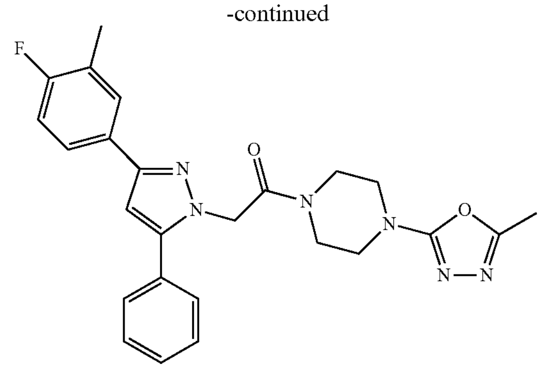
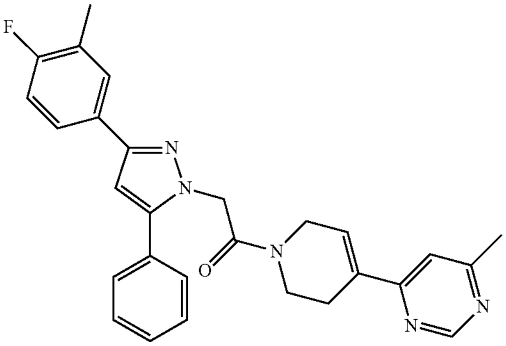
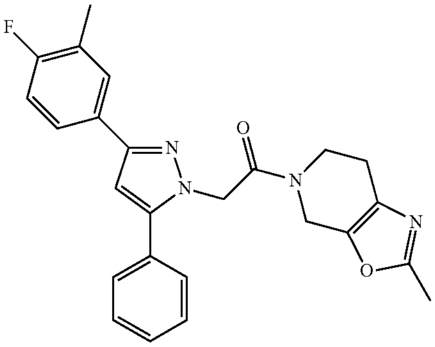
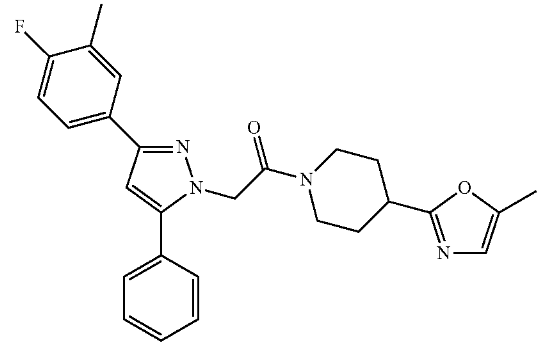
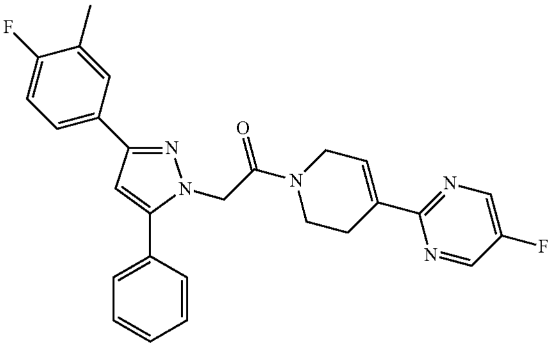
-continued
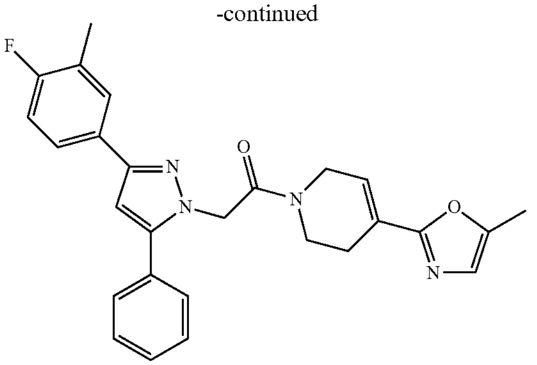
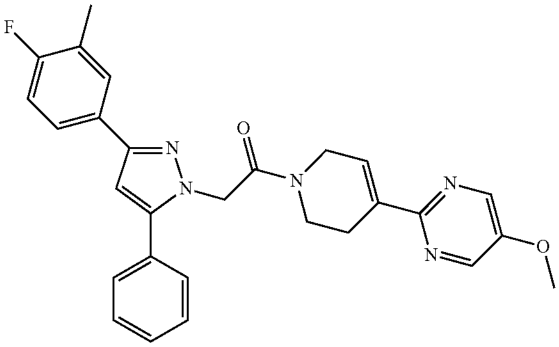
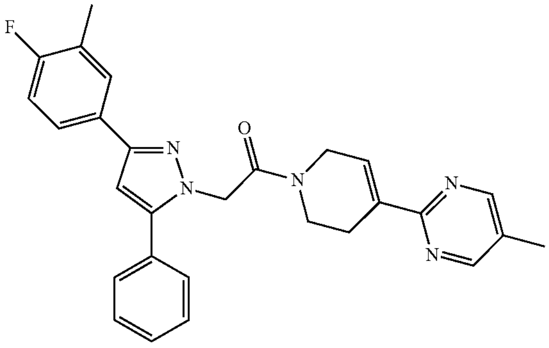
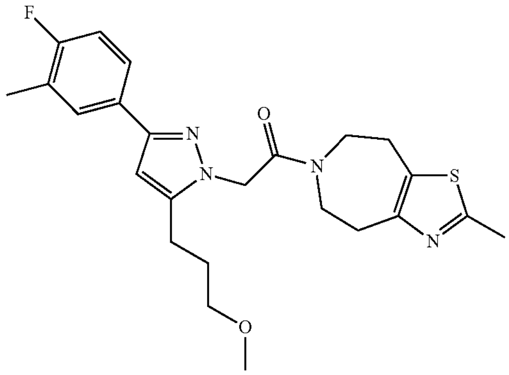

-continued
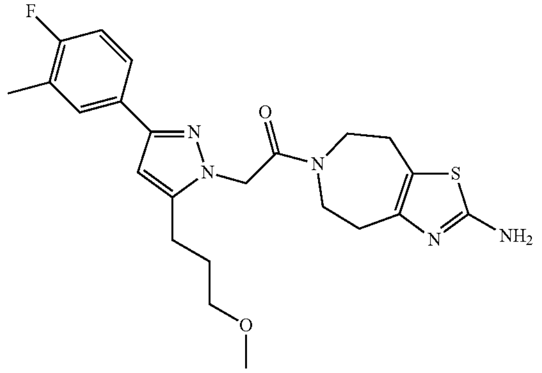
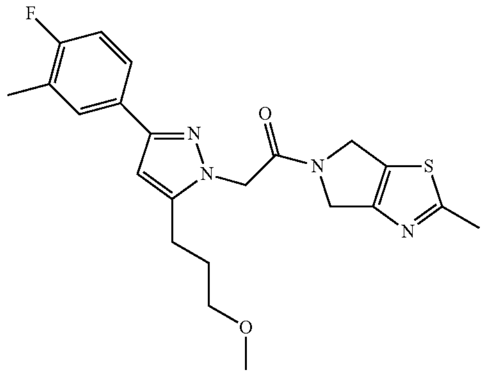
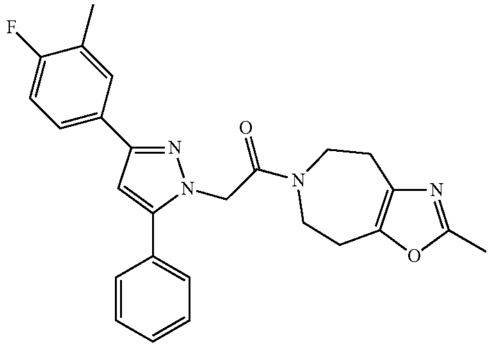
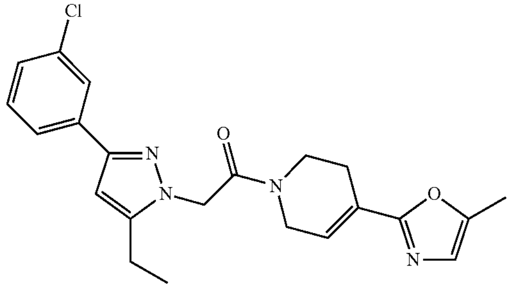
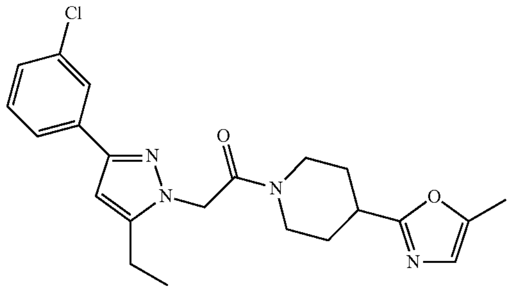
-continued
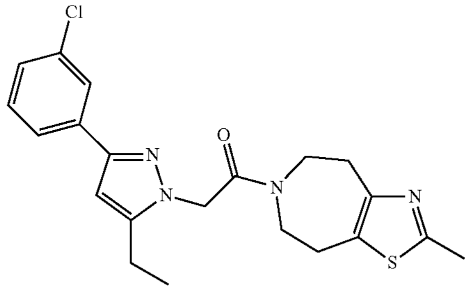
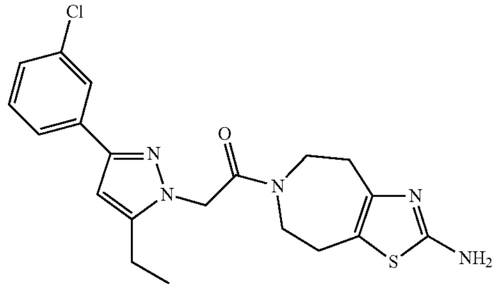
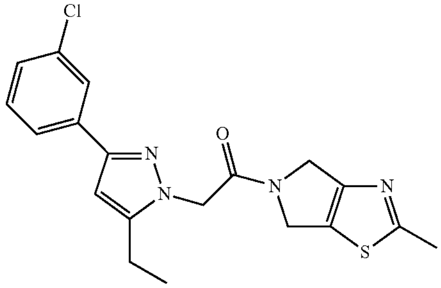
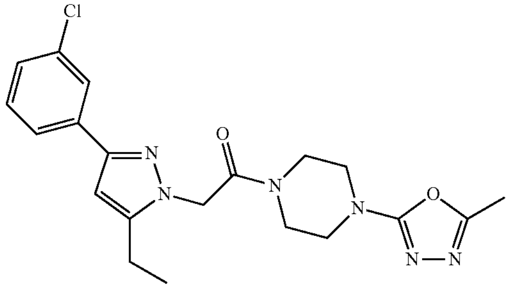
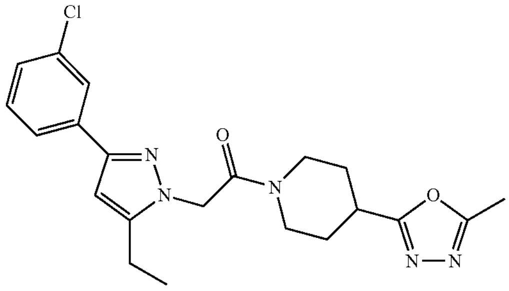

-continued
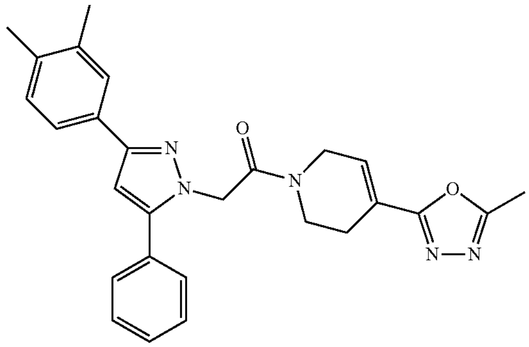
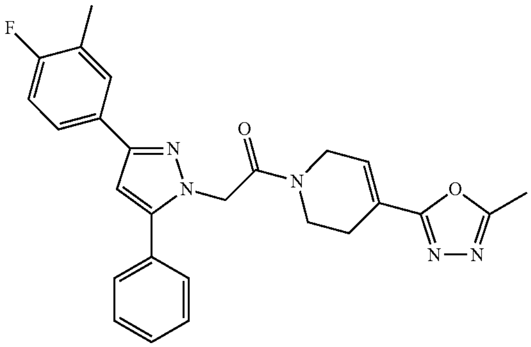
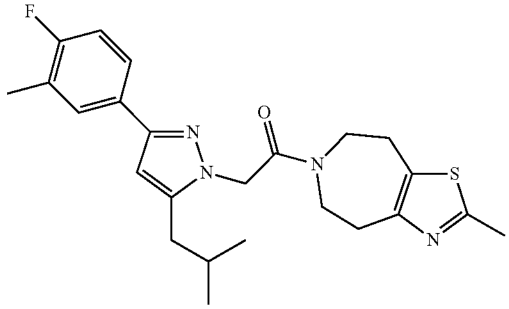
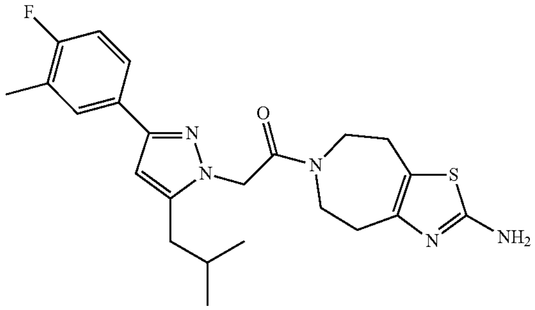
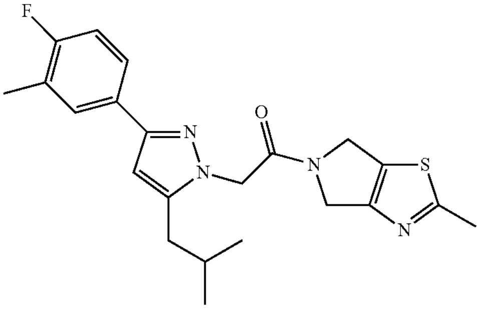
-continued
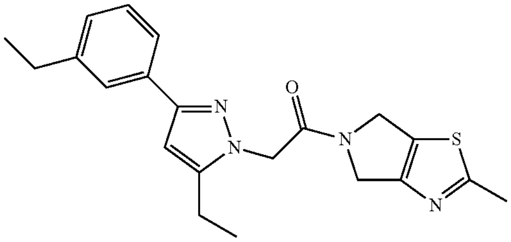
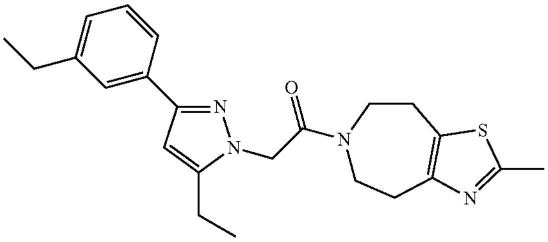
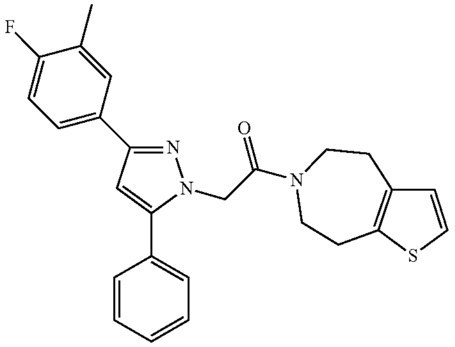
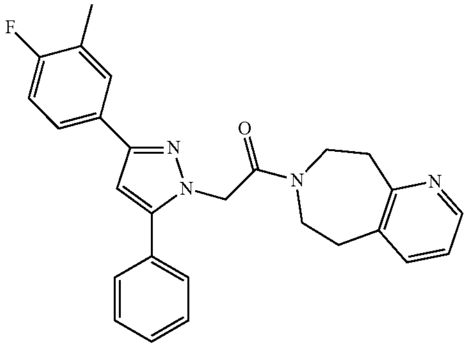
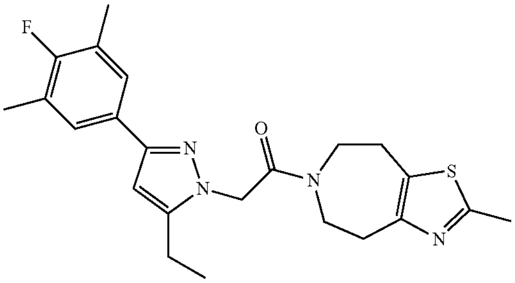

-continued
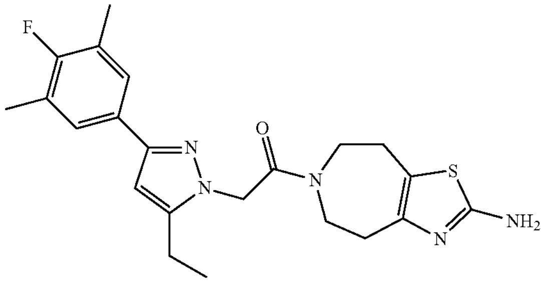
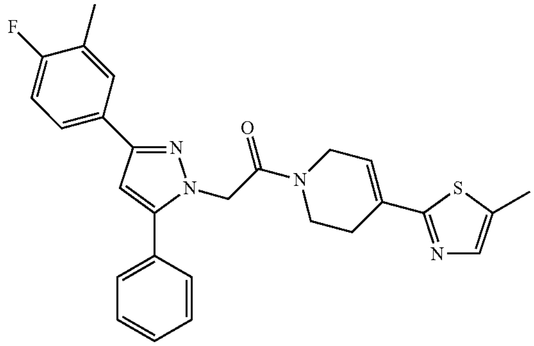
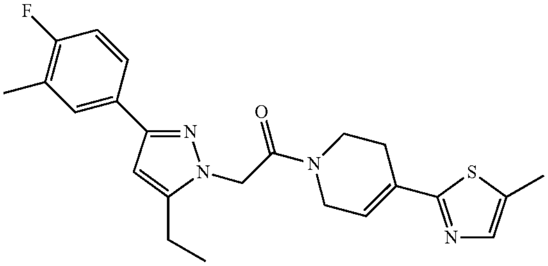
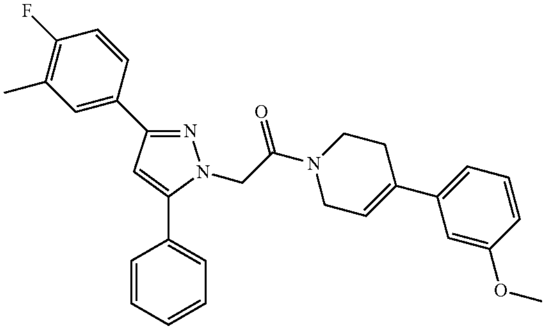
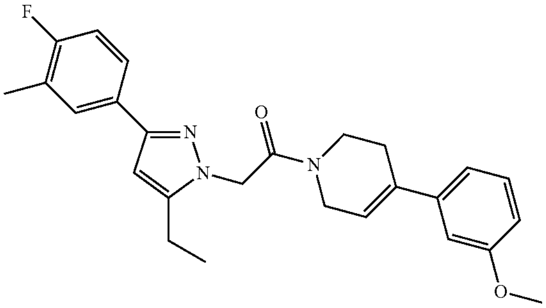
-continued
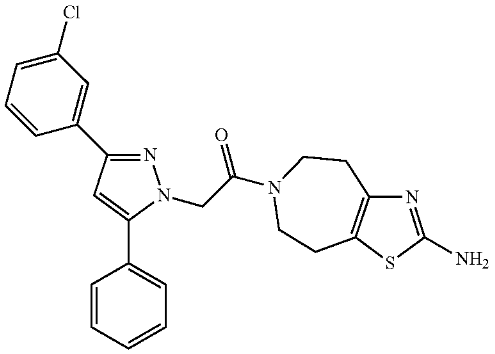
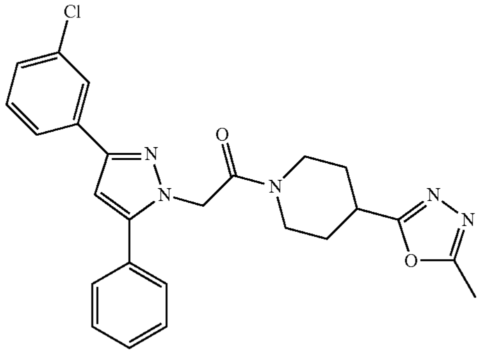
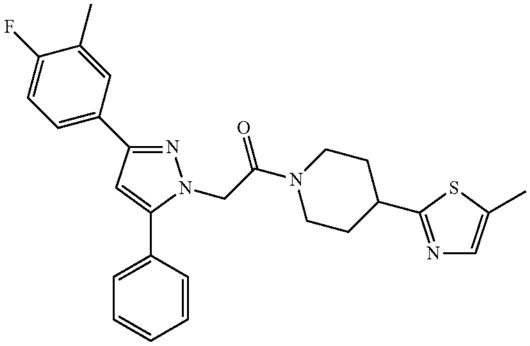
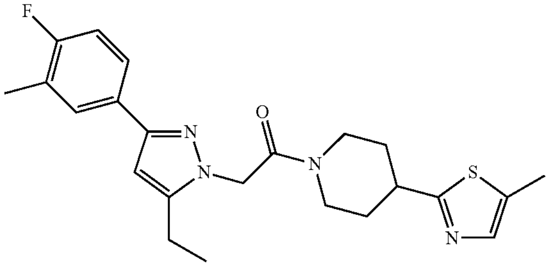
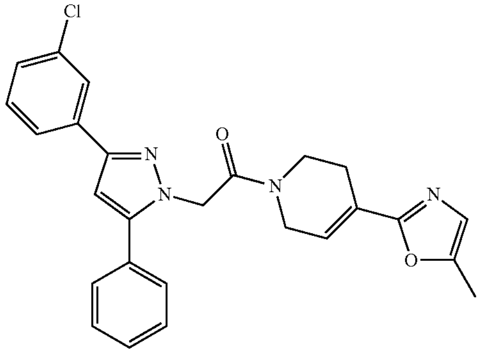

-continued
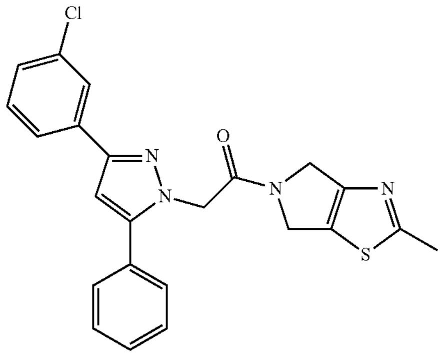
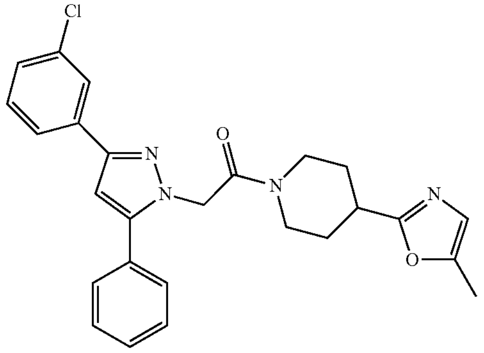
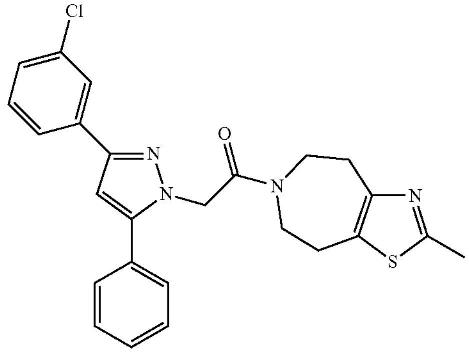
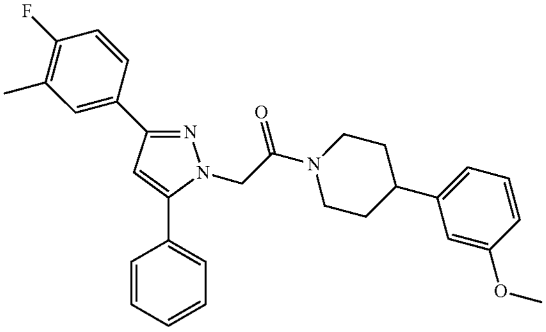
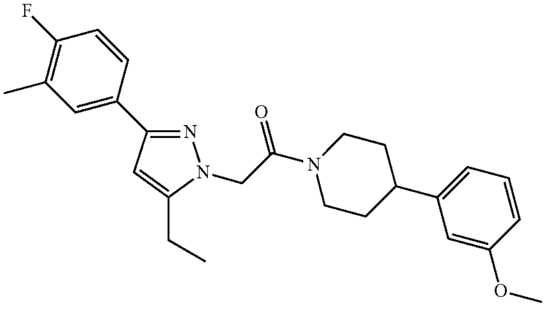
-continued
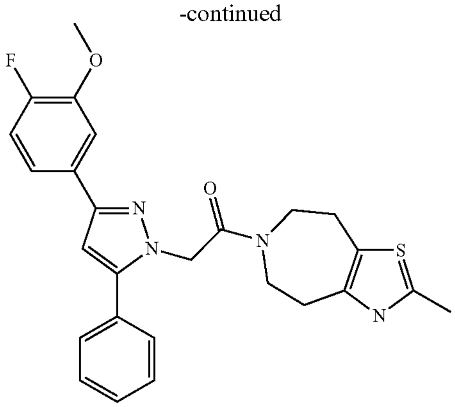
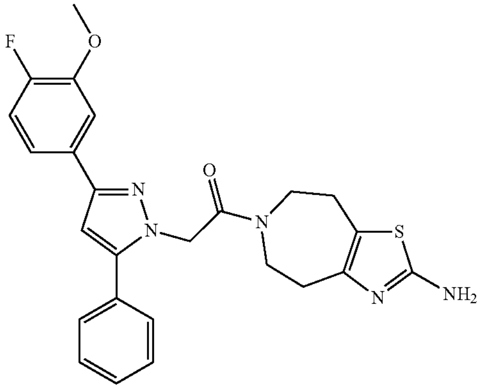
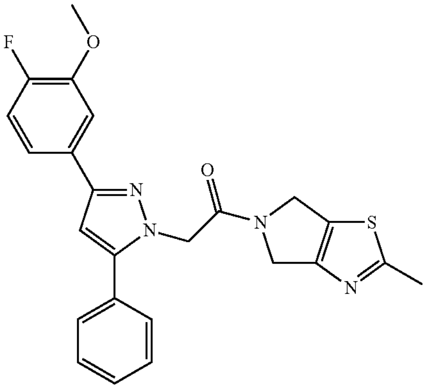
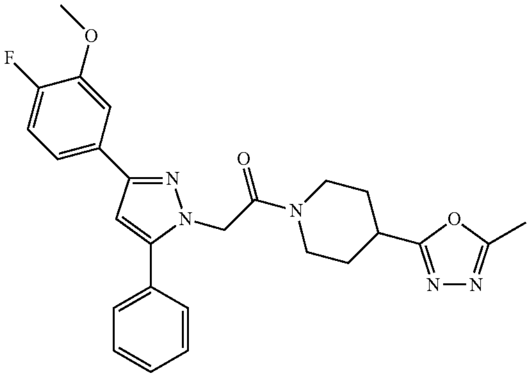

-continued
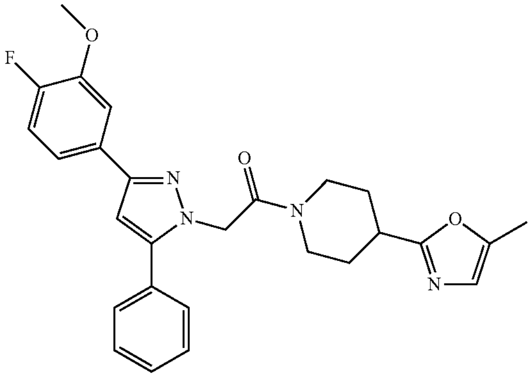
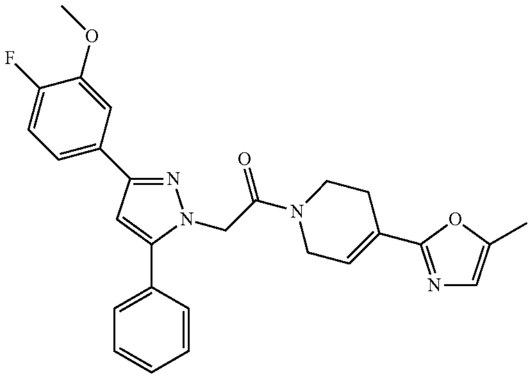
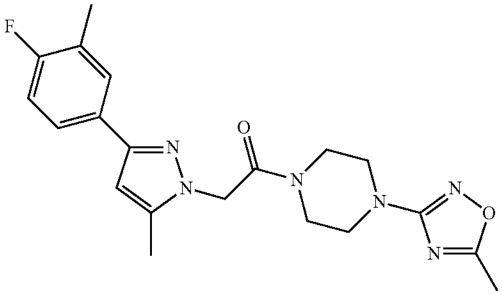
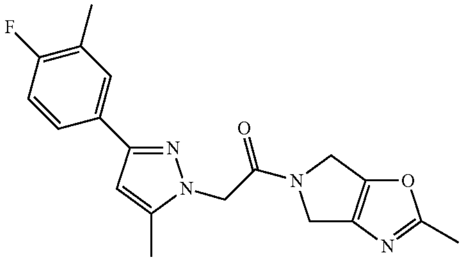
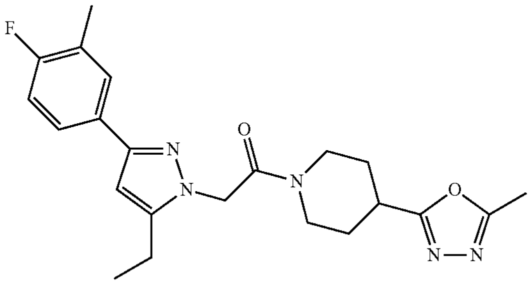
-continued
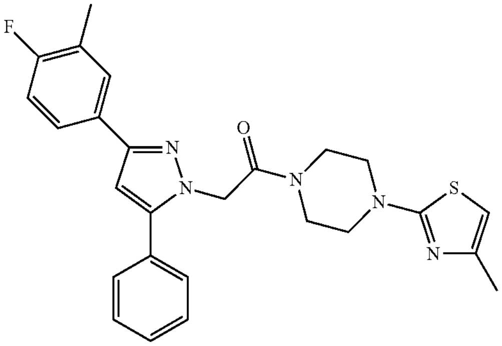
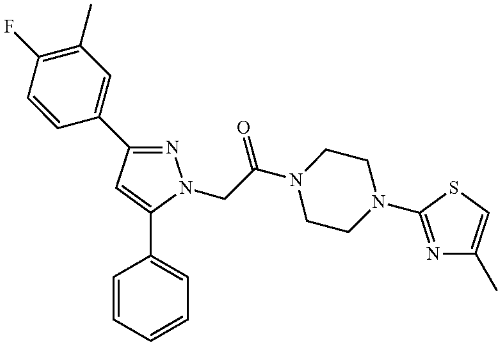
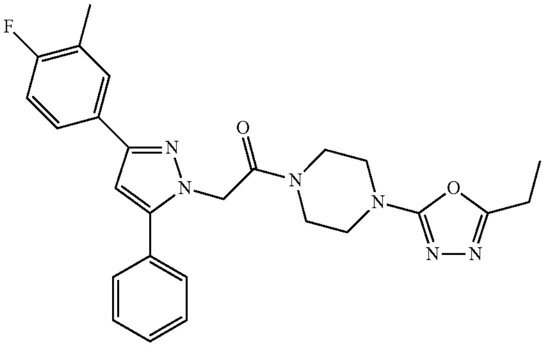
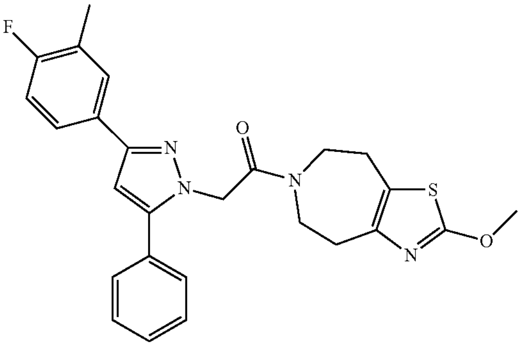
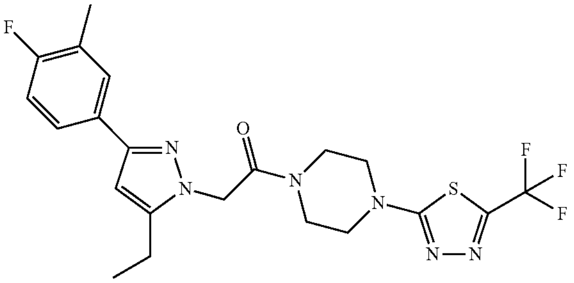

-continued
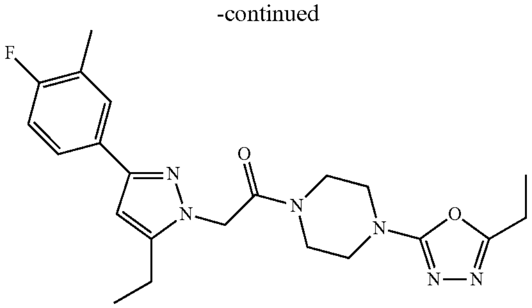
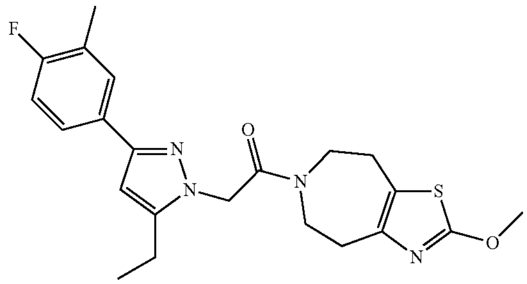
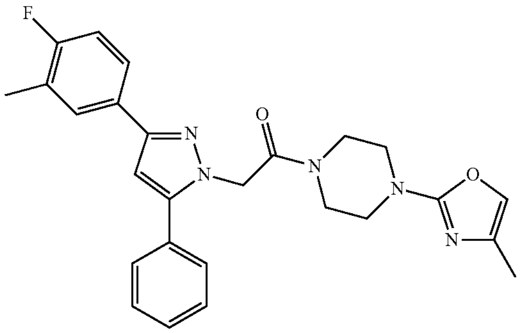
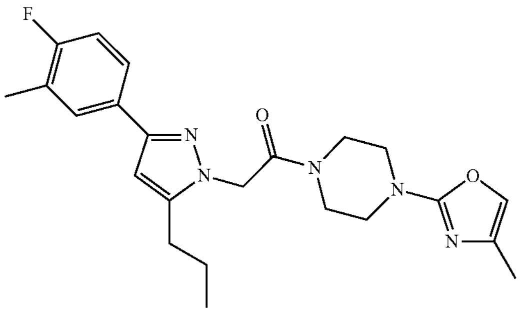
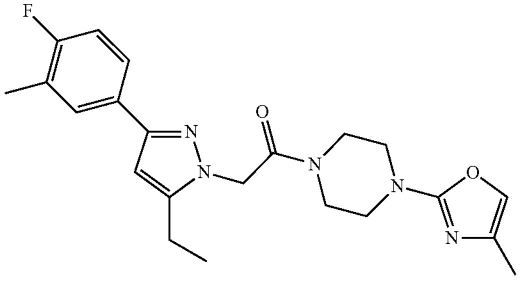
-continued
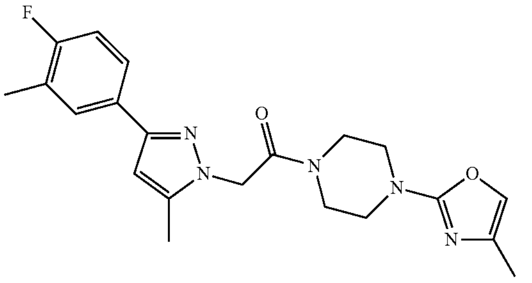
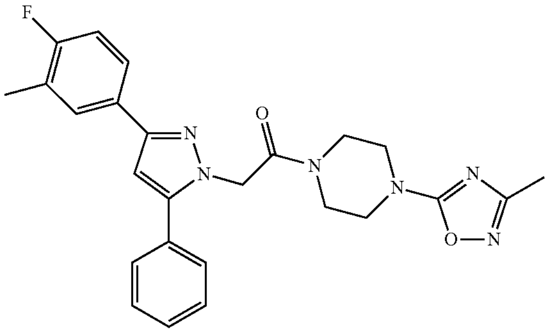
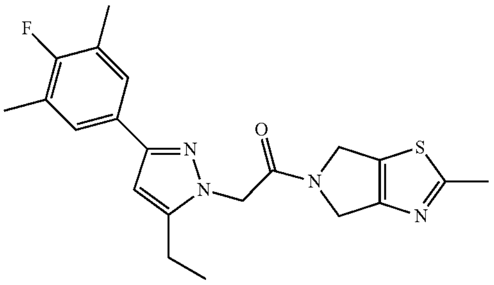
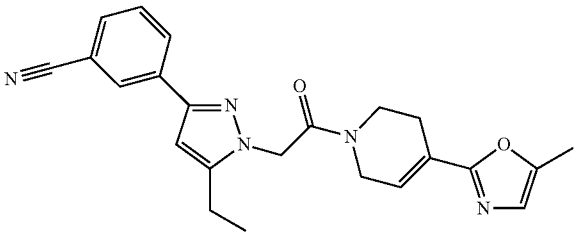
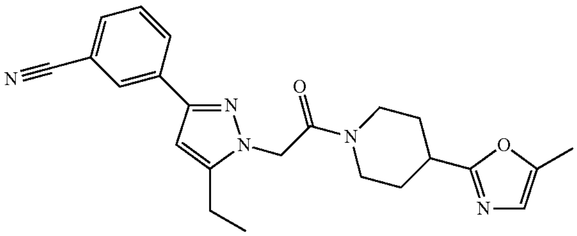
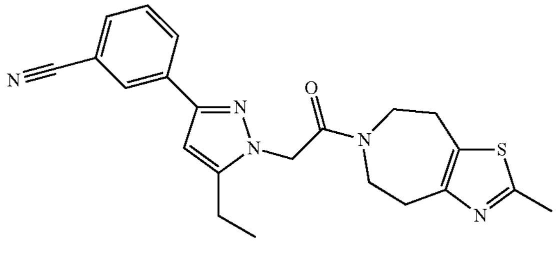

-continued
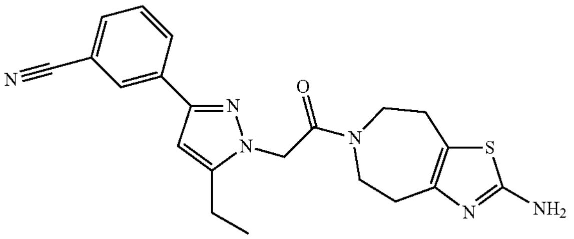
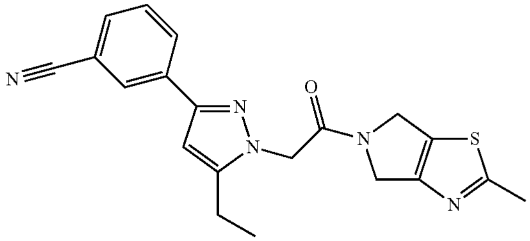
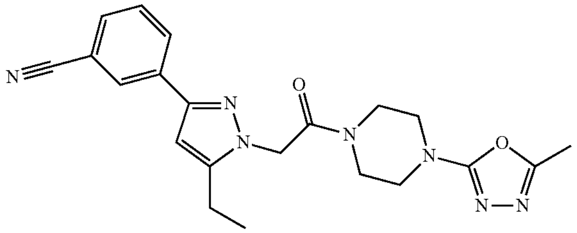
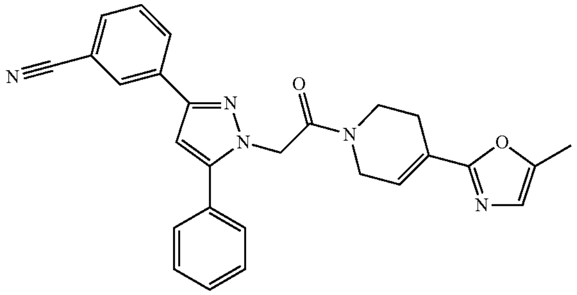
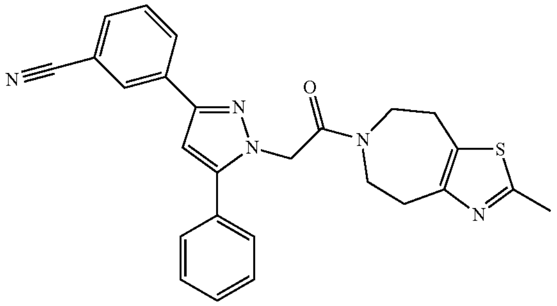
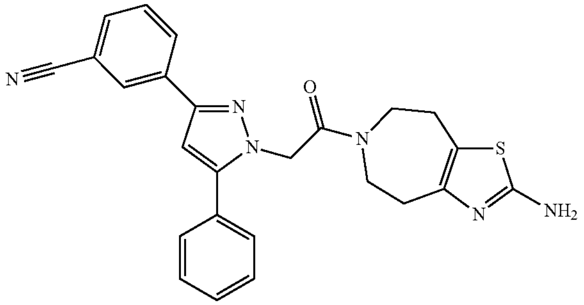
-continued
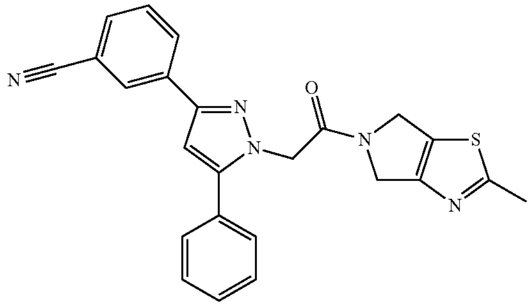
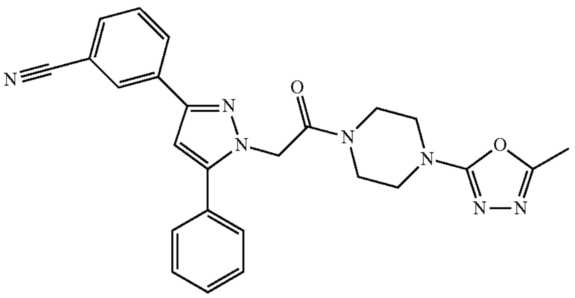
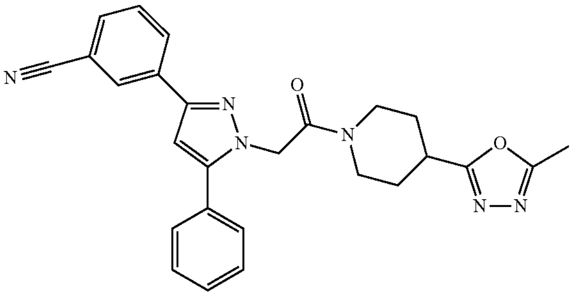
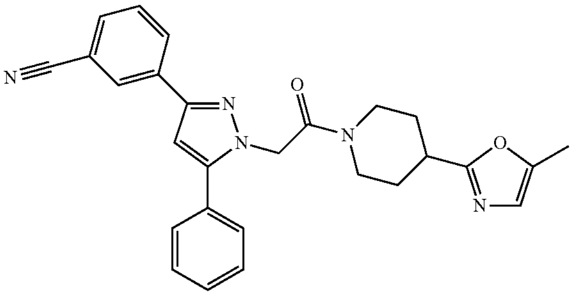
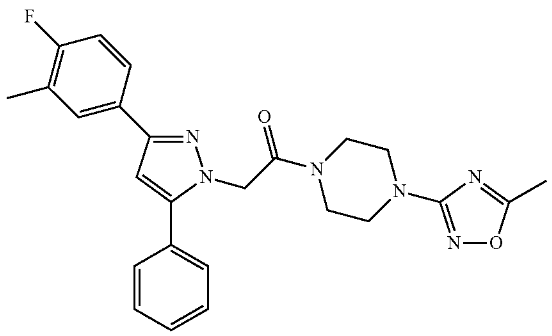

-continued
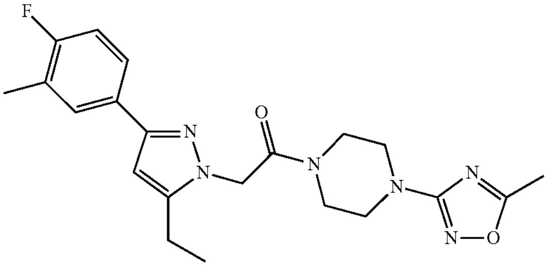
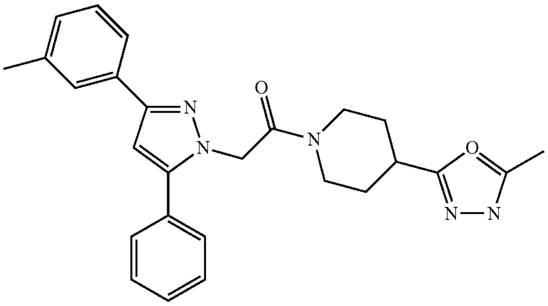
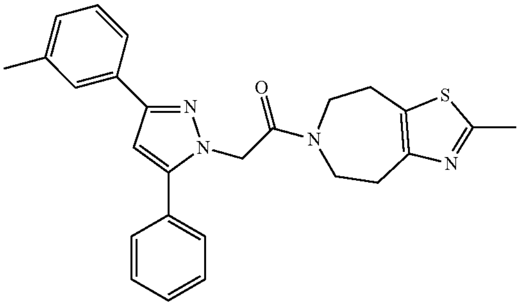
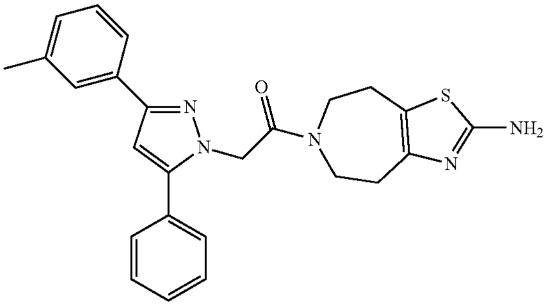
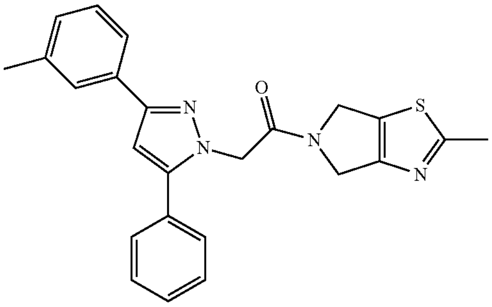
-continued
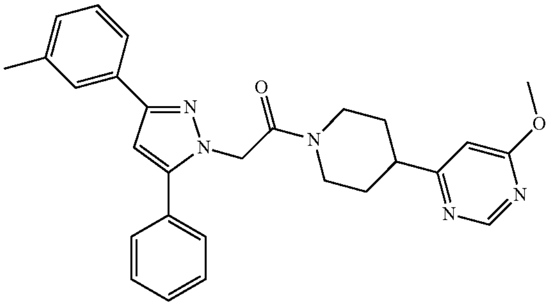
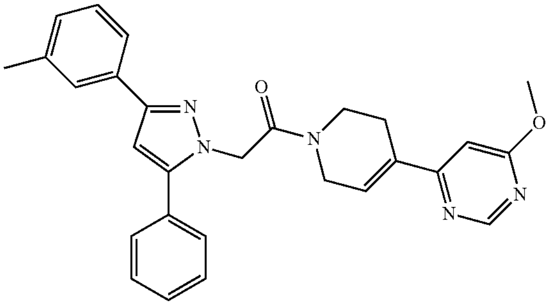
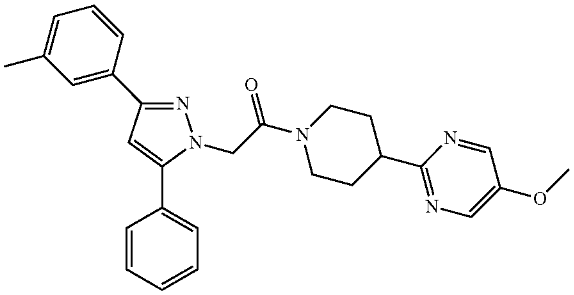
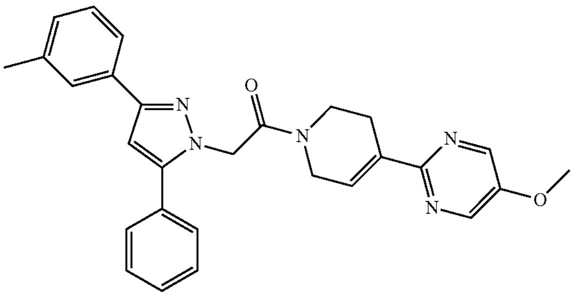
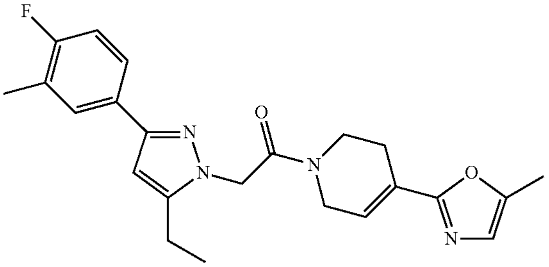

-continued
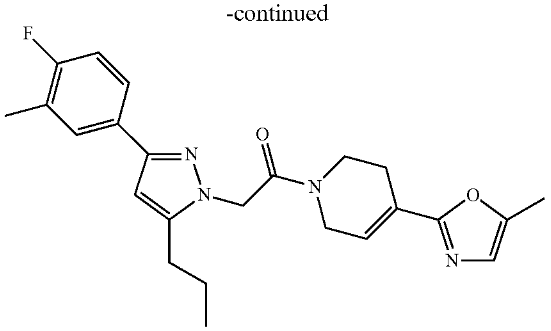
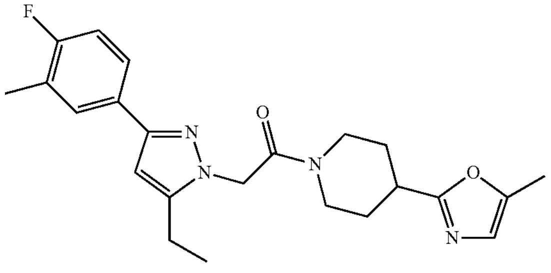
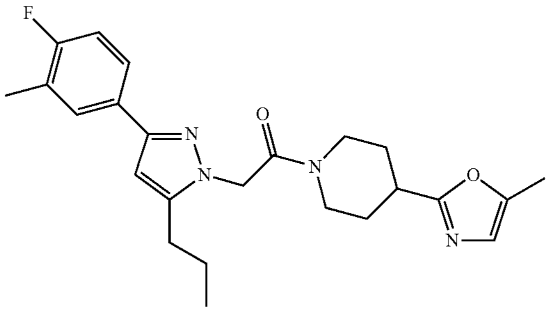
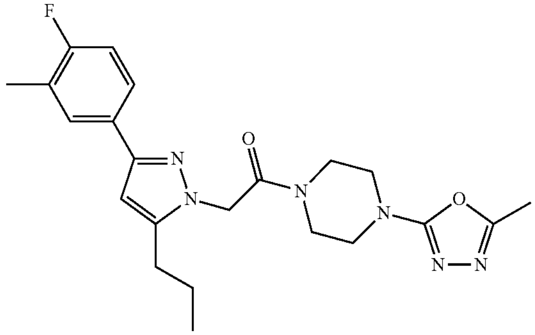
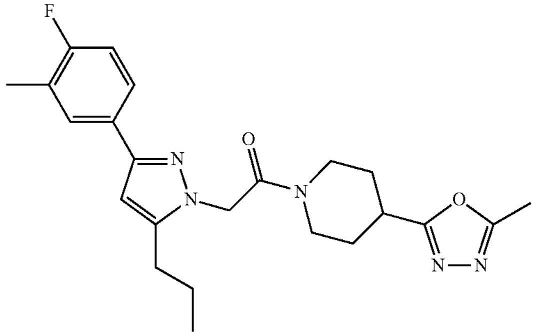
-continued
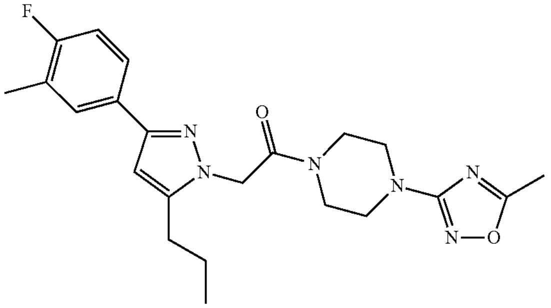
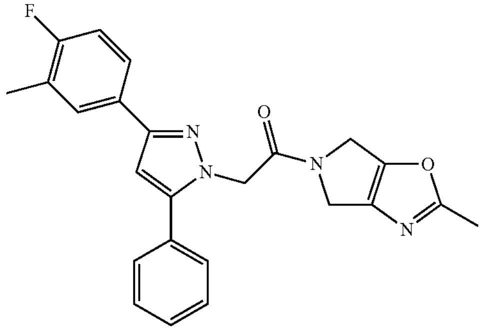
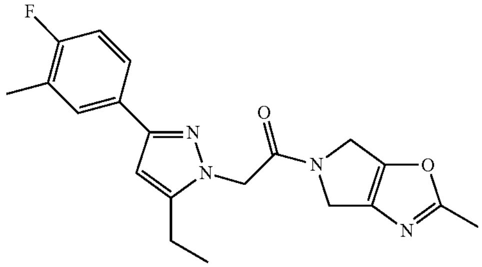
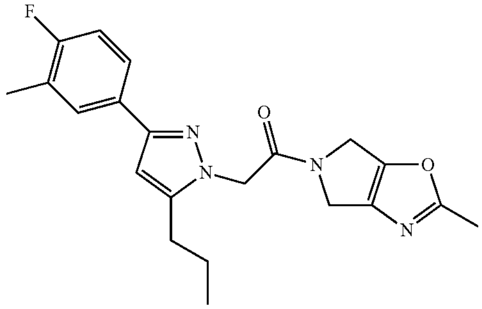
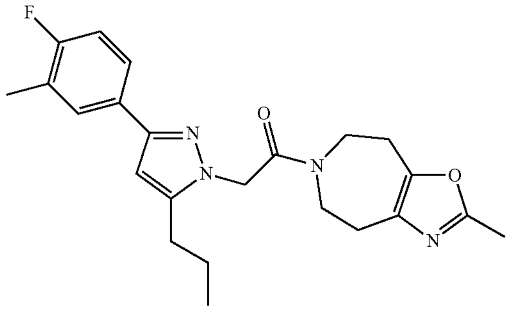

-continued
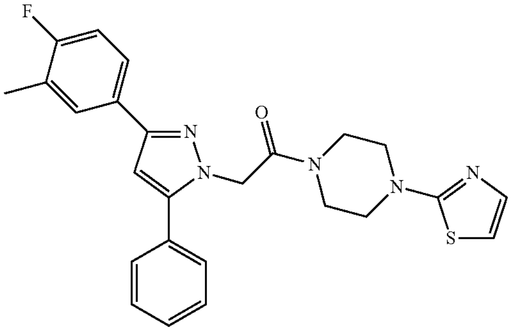
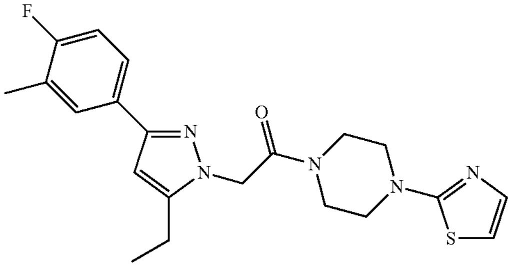
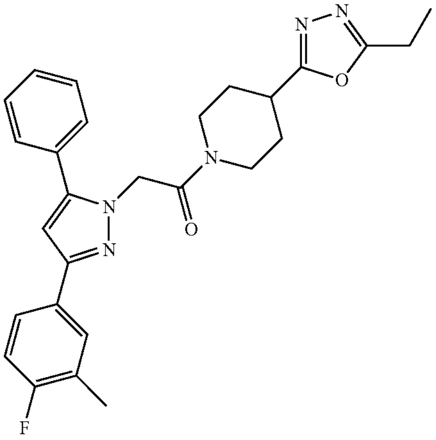
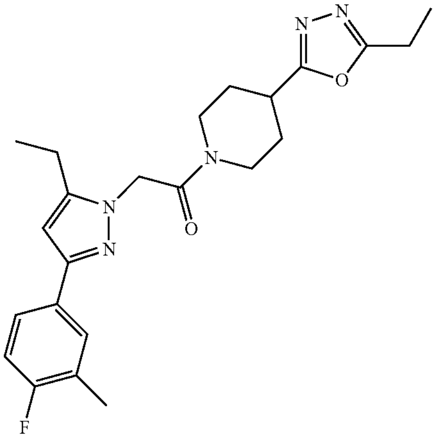
-continued
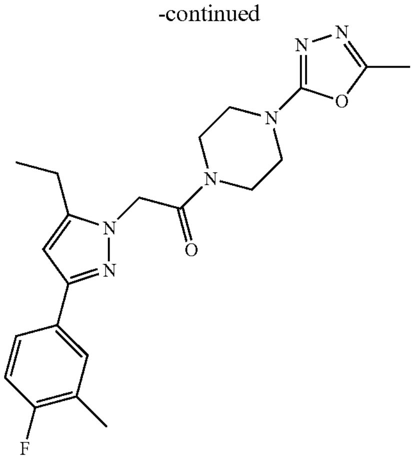
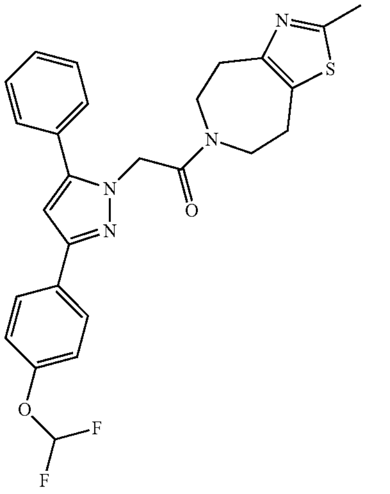
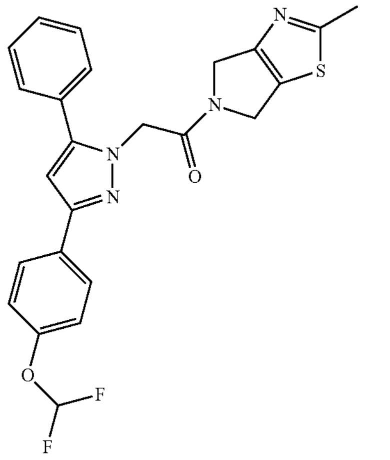

-continued
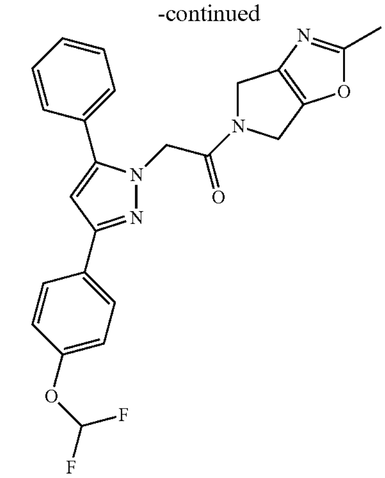
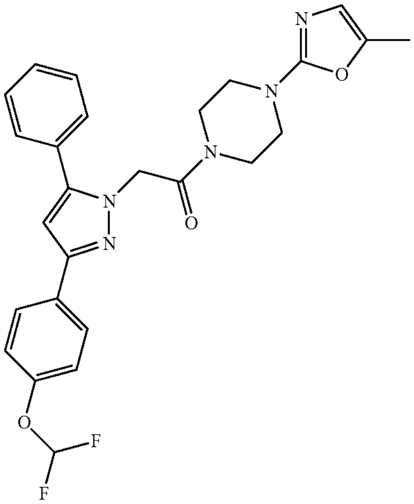
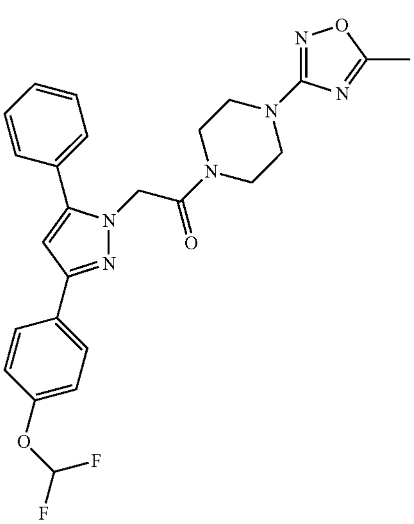
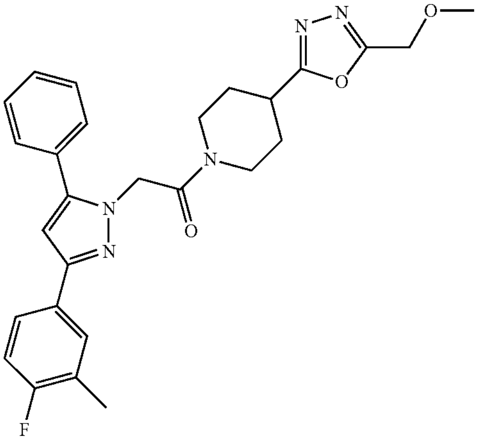
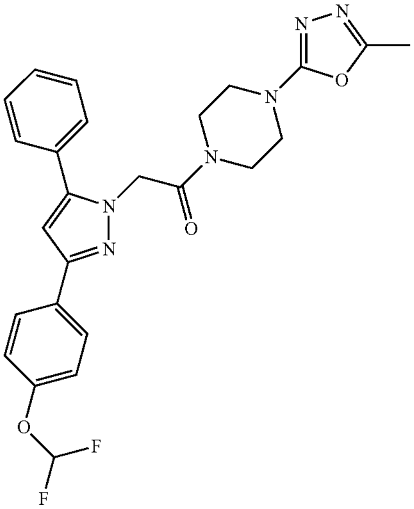
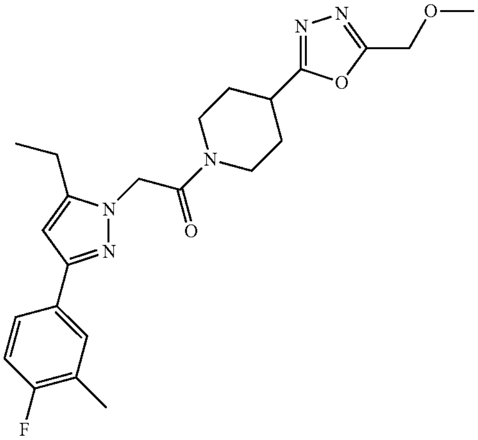

-continued
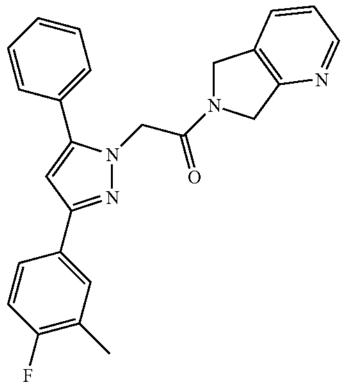
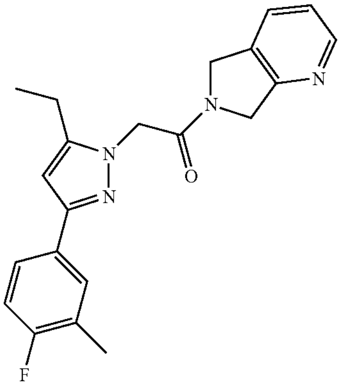
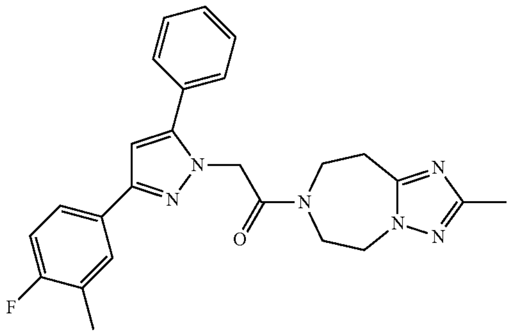
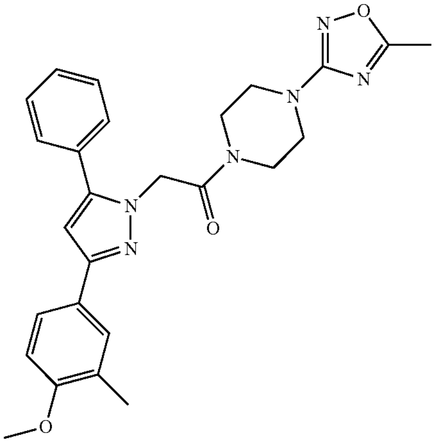
-continued
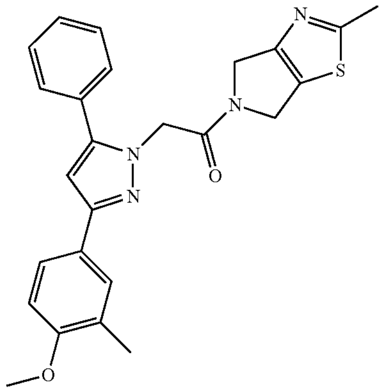
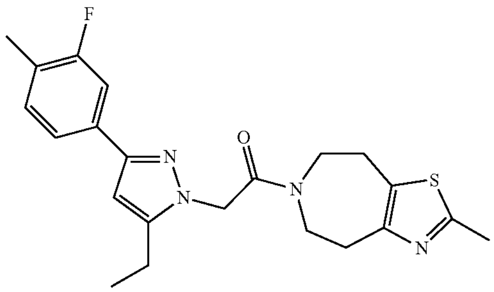
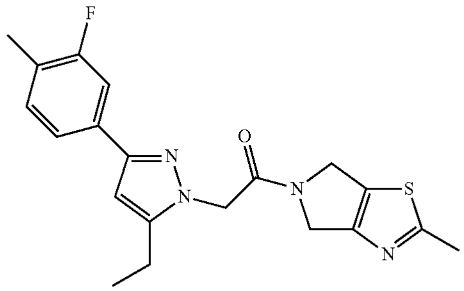
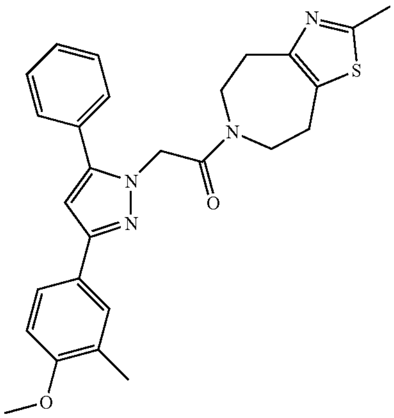

-continued
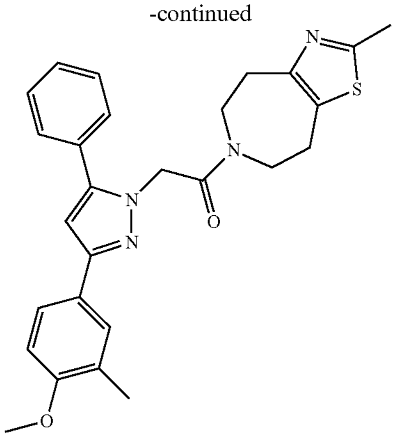
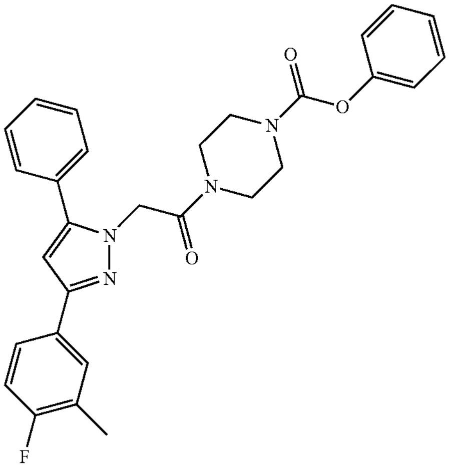
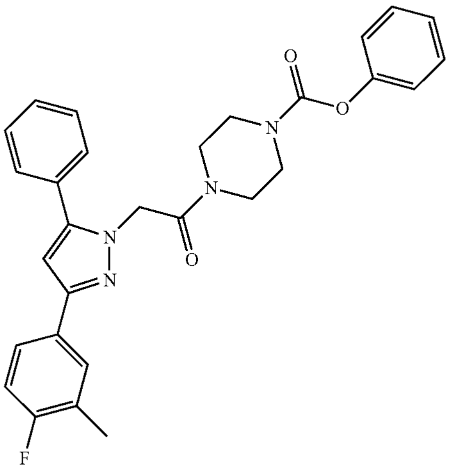
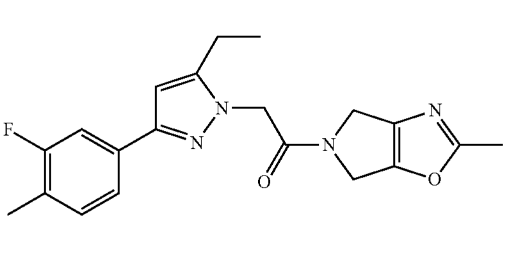
-continued
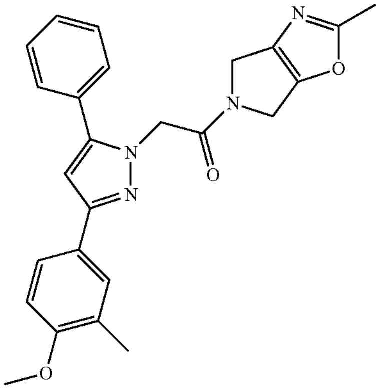
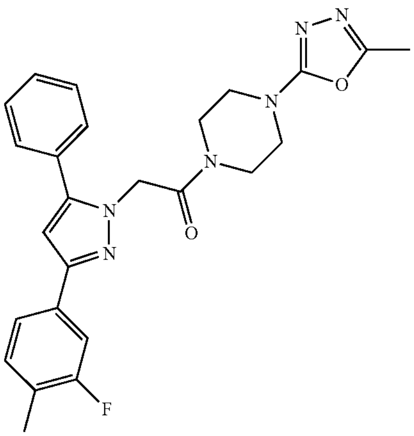
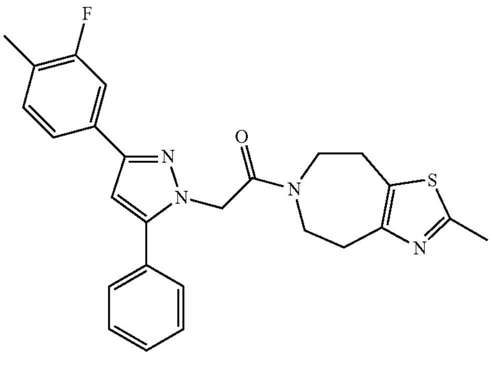
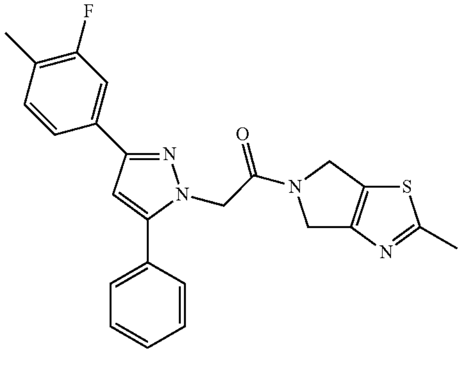

-continued
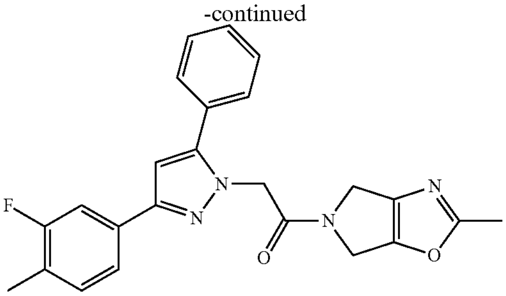
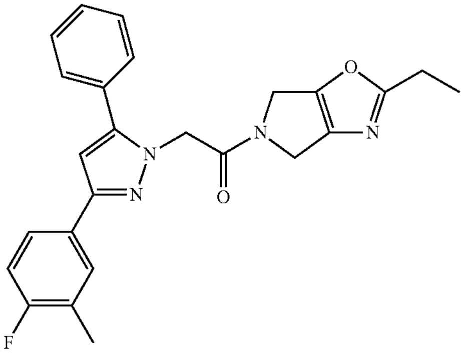
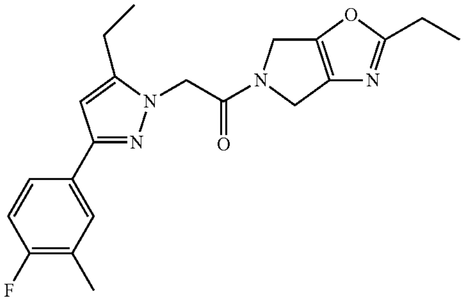
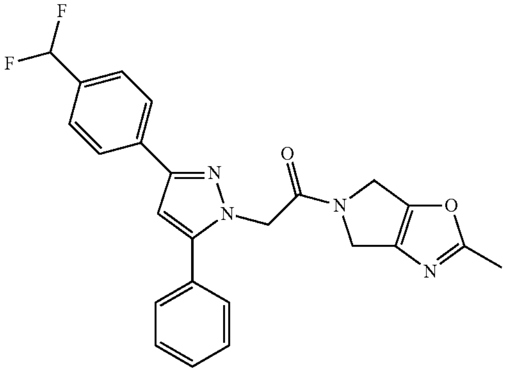
-continued
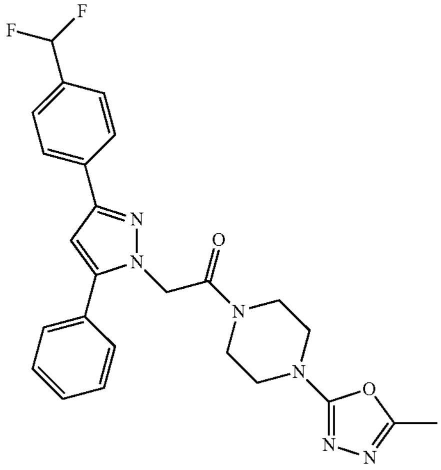
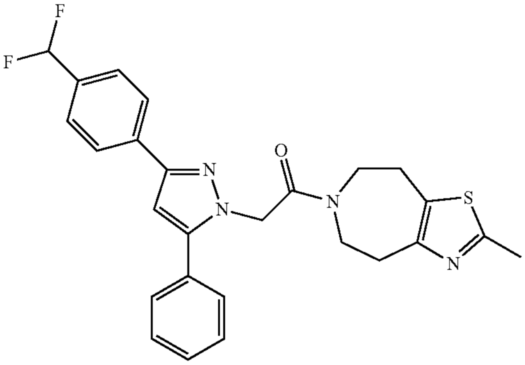
and
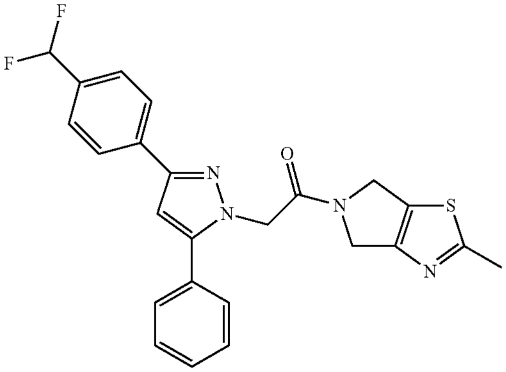
or a physiologically acceptable salt thereof.
3. A pharmaceutical composition comprising a therapeutically effective amount of a compound according to claim 1 or a pharmaceutically acceptable salt thereof in admixture with a pharmaceutically acceptable adjuvant, diluent and/or carrier.
* * * * *